(12) United States Patent
Jinno et al.

(10) Patent No.: US 6,602,898 B1
(45) Date of Patent: Aug. 5, 2003

(54) TRICYCLIC FUSED HETEROCYCLE COMPOUNDS, PROCESS FOR PREPARING THE SAME AND USE THEREOF

(75) Inventors: Shuji Jinno, Tokyo (JP); Takaaki Okita, Tokyo (JP); Naomi Ohtsuka, Tokyo (JP); Shinya Yamashita, Tokyo (JP); Junichiro Hata, Tokyo (JP); Jiro Takeo, Tokyo (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 09/980,581

(22) PCT Filed: Jun. 2, 2000

(86) PCT No.: PCT/JP00/03592

§ 371 (c)(1),
(2), (4) Date: Feb. 26, 2002

(87) PCT Pub. No.: WO00/75127

PCT Pub. Date: Dec. 14, 2000

(30) Foreign Application Priority Data

Jun. 3, 1999 (JP) .......................................... 11-157181

(51) Int. Cl.$^7$ ...................... A61K 31/38; C07D 337/12

(52) U.S. Cl. ........................................ 514/431; 549/12

(58) Field of Search ............................. 549/12; 514/431

(56) References Cited

U.S. PATENT DOCUMENTS

| | | | |
|---|---|---|---|
| 4,104,280 A | 8/1978 | Ackrell | |
| 4,237,160 A | 12/1980 | Hamel et al. | |
| 5,734,067 A | 3/1998 | Jinno et al. | |
| 6,180,659 B1 | 1/2001 | Yamashita et al. | |
| 6,211,227 B1 * | 4/2001 | Yoshida et al. | 514/431 |

FOREIGN PATENT DOCUMENTS

| | | |
|---|---|---|
| CA | 1 176 265 | 1/1982 |
| DE | 1 302 590 | 11/1970 |
| DE | 3203065 A1 | 8/1983 |
| EP | 0 003 893 A1 | 9/1979 |
| EP | 0 011 067 | 5/1980 |
| EP | 0 805 155 A1 | 11/1997 |
| EP | 0885610 A1 | 12/1998 |
| GB | 2 016 466 A | 9/1979 |
| WO | WO96 25927 | 8/1996 |

OTHER PUBLICATIONS

Acton, David et al., "Tricyclic Triarylethylene Antiestrogens; Dibenz[b, f]oxepins, Dibenzo[b,f]thiepins, Dibenzo[a, e]cyclooctenes, and Dibenzo[b,f]thiocins," J. Med. Chem., vol. 26, No. 8, pp. 1131–1137, (1983).

Anjaneyulu, A.S.R. et al,."Pacharin: A New Dibenzo(2.3–6, 7)oxepin Derivative from Bauhinia Racemosa Lamk," Tetrehedron, vol. 40, No. 21, pp. 4245–4252, (1984).

Burden, Peter M. et al., "The Synthesis of 1,8–Disubstituted 10,11–Dihydrodibenz[b,f]oxepin–10–ones. Analogues of Anaesthetic Steroids," J. Chem. Soc. Perkin Trans. 1, pp. 3291–3294, (1991).

Carrier, R. et al., "Studies on L–640,035: a novel antogonist of contractile prostanoids in the lung," British Journal of Pharmacology, vol. 82, No. 2, pp. 389–395 (1984).

de la Fuente, M.C. et al., "A Synthetic Route to (±) Clavizepine through a Dibenzoxepine Intermediate," J. Org. Chem., vol. 61, No. 17, pp. 5818–5822, (1996).

Kametani, Tetsuji et al., Cularine and Related Compounds. XV. Demethylation of Cularine and Cularimine (Studies on the Synthesis of Heterocyclic Compounds. CLXVII.), Journal of the Pharmaceutical Society of Japan, vol. 87, No. 2, pp. 198–201, (1967).

Kushiku, Kazushi et al., "Effects of 2–(10, 11–Dihydro–10–oxodibenzo [b,f]thiepin–2–yl)propionic acid (CN–100) on the cardiovascular and autonomic nervous systems," Folia Pharmacol. Japan, vol. 94, pp. 299–307, (1989).

(List continued on next page.)

*Primary Examiner*—Deborah C. Lambkin
(74) *Attorney, Agent, or Firm*—Fish & Richardson P.C.

(57) ABSTRACT

Compounds represented by formula (1), (Formula 1)

wherein
X is, for example, CH, $CH_2$, CHR (wherein R is a lower alkyl group or a substituted lower alkyl group) or CRR' (wherein R and R' are the same as the above defined R);
Y is, for example, CH, $CH_2$ or C=O;
Z is, for example, O, S, S=O or $SO_2$;
U is C or N;
$R_1$ to $R_4$ are each independently, for example, a hydrogen atom, OR, SR (wherein R is the same as defined above), or an aromatic ring, a substituted aromatic ring or a heterocycle;
at least one of $R_5$ and $R_8$ is, for example, OH and the remaining of $R_5$ and $R_8$ are each independently, for example, a hydrogen atom or OH, optical isomers thereof, conjugates thereof or pharmaceutically acceptable salts thereof are provided. These compounds are characterized in having a wide range of pharmacological actions such as an excellent relaxing action of tracheal smooth muscles, an inhibition of airway hypersensitivity and an inhibition of infiltration of inflammatory cells into the airway and, in addition, high safety.

88 Claims, 4 Drawing Sheets

OTHER PUBLICATIONS

Qian, Tian–Xiu, et al., "Isosalvianolic Acid C, A Depside Possessing a Dibenzooxepin Skeleton," Phytochemistry, vol. 31, No. 3, pp. 1068–1070, (1992).

ăSindeláăr Karel et al., "Synthesis of 2–Acetyl and 3–Acetyl Derivatives of 8–Chloro–10(4–Methylpiperazino)–10, 11–Dihydrodibenzo[b, f]–Thiepin; $^2$–Acyl–7–Substituted Thioxanthenes," Collection Czechoslov, Chem. Commum., vol. 43, pp. 471–497, (1978).

Ueda, Ikuo et al., "Synthesis and Pharmacological Properties of 8–Chloro–10–(2–dimethylamino–ethoxy)dibenzo[b, f]thiepin and Related Compounds. Neurotropic and Psychotropic Agents, III" Chem. Pharm. Bull., vol. 26, No. 10, pp. 3058–3070, (1978).

Ueda, Ikuo et al., "The Synthesis of 10–(4–Methylpiperazino)dibenzo[b,f]thiepin and Related Compounds $^1$), Neurotropic and Psychotropic Agents," Chem. Pharm. Bull., vol. 23, No. 10, pp. 2223–2231, (1975).

Chemical Abstracts, 54319g, vol. 67, No. 11, p. 5118, (1967).

Chemical Abstracts, 93:150129, CS 179268, (Jun. 15, 1979).

Chemical Abstracts, 115:49435, CS 268630, (Mar. 4, 1990).

Chemical Abstracts, 125:86518, (Apr. 4, 1996).

Chemical Abstracts, 125:275677, (Aug. 29, 1996).

* cited by examiner

TRICYCLIC FUSED HETEROCYCLE COMPOUNDS, PROCESS FOR PREPARING THE SAME AND USE THEREOF

This application is a 371 of PCT/JP00/03592 Jun. 2, 2000.

TECHNICAL FIELD

The present invention relates to novel tricyclic condensed heterocyclic compounds, their preparation method and uses. The tricyclic condensed heterocyclic compounds of the present invention have a wide range of pharmacological actions such as the relaxing action of tracheal smooth muscles, the inhibition of airway hypersensitivity and the inhibition of infiltration of inflammatory cells into the airway and are useful as drugs such as antiasthmatic drugs.

BACKGROUND ART

Heretofore, various cyclic compounds have been proposed as the compounds useful for asthma and the like. For example, xanthine derivatives such as theophylline and $\beta_2$-agonists such as salbutamol, steroids, antiallergic drugs and the like are known.

Further, various tricyclic condensed heterocyclic compounds are proposed.

Examples of such prior arts are mentioned below.

*Yakugaku Zasshi*, 87,(2), 198–201 (1967) discloses three dihydrodibenz[b,f]oxepin derivatives as the synthetic intermediates of a natural product but no pharmacological action and the like relating to these compounds are described.

U.S. Pat. No. 4,104,280 describes that tricyclc condensed heterocyclic compounds containing an oxygen atom or a sulfur atom as the heterocyclic atom and a substituent of —CHRCOOH or —CHRCOOCH$_3$ (wherein R is a hydrogen atom or a methyl group) on the benzene ring are useful as anti-inflammatory drugs and relaxants.

European Patent Publication No. 0 011 067 A1 suggests that triclyclic condensed heterocyclic compounds containing a sulfur atom as the heterocyclic atom and —(CH$_2$)$_n$—A (wherein n is 0 to 4; and A is a heterocyclic residue) as one substituent on the benzene ring are effective for asthma, allergy and the like.

British Patent No. 2,016,466 describes that triclyclic condensed heterocyclic compounds containing an oxygen atom or a sulfur atom as the heterocyclic atom and —CH$_2$COR (wherein R is OH, NH$_2$, a C$_{1-5}$ alkyl group or the like) as one substituent on the benzene ring are useful as anti-inflammatory drugs.

German Patent No. 32 03065 discloses that certain types of triclyclic condensed heterocyclic compounds containing an oxygen atom or a sulfur atom as the heterocyclic atom and various substituents on the benzene ring have pharmacological actions such as analgesia, sedation, antidepression, antispastic action.

European Patent Publication No. 0 003 893 discloses that triclyclic condensed heterocyclic compounds containing oxygen or sulfur as the heterocyclic atom and having —CHR$_2$COOR$_3$ (wherein R$_2$ is a hydrogen atom or a methyl group; and R$_3$ is a hydrogen atom or —CH$_2$CH$_2$OCH$_2$CH$_2$OH) as one substituent on the benzene ring have pharmacological actions such as anti-inflammation, analgesia and pyretolysis.

German Patent No. 1,302,590 describes tricyclic condensed heterocyclic compounds containing sulfur as the hetero atom and having various substituents on the benzene ring.

U.S. Pat. No. 4,104,280 teaches that 3-hydroxymethyl-benzo[b,f]thiepin containing a sulfur atom as the heterocyclic atom and its derivatives are used in the treatment of allergic diseases such as allergic asthma.

*Br. J. Pharmac.*, 82, 389–395 (1984) describes 2-hydroxy-methyl-dibenzo[b,f]thiepin-5,5-dioxide which is an antagonist of prostanoids contractile for lung smooth muscles.

*Japanese Pharm. Soc. Bull.*, 94, 299–307 (1989) suggests that 2-(10,11-dihydro-10-oxodibenzo[b,f]thiepin-2-yl) propionic acid possibly becomes a clinically useful substance as an anti-inflammatory, analgesic and antipyretic drug since it only has a slight effect on circulatory organs and the autonomic nervous system when a considerably large amount is used.

WO Publication 96/10021 describes antioxidative tricylic condensed heterocyclic compounds containing oxygen or sulfur as the heterocyclic atom and having various substitutents on the benzene ring.

WO Publication 96/25927 describes glutamic receptor blockers and cerebral function improving drugs containing oxygen or sulfur as the heterocyclic atom and having various substitutents on the benzene ring.

WO Publication 97/25985 describes tracheal smooth muscle relaxants having compounds containing oxygen or sulfur as the heterocyclic atom and having various substituents on the benzene ring as the effective component.

*J. Org. Chem.*, 61,5818–5822 (1996) and *Collection Czechoslov. Chem. Commum.*, 43, 309 (1978) describe the synthesis of dibenzoxepins and dibenzothiepins.

*Terahedron*, 40, 4245–4252 (1984) and *Phytochemistry*, 31, (3) 1068–1070 (1992) describe dibenzoxepin derivatives derived from a natural substance.

*Chem. Pharm. Bull.*, 23, (10) 2223–2231 (1975) and *Chem. Pharm. Bull.*, 26, (10) 3058–3070 (1978) describe the synthetic methods of dibenzothiepin derivatives and the antiemetic action of these compounds.

*J. Chem. Soc. Perkin Trans.* 1, 3291–3294 (1991) and *J. Med. Chem.*, 26, 1131–1137 (1983) describe the synthetic methods of dibenzoxepin and dibenzothiepin derivatives and the anti-estrogenic action of these compounds.

As stated above, heretofore, various tricyclic condensed heterocyclic compounds have been disclosed, but they cannot be said to be sufficient in respect of therapeutic effect, prolonged action, safety (in terms of preventing side effects) when used as therapeutic drugs for airway disorders such as bronchial asthma, acute or chronic bronchitis, pulmonary emphysema and upper esophagitis and the like and lung diseases, allergic diseases, chronic inflammation and the like. Thus, the development of novel compounds having a broad range of pharmacological actions including an airway smooth muscle relaxing action, an inhibition of airway hypersensitivity and an inhibition of infiltration of inflammatory cells into the airway and, at the same time, high safety (reduced side effects) is demanded.

DISCLOSURE OF THE INVENTION

In view of the above described present situations, the object of the present invention is to provide novel compounds which have a wide range of pharmacological actions such as a clinically useful relaxing action of tracheal smooth muscles, an inhibition of airway hypersensitivity and an inhibition of infiltration of inflammatory cells into the airway.

The present inventors have found as a result of strenuous investigations of tricyclic condensed heterocyclic compounds that certain types of tricyclic condensed heterocyclic compounds having an OH group, or an OH group and an OR group (wherein R is a hydrogen atom or a lower alkyl group) as the substitutent have a wide range of pharmacological actions such as a relaxation of tracheal smooth muscles, an inhibition of airway hypersensitivity and an inhibition of infiltration of inflammatory cells into the airway and, in addition, an excellent prolonged action and safety, and have completed the present invention on the basis of this knowledge. Specifically, the present invention relates to the compounds, their preparation method, uses and intermediates described in the following (1) to (25).

(1) A compound represented by formula (1),

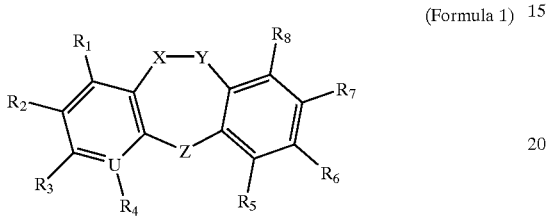

(Formula 1)

wherein
when the X—Y bond is a single bond, X and Y, which may be the same or different, are each independently any one selected from the group consisting of $CW_1W_2$ (wherein $W_1$ and $W_2$, which may be the same or different, are each independently any one of a hydrogen atom, a halogen, a hydroxyl group, a lower alkyl group, a substituted lower alkyl group, a lower alkoxy group, a cycloalkyl group and a cycloalkenyl group), C=O, and C=$NOW_3$ (wherein $W_3$ is a hydrogen atom or a lower alkyl group);

when the X—Y bond is a double bond, X and Y, which may be the same or different, are each independently $CW_4$ (wherein $W_4$ is any one of a hydrogen atom, a halogen, a hydroxyl group, a lower alkyl group, a substituted lower alkyl group, a lower alkoxy group and an acyloxy group);

Z is any one selected from O, S, S=O and $SO_2$;

U is C or N;

$R_1$ to $R_4$, which may be the same or different, are each independently any one selected from the group consisting of a hydrogen atom, a lower alkyl group, a substituted lower alkyl group, a cycloalkyl group, a substituted cycloalkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_1W_5$ (wherein $V_1$ is any one of O, S, S=O and $SO_2$; and $W_5$ is any one of a hydrogen atom, a lower alkyl group, a substituted lower alkyl group, a lower alkylcarbonyl group and a substituted lower alkylcarbonyl group, an acyloxy group and a trihalomethyl group), a nitro group, an amino group, a substituted amino group, a cyano group, an acyl group, an acylamino group, a substituted acyl group, a substituted acylamino group, an aromatic ring, a substituted aromatic ring, a heterocycle and a substituted heterocycle (when U is N, $R_4$ does not exist in some cases);

$R_5$ to $R_8$, which may be the same or different, are each independently any one selected from the group consisting of a hydrogen atom, a lower alkyl group, a substituted lower alkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_2W_7$ (wherein $V_2$ is any one selected from O, S, S=O and $SO_2$; and $W_7$ is any one selected from a hydrogen atom, a lower alkyl group, a substituted lower alkyl group, a lower alkylcarbonyl group, a substituted lower alkylcarbonyl group and a trihalomethyl group), a nitro group, an amino group, a substituted amino group, an acylamino group, an aromatic ring, a substituted aromatic ring, a heterocycle and a substituted heterocycle;

provided that at least one of $R_5$ to $R_8$ is a hydroxyl group [provided that at least one of $R_5$, $R_7$ or $R_8$ is a hydroxy group when the X—Y bond is $CH(C_2H_5)CO$ and $R_6$ is a hydroxyl group] when X is $CHW_0$, $CW_0W_0$ or $CW_0$ (wherein $W_0$ is any one selected from a lower alkyl group and a substituted lower alkyl group) and at least one of $R_5$ to $R_8$ is a hydroxyl group and, at the same time, at least one of the other $R_5$ to $R_8$ is a group of OR (wherein R is any one selected from the group consisting of a hydrogen atom, a lower alkyl group, a substituted lower alkyl group, a lower alkylcarbonyl group and a substituted lower alkylsilyl group) when X is other than $CHW_0$, $CW_0W_0$ or $CW_0$ (wherein $W_0$ is any one selected from a lower alkyl group and a substituted lower alkyl group);

in addition, when the X—Y is $CH_2CH_2$, $CHBrCH_2$, $CH_2CO$, $CHBrCO$, CH=CH, CH=$COCOCH_3$ or CH=$COCH_3$, at least one of $R_1$ to $R_4$ is an aromatic ring, a substituted aromatic ring, a heterocycle or a substituted heterocycle (provided that when both $R_6$ and $R_7$ are hydroxyl groups, any one of $R_1$ to $R_4$ is not a phenyl group); or at least one of $R_1$ to $R_4$ is $SW_8$ (wherein $W_8$ is a lower alkyl group or a substituted lower alkyl group) or $S(O)W_9$ (wherein $W_9$ is a lower alkyl group or a substituted lower alkyl group) (provided that $R_7$ is a hydrogen atom when Z is O); or $R_2$ is either a lower alkyl group or a substituted lower alkyl group and, at the same time, $R_8$ is a hydroxyl group (provided that the number of carbon atoms of the lower alkyl group is 3 or more when Z is O); or at least one of $R_1$ to $R_4$ is a lower alkylcarbonyl group (provided that the number of carbon atoms of the lower alkyl group is 3 or more), a cycloalkylcarbonyl group or a cycloalkenylcarbonyl group and, at the same time, $R_8$ is a hydroxyl group; or at least one of $R_1$ to $R_4$ is a cyano group; or at least one of $R_1$ to $R_4$ is a halogen and, at the same time, Z is any one of S, S=O and $SO_2$; or $R_5$ and $R_6$ are hydroxyl groups and, at the same time, Z is S; or at least one of $R_1$ to $R_4$ is —C(=NOR)$CH_3$ (wherein R is a hydrogen atom or a lower alkyl group), an optical isomer thereof, a conjugate thereof or a pharmaceutically acceptable salt thereof.

(2) The compound stated in the above (1), wherein $R_6$ is a hydroxyl group.

(3) The compound stated in the above (1), wherein $R_6$ and $R_7$ are hydroxyl groups.

(4) The compound stated in the above (1), wherein $R_6$ and $R_8$ are hydroxyl groups.

(5) The compound stated in the above (1), wherein $R_5$ and $R_6$ are hydroxyl groups.

(6) The compound stated in any one of the above (1) to (5), wherein the X—Y bond is a single bond and X is $CW_1W_2$ (wherein at least one of $W_1$ and $W_2$ is any one selected from a lower alkyl group, a substituted lower alkyl group, a cycloalkyl group and a cycloalkenyl group) or the X—Y bond is a double bond and X is $CW_3$ (wherein $W_3$ is any one selected a lower alkyl group, a substituted lower alkyl group, a cycloalkyl group and a cycloalkenyl group).

(7) The compound stated in any one of the above (1) to (6), wherein Y is CO.

(8) The compound stated in the above (6), wherein the lower alkyl group is any one of a methyl group, an ethyl group, a n-propyl group, an isopropyl group, n-butyl group, a sec-butyl group, an isobutyl group and a tert-butyl group.

(9) The compound stated in any one of the above (1) to (5), wherein $R_2$ or $R_3$ is any one of a heterocycle, a substituted heterocycle, an aromatic ring and a substituted aromatic ring.

(10) The compound according to any one of the above (1) to (5), wherein the heterocycle is an aromatic heterocycle.

(11) The compound according to any one of the above (1) to (5), wherein $R_2$ or $R_3$ is $SW_8$ (wherein $W_8$ is a lower alkyl group or a substituted lower alkyl group) or $S(O)W_9$ (wherein $W_9$ is a lower alkyl group or a substituted alkyl group).

(12) The compound stated in the above (11), wherein the lower alkyl group is any one of a methyl group, an ethyl group, a n-propyl group, an isopropyl group, an n-butyl group, a sec-butyl group, an isobutyl group and a tert-butyl group.

(13) The compound stated in any one of the above (1) to (12), wherein Z is S.

(14) The compound stated in the above (1) which is 7,8-dihydroxy-11-ethyl-10,11-dihydrodibenzo[b,f]thiepin-10-one.

(15) The compound stated in the above (1) which is 11-diethyl-7,8-dihydroxy-10,11-dihydrodibenzo[b,f]thiepin-10-one.

(16) The compound stated in the above (1) which is 7,9-dihydroxy-2-methylthio-10,11-dihydrodibenzo[b,f]thiepin-10-one.

(17) A method of preparing a compound represented by formula (1),

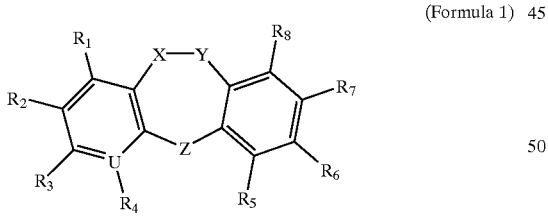

(Formula 1)

wherein
when the X—Y bond is a single bond, X and Y, which may be the same or different, are each independently any one selected from the group consisting of $CW_1W_2$ (wherein $W_1$ and $W_2$, which may be the same or different, are each independently any one of a hydrogen atom, a halogen, a hydroxyl group, a lower alkyl group, a substituted lower alkyl group, a lower alkoxy group, a cycloalkyl group and a cycloalkenyl group), C=O, and C=NOW$_3$ (wherein $W_3$ is a hydrogen atom or a lower alkyl group);
when the X—Y bond is a double bond, X and Y, which may be the same or different, are each independently $CW_4$ (wherein $W_4$ is any one of a hydrogen atom, a halogen, a hydroxyl group, a lower alkyl group, a substituted lower alkyl group, a lower alkoxy group and an acyloxy group);

Z is any one selected from O, S, S=O and $SO_2$;

U is C or N;

$R_1$ to $R_4$, which may be the same or different, are each independently any one selected from the group consisting of a hydrogen atom, a lower alkyl group, a substituted lower alkyl group, a cycloalkyl group, a substituted cycloalkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_1W_5$ (wherein $V_1$ is any one of O, S, S=O and $SO_2$; and $W_5$ is any one of a hydrogen atom, a lower alkyl group, a substituted lower alkyl group, a lower alkylcarbonyl group and a substituted lower alkylcarbonyl group, an acyloxy group and a trihalomethyl group), a nitro group, an amino group, a substituted amino group, a cyano group, an acyl group, an acylamino group, a substituted acyl group, a substituted acylamino group, an aromatic ring, a substituted aromatic ring, a heterocycle and a substituted heterocycle (when U is N, $R_4$ does not exist in some cases);

$R_5$ to $R_8$, which may be the same or different, are each independently any one selected from the group consisting of a hydrogen atom, a lower alkyl group, a substituted lower alkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_2W_7$ (wherein $V_2$ is any one selected from O, S, S=O and $SO_2$; and $W_7$ is any one selected from a hydrogen atom, a lower alkyl group, a substituted lower alkyl group, a lower alkylcarbonyl group, a substituted lower alkylcarbonyl group and a trihalomethyl group), a nitro group, an amino group, a substituted amino group, an acylamino group, an aromatic ring, a substituted aromatic ring, a heterocycle and a substituted heterocycle;

provided that at least one of $R_5$ to $R_8$ is a hydroxyl group [provided that at least one of $R_5$, $R_7$ or $R_8$ is a hydroxy group when the X—Y bond is $CH(C_2H_5)CO$ and $R_6$ is a hydroxyl group] when X is $CHW_0$, $CW_0W_0$ or $CW_0$ (wherein $W_0$ is any one selected from a lower alkyl group and a substituted lower alkyl group) and at least one of $R_5$ to $R_8$ is a hydroxyl group and, at the same time, at least one of the other $R_5$ to $R_8$ is a group of OR (wherein R is any one selected from the group consisting of a hydrogen atom, a lower alkyl group, a substituted lower alkyl group, a lower alkylcarbonyl group and a substituted lower alkylsilyl group) when X is other than $CHW_0$, $CW_0W_0$ or $CW_0$ (wherein $W_0$ is any one selected from a lower alkyl group and a substituted lower alkyl group);

in addition, when the X—Y is $CH_2CH_2$, $CHBrCH_2$, $CH_2CO$, $CHBrCO$, CH=CH, $CH=COCOCH_3$ or $CH=COCH_3$, at least one of $R_1$ to $R_4$ is an aromatic ring, a substituted aromatic ring, a heterocycle or a substituted heterocycle (provided that when both $R_6$ and $R_7$ are hydroxyl groups, any one of $R_1$ to $R_4$ is not a phenyl group); or at least one of $R_1$ to $R_4$ is $SW_8$ (wherein $W_8$ is a lower alkyl group or a substituted lower alkyl group) or S(O)W$_9$ (wherein W$_9$ is a lower alkyl group or a substituted lower alkyl group) (provided that R$_7$ is a hydrogen atom when Z is O); or R$_2$ is either a lower alkyl group or a substituted lower alkyl group and, at the same time, R$_8$ is a hydroxyl group (provided that the number of carbon atoms of the lower alkyl group is 3 or more when Z is O); or at least one of R$_1$ to R$_4$ is a lower alkylcarbonyl group (provided that the number of carbon atoms of the lower alkyl group is 3 or more), a cycloalkylcarbonyl group or a cycloalkenylcarbonyl group and, at the same time, R$_8$ is a hydroxyl group; or at least one of R$_1$ to R$_4$ is a cyano group; or at least one of R$_1$ to R$_4$ is a halogen and, at the same time, Z is any one of S, S=O and SO$_2$; or R$_5$ and R$_6$ are hydroxyl groups and, at the same time, Z is S; or at least one of R$_1$ to R$_4$ is —C(=NOR)CH$_3$ (wherein R is a hydrogen atom or a lower alkyl group), an optical isomer thereof, a conjugate thereof or a pharmaceutically acceptable salt thereof, which comprises, in any order, the reaction steps of ① bonding a ring A to a ring C by the Ullmann reaction as shown in formula 2 and ② bonding a ring A to a ring C by the Friedel-Crafts reaction or photoreaction as shown in formula 3,

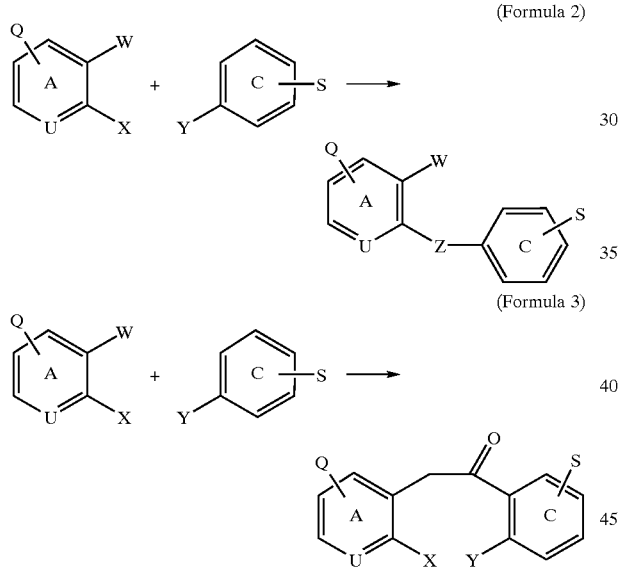

(Formula 2)

(Formula 3)

wherein

Q, S and W are each any substitutent;

U is C or N;

one of X and Y is a leaving group and the other is a nucleophilic group; and

Z is any one of O, S, SO and SO$_2$.

(18) The method stated in the above (17) further comprising at least one step of the step of carbon atom increasing reaction, the step of conversion reaction of a substituent, the step of introduction reaction of a substituent, the step of removal of the protection of a substituent, the step of forming a salt and the step of performing optical resolution. The order of these steps and step1 and step2 of (17) is not limited. A person skilled in the art can decide the order considering a structure of the target compound and other conditions.

(19) A pharmaceutical composition comprising an effective amount of the compound stated in any one of the above (1) to (16) and a pharmaceutically acceptable carrier or diluent.

(20) The pharmaceutical composition stated in the above (19) which utilizes the tracheal smooth muscles relaxing action of the compound.

(21) The pharmaceutical composition stated in the above (19) which utilizes the Inhibitory effect on airway hypersensitivity of the compound.

(22) The pharmaceutical composition stated in the above (19) which utilizes the inhibitory effect on inflammatory cells filtration of the compound.

(23) The pharmaceutical composition stated in the above (19) which is used as the antiasthmatic drug.

(24) A compound of the following formula,

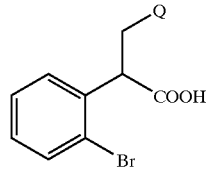

wherein Q is a lower alkyl group,
an optical isomer thereof or a salt thereof.

(25) A compound of the following formula,

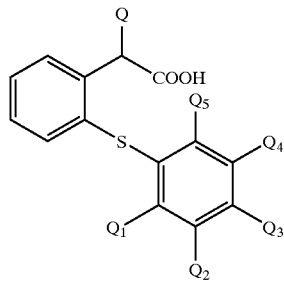

wherein

Q is a lower alkyl group; and

Q$_1$ to Q$_5$ which may be the same or different are each independently any one selected from a hydrogen atom, a lower alkoxy group and a hydroxyl group, an optical isomer thereof or a salt thereof.

Further, when the compounds and their salts described in the above (1) contain an asymmetric carbon atom in the structure, the optical active compounds and the racemic compounds are also included in the scope of the present invention. In addition, the compounds and their salts described in the above (1) may be either the hydrates or nonhydrates and may be the solvates.

BEST MODE FOR CARRYING OUT THE INVENTION

Figure 1:
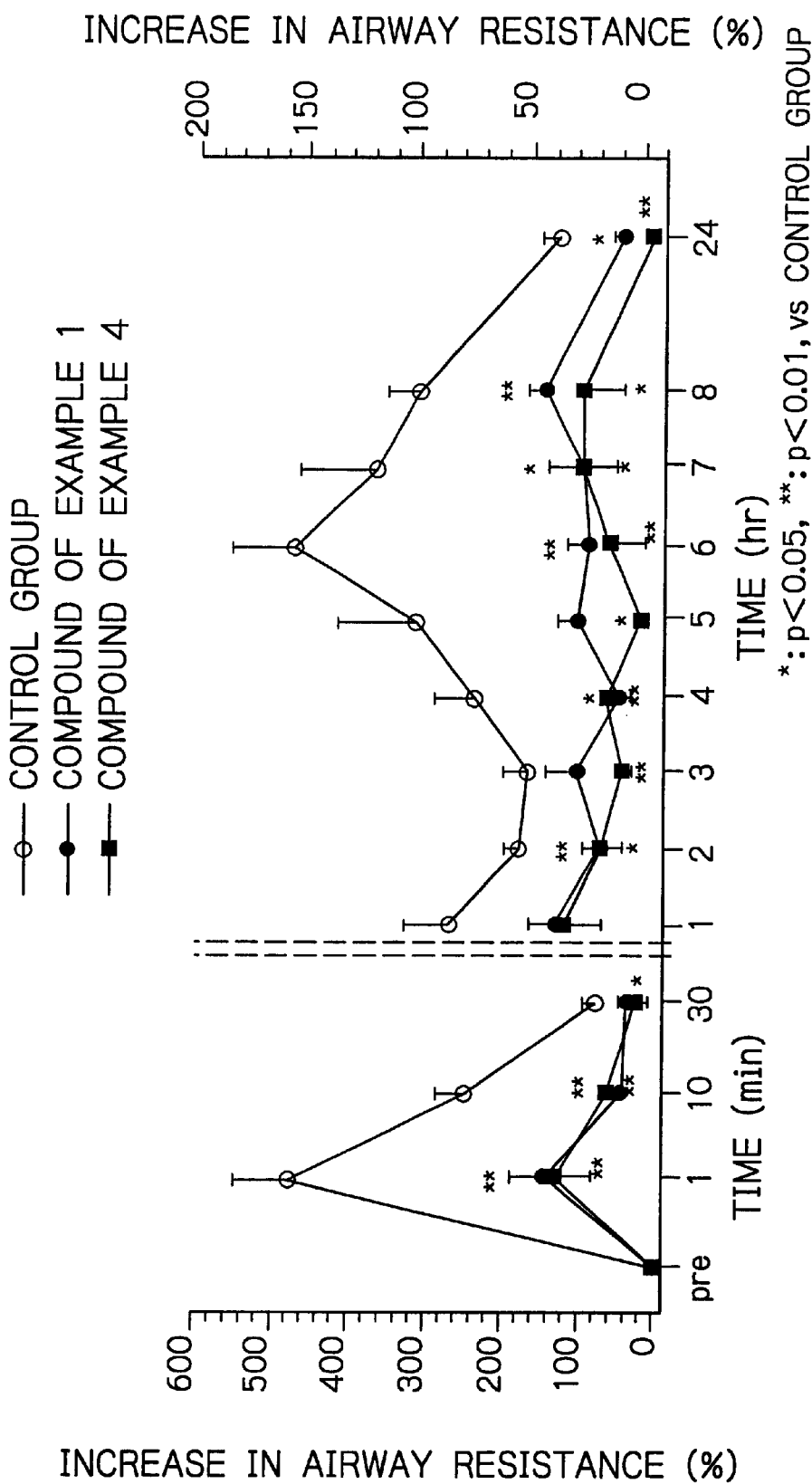
FIG. 1 is a graph showing the inhibitory effects of the compounds of the present invention on the immediate and late asthmatic responses in actively sensitized guinea pigs.

The term "halogen" as used in the specification of the present application refers to any atom of fluorine, chlorine, bromine and iodine. Further, the term "trihalomethyl group" as used herein refers to a group in which three hydrogen atoms are substituted with halogen atoms, and these three halogen atoms may be all the same or may be constituted of two or more different halogen atoms.

The term "lower alkyl group" as used herein refers to, for example, a straight-chain or branched chain $C_{1-6}$ alkyl group, and the $C_{1-6}$ alkyl group includes, for example, methyl, ethyl, n-propyl, isopropyl, n-butyl, isobutyl, tert-butyl, n-pentyl and n-hexyl. As the substituent which the "lower alkyl group" may have, one or more selected from, for example, hydroxyl, amino, carboxyl, nitro, an aryl group, a substituted aryl group, a mono- or di-lower alkylamino group (including, for example, mono- or di-$C_{1-6}$ alkylamino such as methylamino, ethylamino, propylamino, dimethylamino and diethylamino), lower alkoxy (including, for example, $C_{1-6}$ alkoxy such as methoxy, ethoxy, propoxy and hexyloxy), lower alkylcarbonyloxy (including, for example, $C_{1-6}$ alkylcarbonyloxy such as acetoxy and ethylcarbonyloxy) and a halogen atom are employed. Further, the lower alkyl moiety in the "lower alkoxy group" as used herein refers to the above described "lower alkyl group".

The term "cycloalkyl group" as used herein refers to, for example, a $C_{3-8}$ cyclic alkyl group. The $C_{3-8}$ cycloalkyl group includes, for example, cyclopropyl, cyclobutyl, cyclopentyl, cyclohexyl and cyclooctyl. As the substituent which the "cycloalkyl group" may have, one or more selected from, for example, hydroxyl, amino, carboxyl, nitro, a mono- or di-lower alkylamino group (including, for example, mono- or di-$C_{1-6}$ alkylamino such as methylamino, ethylamino, propylamino, dimethylamino and diethylamino), a lower alkoxy (including, for example, $C_{1-6}$ alkoxy such as methoxy, ethoxy, propoxy and hexyloxy), a lower alkylcarbonyloxy (including, for example, alkylcarbonyloxy such as acetoxy and ethylcarbonyloxy) and a halogen atom are employed.

The term "cycloalkenyl group" as used herein refers to a cycloalkenyl group having one or more double bonds on the ring moiety.

The term "lower alkenyl group" as used herein refers to, for example, a straight chain or branched chain $C_{2-6}$ alkenyl group. The $C_{2-6}$ alkenyl group includes, for example, vinyl, allyl, 2-methylallyl, isopropenyl, 2-butenyl, 3-butenyl, 2-pentenyl, 3-pentenyl, 2-hexenyl and 3-hexenyl. As the substituent which the "lower alkenyl group" may have, one or more selected from, for example, hydroxyl, amino, carboxyl, nitro, mono- or di-lower alkylamino group (including, for example, mono- or di-$C_{1-6}$ alkylamino such as methylamino, ethylamino, propylamino, dimethylamino and diethylamino), lower alkoxy such as methoxy, ethoxy, propoxy and hexyloxy), lower alkylcarbonyloxy (including, for example, $C_{1-6}$ alkylcarbonyloxy such as acetoxy and ethylcarbonyloxy) and a halogen atom are employed.

The term "lower alkynyl group" as used herein refers to, for example, a straight chain or branched chain $C_{2-6}$ alkynyl group. The $C_{2-6}$ alkynyl group includes, for example, ethynyl, 2-propynyl, 2-butynyl, 3-butynyl, 2-pentynyl, 3-pentynyl, 2-hexynyl and 3-hexynyl. As the substituent which the "lower alkynyl group" may have, one or more selected from, for example, hydroxyl, amino, carboxyl, nitro, mono- or di-lower alkylamino (including, for example, a mono- or di-$C_{1-6}$ alkylamino such as methylamino, ethylamino, propylamino, dimethylamino and diethylamino), lower alkoxy (including, for example, $C_{1-6}$ alkoxy such as methoxy, ethoxy, propoxy and hexyloxy), lower alkylcarbonyloxy (including, for example, $C_{1-6}$ alkylcarbonyloxy such as acetoxy and ethylcarbonyloxy) and a halogen atom are employed.

The lower alkyl moiety in the "lower alkylcarbonyl group" as used herein refers to the above described "lower alkyl group".

As the substituent in the term "substituted amino group" as used herein, one or more selected from, for example, hydroxyl, carboxyl, nitro, mono- or di-lower alkyl (including, for example, mono- or di-$C_{1-6}$ alkyl such as methyl, ethyl, n-propyl, isopropyl, dimethyl and diethyl), lower alkoxy (including, for example, $C_{1-6}$ alkoxy such as methoxy, ethoxy, propoxy and hexyloxy), lower alkylcarbonyloxy (including, for example, $C_{1-6}$ alkylcarbonyloxy such as acetoxy and ethylcarbonyloxy) and a halogen atom are employed.

The term "acyl group" as used herein refers to —COR wherein R is any one of a hydrogen atom, a lower alkyl group, a lower alkenyl group, a lower alkynyl group, a $C_{3-8}$ cycloalkyl group and a monocyclic or polycyclic aromatic ring or a hereocycle. The acyl moiety in the terms "acyloxy group" and "acylamino group" as used herein refers to the above described acyl group. The substituent which the "acyl group" and the "acylamino group" may have refers to a substituent on the carbon atom of R, and one or more selected from, for example, hydroxyl, amino, carboxyl, nitro, mono- or di-lower alkylamino (including, for example, a mono- or di-$C_{1-6}$ alkylamino such as methylamino, ethylamino, propylamino, dimethylamino and diethylamino), lower alkoxy (including, for example, $C_{1-6}$ alkoxy such as methoxy, ethoxy, propoxy and hexyloxy), lower alkylcarbonyloxy (including, for example, $C_{1-6}$ alkylcarbonyloxy such as acetoxy and ethylcarbonyloxy) and a halogen atom are employed.

The term "aromatic ring" as used herein refers to a group of atoms remaining after removal of one hydrogen atom from an aromatic hydrocarbon, that is, an aryl group. Particularly, $C_{6-14}$ alkyl groups are preferred. Such $C_{6-14}$ alkyl groups that can be used include, for example, phenyl, naphthyl, tolyl, xylyl, biphenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenathryl, 1-azulenyl, 2-azulenyl, 4-azulenyl, 5-azulenyl and 6-azulenyl. As the substituent which the "aromatic ring" may have, one or more selected from, for example, lower alkyl, hydroxyl, amino, carboxyl, nitro, mono- or di-lower alkylamino (including, for example, a mono- or di-$C_{1-6}$ alkylamino such as methylamino, ethylamino, propylamino, dimethylamino and diethylamino), lower alkoxy (including, for example, $C_{1-6}$ alkoxy such as methoxy, ethoxy, propoxy and hexyloxy), lower alkylcarbonyloxy (including, for example, $C_{1-6}$ alkylcarbonyloxy such as acetoxy and ethylcarbonyloxy), trihalomethane, trihalomethoxy, a halogen atom and aryl such as phenyl are used.

The term "heterocycle" as used herein refers to a group of atoms remaining after removal of one hydrogen atom from a 3- to 7-membered heterocycle which contains one to four hetero atoms selected from, for example, a nitrogen atom, an oxygen atom, and a sulfur atom in addition to carbon atoms. The heterocycle may be condensed. Exemplary heterocycles include, for example, oxetane, tetrahydrofuran, tetrahydrothiophene, tetrahydropyran, pyrrole, azetidine, pyrrolidine, piperidine, piperazine, homopiperidine, morpholine, furan, pyridine, benzofuran and benzothiophene. As the substituent which the "heterocycle" may have, one or more selected from, for example, hydroxyl, amino, carboxyl, nitro, mono- or di-lower alkylamino (including, for example, a mono- or di-$C_{1-6}$ alkylamino such as methylamino, ethylamino, propylamino, dimethylamino and diethylamino), lower alkoxy (including, for example, $C_{1-6}$ alkoxy such as methoxy, ethoxy, propoxy and hexyloxy), lower alkylcarbonyloxy (including, for example, $C_{1-6}$ alkylcarbonyloxy such as acetoxy and ethylcarbonyloxy) and a halogen atom are used.

Further, examples of particularly preferred compounds in the present invention include the following compounds, their optical isomers, conjugated compounds and salts.
(1) Compounds in which two hydroxyl groups are present on ring C ($R_5$ to $R_8$) and a lower alkyl group is present in the 11-position (X-position). Specifically, 7,8-dihydroxy-11-ethyl-10,11-dihydrodibenzo[b,f]thiepin-10-one, 11-diethyl-7,8-dihydroxy-10,11-dihydrodibenzo[b,f]thiepin-10-one, 11-methyl-7,8-dihydroxy-10,11-dihydrodibenzo[b,f]thiepin-10-one and the like can be illustrated.
(2) Compounds in which two hydroxyl groups are present on ring C ($R_5$ to $R_8$) and a thio-lower alkyl group is present on ring A ($R_1$ to $R_4$). Specifically, 7,9-dihydroxy-2-methylthio-10,11-dihydrodibenzo[b,f]thiepin-10-one, 8-methylthio-10,11-dihydrodibenzo[b,f]thiepin-1,3-diol and the like can be illustrated.
(3) Compounds in which two hydroxyl groups are present on ring C ($R_5$ to $R_8$) and a heterocycle is bonded to ring A ($R_1$ to $R_4$). Specifically, 7,9-dihydroxy-3-(2-furyl)-10,11-dihydrodibenzo[b,f]thiepin-10-one, 7-(2-thienyl)-10,11-dihydrodibenzo[b,f]thiepin-1,3-diol, 7-(2-furyl)-10,11-dihydrodibenzo[b,f]thiepin-1,3-diol and the like can be illustrated.

As the salts of the compounds of the present invention, acid addition salts whose acids are pharmaceutically or physiologically acceptable ones are preferably employed. Such salts which can be used include, for example, salts with inorganic acids (such as hydrochloric acid, phosphoric acid, hydrobromic acid and sulfuric acid); organic acids(such as acetic acid, formic acid, propionic acid, fumaric acid, maleic acid, succinic acid, tartaric acid, lactic acid, citric acid, malic acid, oxalic acid, benzoic acid, methanesulfonic acid, p-toluenesulfonic acid and benzenesulfonic acid); and alkalis (such as sodium, potassium, magnesium, calcium, ammonium, pyridine and triethylamine).

The conjugates of the compounds of the present invention include, for examples, glucuronic acid conjugates and sulfuric acid conjugates of the compounds represented by formula (1), their optical isomers and their salts.

Next, the method for the preparation of the compounds of the present invention or their salts will be described.

The tricyclic condensed heterocyclic compound of the present invention is a 6-7-6-membered tricyclic compounds consisting of three rings of A, B and C as shown in formula (4) below.

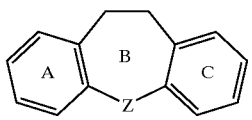

(Formula 4)

The skeleton of this compound can be prepared by the combination of bonding of ring A to ring C by the Ullmann reaction and bonding of ring A to ring C by the Friedel-Crafts reaction or photoreaction. Depending on the starting material and the target compound, it is necessary to add a carbon atom increasing reaction. Furthermore, if necessary or desired, the target compound can be obtained by carrying out a substituent introduction reaction and a substituent conversion reaction.

For example, the first step is to bond ring A to ring C by the Ullmann reaction. Then, the second step (carbon atom increasing reaction) is to increase W of carbon atoms to make ring B 7-membered. Furthermore, the third step is to form ring B by the Friedel-Crafts reaction. The fourth step (substituent introduction reaction) is to introduce a necessary substituent such as a halogen and a lower alkyl group into the tricyclic compound thus formed.

As regards the introduction of a substituent, it is possible to introduce the substituent either into the starting material of the first step or in the middle of the carbon atom increasing reaction of the second step and thus, the introduction of the substituent can be selected by taking the type of the target compound or the like into consideration when the occasion demands. Furthermore, if necessary or desired, the carbonyl group of the 10-position can be reduced or the substituent, OR (for example; $OCH_3$), can be converted into OH by the reaction of removing the protection.

Now the reaction scheme of each step will be illustrated.
① Ullmann Reaction

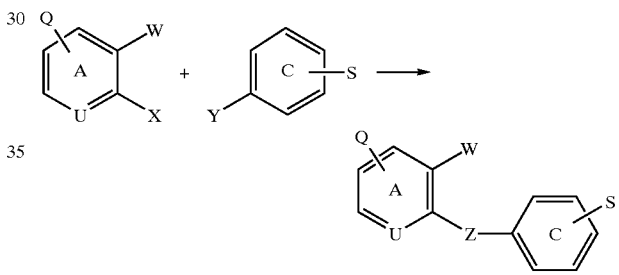

wherein
one of X and Y is a leaving group: and the other is a nucleophilic agent.
②-1 Friedel-Crafts Reaction
②-2 Photoreaction

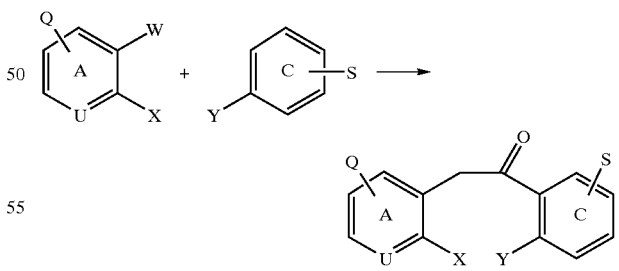

③ Carbon Atom Increasing Reaction

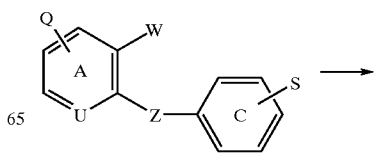

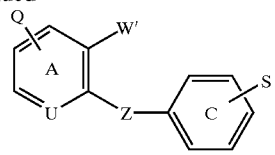

④ Conversion Reaction of Halogen to Another Functional Group
⑤ Introduction Reaction of Alkyl Group or Alkylcarbonyl Group
⑥ Conversion Reaction at 10-Position

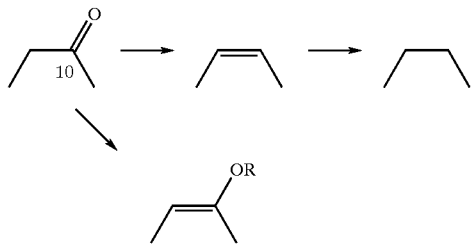

⑦ Reaction of Deprotection

The above mentioned reaction scheme of each step will be explained as follows.

① Ullmann Reaction

Ring A having a necessary substituent and a substituted benzene corresponding to ring C are formed into a coupled compound by the Ullmann reaction. The leaving group in the Ullmann reaction which can be used includes, for example, a halogen (for example, chlorine, bromine or iodine), $C_{6-10}$ arylsulfonyloxy (for example, benzenesulfonyloxy or p-toluenesulfonyloxy) and $C_{1-4}$ alkylsulfonyloxy (for example, methanesulfonyloxy) and above all, a halogen (for example, chlorine, bromine or iodine) is preferred. The nucleophilic side which can be used includes, for example, a precursor having a functional group containing oxygen or sulfur and above all, a substituted phenol, a substituted thiophenol and a substituted disulfide are preferred.

② Friedel-Crafts Reaction or Photoreaction

The reaction of further bonding ring A to ring C can use a method which is conventionally carried out as the Friedel-Crafts reaction. For example, the methods of "Comprehensive Organic Synthesis: The Intramolecular Aromatic Friedel-Crafts Reaction", Vol. 2, pp753 (1991), *J. Org. Chem.*, 52, 849 (1987) and *Synthesis*, 1257 (1995) or the ones corresponding thereto can be used. Further, by using the photocyclization method as shown in Japanese Patent Publication (Kokai) No. Hei 10-204079/1998) or the one corresponding thereto, a substituted acetophenone compound can be directly led to a cyclized compound. Further, the order of the Ullmann reaction and these reactions can also be changed.

③ Carbon Atom-increasing Reaction

When a substituted phenyl acetate derivative is used in the Ullmann reaction, it can be directly led to a cyclized compound but when a substituted benzoic acid derivative is used, the moiety corresponding to ring B is subjected to a carbon atom-increasing reaction. In this instance, a substituted benzoic acid derivative can be led to the substituted phenyl acetate via the substituted benzyl alcohol compound, the substituted benzyl halide compound and the substituted benzyl nitrile compound. Further, the substituted benzyl halide compound can also be directly led to the substituted phenyl acetate with carbon dioxide. By the Willgerodt reaction, the substituted acetophenone compound is formed into the substituted morpholine compound which can be then led to the substituted phenyl acetate.

④ Conversion Reaction of Halogen to Another Functional Group

The introduction reaction of a heterocycle, a substituted phenyl ring or a lower alkyl group can be carried with palladium by using the methods of *Chem. Rev.*, 95, 2457 and "Organic Reactions", Vol. 50 (1997) or one corresponding thereto.

⑤ Reaction of Introduction of Alkyl Group or Alkylcarbonyl Group

The introduction of an alkyl group such as an ethyl group can be carried out in the presence of a base for the cyclized compound in an anhydrous solvent in the presence of an alkyl halogenating agent or an alkali with the use of a phase transfer catalyst and an alkyl halogenating agent. Further, the alkyl group can be introduced into either an intermediate of the carbon atom increasing reaction before cyclization or the starting material before the Ullmann reaction. The introduction of an alkylcarbonyl group can be carried out by using the Friedel-Crafts reaction.

⑥ Conversion Reaction at 10-Position

The carbonyl group of the cyclized compound is reduced to an alcohol compound of the cyclized compound which is then formed into the olefinic compound by dehydration reaction, and this oleinic compound can be led to the decarbonylated compound by catalytic reduction. Further, the alcohol compound of the cyclized compound is subjected to the reaction ⑦ of Deprotection to form the olefinic compound which can be then led to the decarbonylated compound by reduction. Alternatively, the cyclized compound can be directly led to the decarbonylated compound by Wolff-Kishner reduction.

⑦ Reaction of Deprotection

The reaction of deprotection can be carried out with a pyridine salt or a boron halide.

The preparation of the compounds of the present invention is preferably carried out in a solvent, and such a solvent that can be used include, for example, aromatic hydrocarbons such as benzene, toluene and xylene; ethers such as diethyl ether, tetrahydrofuran and dioxane; amides such as dimethylformamide and dimethylacetamide; sulfoxide such as dimethyl sulfoxide; nitrites such as acetonitrile; N-methyl-2-pyrrolidone and anhydrous solvents thereof. The reaction temperature is −78° C. to 200° C., and the reaction time is 30 minutes to several days, and the reaction is advantageously carried out under a stream of nitrogen or argon. The reaction product can be isolated and purified by known means such as solvent extraction, acidity or alkalinity conversion, transdissolution, salting out, crystallization, recrystallization and chromatography.

In the method of the present invention, when the substituent is an amino group, the amino group is preferably protected, and a protective group which is commonly used in the field of peptide chemistry and the like can be used, and a protective group of the type which forms an amide, such as formyl, acetyl and benzoyl; a protective group of the type which forms a carbamate, such as tert-butoxycarbonyl and benzyloxycarbonyl; a protective group of the imino type such as dimethylaminomethylene, benzylidene, p-methoxybenzylidene and diphenylmethylene are preferably used. Preferred protective groups which can be used are, for example, formyl, acetyl and dimethylaminomethylene. Further, when the product obtained in the above described reactions has a protective group, the protective group can be removed by the conventional method. For example, the protective group can be removed by hydrolysis with an acid or a base or by procedure of deprotection such as catalytic reduction or the like.

Further, when the compound of the present invention has an asymmetric carbon, an optical isomer can be obtained by using conventionally known various optically resolving methods such as an optical isomer resolving column.

In addition, the compounds of the present invention or their pharmaceutically or physiologically acceptable salts thereof have a wide range of pharmacological actions such as the excellent relaxing action of tracheal smooth muscles, the inhibition of airway hypersensitivity and the inhibition of infiltration of inflammatory cells into the airway and can be used as safe antiasthmatic drugs and the like for mammals (humans, mice, dogs, rats, cattle and the like). Specifically, when they are used as antiasthmatic drugs for humans, the dose may vary depending on the age, weight, symptom of disease, route of administration, frequency of administration and the like, and they are administered with a dose of 0.1 to 100 mg/kg daily, preferably 1 to 50 mg/kg daily once or dividedly twice. The route of administration may be either oral or parenteral.

The compounds of the present invention or their salts may be administered as the bulk drug but they are usually administered in the form of preparations with a drug carrier. As concrete examples, tablets, capsules, granules, fine granules, powders, syrups, injections, inhalants and the like are employed. These pharmaceutical preparations can be prepared according to conventional techniques. As carriers of oral preparations, the substance which is conventionally employed in the field of pharmaceutical preparation, such as starch, mannitol, crystalline cellulose and sodium carboxymethyl cellulose can be used. As carriers for injections, distilled water, a physiological saline, glucose solution, a transfusion and the like can be used. Other additives which are commonly employed in pharmaceutical preparations can suitably be added.

REFERENTIAL EXAMPLES

Examples of the method for preparing the starting material substances of the present invention and each of the above described reactions will be explained below but the present invention is not limited to them and may be changed without departing from the scope of the present invention. The elution in the chromatography of Referential Example was carried out under observation by thin-layer chromatography (TLC) unless expressly stated. In the TLC observation, "60F$_{254}$" of Merck was used as the TLC plate and as the developing solvent, a solvent which was used as the eluting solvent in column chromatography was used. Further, an UV detector was employed in detection. As the silica gel for the column chromatography, "Silica Gel 60" (70 to 230 mesh) of Merck or "Microsphere Gel D75-60A" of Asahi Glass was used. The term "room temperature" means from about 10° C. to about 35° C.

Referential Example 1

Method of Preparing 4-Bromo-2-chlorobenzoic Acid (3)

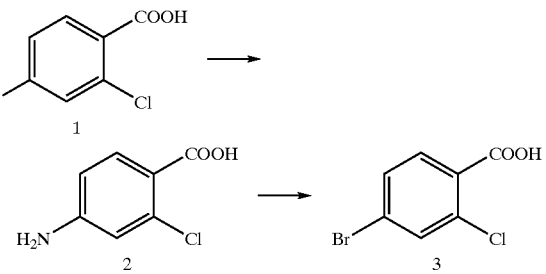

Synthesis of 4-Amino-2-chlorobenzoic Acid (2)

In ethanol (250 mL) was dissolved 100 g (F.W. 201.57, 496 mmol) of 2-chloro-4-nitrobenzoic acid (1) and after replacing with argon, a 10% palladium carbon catalyst (4.0+1.5 g) was added thereto. After replacing with hydrogen, the mixture was stirred at room temperature for 72 hours. The formed crystal was dissolved with acetone and filtered to remove the catalyst. The solvent was distilled under reduced pressure to quantitatively obtain 88 g of the target 4-amino-2-chlorobenzoic acid (2).

Melting point: 215–217° C.

Synthesis of 4-Bromo-2-chlorobenzoic Acid (3)

Eighty-eight grams (F.W. 171.58, 513 mmol) of 4-amino-2-chlorobenzoic acid (2), 48% hydrobromic acid (304 mL) and water (304 mL) were heated at 120° C. for one hour and dissolved to form a hydrobromate salt. Under stirring, the solution was cooled (ice-sodium chloride), and an aqueous solution (water, 250 mL) of 44.4 g (F.W. 69.00, 643 mmol) of sodium nitrite was added thereto while maintaining 5° C. or below.

In a beaker 120.8 g (F.W. 80.79, 2.83 mmol) of copper bromide in 48% hydrobromic acid (331 mL) was made 0° C. and the prepared diazonium salt solution was slowly added thereto with stirring so as not to foam. After completion of the addition, the resulting solution was heated in a hot water bath until the generation of nitrogen ceased. The reaction solution was cooled by standing and then, extracted with ethyl acetate. The extract was treated according to the conventional method to obtain 88.3 g (73%) of a desired 4-bromo-2-chlorobenzoic acid (3).

Melting Point: 152–160° C.; IR (KBr) $v_{max}$ cm$^{-1}$: 3090, 1682, 1578; $^1$H NMR (400 MHz, CDCl$_3$) δ: 7.50 (1H, dd, J=8.5, 2.0 Hz, Ar—H), 7.69 (1H, J=2 Hz, Ar—H), 7.89 (1H, J=8.5 Hz, Ar—H).

Referential Example 2

Method of Preparing of di-(3,5-Dimethoxyphenyl) disulfide (9)

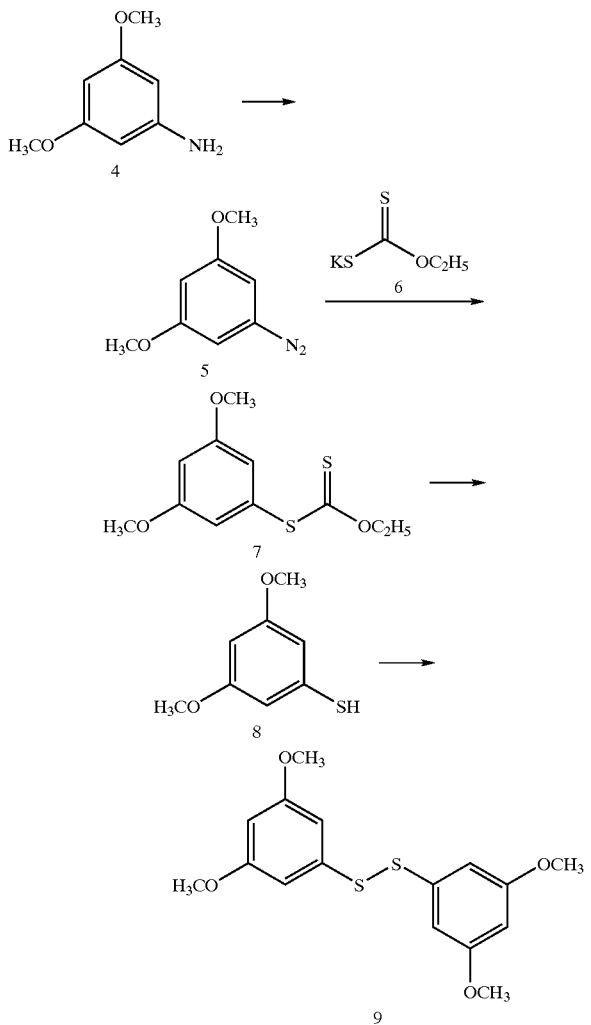

To a suspension of 25.0 g (F.W. 153.18, 163.2 mmmol) of 3,5-dimethoxyaniline (4) in 500 mL of water was added 40.8 mL (489.6 mmol) of concentrated hydrochloric acid to completely dissolve the hydrochloride by stirring and heating. To the resulting solution was added 400 mL of water and then, ice-cooled. While maintaining the reaction temperature (inner temperature) at 5° C. or below and vigorously stirring, a solution of 11.8 g (F.W. 69.00, 171.4 mmol) of sodium nitride in 40 mL of water was carefully added to the resulting solution. The obtained solution was stirred at the same temperature for about 30 minutes to prepare a dizaonium salt solution.

A suspension of 680.5 g (F.W. 160.30, 4243.2 mol) of potassium xanthogenate (6) in 550 mL of water was completely dissolved by raising the temperature to 65 to 70° C. to prepare a potassium xanthogenate solution.

To this solution maintained at 65 to 70° C. was slowly added dropwise the dizaonium salt solution maintained at 5° C. of below over 30 minutes. This procedure was repeated four times.

The resulting solution was stirred at 65 to 70° C. for about one hour and then, cooled to room temperature by standing. The resulting solution was extracted with ethyl acetate three times. The extract was washed with 1N sodium hydroxide, water and a saturated sodium chloride aqueous solution in the order named. After drying with anhydrous sodium sulfate, the solvent was removed under reduced pressure to obtain a crude product (7). By column chromatography (developing solvent; hexane:ethyl acetate=7:1) 122.31 g of product (7)[and a mixture with compound (9)] was obtained.

In 450 mL of ethanol was dissolved 85.7 g of product (7)[and a mixture with compound (9)] and then, 50 mL of water and 200.0 g (F.W. 56.11, 4986.0 mmol) of potassium hydroxide were added thereto. The reaction solution was stirred under refluxing for 10 minutes. After having confirmed the absence of compound (7) by TLC, the reaction solution was cooled by standing and neutralized with 3N hydrochloric acid. Under reduced pressure, ethanol was distilled off and then, the residue was extracted with ethyl acetate three times and the extract was washed with a saturated sodium chloride aqueous solution. To the organic layer was added 25.0 g (F.W. 79.54, 314.3 mmol) of copper (II) oxide (powder) and stirred at room temperature while bubbling air (or oxygen) thereinto until thiol (8) disappeared. After removing insolubles by filtration, water was added to the solution thus obtained and the resulting solution was extracted with ethyl acetate three times and the extract was washed with 1N hydrochloric acid, water and a saturated sodium chloride aqueous solution in the order named. After drying with anhydrous sodium sulfate, the solvent was removed under reduced pressure to obtain 53.65 g of a crude product (9). This crude product (9) was purified by column chromatography (developing solvent; hexane: ethyl acetate= 19:1) to obtain 34.87 g (pure)(F.W.338.44, 103.0 mmol) and 11.05 g (crude) of disulfide (9) in 41% yield.

Melting Point: 152–160° C.; IR (KBr) $v_{max}$ cm$^{-1}$: 3090, 1682, 1578; $^1$H NMR (400 MHz, CDCl$_3$) δ: 7.50 (1H, dd, J=8.5, 2 Hz, Ar—H), 7.69 (1H, J=2 Hz, Ar—H), 7.89 (1H, J=8.5 Hz, Ar—H).

Referential Example 3

Method of Preparing of di-(3,4-Dimethoxyphenyl) disulfide (11)

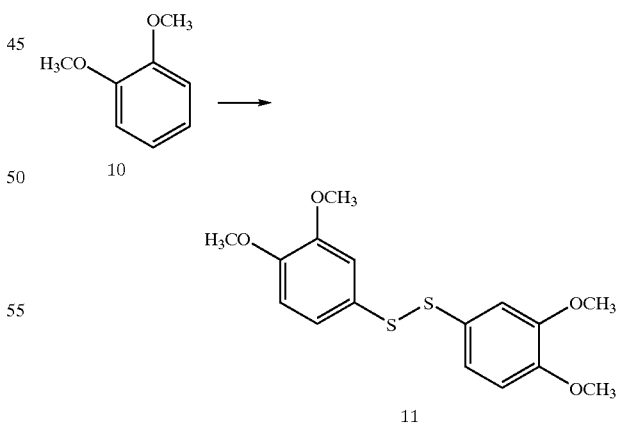

To 100 g of veratrole (10) was added 500 mL of anhydrous methylene chloride and stirred at 0° C. To this solution was added 235 mL of chlorosulfonic acid over one hour and stirred at 50° C. for 30 minutes. The resulting solution was added dropwise to 1.5 L of methanol at 0° C. over 40 minutes and then, 290 mL of hydrochloric acid and 570 g of stannous chloride were added thereto at room temperature and stirred for two hours. The obtained solution was concentrated under reduced pressure to half the volume and then, the resulting solution was extracted with toluene and the organic layer was washed with 12% hydrochloric acid, water and a saturated sodium chloride solution in the order named, and subsequently dried with anhydrous magnesium sulfate and the solvent was distilled off under reduced pressure. The residue was dissolved in ethyl acetate and then, 20 g of cupric oxide was added thereto and stirred while bubbling air. The catalyst was filtered and the filtrate was washed with ethyl acetate and then, recrystallized from ethyl acetate-hexane to obtain a desired compound (11). (Total yield 21%)

EM-MS: 338 (M$^+$), 169 (Base); NMR (CDCl$_3$): 3.83 (6H, s), 3.87 (6H, s), 6.79 (2H, d, J=8.3 Hz), 7.01 (2H, d, J=2.1 Hz), 7.05 (2H, dd, J=2.1, 8.3 Hz).

Referential Example 4

Method of Preparing 8-Bromo-10,11-dihydrodibenz[b,f]oxepin-1,3-diol (21)

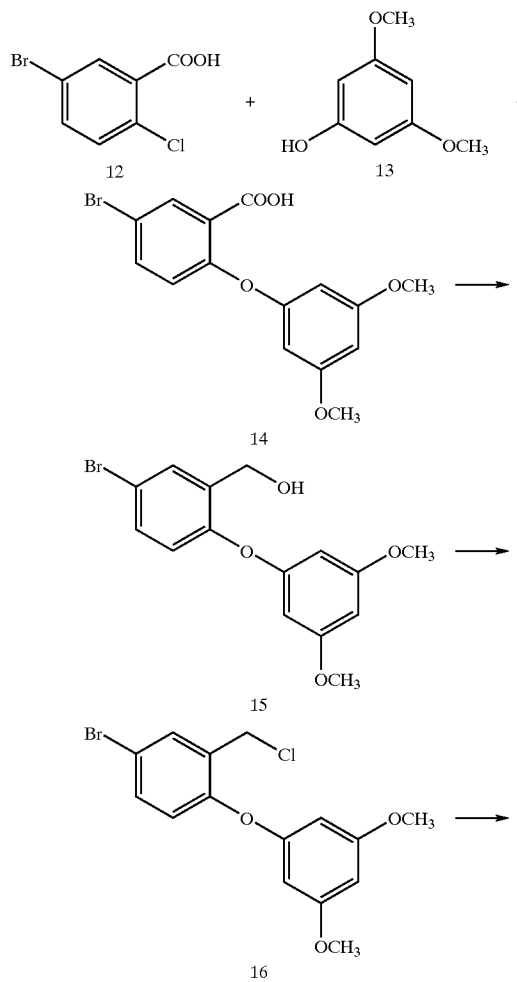

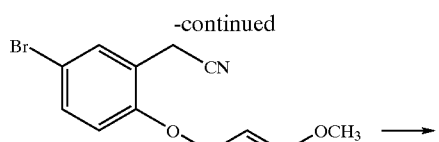

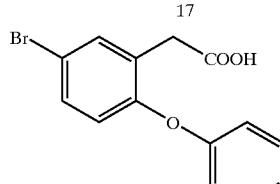

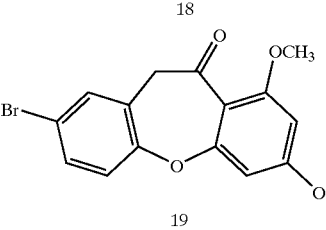

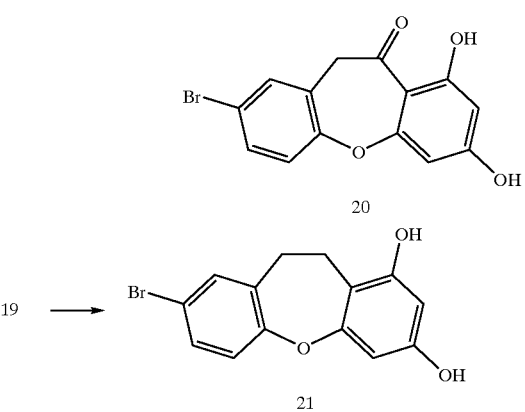

Synthesis of Carboxylic Acid (14)

To a mixture of 30.0 g (F.W. 235.46, 127 mmol) of 5-bromo-2-chlorobenzoic acid (12), 21.6 g (F.W. 154.165, 140 mmol) of 3,5-dimethoxyphenol (13), 35.3 g (F.W. 138.21, 325.6 mmol) of potassium carbonate and 180 mL of N-methyl-2-pyrrolidone was added benzene (100 mL) and the resulting solution was dried by a Dean-Stark water separator (140–170° C.) for three hours and then, 1.59 g (F.W. 63.55, 25.0 mmol) of copper (powder) and 6.05 g (F.W. 190.45, 25.0 mmol) of copper (I) iodide were added thereto and stirred at 120° C. for 1.5 hours. This reaction mixture was cooled by standing and ice water and ethyl acetate were added thereto and then, the obtained solution was made pH 2 with concentrated hydrochloric acid and filtered. The organic layer was separated and then, thoroughly washed with water and subjected to salting out with a saturated sodium chloride aqueous solution. After drying with anhydrous magnesium sulfate and concentration, the residue was recrystallized from benzene to obtain 25.47 g of carboxylic acid (14). The mother liquor was purified by column chromatography (silica gel, water content of 6%; 250 g, ethyl acetate:hexane=1:2) to obtain 4.58 g of crystals. Total yield: 30.05 g (67%)+9.23 g of mother liquor (purity 40%) (TLC; ethyl acetate:hexane=1:2 or 1:1).

MS (EI): 354, 352, 269; NMR (CDCl$_3$): 3.76 (2H, s, CH$_2$), 3.77 (6H, s, CH$_3$×2), 6.22 (2H, d, J=2.5 Hz, Ar—H), 6.33 (1H, d, J=2.5 Hz, Ar—H), 6.85 (1H, d, J=8.5 Hz, Ar—H), 7.57 (1H, dd, J=8.5, 2.2 Hz, Ar—H), 8.26 (1H, d, J=2.2 Hz, Ar—H).

Synthesis of Alcohol (15)

To a solution of 21.5 g (F.W. 353.168, 60.9 mmol) of carboxylic acid (14) in 75 mL of tetrahydrofuran was added potionwise 2.65 g (F.W. 37.83, 70.05 mmol) of sodium borohydride at room temperature and then, 9.49 mL (F.W. 141.93, d=1.154, 77.16 mmol) of boron trifluoride diethyl etherate was added dropwise thereto. The resulting solution was stirred at room temperature for one hour. A 200 mL of ice water was slowly added to the reaction solution. The resulting solution was extracted with ethyl acetate and the extract was washed with a saturated sodium chloride aqueous solution three times. After drying with anhydrous magnesium sulfate, the solvent was removed under reduced pressure. The residue was recrystallized from benzene-diisopropyl ether to obtain 19.04 g (98%) of alcohol (15). (TLC; ethyl acetate:hexane=1:4).

MS (EI): 340, 338, 291, 289; NMR (CDCl$_3$): 3.75 (6H, s, CH$_3$×2), 4.70 (2H, s, CH$_2$), 6.02; (2H, d, J=2.5 Hz, Ar—H), 6.07 (1H, d, J=2.5 Hz, Ar—H), 6.85; (1H, d, J=8.5 Hz, Ar—H), 7.39 (1H, dd, J=8.5, 2.2 Hz, Ar—H), 7.64 (1H, d, J=2.2 Hz, Ar—H).

Synthesis of Chloride (16)

By azeotropy with benzene, 20.0 g (F.W. 339.185, 62.6 mmol) of alcohol (15) was dried. A 40 mL of benzene and 10 mL of methylene chloride to which 5.63 mL (F.W. 118.97, d=1.631, 76.7 mmol) of thionyl chloride and 5.6 mL of methylene chloride were added at 0° C. were added to the dried alcohol to give a mixture. The mixture was stirred at the same temperature for 30 minutes. The reaction solution was further stirred at room temperature overnight. To the reaction mixture was added ice water and the resulting solution was extracted with ethyl acetate and the extract was washed with water and then with a saturated sodium chloride aqueous solution. After drying with anhydrous magnesium sulfate, the solvent was removed under reduced pressure. The residue was purified by silica gel column chromatography (developing solvent; ethyl acetate:hexane=1:4) to obtain 14.03 g (65%) of chloride (16). (TLC; ethyl acetate:hexane=1:4)

NMR (CDCl$_3$): 3.75 (6H, s, CH$_3$×2), 4.49 (2H, s, CH$_2$), 6.16 (2H, d, J=2.5 Hz, Ar—H), 6.25 (1H, d, J=2.5 Hz, Ar—H), 6.78 (1H, d, J=8.7 Hz, Ar—H), 7.35 (1H, dd, J=8.7, 2.4 Hz, Ar—H), 7.57 (1H, d, J=2.4 Hz, Ar—H).

Synthesis of Nitrile Compound (17)

In 30 mL of dimethyl sulfoxide was dissolved 27.9 g (F.W. 357.631, 78.0 mmol) of chloride (16). To this solution was added 5.49 g (F.W. 49.01, 112.0 mmol) of sodium cyanide and stirred at 80° C. for one hour. Under cooling with ice water, water was added to the reaction solution and then, the resulting solution was extracted with ethyl acetate three times. The extract was washed with water and then with a saturated sodium chloride aqueous solution. After drying with anhydrous magnesium sulfate, the solvent was removed under reduced pressure. The residue was recrystallized from methylene chloride-hexane to obtain 16.91 g (65%) of nitrile compound (17). (TLC; ethyl acetate:hexane=1:4).

MS (EI): 349, 347; NMR (CDCl$_3$): 3.70 (2H, s, CH$_2$), 3.74 (3H, s, CH$_3$), 3.75 (3H, s, CH$_3$), 6.11 (2H, d, J=2.5 Hz, Ar—H), 6.26 (1H, d, J=2.5 Hz, Ar—H), 6.81 (1H, d, J=8.5 Hz, Ar—H), 7.40 (1H, dd, J=8.5, 2.2 Hz, Ar—H), 7.62 (1H, d, J=2.2 Hz, Ar—H).

Synthesis of Phenylacetic Acid (18)

To 14.00 g (F.W. 348.196, 40.0 mmol) of nitrile compound (17) were added 33.6 mL of ethanol and 33.6 mL of a 6N sodium hydroxide aqueous solution [8.06 g (F.W. 40.00, 201.5 mmol) of sodium hydroxide being dissolved in water] and stirred at 110° C. overnight. To the reaction solution was added ice and the resulting solution was made pH 2 with concentrated hydrochloric acid. The reaction solution thus obtained was extracted with ethyl acetate and the extract was washed with water and then with a saturated sodium chloride aqueous solution. After drying with anhydrous magnesium sulfate, the solvent was completely removed and the residue was crystallized from benzene-hexane to obtain 13.33 g (90%) of phenylacetic acid (18). (TLC; ethyl acetate:hexane=1:2 or 1:1).

NMR (CDCl$_3$): 3.70 (3H, s, CH$_3$), 3.90 (3H, s, CH$_3$), 3.95 (1H, s, CH$_2$), 6.26 (1H, d, J=2.5 Hz, Ar—H), 6.46 (1H, d, J=2.5; Hz, Ar—H), 7.08 (1H, d, J=8.5 Hz, Ar—H), 7.33 (1H, dd, J=8.5, 2.3 Hz, Ar—H), 7.41 (1H, d, J=2.3 Hz, Ar—H), 12.91; (1H, s, OH).

Synthesis of Cyclized Compound (19)

To 11.75 g (F.W. 367.195, 32.0 mmol) of carboxylic acid (18) was added 60 mL of methanesulfonic acid to dissolve carboxylic acid (18). The resulting solution was stirred at 40° C. for three days. To the reaction solution was added 300 mL of ice water to deposit a cyclized compound. The deposited cyclized compound was separated by filtration and extracted with ethyl acetate and treated by the conventional method to obtain a crude product. This crude product was recrystallized from hexane-methylene chloride to obtain 6.0 g (54%) of cyclized compound (19). (TLC; ethyl acetate:hexane=1:2).

MS (EI): 349, 347, 269; NMR (CDCl$_3$): 3.84 (3H, s, CH$_3$), 3.90 (3H, s, CH$_3$), 3.95 (1H, s, CH$_2$), 6.26 (1H, d, J=2.5 Hz, Ar—H), 6.46 (1H, d, J=2.5; Hz, Ar—H), 7.08 (1H, d, J=8.5 Hz, Ar—H), 7.33 (1H, dd, J=8.5, 2.3 Hz, Ar—H), 7.41 (1H, d, J=2.3 Hz, Ar—H), 12.91; (1H, s, OH).

Synthesis of 2-Bromo-7,9-dihydroxy-10,11-dihydrodibenz[b,f]oxepin-10-one (20)

To 395 mg (F.W. 349.18, 1.13 mmol) of dimethoxylated compound (19) was added 2.0 g of pyridine hydrochloride and stirred at 195° C. for 1.5 hours under heating and then, ice water was slowly added. The resulting solution was extracted with ethyl acetate and the extract was washed with 1N hydrochloric acid, water and a saturated sodium chloride aqueous solution in the order named. After drying with anhydrous magnesium sulfate, the dried extract was concentrated. The residue was purified by silica gel column chromatography (developing solvent; ethyl acetate:hexane=1:2). Furthermore, the product thus obtained was recrystallized from diisopropyl ether-hexane to obtain 223 mg (61%) of the title compound. (TLC; ethyl acetate:hexane=1:2).

Melting Point: 194–195° C.; MS (EI): 322, 320, 241; NMR (CDCl$_3$): 4.03 (2H, s, CH$_2$), 5.88 (1H, s, OH), 6.17

(1H, d, J=2.5 Hz, Ar—H), 6.35 (1H, d, J=2.5 Hz, Ar—H), 7.10 (1H, d, J=8.5 Hz, Ar—H), 7.36 (1H, dd, J=8.5, 2.3 Hz, Ar—H), 7.43 (1H, d, J=2.3 Hz, Ar—H), 12.91 (1H, s, OH).

Synthesis of 8-Bromo-10,11-dihydrodibenz[b,f]oxepin-1,3-diol (21)

To 2.00 g (F.W. 321.126, 6.23 mmol) of dimethoxylated compound (19) was added 50 mL of methanol and stirred. The obtained suspension was cooled to 0° C. Thereto 500 mg of sodium borohydride was dividedly added several times. The reaction solution was returned to room temperature and stirred for one hour. To the reaction solution was added dilute hydrochloric acid to stop the reaction, and methanol was distilled off under reduced pressure. The resulting reaction solution was partitioned with ethyl acetate. The organic layer was washed with water and then with a saturated sodium chloride aqueous solution, and subsequently dried with anhydrous magnesium sulfate and the solvent was distilled off under reduced pressure to obtain an oily substance, and 10 g of pyridine hydrochloride was added to the oily substance and stirred at 200° C. for two hours under heating. After completion of the reaction, the reaction solution was partitioned with ethyl acetate and dilute hydrochloric acid. The organic layer was washed with water and then with a saturated sodium chloride aqueous solution, and subsequently dried with anhydrous magnesium sulfate and the solvent was distilled off under reduced pressure. The residue was purified by silica gel column chromatography (developing solvent; hexane:ethyl acetate= 1:1). The oily substance thus obtained was dissolved in 20 mL of ethyl acetate. To the resulting solution was added 100 mg of palladium (IV) oxide to effect catalytic reduction at room temperature for three days. After completion of the reaction, the reaction solution was filtered and concentrated and the residue was purified by silica gel column chromatography (developing solvent; hexane:ethyl acetate=2:1). The product thus obtained was recrystallized from chloroform-hexane to obtain the title compound (901.0 mg, 52.2%) as orange plates.

Melting Point: 173.8–175.8° C.; NMR (DNSO-$d_6$): 2.74 (2H, t, J=6.3 Hz, $CH_2$), 2.99 (2H, t, J=6.3 Hz, $CH_2$), 6.05 (1H, d, J=2.3 Hz, Ar—H), 6.10 (1H, d, J=2.3 Hz, Ar—H), 7.04 (1H, d, J=8.5 Hz, Ar—H), 7.32 (1H, dd, J=8.5, 2.5 Hz, Ar—H), 7.42 (1H, d, J=2.5 Hz, Ar—H), 9.19; (1H, s, Ph-OH), 9.39 (1H, s, Ph-OH).

Referential Example 5

Method of Preparing 7-Bromo-10,11-dihydrodibenz[b,f]-oxepin-1,3-diol (29)

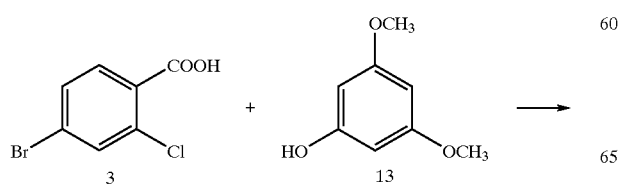
3 + 13

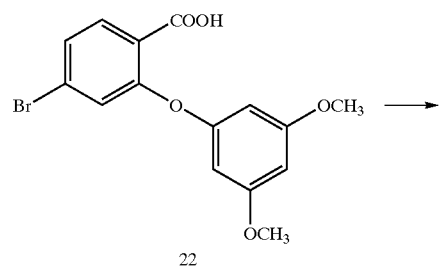
22

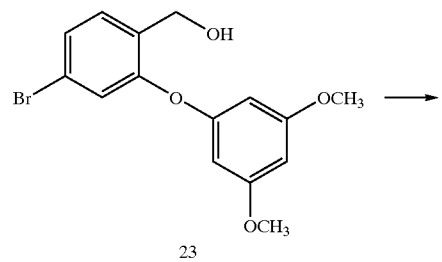
23

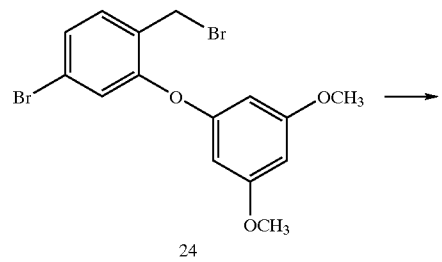
24

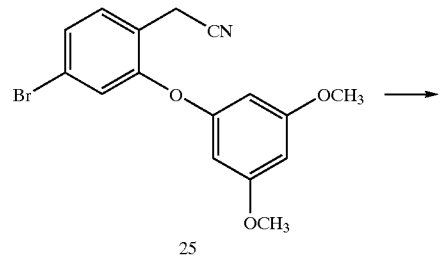
25

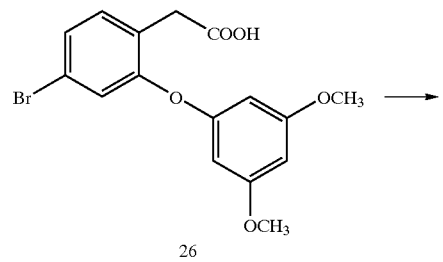
26

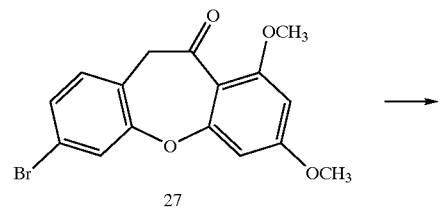
27

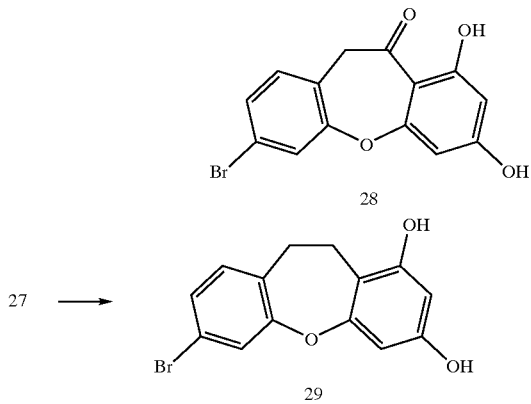

Synthesis Of 4-Bromo-2-(3,5-dimethoxyphenoxy) benzoic Acid (22)

To a mixture of 88.3 g (F.W. 235.46, 375 mmol) of 4-bromo-2-chlorobenzoic acid (3), 57.8 g (F.W. 154.165, 375 mmol) of 3,5-dimethoxyphenol (13), 93.2 g (F.W. 138.21, 670 mmol) of potassium carbonate and 400 mL of N-methyl-2-pyrrolidone was added benzene (200 mL), and the resulting solution was dried by a Dean-Stark water separator (140–170° C.) for three hours and then, 6.0 g (F.W. 63.55, 93.7 mmol) of copper (powder) and 17.8 g (F.W. 190.45, 93.7 mmol) of copper (I) iodide were added thereto and stirred at 120° C. for 30 minutes. This reaction mixture was cooled by standing and ice water and ethyl acetate were added thereto and then, the obtained solution was made pH 2 with concentrated hydrochloric acid and filtered. The organic layer was separated and then, thoroughly washed with water and subjected to salting out with a saturated sodium chloride aqueous solution. The resulting solution was dried with anhydrous magnesium sulfate and concentrated and the residue was purified by silica gel column chromatography (developing solvent; ethyl acetate:hexane=1:3) and recrystallized from ethyl acetate-hexane to obtain 75.4 g (57%) a desired compound (20). (TLC; ethyl acetate:hexane=1:2 or 1:1)

Melting Point: 112–117° C.; UV (EtOH) $\lambda_{max}(\epsilon)$: 292 (2000)nm; IR (KBr) $v_{max}$ cm$^{-1}$:3411, 1699, 1605; $^1$H NMR (400 MHz, CDCl$_3$) δ: 3.75 (2H, s, CH$_2$), 3.77 (6H, s, CH$_3$×2), 6.23 (1H, d, J=2.1 Hz, Ar—H), 6.34 (1H, d, J=2.1 Hz, Ar—H), 7.09 (2H, m, Ar—H), 7.32 (1H, m, Ar—H), 7.98 (1H, m, Ar—H); MS (EI) m/z: 354, 352, 309, 307.

Synthesis of 4-Bromo-2-(3,5-dimethoxyphenoxy) benzyl Alcohol (23)

To a solution of 75.4 g (F.W. 353.168, 213 mmol) of 4-bromo-2-(3,5-dimethoxyphenoxy)benzoic acid (22) in 300 mL of tetrahydrofuran was added 8.9 g (F.W. 37.83, 235 mmol) of sodium borohydride portionwise at room temperature and then, 31 mL (F.W. 141.93, d=1.154, 252 mmol) of boron trifluoride diethyl etherate was added thereto dropwise. The resulting solution was stirred at room temperature for one hour. To this reaction solution was added 200 mL of ice water slowly. The resulting solution was extracted with ethyl acetate and the extract was washed with a saturated sodium chloride aqueous solution three times. After drying with anhydrous magnesium sulfate, the solvent was removed under reduced pressure. The residue was recrystallized from benzene-diisopropyl ether to obtain 46.6 g (64%) of alcohol (23). (TLC; ethyl acetate:hexane=1:4).MS (EI) m/z: 340, 338

Synthesis of 4-Bromo-2-(3,5-dimethoxyphenoxy) benzyl Bromide (24)

In an argon atmosphere, 4.7 mL (F.W. 270.70, d=2.850, 49.5 mmol) of phosphorus tribromide was added to a solution of 46 g (F.W. 339.19, 135 mmol) of alcohol (23) in 100 mL of methylene chloride at 0° C. and stirred at room temperature for 30 minutes. To the reaction mixture was added ice water and the resulting solution was further stirred at room temperature for 30 minutes. The obtained solution was extracted with ethyl acetate and the extract was washed with water and then with a saturated sodium chloride aqueous solution. The resulting extract was dried with anhydrous magnesium sulfate and then, concentrated. The residue was purified by silica gel column chromatography (developing solvent; ethyl acetate:hexane=1:5) to obtain 44.6 g (84%) of a bromide (24). (TLC; ethyl acetate:hexane=1:4)

Synthesis of 4-Bromo-2-(3,5-dimethoxyphenoxy) benzyl Nitrile (25)

In 50 mL of dimethyl sulfoxide was dissolved 44.6 g (F.W. 357.631, 111 mmol) of bromide (24). To this solution was added 8.15 g (F.W. 49.01, 166 mmol) of sodium cyanide and stirred at 80° C. for one hour. Under cooling with ice water, to the reaction solution was added water and then, the resulting solution was extracted with ethyl acetate three times. The extract was washed with water and then with a saturated sodium chloride aqueous solution. After drying with anhydrous magnesium sulfate, the solvent was removed under reduced pressure. The residue was purified by silica gel column chromatography (developing solvent: ethyl acetate:hexane=1:4) to obtain 34.5 g (89%) of nitrile compound (25). (TLC; ethyl acetate:hexane=1:4).

$^1$H NMR (400 MHz, CDCl$_3$) δ: 3.70 (2H, s, CH$_2$), 3.77 (6H, s, CH$_3$×2), 6.14 (1H, d, J=2.1 Hz, Ar—H), 6.28 (1H, d, J=2.1 Hz, Ar—H), 7.02 (1H, m, Ar—H), 7.15 (1H, m, Ar—H), 7.21 (1H, m, Ar—H); MS (EI) m/z: 349, 347, 269.

Synthesis of 4-Bromo-2-(3,5-dimethoxyphenoxy) phenylacetic Acid (26)

To 34.5 g (F.W. 348.196, 99.1 mmol) of nitrile compound (25) were added 83 mL of ethanol and 83 mL [19.9 g (F.W. 40.00, 497 mmol) of sodium hydroxide] of a 6N sodium hydroxide aqueous solution and stirred at 110° C. overnight. To the reaction solution was added ice and the obtained solution was made pH 2 with concentrated hydrochloric acid. The reaction solution thus obtained was extracted with ethyl acetate and the extract was washed with water and then with a saturated sodium chloride aqueous solution. After drying with anhydrous magnesium sulfate, the solvent was completely removed and the residue was purified by silica gel column chromatography (developing solvent; ethyl acetate:hexane=2:3) and crystallized from ethyl acetate-hexane to obtain 27.3 g (75%) of carboxylic acid (26). (TLC; ethyl acetate:hexane=1:2 or 1:1).

Melting Point: 121.9–123.6° C.; UV (EtOH) $\lambda_{max}(\epsilon)$: 272 (2200)nm; IR (KBr) $v_{max}$ cm$^{-1}$: 2954, 1705, 1606, 1576; $^1$H NMR (400 MHz, CDCl$_3$) δ: 3.60 (2H, s, CH$_2$), 3.60 (6H, s, CH$_3$×2), 6.13 (1H, d, J=2.1 Hz, Ar—H), 6.25 (1H, d, J=2.1 Hz, Ar—H), 7.02 (1H, m, Ar—H), 7.15 (1H, m, Ar—H), 7.21 (1H, m, Ar—H), MS (EI) m/z: 368, 366.

Synthesis of 3-Bromo-7,9-dimethoxy-10,11-dihydrodibenz[b,f]oxepin-10-one (27)

To 27.3 g (F.W. 367.195, 74.3 mmol) of carboxylic acid (26) was added 140 mL of methanesulfonic acid to dissolve carboxylic acid (26). This solution was stirred at 40° C. for three days. To the resulting reaction solution was added 300 mL of ice water to deposit a cyclized compound. The cyclized compound was separated by filtration and extracted with ethyl acetate and treated according to the conventional method to obtain a crude product. This crude product was purified by silica gel column chromatography (developing solvent; ethyl acetate:hexane=1:2) and recrystallized from hexane-ethyl acetate to obtain 17.1 g (66%) of cyclized compound (27). (TLC; ethyl acetate: hexane=1:2).

Melting Point: 95–103° C.; UV (EtOH) $\lambda_{max}(\epsilon)$: 272 (2800)nm; IR (KBr) $v_{max}$ cm$^{-1}$: 2977, 1679, 1604; $^1$H NMR (400 MHz, CDCl$_3$) δ: 3.84 (3H, s, CH$_3$), 3.88 (3H, s, CH$_3$), 3.95 (2H, s, CH$_2$), 6.27 (1H, d, J=2.1 Hz, Ar—H), 6.47 (1H, d, J=2.1 Hz, Ar—H), 7.15 (1H, m, Ar—H), 7.30 (1H, m, Ar—H), 7.40 (1H, m, Ar—H), MS (EI) m/z: 350, 348.

Synthesis of 3-Bromo-7,9-dihydroxy-10,11-dihydrodibenz[b,f]oxepin-10-one (28)

To 395 mg (F.W. 349.18, 15.75 mmol) of dimethoxylated compound (27) was added 2.0 g of pyridine hydrochloride and stirred at 195° C. for 1.5 hours and then, ice water was slowly added thereto. The resulting solution was extracted with ethyl acetate and the extract was washed with 1N hydrochloric acid, water and a saturated sodium chloride aqueous solution in the order named. The extract thus washed was dried with anhydrous magnesium sulfate and then, concentrated. The residue was purified by silica gel column chromatography (developing solvent; ethyl acetate:hexane=1:2). Furthermore, the product thus obtained was recrystallized from dioxane and dioxane-hexane to obtain 223 mg (61%) of the title compound. (TLC; ethyl acetate:hexane=1:2).

Melting Point: 194–195° C.; $^1$H NMR (400 MHz, CDCl$_3$) δ: 4.03 (2H, s, CH$_2$), 6.09 (1H, d, J=2.1 Hz, Ar—H), 6.39 (1H, d, J=2.1 Hz, Ar—H), 7.43 (2H, m, Ar—H), 7.64 (1H, m, Ar—H), 11.07 (1H, s, OH), 12.95 (1H, s, OH); MS (EI) m/z: 322, 320.

Synthesis of 7-Bromo-10,11-dihydrodibenz [b,f] oxepin-1,3-diol (29)

To 5.5 g (F.W. 349.18, 15.75 mmol) of dimethoxylated compound (27) was added 80 mL of methanol and stirred. The obtained suspension was cooled to 0° C. Thereto 890 mg of sodium borohydride was dividedly added several times. The reaction solution was returned to room temperature and stirred for one hour. To the reaction solution was added dilute hydrochloric acid to stop thereaction, and methanol was distilled off under reduced pressure. To the resulting reaction solution was added ethyl acetate to effect partition. The organic layer was washed with water and then with a saturated sodium chloride aqueous solution, and subsequently dried with anhydrous magnesium sulfate and the solvent was distilled off under reduced pressure to obtain an oily substance, and 20 mL of pyridine and 3.6 g of tosyl chloride were added to the oily substance and stirred at 90° C. overnight. The reaction solution was partitioned with ethyl acetate and dilute hydrochloric acid. The organic layer was washed with water and then with a saturated sodium chloride aqueous solution, and subsequently dried with anhydrous magnesium sulfate and the solvent was distilled off under reduced pressure. The residue was purified by silica gel column chromatography (developing solvent; hexane:ethyl acetate=5:1)(4.96 g, yield 95%). The oily substance thus obtained was dissolved in 50 mL of ethyl acetate and 150 mg of palladium (IV) oxide added thereto to effect catalytic reduction at room temperature for one day. After completion of the reaction the reaction solution was filtered and concentrated and the residue was purified by silica gel column chromatography (developing solvent: hexane:ethyl acetate=10:1) (4.21 g, yield 84%; melting point 60.0–66.2° C.). To the obtained crystals 150 mg (F.W. 335.20, 0.45 mmol) was added 2 g of pyridine hydrochloride and the resulting solution was stirred at 200° C. under heating for two hours. After completion of the reaction, the reaction solution was partitioned with ethyl acetate and dilute hydrochloric acid. The organic layer was washed with water and then with a saturated sodium chloride aqueous solution, and subsequently dried with anhydrous magnesium sulfate and the solvent was distilled off under reduced pressure. The residue was purified by silica gel column chromatography (developing solvent; hexane:ethyl acetate=1:1). The product thus obtained was recrystallized from chloroform-hexane to obtain 80 mg (58%) of the title compound as pink plates.

Melting Point: 177.5–179.5° C.; $^1$H NMR (90 Mz, DMSO-d$_6$) δ: 2.7–2.9 (2H, m, CH$_2$), 2.9–3.1 (2H, m, CH$_2$), 6.0–6.2 (2H, m, Ar—H), 7.1–7.4 (3H, m, Ar—H), 9.22; (1H, s, OH), 9.41 (1H, s, OH); MS (EI) m/z: 308, 306, 227.

Referential Example 6

Method of Preparing 1-Chloro-7,9-dihydroxy-10,11-dihydrodibenz[b,f]oxepin-10-one (38)

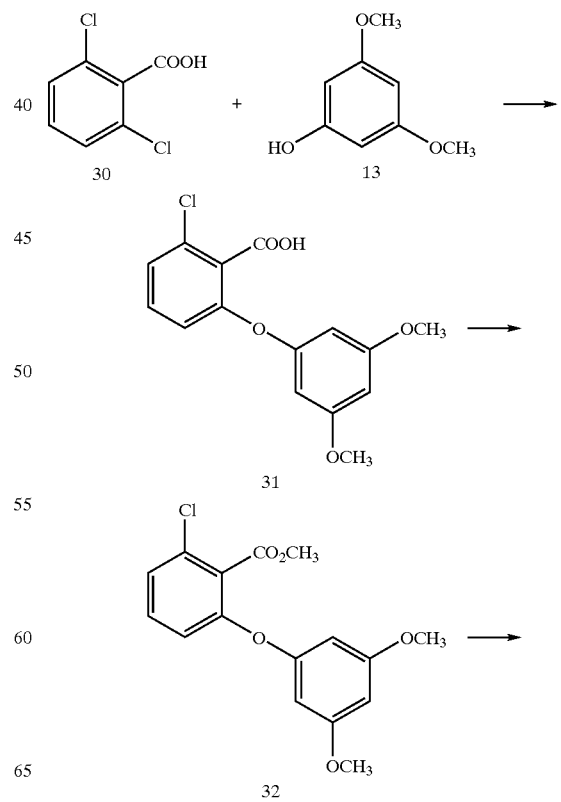

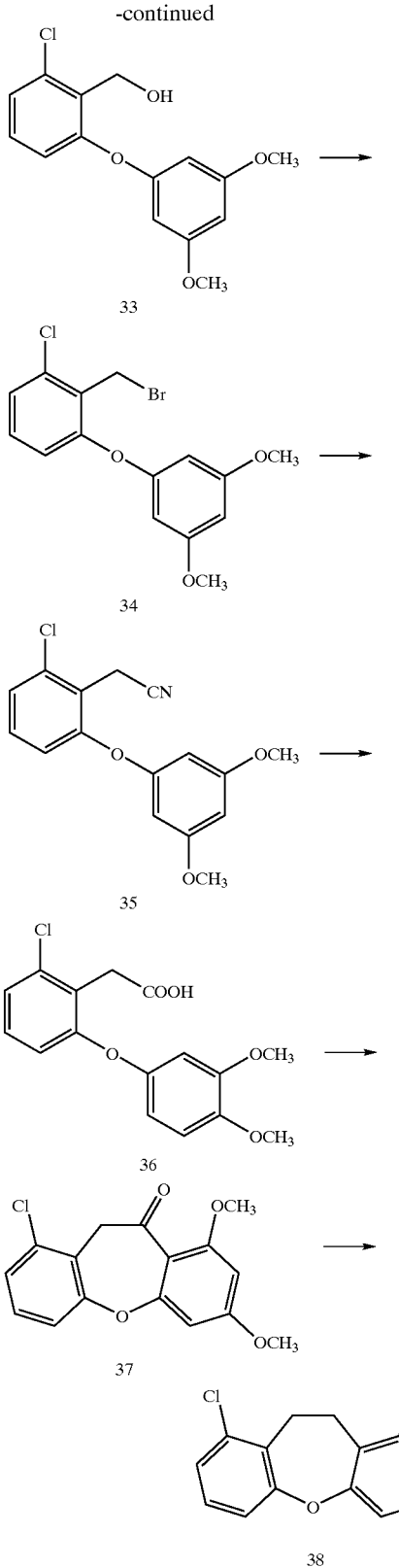

mmol) of 3,5-dimethoxyphenol (13), 9.32 g (F.W. 138.21, 67.4 mmol) of potassium carbonate and 56 mL of N-methyl-2-pyrrolidone was added benzene (40 mL), and the resulting solution was dried by a Dean-Stark water separator (140–170° C.) for three hours and then, 614 mg (F.W. 63.55, 9.67 mmol) of copper (powder) and 2.30 mg (F.W. 190.45, 12.1 mmol) of copper (I) iodide were added thereto and the obtained solution was stirred at 140° C. for one hour. This reaction mixture was cooled by standing and ice water and ethyl acetate were added thereto and then, the resulting solution was made pH 2 with concentrated hydrochloric acid and filtered. The organic layer was separated and then, thoroughly washed with water and subjected to salting out with a saturated sodium chloride aqueous solution. The resulting solution was dried with anhydrous magnesium sulfate and concentrated. The residue (17 g) was purified by column chromatography (silica gel, water content of 6%; 340 g, ethyl acetate:hexane=1:2) to obtain 5.05 g (38%) of crystals (31).

Synthesis of Esterified Compound (32)

To a mixed solution of 2.5 g (F.W. 353.168, 8.10 mmol) of carboxylic acid (31) in 10 mL of dichloromethane and 10 mL of methanol was added an ether solution of diazomethane until the yellow color disappeared. The reaction solution was concentrated and purified by column chromatography (silica gel; 90 g, ethyl acetate:hexane=1:4) to obtain 2.507 g (98%) of an esterified compound (32)(TLC; ethyl acetate:hexane=1:4).

Synthesis of Alcohol (33)

To a mixture of 250 mg (F.W. 37.83, 6.60 mmol) of lithium aluminum hydride and 10 mL of diethyl ether was added a solution of 2.51 g (F.W. 322.744, 7.76 mmol) of esterified compound (32) in ether (5+3 mL) portionwise at 0° C. under stirring. After stirring at room temperature for three hours, a 90% methanol solution and a saturated ammonium chloride aqueous solution were added to the resulting reaction solution. The organic layer was separated and washed with a saturated sodium chloride aqueous solution three times. After drying with anhydrous magnesium sulfate, the solvent was removed under reduced pressure. The residue was purified by column chromatography (silica gel; 150 g, ethyl acetate:hexane=3:7) to obtain 1.53 g (64%) of alcohol (33). (TLC; ethyl acetate:hexane=1:4).

Synthesis of Bromide (34)

By azeotropy with benzene, 2.24 g (F.W. 308.761, 7.28 mmol) of alcohol (33) was dried. A 5 mL of methylene chloride to which 0.254 mL (F.W. 270.70, d=2.85, 2.67 mmol) of phosphorus tribromide had been added and 5.6 mL of methylene chloride were added thereto at 0° C. and stirred at room temperature for two hours. To the reaction mixture was added ice water and the resulting solution was extracted with ethyl acetate and the extract was washed with water and then with a saturated sodium chloride aqueous solution. After drying with anhydrous magnesium sulfate, the solvent was removed under reduced pressure. The residue was purified by silica gel column chromatography (developing solvent; ethyl acetate:hexane=1:4) to obtain 2.58 g (99%) of bromide (34) as crystals. (TLC; ethyl acetate:hexane=1:4)

Synthesis of Nitrile Compound (35)

In 5 mL of dimethyl sulfoxide was dissolved 2.58 g (F.W. 357.631, 7.21 mmol) of bromide (34). To this solution was Synthesis of Carboxylic Acid (31)

To a mixture of 9.32 g (F.W. 191.01, 48.8 mmol) of 2,6-dichlorobenzoic acid (30), 6.60 g (F.W. 154.165, 4.29 added 530 mg (F.W. 49.01, 10.82 mmol) of sodium cyanide and stirred at 80° C. for 30 minutes. Under cooling with ice water, to the reaction solution was added water and then, the resulting solution was extracted with ethyl acetate three times. The extract was washed with water and then with a saturated sodium chloride aqueous solution. After drying with anhydrous magnesium sulfate, the solvent was removed under reduced pressure. The residue was purified by silica gel column chromatography (developing solvent; ethyl acetate:hexane=1:4) to obtain 1.95 g (89%) of nitrile compound (35). (TLC; ethyl acetate:hexane=1:4).

Synthesis of Phenylacetic Acid (36)

To 1.93 g (F.W. 303.745, 6.35 mmol) of nitrile compound (35) were added 4.56 mL of ethanol and 4.56 mL [1.13 g (F.W. 40.00, 28.3 mmol) of sodium hydroxide] of a 6N sodium hydroxide and stirred at 110° C. overnight. To the reaction solution was added ice and the resulting solution was made pH 2 with concentrated hydrochloric acid. The reaction solution thus obtained was extracted with ethyl acetate and the extract was washed with water and then with a saturated sodium chloride aqueous solution. After drying with anhydrous magnesium sulfate, the solvent was completely removed under reduced pressure and the residue was crystallized from benzene-hexane to obtain 1.36 g (66%) of phenylacetic acid (36). (TLC; ethyl acetate: hexane=1:2 or 1:1).

Synthesis of Cyclized Compound (37)

To 1.30 g (F.W. 332.74, 4.03 mmol) of carboxylic acid (36) was added 6 mL of toluene to dissolve carboxylic acid (36) and then, polyphosphoric acid (10 mL of phosphoric acid and 7 g of phosphorus pentoxide having been heated at 150° C.) was added thereto and the obtained solution was concentrated. This solution was stirred at 100° C. for 1.5 hours. To the resulting reaction solution was added ice water and the solution thus obtained was extracted with ethyl acetate and treated according to the conventional method to obtain a crude product. This crude product was recrystallized from hexane-methylene chloride to obtain 1.17 g (85%) of cyclized compound (37). (TLC; ethyl acetate:hexane=1:2).

Synthesis of 1-Chloro-7,9-dihydroxy-10,11-dihydrodibenz[b,f]oxepin-10-one (38)

To 150 mg (F.W. 304.729, 0.492 mmol) of dimethoxylated compound (37) and 0.15 mL of benzene was added 2.0 g of pyridine hydrochloride and stirred at 195° C. for 1.5 hours with heating and then, ice water was slowly added thereto. The resulting solution was extracted with ethyl acetate and the extract was washed with 1N hydrochloric acid, water and a saturated sodium chloride aqueous solution in the order named. After drying with anhydrous magnesium sulfate, the dried extract was concentrated. The residue was purified by silica gel column chromatography (developing solvent; ethyl acetate:hexane=1:2). Furthermore, the product thus obtained was recrystallized from dichloromethane-hexane to obtain 104 mg (77%) of the title compound. (TLC; ethyl acetate:hexane=1:2).

Referential Example 7

Method of Preparing of 9-Chloro-10,11-dihydrodibenz[b,f]oxepin-1,3-diol (40)

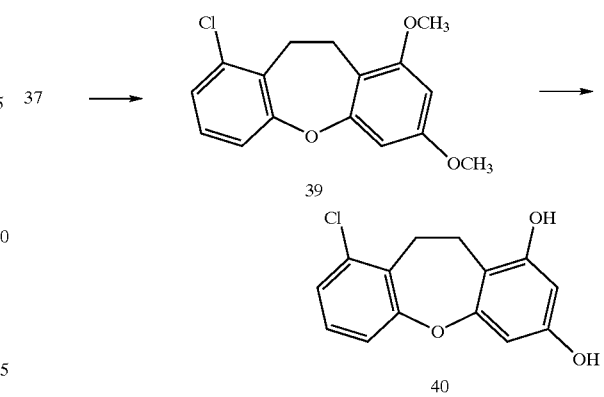

Reduction of Ketone of Ring B

In 20 mL of ethylene glycol was dissolved 475 mg (F.W. 304.729, 1.56 mmol) of ring B-ketone compound (37) and 2.25 mL (F.W. 50.06. d=1.032, 46.5 mmol) of hydrazine-monohydrate and 3.05 g (F.W. 56.11, 54.3 mmol) of potassium hydroxide were added thereto and stirred at 70° C. for 4.5 hours. After raising the temperature up to 140° C., the reaction solution was further stirred for two hours. Under cooling with ice, the reaction solution was neutralized by addition of 4N hydrochloric acid. The reaction solution thus neutralized was extracted with ethyl acetate and the extract was washed with water and then with a saturated sodium chloride aqueous solution. After drying with anhydrous sodium sulfate, the solvent was removed under reduced pressure. The residue was purified by silica gel column chromatography (developing solvent; hexane:ethyl acetate= 19:1) to obtain 347 mg (F.W. 290.746, 1.19 mmol, 76%) of a reduced compound (39).

Deprotection

To 347 mg (F.W. 290.746, 1.19 mmol) of dimethoxy compound (39) was added 3.5 g of pyridine hydrochoride and stirred at 200° C. for two hours with heating and then, ice water was slowly added thereto. The reaction solution was extracted with ethyl acetate and the extract was washed with 1N hydrochloric acid, water and a saturated sodium chloride aqueous solution in the order named. After drying with anhydrous sodium sulfate, the extract thus washed was concentrated. The residue was purified by silica gel column chromatography (developing solvent; ethyl acetate: hexane= 3:1) and further recrystallized from chloroform-hexane to obtain 225 mg (F.W. 262.692, 0.86 mmol, 72%) of the title compound (40).

EXAMPLES

The present invention will now be explained in more detail based on Examples but the present invention is not limited to them or the like and may be changed without departing from the scope of the present invention. The elution in the chromatography of Example was carried out under observation by thin-layer chromatography (TLC) unless expressly stated otherwise. In the TLC observation, "60F$_{254}$" of Merck was used as the TLC plate and as the developing solvent, a solvent which was used as the eluting solvent in column chromatography was used. Further, an UV detector was employed in detection. As the silica gel for the column chromatography, "Silica Gel 60" (70 to 230 mesh) of Merck or "Microsphere Gel D75-60A" of Asahi Glass was used. The term "room temperature" means about 10° C. to about 35° C.

Example 1

Preparation of 2-Methylthio-7,9-dihydroxy-10,11-dihydrodibenzo[b,f]thiepin-10-one (Compound of Example 1)

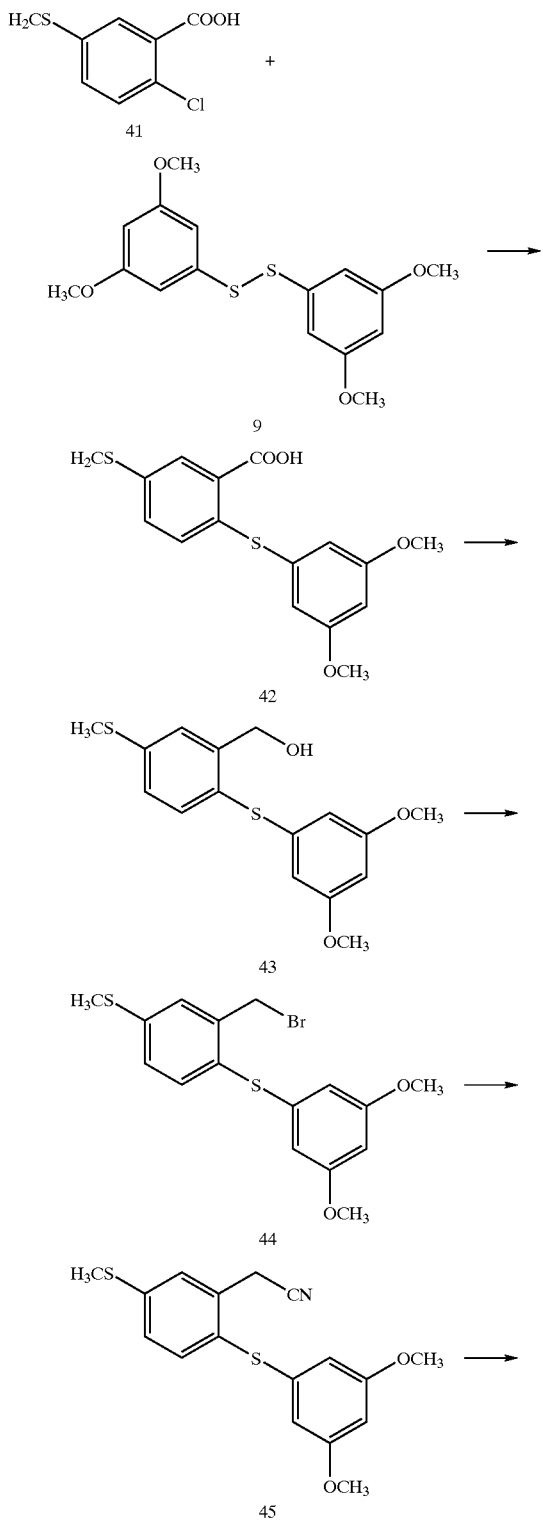

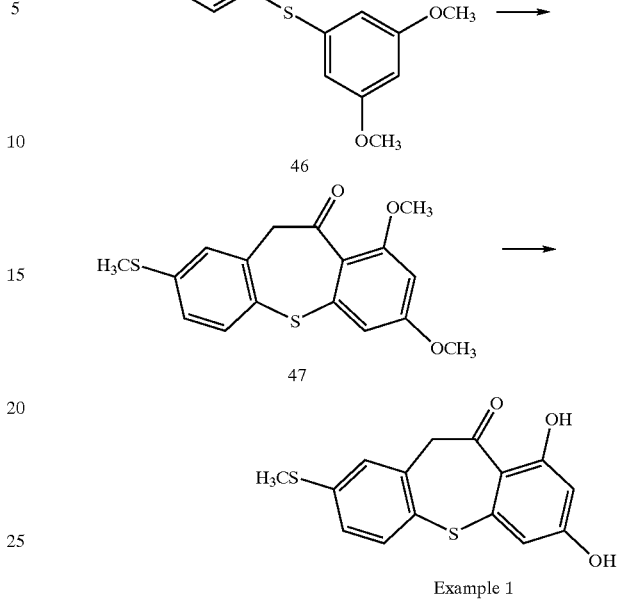

Synthesis of Carboxylic Acid (42)

To a mixture of 60.8 g (F.W. 202.66, 0.30 mmol) of 5-thiomethyl-2-chlorobenzoic acid (41), 21.0 g (F.W. 338.448, 0.15 mmol) of 3,5-dimethoxy disulfide (9), 21.0 g (F.W. 138.21, 0.15 mmol) of potassium carbonate and 300 mL of N-methyl-2-pyrrolidone was added benzene (100 mL×3), and the resulting mixture was subjected to azeotropic drying by a Dean-Stark water separator and then, heated at 135° C. To this reaction solution were added 9.53 g (F.W. 63.55, 0.15 mol) of copper (powder) and 28.57 g (F.W. 190.45, 0.15 mol) of copper (I) iodide and stirred at 135° C. for 5.5 hours. This reaction mixture was cooled by standing and ice water and ethyl acetate were added thereto and then, the resulting solution was made pH 2 with concentrated hydrochloric acid and filtered. The organic layer was separated and then, thoroughly washed with water and subjected to salting out with a saturated sodium chloride aqueous solution. After drying with anhydrous magnesium sulfate and concentrating, the resulting crude carboxylic acid was recrystallized from 2-butanone-isopropyl ether to obtain 65.08 g of carboxylic acid (42). Total yield: 65.08 g(65%)+ 11.03 g of mother liquor (purity 40%) (TLC; ethyl acetate:hexane=1:2 or 1:1).

MS (EI): 336, 318, 303, 244; NMR (CDCl$_3$): 2.48 (3H, s, CH$_3$), 3.78 (6H, s, CH$_3$×2), 6.50; (1H, d, J=2.2 Hz, Ar—H), 6.69 (1H, d, J=2.2 Hz, Ar—H), 6.91; (1H, d, J=8.5 Hz, Ar—H), 7.22 (1H, dd, J=8.5, 2.2 Hz, Ar—H), 7.97 (1H, d, J=2.2 Hz, Ar—H).

Synthesis of Alcohol (43)

To a solution of 50.45 g (F.W. 336.432, 150 mmol) of carboxylic acid (42) in 200 mL of tetrahydrofuran was added 6.24 g (F.W. 37.83, 165.0 mmol) of sodium borohydride in small portions at room temperature and then, 20.29 mL (F.W. 141.93, d=1.154, 165.0 mmol) of boron trifluoride diethyl etherate was added dropwise thereto. The resulting mixture was stirred at room temperature for one hour. To the reaction solution was slowly added ice water. The resulting solution was extracted with ethyl acetate and washed with a saturated sodium chloride aqueous solution three times. After drying with magnesium sulfate, the solvent was removed under reduced pressure. The residue was recrystallized from diisopropyl ether to give 46.23 g of alcohol (43). These crystals were recrystallized from ethyl acetate-hexane again to obtain 43.61 g (77%) of a product. (TLC; ethyl acetate:hexane=1:2).

MS (EI): 322, 303, 289, 273; NMR (CDCl₃): 2.51 (3H, s, CH₃), 3.71 (6H, s, CH₃×2), 4.74; (2H, d, J=6.3 Hz, CH₂), 6.26 (3H, s, Ar—H), 6.85 (1H, dd, J=8.5, 2.2 Hz, Ar—H), 7.40 (1H, d, J=2.2 Hz, Ar—H), 7.42; (1H, d, J=8.5 Hz, Ar—H).

Synthesis of Bromide (44)

To a solution of 59.06 g(F.W. 322.449, 175.5 mmol) of alcohol (43) in methylene chloride (127 mL) was added 6.4 mL (F.W. 118.97, d=1.631, 64.4 mmol) of phosphorus tribromide at 0° C. and stirred at the same temperature for 30 minutes. The reaction solution was further stirred at room for 15 minutes. To the reaction mixture was added ice water and the resulting solution was extracted with ethyl acetate and washed with water and then with a saturated sodium chloride aqueous solution. After drying with anhydrous magnesium sulfate, the solvent was removed under reduced pressure. The residue was purified by silica gel column chromatography (developing solvent; ethyl acetate:hexane=1:5) and then, recrystallized from ethyl acetate-hexane to obtain 57.74 g (82%) of bromide (44). (TLC; ethyl acetate:hexane=1:4)

MS (EI): 386, 384; NMR (CDCl₁₃): 2.50 (3H, s, CH₃), 3.73 (6H, s, CH₃×2), 4.64 (2H, s, CH₂), 6.28 (1H, d, J=2.2 Hz, Ar—H), 6.33 (2H, d, J=2.2 Hz, Ar—H), 7.12 (1H, dd, J=8.2, 2.4 Hz, Ar—H), 7.33; (1H, d, J=8.2 Hz, Ar—H ), 7.35 (1H, d, J=2.4 Hz, Ar—H).

Synthesis of Nitrile Compound (45)

In 127 mL of dimethyl sulfoxide was dissolved 57.74 g (F.W. 385.346, 149.8 mmol) of bromide (44). To this solution was added 11.02 g (F.W. 49.01, 224.8 mmol) of sodium cyanide and stirred at 80° C. for 45 minutes. Under cooling with ice water, to the reaction solution was added water and then, the obtained solution was extracted with ethyl acetate three times. The extract was washed with water and then with a saturated sodium chloride aqueous solution. After drying with anhydrous magnesium sulfate, the solvent was removed under reduced pressure. The residue was recrystallized from ethyl acetate-hexane to obtain 34.83 g (70%) of nitrile compound (45). (TLC; ethyl acetate:hexane=1:4).

MS (EI): 331; NMR (CDCl₃): 2.53 (3H, s, CH₃), 3.72 (6H, s, CH₃), 3.85 (3H, s, CH₃), 6.20 (2H, d, J=2.5 Hz, Ar—H), 6.27 (1H, d, J=2.5; Hz, Ar—H), 7.19 (1H, dd, J=8.5, 2.3 Hz, Ar—H), 7.44 (1H, d, J=2.3 Hz, Ar—H ), 7.45 (1H, d, J=8.5 Hz, Ar—H).

Synthesis of Phenylacetic Acid (46)

To 30.07 g (F.W. 331.46, 90.8 mmol) of nitrile compound (45) were added 75 mL of ethanol and 75 mL of a 6N sodium hydroxide aqueous solution [18.06 g (F.W. 40.00, 450 mmol) of sodium hydroxide] and stirred at 110° C. overnight. To the reaction solution was added ice and the resulting solution was made pH 2 with concentrated hydrochloric acid. The reaction solution thus obtained was extracted with ethyl acetate and the extract was washed with water and then with a saturated sodium chloride aqueous solution. After drying with anhydrous magnesium sulfate, the solvent was completely removed under reduced pressure and the residue was crystallized from benzene-hexane to obtain 28.86 g (91%) of phenylacetic acid (46). (TLC; ethyl acetate:hexane=1:2 or 1:1).

MS (EI): 350, 273; NMR (CDCl₃): 2.49 (3H, s, CH₃), 3.70 (6H, s, CH₃), 3.84 (1H, s, CH₂), 6.25 (3H, m, Ar—H), 7.15 (1H, dd, J=8.5, 2.3 Hz, Ar—H), 7.21 (1H, d, J=2.3 Hz, Ar—H), 7.42 (1H, d, J=8.5 Hz, Ar—H), 12.91 (1H, s, OH).

Synthesis of Cyclized Compound (47)

To 27.89 g (F.W. 350.459, 32.0 mmol) of carboxylic acid (46) was added 140 mL of methanesulfonic acid to dissolve carboxylic acid (46). The resulting solution was stirred at 40° C. for one day. To the reaction solution was added ice water to deposit a cyclized compound. The deposited cyclized compound was separated by filtration and extracted with ethyl acetate and treated by the conventional method to obtain a crude product. This crude product was recrystallized from hexane-methylene chloride to obtain 15.22 g (58%) of cyclized compound (47). (TLC; ethyl acetate:hexane=1:2).

MS (EI): 332, 347, 269; NMR (CDCl₃): 2.49 (3H, s, CH₃), 3.81 (3H, s, CH₃), 3.85 (3H, s, CH₃), 4.19 (1H, s, CH₂), 6.36 (1H, d, J=2.5 Hz, Ar—H), 6.66 (1H, d, J=2.3 Hz, Ar—H), 7.04 (1H, dd, J=8.5, 2.2 Hz, Ar—H), 7.22 (1H, d, J=2.2 Hz, Ar—H ), 7.46 (1H, d, J=8.5 Hz, Ar—H).

Synthesis of 7-Methylthio-7,9-dihydroxy-10,11-dihydrodibenzor[b,f]thiepin-10-one (Compound of Example 1)

To 27.88 g (F.W.332.44, 1.13 mmol) of dimethoxy compound (47) was added 120 g of pyridine hydrochloride and stirred at 195° C. for 1.5 hours with heating and then, ice water was slowly added thereto. The reaction solution was extracted with ethyl acetate and the extract was washed with 1N hydrochloric acid, water, a saturated sodium chloride aqueous solution in the order named. After drying with anhydrous magnesium sulfate, the extract thus obtained was concentrated. The residue was purified by silica gel column chromatography (developing solvent: ethyl acetate:hexane=1:2). Furthermore, the residue was recrystallized from isopropyl alcohol-2-butanone to obtain 19.40 g (64%) of the title compound.

Example 2

Preparation of 8-Methylthio-10,11-dihydrodibenzo[b,f]thiepin-1,3-diol (Compound of Example 2)

47 ⟶ 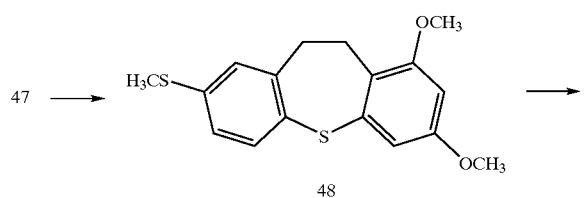 ⟶

48

-continued

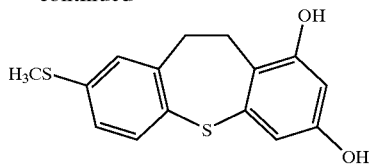

Example 2

In 50 mL of ethylene glycol was dissolved 665 mg (F.W. 332.43, 2.0 mmol) of cyclized compound (47) and 2.9 mL (F.W. 50.06, d=1.032, 60.0 mmol) of hydrazine monohydrate and 4.04 g (F.W. 56.11, 72.0 mmol) of potassium chloride aqueous solution in the order named. After drying with anhydrous sodium sulfate, the obtained solution was concentrated. The residue was purified by silica gel column chromatography (developing solvent;hexane: ethyl acetate= 19:1) and further recrystallized from hexane-ethyl acetate to obtain 132.7 mg (61%) of the title compound.

Example 3

Preparation of 11-Diethyl-7,9-dihydroxy-10,11-dihydrodibenzo[b,f]thiepin-10-one (Compound of Example 3)

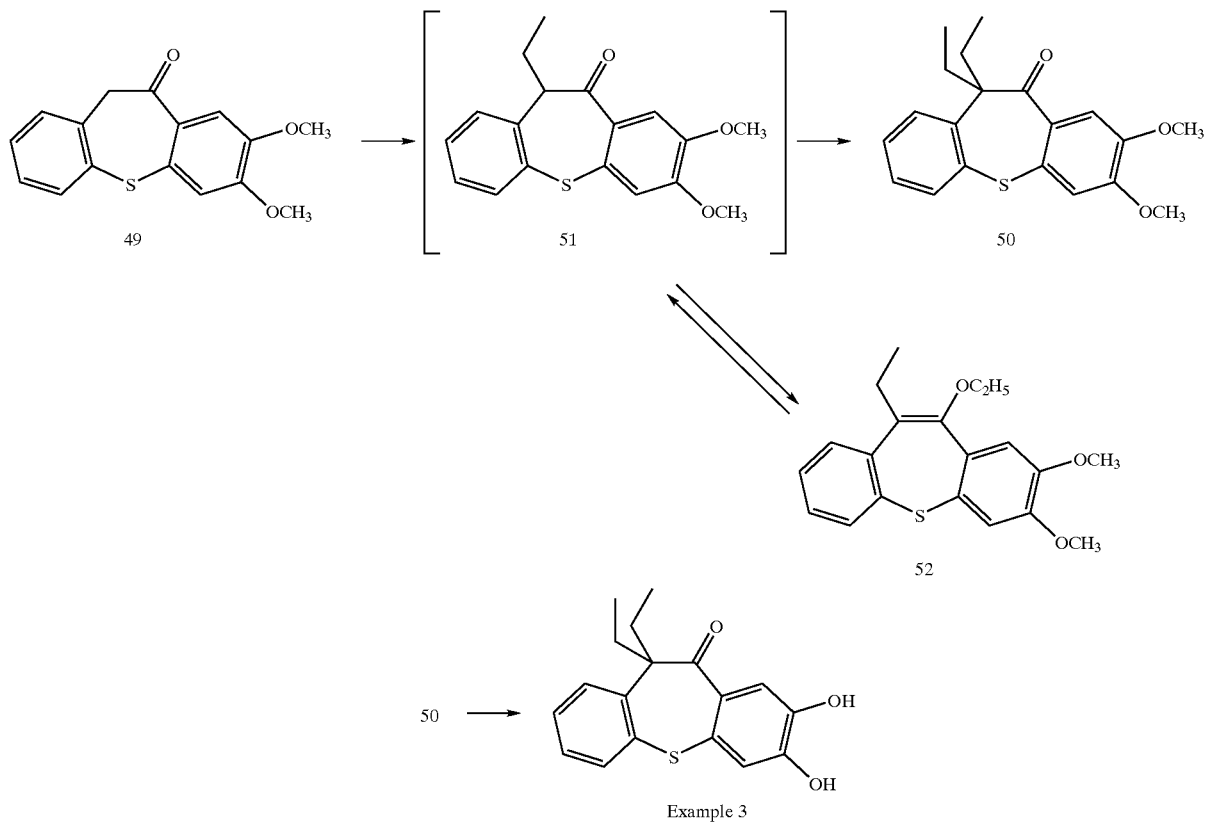

Example 3 hydroxide were added thereto and stirred at 80° C. for 1.5 hours. After raising the temperature to 140° C., the reaction solution was further stirred for five hours. Under cooling with ice, the reaction solution was neutralized by addition of 1N hydrochloric acid. The reaction solution thus neutralized was extracted with ethyl acetate and washed with water and then with a saturated sodium chloride aqueous solution. After drying with anhydrous sodium sulfate, the solvent was completely removed under reduced pressure to obtain a crude product. The residue was purified by silica gel column chromatography (developing solvent; hexane: ethyl acetate= 19:1) to obtain 238.5 mg (37.5%) of a reduced compound (48).

To 238.5 mg (F.W. 318.45, 0.75 mmol) of reduced compound (48) was added 3.0 g of pyridine hydrochloride and stirred at 200° C. under heating for six hours and then, ice water was slowly added thereto, and the resulting solution was extracted with ethyl acetate and the extract was washed with 1N hydrochloric acid, water and a saturated sodium To a suspension of 1.92 g (60% content, F.W. 24.00, 48.0 mmol) of sodium hydride and 50 mL of tetrahydrofuran was added dropwise a solution of 5.72 g (F.W. 286.34, 20.0 mmol) of compound (49) dissolved in 200 mL of tetrahydrofuran. The resulting suspension was stirred at room temperature for 30 minutes and then, 3.84 mL (F.W. 155.97, d=1.94, 48.0 mmol) of ethyl iodide was added thereto and further stirred at room temperature for two days. Under cooling with ice, ammonium chloride was added to the reaction solution and the tetrahydrofuran was completely removed under reduced pressure and then, the residue was partitioned with ethyl acetate and water and washed with water and then with a saturated sodium chloride aqueous solution. After drying with anhydrous sodium sulfate, the solvent was completely removed under reduced pressure to obtain 9.34 g of a crude product. The residue was purified by silica gel column chromatography (developing solvent; hexane:ethyl acetate=9:1 to 3:1) to obtain 3.62 g of a mixture of compound (50) with compound (51) and 2.62 g (F.W.

342.45, 7.65 mmol, 38.2%) of compound (52). The by-product of compound (52) was subjected to acid treatment with ethanol-concentrated hydrochloric acid to be converted to compound (51). With compound (51) the above described reaction was repeated to be led to compound (50).

The crude products (50) were combined and purified by silica gel column chromatography (developing solvent; hexane: ethyl acetate=9:1 to 5:1) to obtain 3.73 g (F.W. 342.45, 10.89 mmol, 54.5%) of compound (50). Demethylation reaction was carried out according to the method of Example 1 to obtain the title compound.

Example 4

Preparation of 11-Ethyl-7,9-dihydroxy-10,11-dihydrodibenzo[b,f]thiepin-10-one (Compound of Example 4)

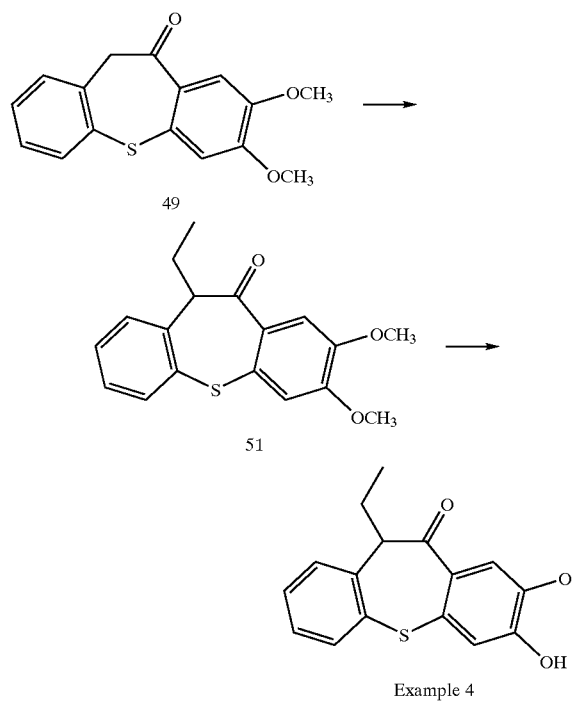

Example 4

To a suspension of potassium tert-butoxide (12.3 g, 110 mmol) and 500 mL of tetrahydrofuran was added dropwise a solution of 30 g (F.W. 286.34, 105 mmol) of compound (49) in 500 mL of tetrahydrofuran at 0° C. This suspension was stirred at room temperature for two hours and then, cooled to 0° C., and 16.8 mL (F.W. 155.97, d=1.94, 210 mmol) of ethyl iodide was added thereto and stirred at room temperature for 20 hours. Under cooling with ice, hydrochloric acid was added to the reaction solution, and tetrahydrofuran was completely removed under reduced pressure and then, the residue was partitioned with ethyl acetate and water and the organic layer was washed with water and then with a saturated sodium chloride aqueous solution and dried with anhydrous magnesium sulfate, and the solvent was removed under reduced pressure. The residue was purified by silica gel column chromatography (developing solvent; hexane:ethyl acetate=4:1) and then, recrystallized from methanol to obtain 18.7 g (yield 57%) of compound (51). The demethylation reaction of compound (51) was carried out according to the method of Example 1 to obtain 14.8 g of the title compound.

Example 5

Preparation of 3-(2-Thiophene)-7,9-dihydroxy-10,11-dihydrodibenz[b,f]oxepin-10-one (Compound of Example 5)

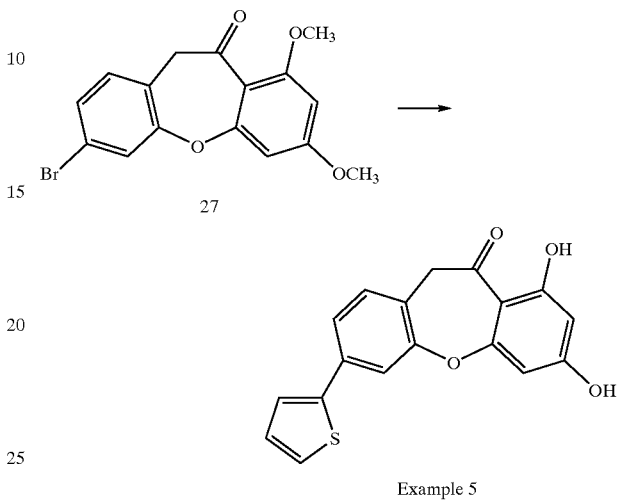

Example 5

To 3-bromo-7,9-dimethoxy-10,11-dihydrodibenz[b,f]oxepin-10-one (27) (500 mg, 1.4 mmol), 2-(tributylstannyl)thiophene (0.9 mL, 2.8 mmol) and tetrakis(triphenylphosphine) palladium (82.5 mg, 0.07 mmol) was added 5 mL of hexamethylphosphoric triamide and stirred at 100° C. for one hour. After completion of the reaction, the reaction solution was partitioned with diethyl ether and water, and the organic layer was washed with water and then with a saturated sodium chloride aqueous solution and dried with anhydrous magnesium sulfate, and the solvent was distilled off under reduced pressure. The residue was purified by silica gel column chromatography (developing solvent; hexane:ethyl acetate=1:1) to obtain 538 mg (yield 89%) of 3-(2-thiophene)-7,9-dimethoxy-10,11-dihydrodibenz[b,f]oxepin-10-one. Demethylation reaction was carried out according to the method of Example 1 to obtain the title compound.

Example 6

Preparation of 3-Phenyl-7,9-dihydroxy-10,11-dihydrodibenz[b,f]oxepin-10-one (Compound of Example 6)

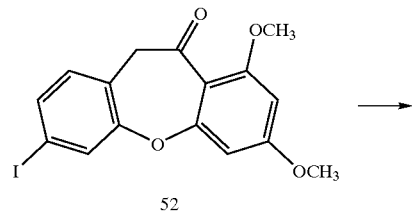

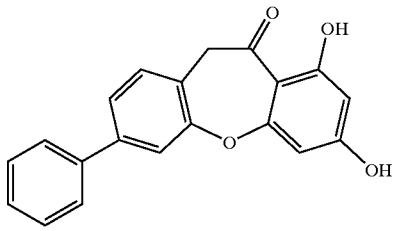

Example 6

To 3-iodo-7,9-dimethoxy-10,11-dihydrodibenz[b,f]oxepin-10-one (52) (403 mg, 1.0 mmol), phenyl boronic acid (186 mg, 1.5 mmol), a 2M potassium carbonate aqueous solution (0.6 mL, 1.2 mmol) and tetrakis(triphenylphosphine) palladium (118 mg, 0.10 mmol) was added 5 mL of toluene and stirred at 125° C. for 19 hours. After completion of the reaction, the reaction solution was neutralized with dilute hydrochloric acid and extracted with ethyl acetate. The organic layer was washed with water and then with a saturated sodium chloride aqueous solution and dried with anhydrous magnesium sulfate, and the solvent was distilled off under reduced pressure. The residue was purified by silica gel column chromatography (developing solvent; hexane:ethyl acetate=2:1) to obtain 108 mg (yield 31%) of 3-phenyl-7,9-dimethoxy-10,11-dihydrodibenz[b,f]oxepin-10-one. Demethylation reaction was carried out according to the method of Example 1 to obtain the title compound.

Example 7

Preparation of 7-Phenyl-10,11-dihydrodibenz[b,f]oxepin-1,3-diol (Compound of Example 7)

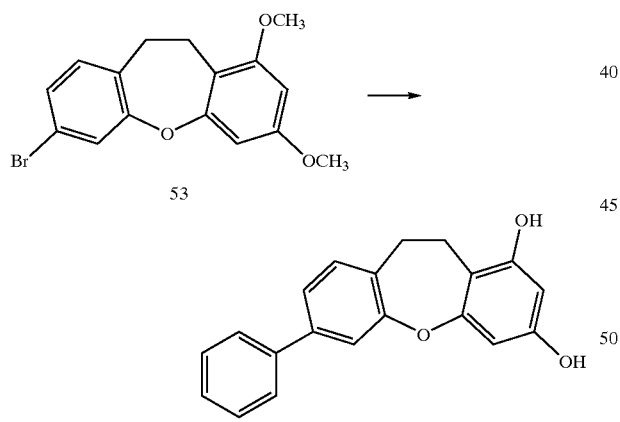

Example 7

To 1,3-dimethoxy-7-bromo-10,11-dihydrodibenz[b,f]oxepin (53) (970 mg, 2.9 mmol) obtained by reducing the 10-position of the carbonyl group of the previous compound (27), phenylboronic acid (380 mg, 3.1 mmol), potassium carbonate (1.98 mg, 14.3 mmol), palladium acetate (20 mg, 0.09 mmol) and tetra-n-butylammonium bromide (920 mg, 2.9 mmol) was added 5 mL of water and stirred at 70° C. for one hour. After completion of the reaction, the reaction solution was neutralized with dilute hydrochloric acid and extracted with ethyl acetate. The organic layer was washed with water and then with a saturated sodium chloride aqueous solution and dried with anhydrous magnesium sulfate, and the solvent distilled off under reduced pressure. The residue was purified by silica gel column chromatography (developing solvent;hexane: ethyl acetate=10:1) to quantitatively obtain 1.05 g of 1,3-dimethoxy-7-phenyl-10,11-dihydrodibenz[ b,f]oxepin. Demethylation reaction was carried out according to the method of Example 1 to obtain the title compound.

Example 8

Preparation of 3-Iodo-7,9-dihydroxy-10,11-dihydrodibenzo[b,f]thiepin-10-one (Compound of Example 8)

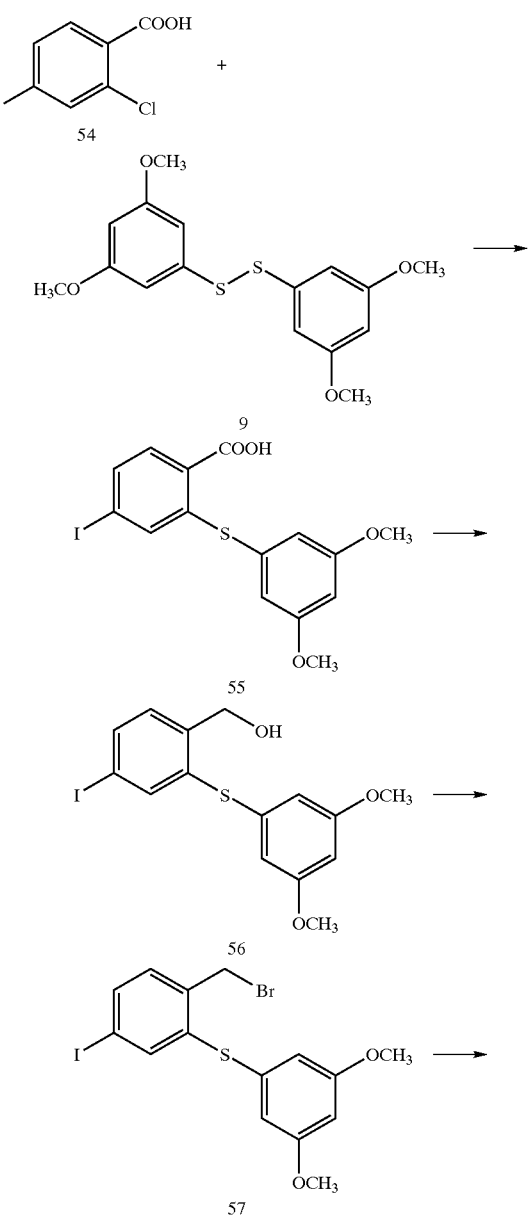

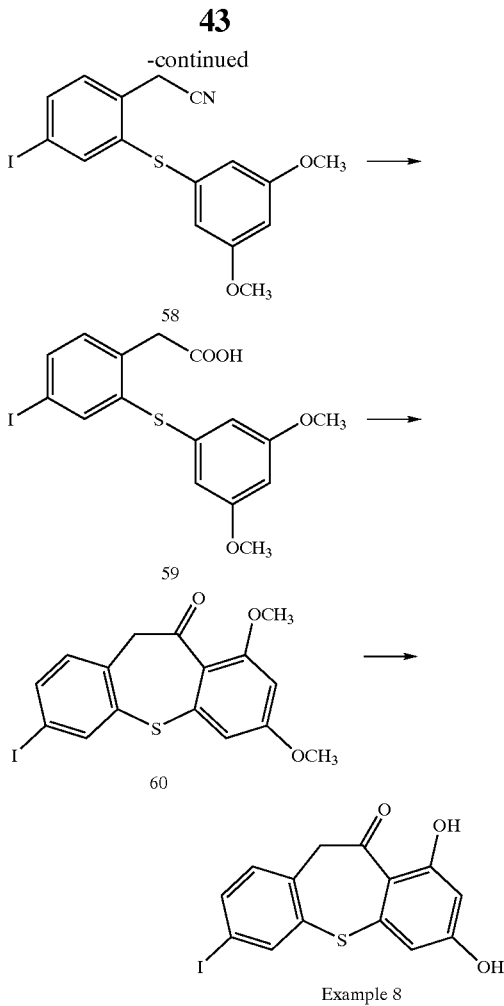

Example 8

Synthesis of Carboxylic Acid (55)

A mixture of 14.1 g (F.W. 282.46, 50.0 mmol) of 2-chloro-3-iodobenzoic acid (54), 8.46 g (F.W. 338.44, 25.0 mmol) of disulfide (9), 1.58 g (F.W. 63.55, 25.0 mmol) of copper (powder), 4.76 g (F.W. 190.45, 25.0 mmol) of copper (I) iodide, 12.4 g (F.W. 138.21, 90.0 mmol) of potassium carbonate and 100 mL of N-methyl-2-pyrrolidone was stirred at 120° C. for 1.5 hours. This reaction solution was cooled by standing, and made pH 2 with 4N hydrochloric acid. The resulting solution was extracted with ethyl acetate and washed with water and a saturated sodium chloride aqueous solution in the order named. After drying with anhydrous sodium sulfate, the solvent was removed under reduced pressure, and the resulting crude carboxylic acid was recrystallized from ethyl acetate to obtain 4.21 g (F.W. 416.23, 10.1 mmol) of carboxylic acid (55). The filtrate after recrystallization was further crystallized (from ethyl acetate) to obtain 3.45 g (F.W. 416.23, 8.3 mmol) of carboxylic acid (55). The yield was 36.8%.

Synthesis of Alcohol (56)

To a solution of 7.66 g (F.W. 416.23, 18.4 mmol) of carboxylic acid (55) in 20 mL of tetrahydrofuran was added 722 mg of sodium borohydride and then, 2.74 mL of boron trifluoride diethyl etherate was added dropwise thereto. The resulting mixture was stirred at room temperature for 45 minutes. Ice water was slowly added to this reaction solution. The reaction solution thus obtained was extracted with ethyl acetate and washed with a saturated sodium chloride aqueous solution. After drying with anhydrous magnesium sulfate, the solvent was removed under reduced pressure. The resulting crude product was purified by column chromatography (developing solvent; hexane:ethyl acetate=4:1) to quantitatively obtain 7.59 g (F.W. 402.25) of alcohol (56).

Synthesis of Bromide Compound (57)

To a solution of 7.49 g (F.W. 402.25) of crude alcohol (56) in 20 mL of methylene chloride was added 0.62 mL of phosphorus tribromide at 0° C. and stirred at room temperature for 30 minutes. To this reaction solution was added slowly ice water. The reaction solution was further stirred at room temperature for 30 minutes and then, extracted with methylene chloride and the extract was washed with water and then with a saturated sodium chloride aqueous solution. After drying with anhydrous magnesium sulfate, the solvent was removed under reduced pressure. As a result, a crude product was obtained. This crude product was purified by silica gel column chromatography (developing solvent; hexane:ethyl acetate=4:1) to obtain 5.14 g (F.W. 465.14, 11.05 mmol) of bromide (57). The yield was 61.4% in two steps.

Synthesis of Nitrile Compound (58)

In 20 mL of dimethyl sulfoxide was dissolved 5.00 g (F.W. 465.14, 10.75 mmol) of bromide (57). To this solution was added 630 mg of sodium cyanide and stirred at 80° C. for one hour. Under cooling with ice, to the resulting solution was added water and then, the obtained solution was extracted with ethyl acetate, and the extract was washed with water and a saturated sodium chloride aqueous solution in the order named. After drying with anhydrous magnesium sulfate, the solvent was removed under reduced pressure and the crude product thus obtained was purified by silica gel column chromatography (developing solvent; hexane:ethyl acetate=3:1) to obtain 2.30 g (F.W. 411.26, 5.59 mmol) of nitrile compound (58) and 2.06 g (F.W. 411.26) of crude nitrile compound (58).

Synthesis of Carboxylic Acid (59)

To 30 ml of ethanol 2.27 g (F.W. 411.26, 5.5 mmol) of nirile compound (58) was added and completely dissolved by raising the temperature to 110° C. To this solution was added 2.35 mL of a 1N sodium hydroxide aqueous solution. The resulting solution was further stirred at 110° C. overnight. To the reaction solution was added ice and the obtained solution was neutralized with 1N hydrochloric acid. The resulting solution was extracted with ethyl acetate and the extract was washed with water and then with a saturated sodium chloride aqueous solution. After drying with anhydrous magnesium sulfate, the solvent was completely removed under reduced pressure to obtain 2.36 g (F.W. 430.26) of crude carboxylic acid (59).

Synthesis of Cyclized Compound (60)

To 4.40 g (F.W. 430.26 mmol) of crude carboxylic acid (59) was added 60 mL of methanesulfonic acid to dissolve crude carboxylic acid (59). The resulting solution was stirred at room temperature overnight. To the reaction solution was added water under cooling with ice and then, the resulting solution was extracted with ethyl acetate and the extract was washed with water and then with a saturated sodium chloride aqueous solution. After drying with anhydrous magnesium sulfate, the solvent was completely removed to obtain a crude product which was then purified by silica gel column chromatography (developing solvent; hexane:ethyl acetate= 4:1). Furthermore, recrystallization of the product thus obtained was repeated from hexane and methylene chloride and from hexane and ethyl acetate to obtain 1.82 g (F.W. 412.24, 4.4 mmol) of cyclized compound (60). The yield was 41.1% in three steps.

Synthesis of 3-Iodo-7,9-dihydroxy-10,11-dihydrodibenzo[b,f]thiepin-10-one (Compound of Example 8)

To 412.2 mg (F.W. 412.24, 1.0 mmol) was added 2.0 g of pyridine hydrochloride and the temperature was raised up to 200° C. The resulting solution was stirred at 200° C. for two hours and then, ice water was slowly added thereto. The reaction solution thus obtained was extracted with ethyl acetate to which a small amount of tetrahydrofuran had been added and the extract was washed with 1N hydrochloric acid, water and a saturated sodium chloride aqueous solution in the order named. After drying with anhydrous magnesium sulfate, the solvent was completely removed under reduced pressure to obtain 289.1 mg of a crude product. This crude product was purified by silica gel column chromatography (developing solvent; hexane:ethyl acetate=9:1 to 4:1). Furthermore, the product thus obtained was recrystallized from chloroform to obtain 150.1 mg (F.W. 384.19, 39.1 mmol) of the title compound. The yield was 39.1%.

Example 9

Preparation of 3-Bromo-7,9-dihydroxy-10,11-dihydrodibenzo[b,f]thiepin-10-one (Compound of Example 9)

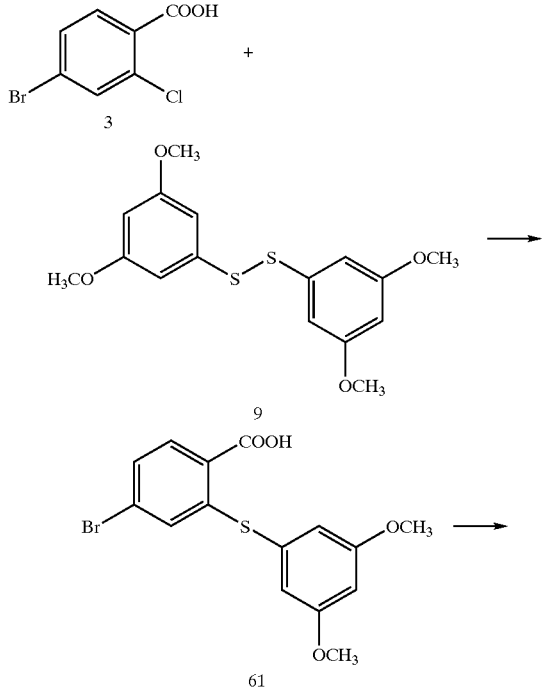

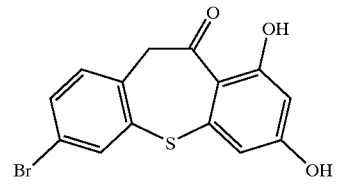

Example 9

Synthesis of Carboxylic Acid (61)

A mixed solution of 58.87 mg (F.W. 235.47, 0.25 mmol) of 3-bromo-2-chlorobenzoic acid (3), 42.31 mg (F.W. 338.44, 0.10 mmol) of disulfide (80%) (9), 7.94 mg (F.W. 63.55, 0.125 mmol) of copper (powder), 23.81 mg (F.W. 190.45, 0.125 mmol) of copper (I) iodide, 41.46 mg (F.W. 138.21, 0.30 mmol) of potassium carbonate and 3 mL of N-methyl-2-pyrrolidone was stirred at 150° C. for 2.5 hours. This reaction solution was cooled by standing, and made pH 2 with 1N hydrochloric acid. The resulting solution was extracted with ethyl acetate and washed with water and a saturated sodium chloride aqueous solution in the order named. After drying with anhydrous sodium sulfate, the solvent was removed under reduced pressure to give crude carboxylic acid (61) (F.W. 369.23). The yield was 64.5% by HPLC.

The procedure after the synthesis of carboxylic acid (61) was carried out according to the method of Example 8 to obtain the title compound.

Example 10

Preparation of 8-Propionyl-10,11-dihydrodibenz[b,f]oxepin-1,3-diol (Compound of Example 10)

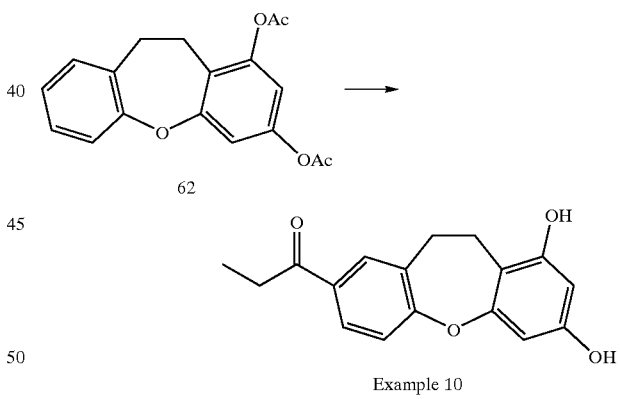

Example 10

To a suspension of aluminum chloride (1 g, 7.5 mmol) in anhydrous methylene chloride (3 mL) was added propionyl chloride (668 μL, 7.7 mmol) and stirred at room temperature for one hour. This solution was added dropwise to a solution of 10,11-dihydrodibenz[b,f]oxepin-1,3-diol diacetate (62) (300 mg, 0.96 mmol) in methylene chloride (5 mL) at 0° C. and stirred at room temperature for one hour. To the reaction solution was added dropwise methanol (10 mL) at 0° C. and a 20% sodium hydroxide aqueous solution (3 mL) was added thereto and stirred at room temperature for 30 minutes. After completion of the reaction, the reaction solution was poured into hydrochloric acid-ice water and extracted with ethyl acetate, and the organic layer was washed with water and then with a saturated sodium chloride aqueous solution and dried with anhydrous magnesium sulfate and the solvent was distilled off under reduced pressure. The residue was purified by silica gel column chromatography (developing solvent; hexane:ethyl acetate=2:1), and recrystallization was carried out from ethyl acetate and hexane to obtain 190 mg (yield 70%) of skin-colored needles of the title compound.

Example 11

Preparation of 8-(1-Hydroxyiminoethyl)-10,11-dihydrodibenzo[b,f]thiepin-1,3-diol (Compound of Example 11)

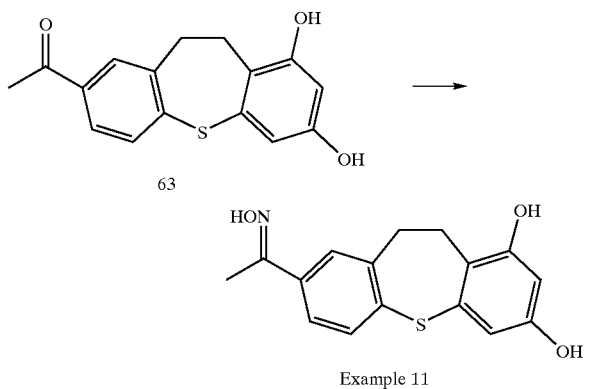

Example 11

In ethanol, 180 mg of 8-acetyl-10,11-dihydrodibenzo[b,f]thiepin-1,3-diol (63) was dissolved, and an aqueous solution of 49 mg of hydroxylamine hydrochloride and 100 mg of sodium acetate dissolved in 1 mL of water was added thereto. The mixed solution was stirred at 120° C. for 3 hours, concentrated under reduced pressure and then, extracted with ethyl acetate. The organic layer was washed with water and a saturated sodium chloride solution and then, dried with anhydrous magnesium sulfate and the solvent was distilled off under reduced pressure. The residue was purified by silica gel column chromatography (developing solvent; hexane:ethyl acetate=1:1). Upon recrystallization from chloroform-hexane, 120 mg of skin-colored amorphous title compound was obtained (yield 63%). Melting Point: 215.4 to 217.5° C.

Example 12

Preparation of 8-Hexyl-10,11-dihydrodibenz[b,f]oxepin-1,3-diol (Compound of Example 12)

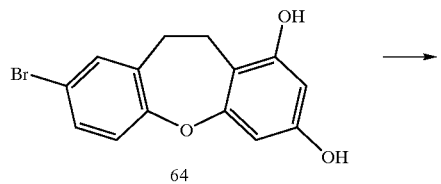

64

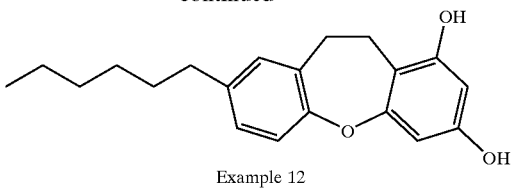

Example 12

In a pressure reaction vessel, 200 mg of 2-bromo-7,9-dimethoxy-10,11-dihydrodibenz[b,f]oxepin-10-one (64), 32 mg of a palladium complex, 34 mg of triphenylphosphine and further 11.8 mg of copper iodide were charged and 3 mL of acetonitrile (dehydrated) was added thereto and stirred. To this solution O,N-bis(trimethylsilyl)acetamide (hereinafter referred to as "BSA") was added at room temperature and stirred for 5 minutes to effect silylation. After silylation, 110 μL of 1-hexyne and 250 μL of N,N-diisopropylethylamine were added and the vessel was heat sealed, and stirred at 120° C. under heating for 17 hours. After completion of the reaction, the reaction solution was partitioned with ethyl acetate and dilute hydrochloric acid. The organic layer was washed with water and a saturated sodium chloride solution and then, dried with anhydrous magnesium sulfate and the solvent was distilled off under reduced pressure. The residue was purified by silica gel column chromatography (developing solvent; hexane:ethyl acetate=3:1). To the obtained oily substance was added 5 mL of ethyl acetate to dissolve the oily substance and 20 mg of palladium-carbon was added thereto to effect hydrogenation overnight. After completion of the reaction, the reaction solution was filtered, concentrated and the residue as purified by silica gel column chromatography (developing sovent; hexane:ethyl acetate=7:1). Upon recrystallization from chloroform-hexane, 49.3 mg of colorless plates of the title compound was obtained (yield 24.3%).

Various compounds of the present invention were synthesized in the same manner as in each of the above described Examples. The structures of a total of 178 compounds synthesized including the compounds synthesized in Examples 1 to 12, and the compounds of Examples used in the following Experimental Examples are collectively shown below. These compounds can be prepared by combinations of ①: Ullmann reaction; ②-1: Friedel-Crafts reaction or ②-2: photoreaction; ③: carbon atom increasing reaction; ④: conversion reaction of a halogens to another functional group; ⑤: introduction reaction of an alkyl group or an alkylcarbonyl group; ⑥: conversion reaction at 10-position; and ⑦: reaction of Deprotection according to the same methods as the preparation methods of Referential Examples and Examples, and the preparation steps of each compound will be explained in Table 1.

Further, the data of the properties of these compounds are listed in Table 2 to Table 18.

TABLE 1
| Example Nos. | Preparation Steps |
|---|---|
| Examples 13 to 23 | ①→②-1→③→⑦ |
| Examples 24 to 36 | ①→②-1→③→⑥→⑦ |
| Examples 37 to 46 | ①→②-1→③→⑤→⑦ |
| Examples 47 to 101 | ①→②-1→③→④→⑦ |
| Examples 102 to 127 | ①→②-1→③→④→⑥→⑦ |
| Examples 128 to 151 | ①→②-1→③→⑤→⑥→⑦ |
| Example 4, Example 37, Example 152 | ①→②-2→⑤→⑦ |
| Examples 153 to 163, Examples 168 to 179 | ①→②-1→③→④→⑤→⑦ |
Example 1
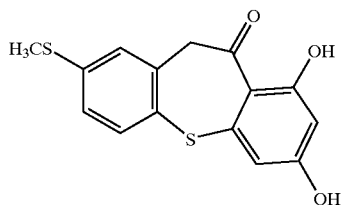
Example 2
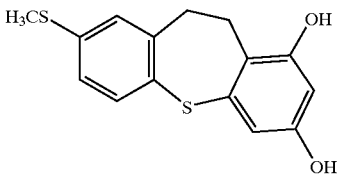
Example 3
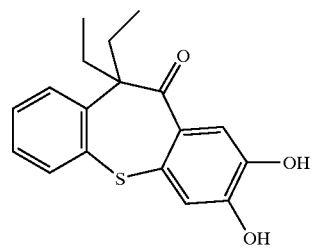
Example 4
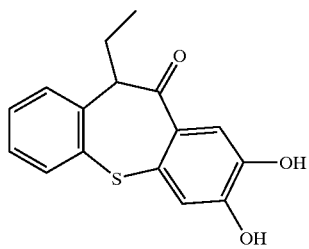
Example 5
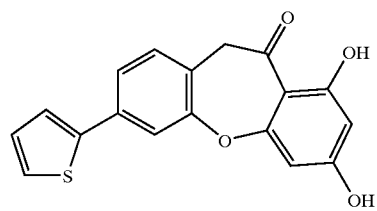
Example 6
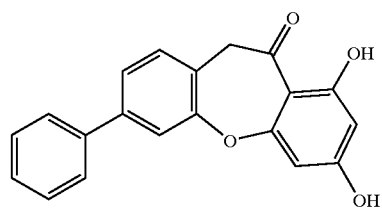
Example 7
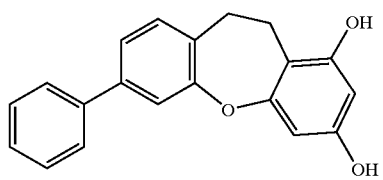
Example 8
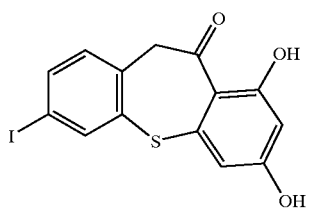
Example 9
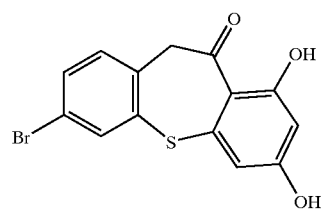
Example 10
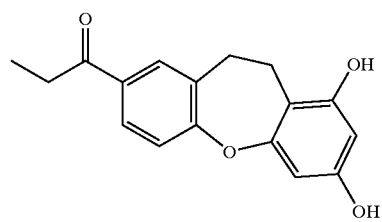

TABLE 1-continued
Example 11
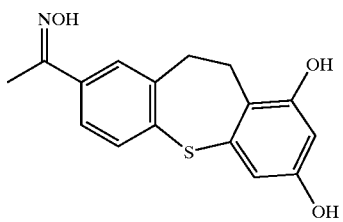
Example 12
Example 13
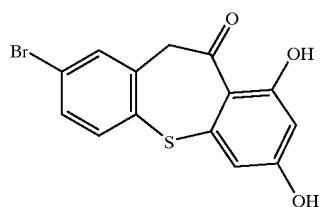
Example 14
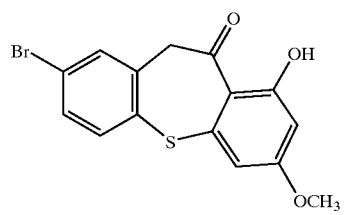
Example 15
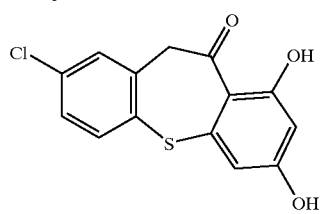
Example 16
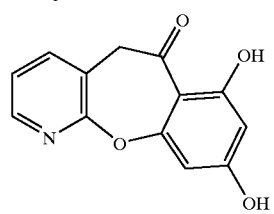
Example 17
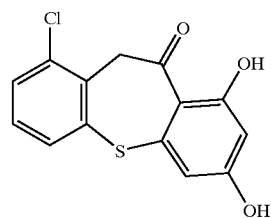
Example 18
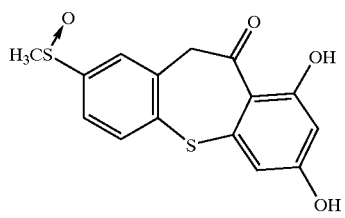
Example 19
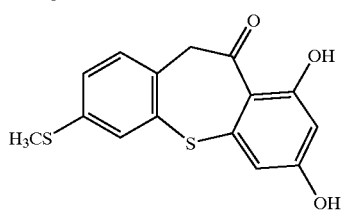
Example 20
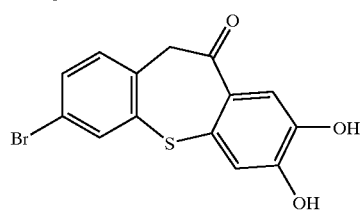
Example 21
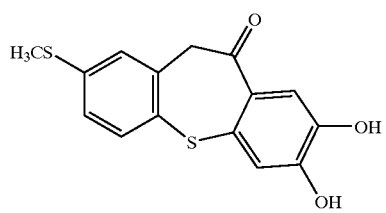
Example 22
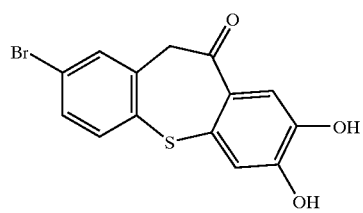

TABLE 1-continued
Example 23 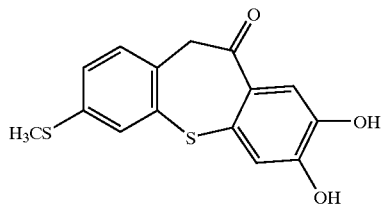
Example 24 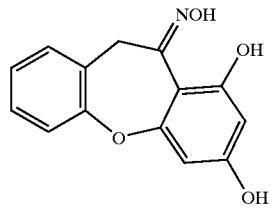
Example 25 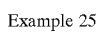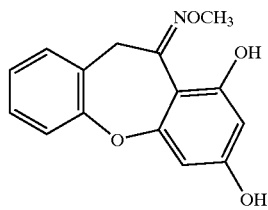
Example 26 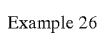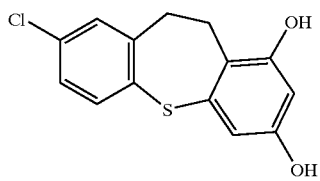
Example 27 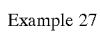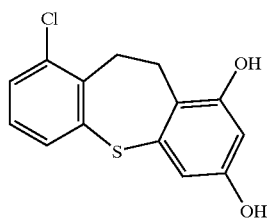
Example 28 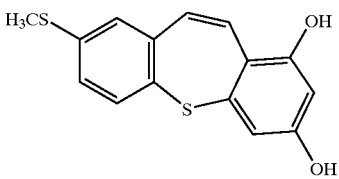
Example 29 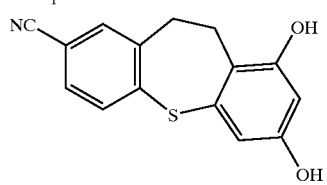
Example 30 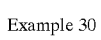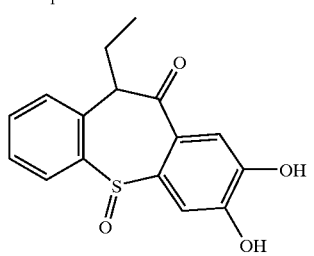
Example 31 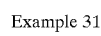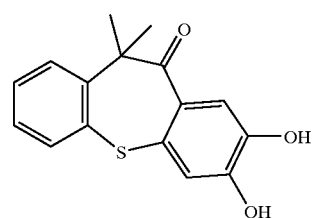
Example 32 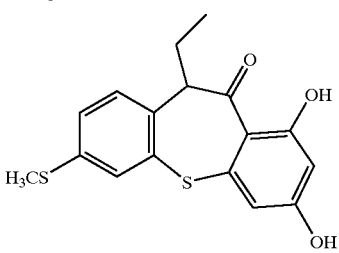
Example 33 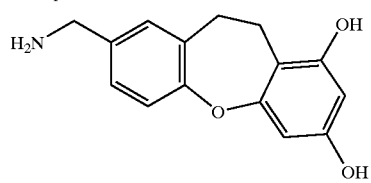
Example 34 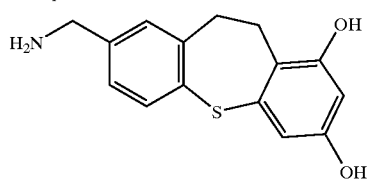

TABLE 1-continued
Example 35
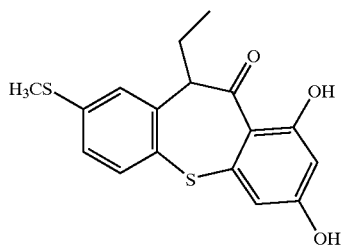
Example 36
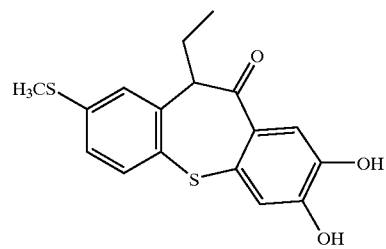
Example 37
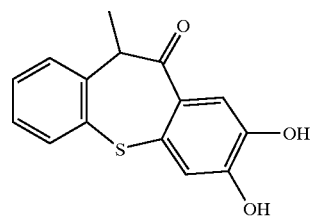
Example 38
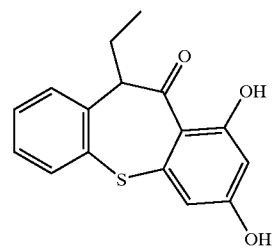
Example 39
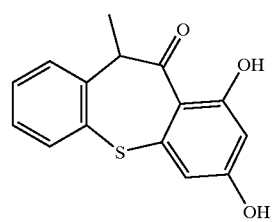
Example 40
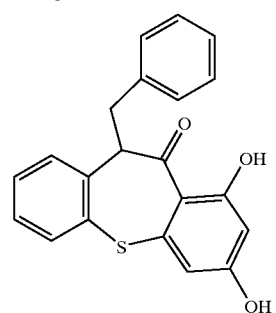
Example 41
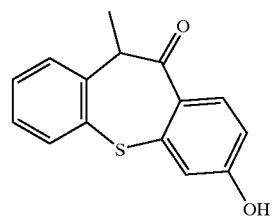
Example 42
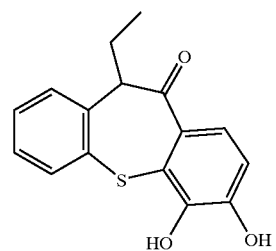
Example 43
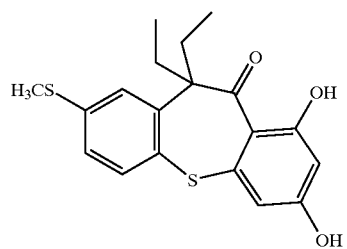
Example 44
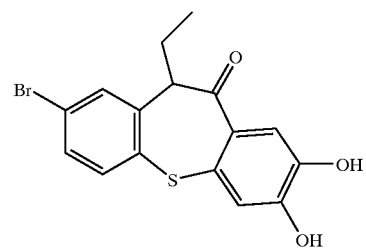

TABLE 1-continued
Example 45
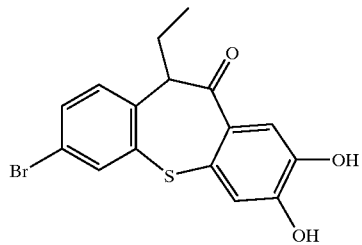
Example 46
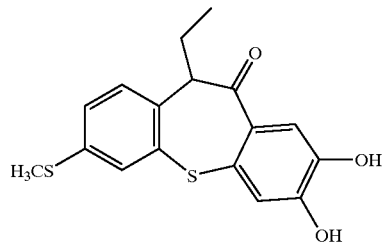
Example 47
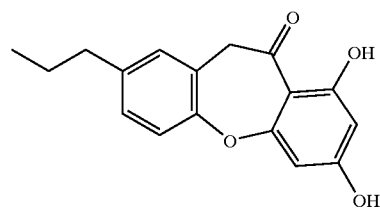
Example 48
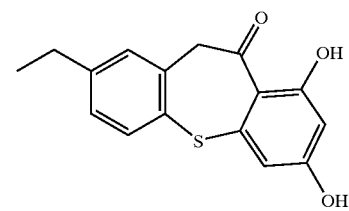
Example 49
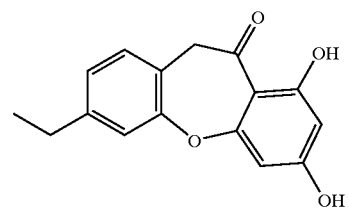
Example 50
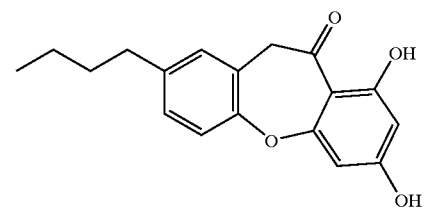
Example 51
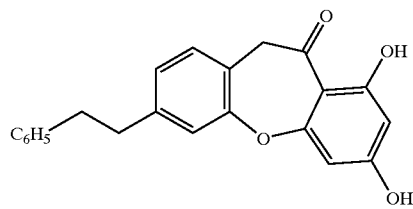
Example 52
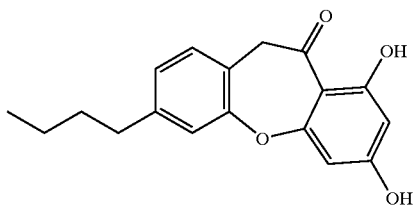
Example 53
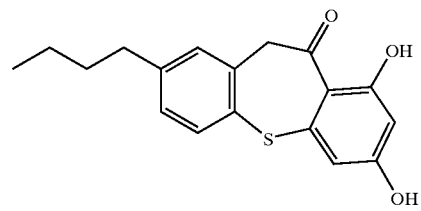
Example 54
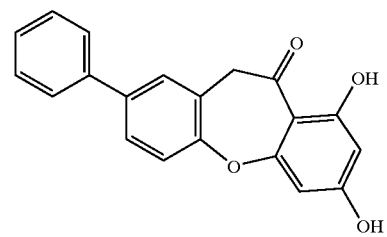
Example 55
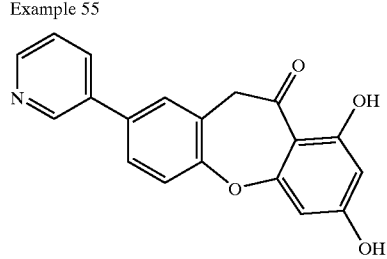
Example 56
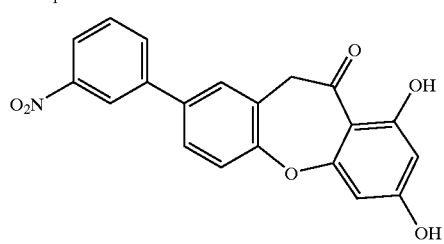

TABLE 1-continued
Example 57
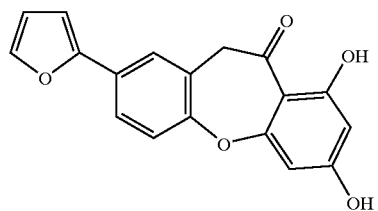
Example 58
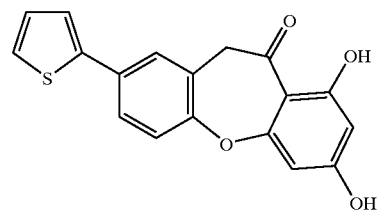
Example 59
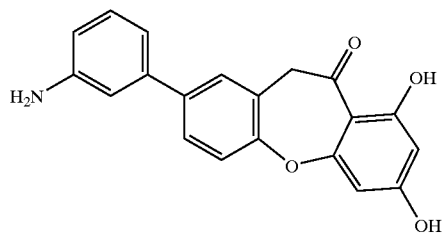
Example 60
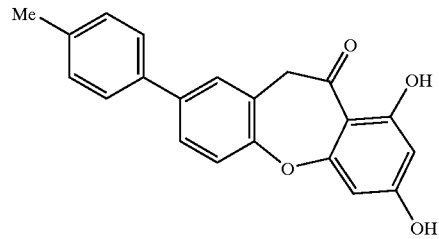
Example 61
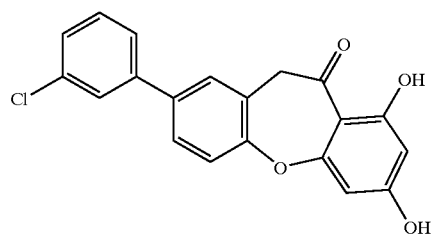
Example 62
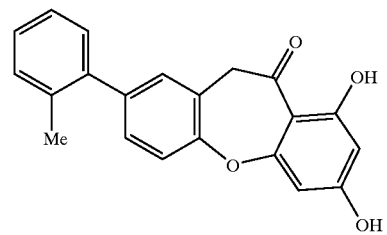
Example 63
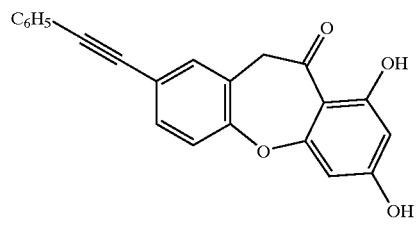
Example 64
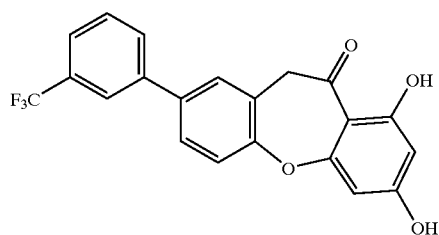
Example 65
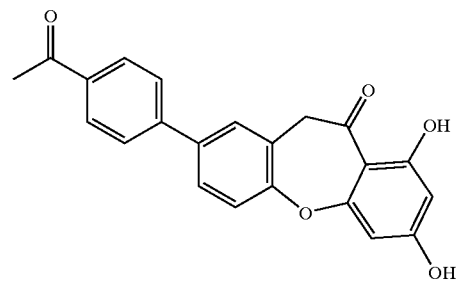
Example 66
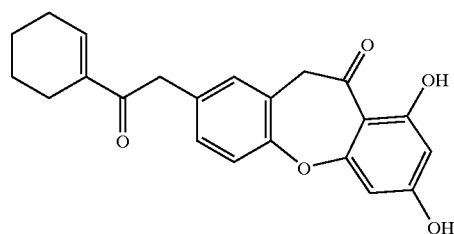

TABLE 1-continued
Example 67
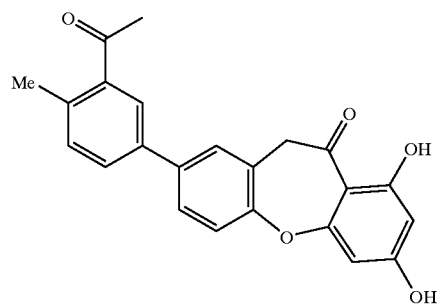
Example 68
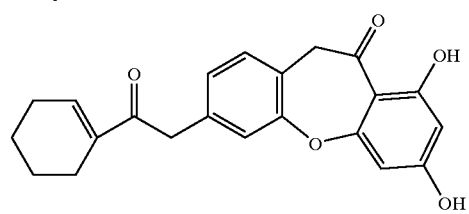
Example 69
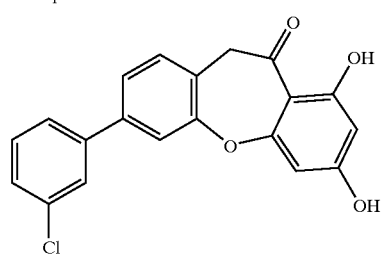
Example 70
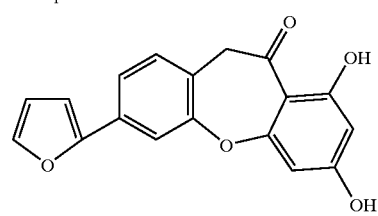
Example 71
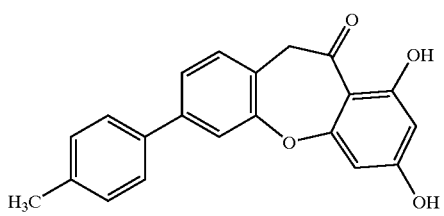
Example 72
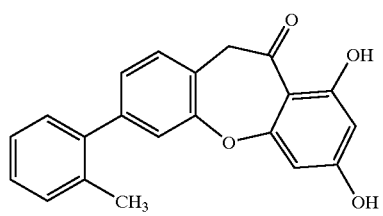
Example 73
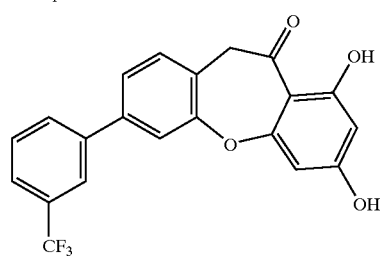
Example 74
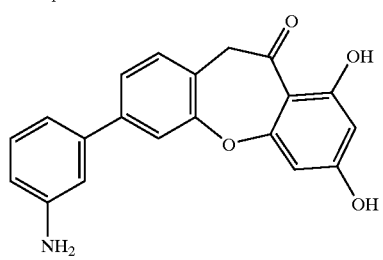
Example 75
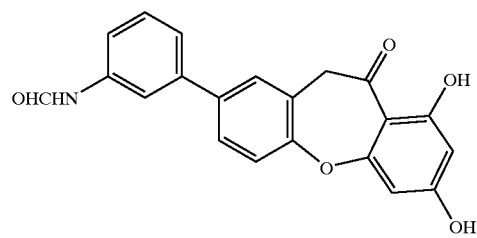
Example 76
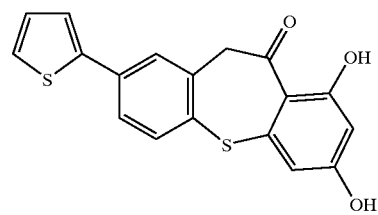

TABLE 1-continued
Example 77
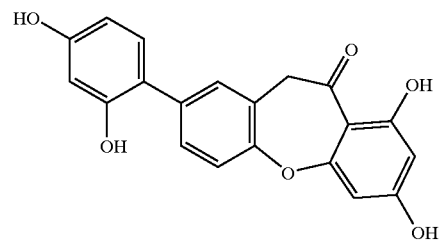
Example 78
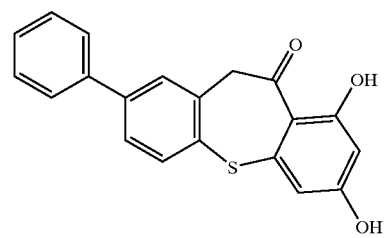
Example 79
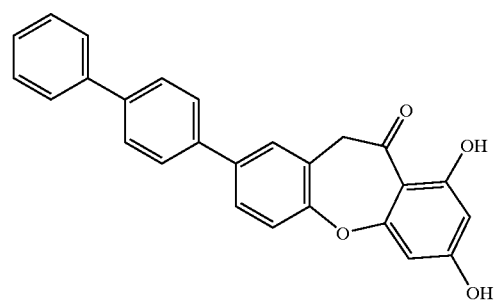
Example 80
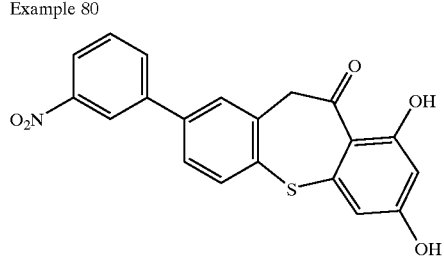
Example 81
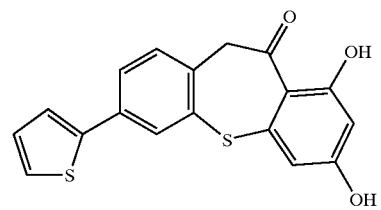
Example 82
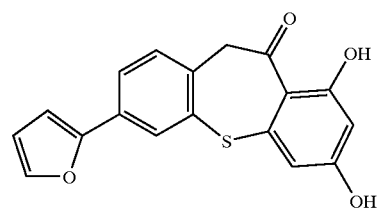
Example 83
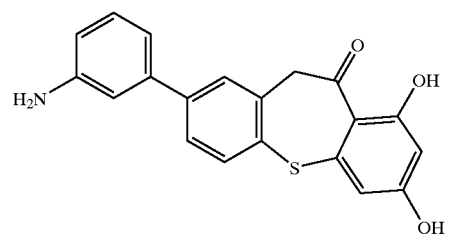
Example 84
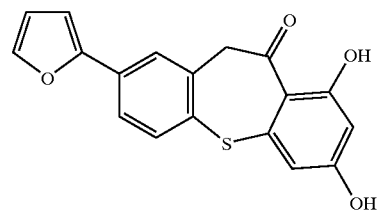
Example 85
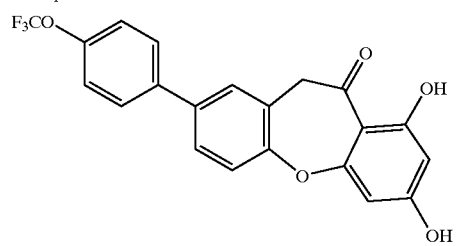
Example 86
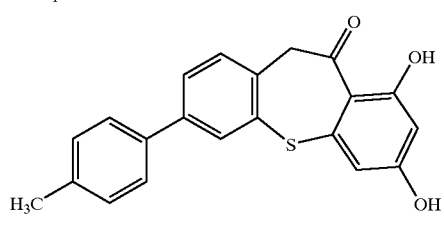

TABLE 1-continued
Example 87
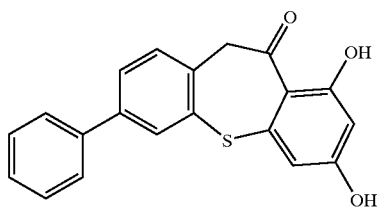
Example 88
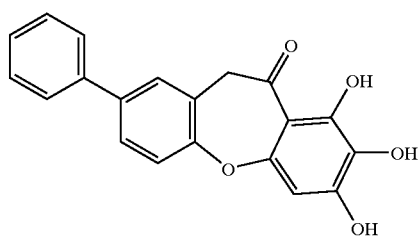
Example 89
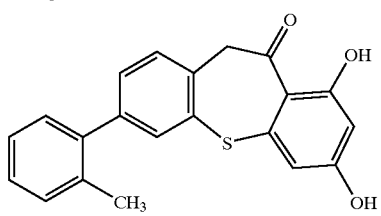
Example 90
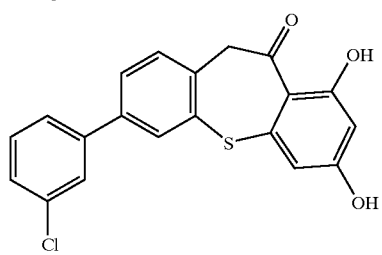
Example 91
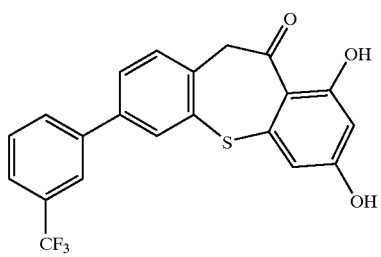
Example 92
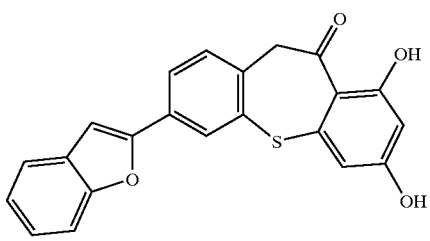
Example 93
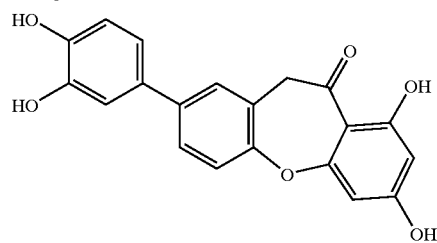
Example 94
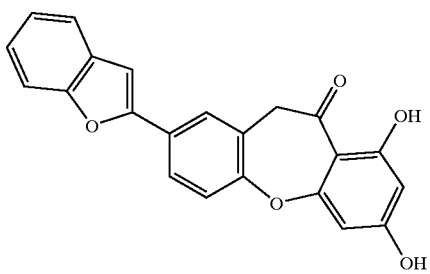
Example 95
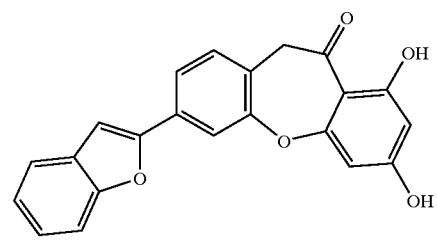
Example 96
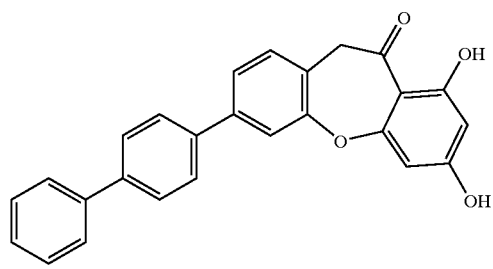

TABLE 1-continued
Example 97
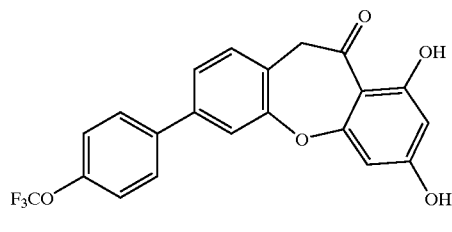
Example 98
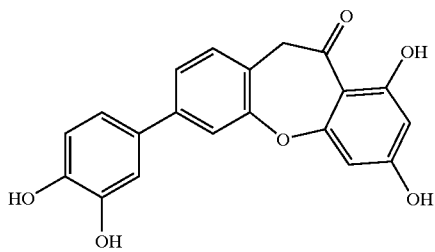
Example 99
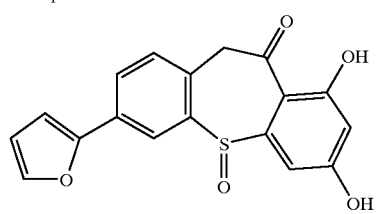
Example 100
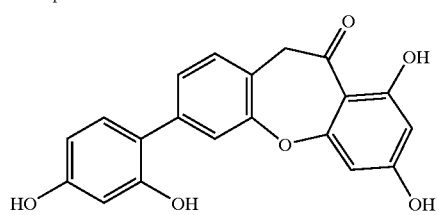
Example 101
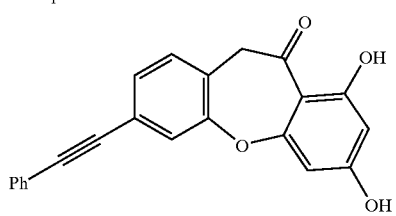
Example 102
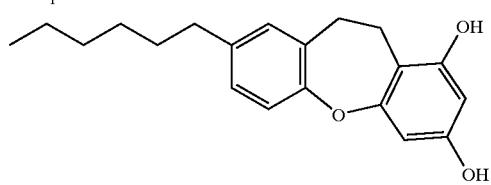
Example 103
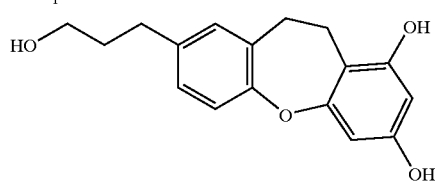
Example 104
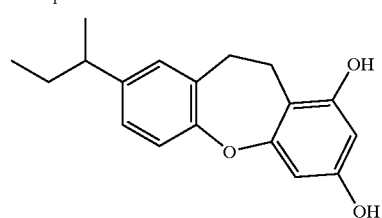
Example 105
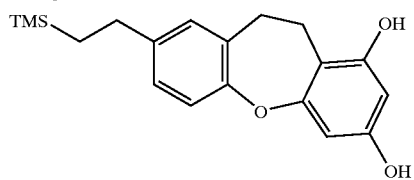
Example 106
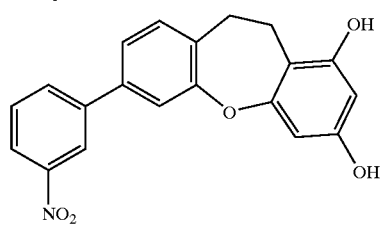
Example 107
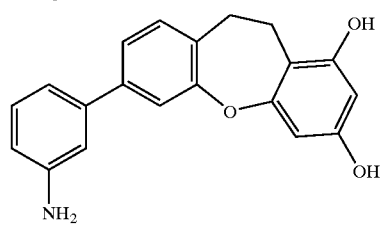
Example 108
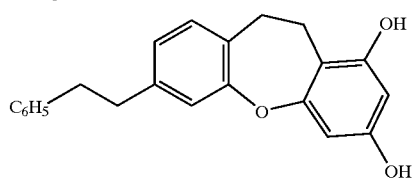

TABLE 1-continued
Example 109
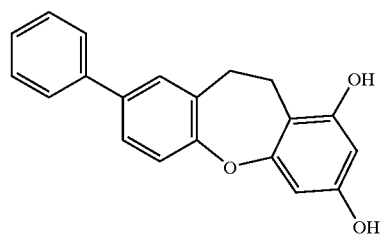
Example 110
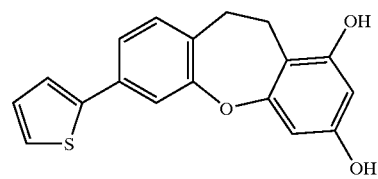
Example 111
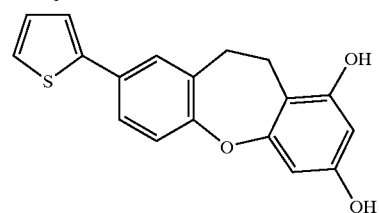
Example 112
Example 113
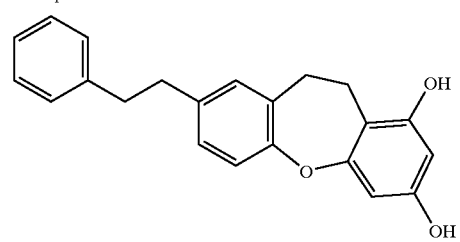
Example 114
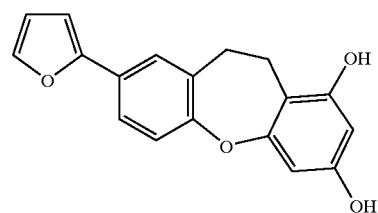
Example 115
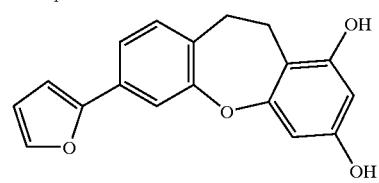
Example 116
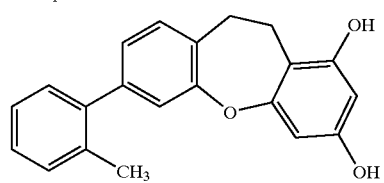
Example 117
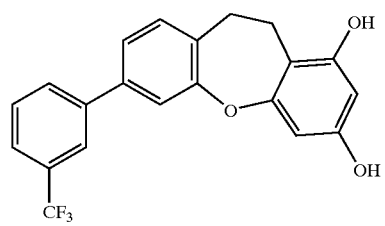
Example 118
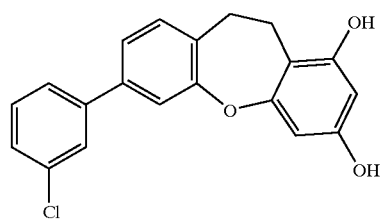
Example 119
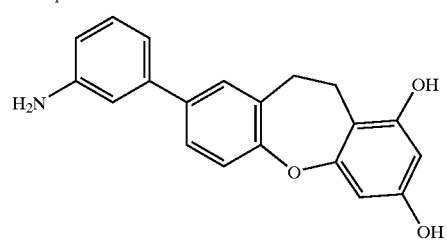
Example 120
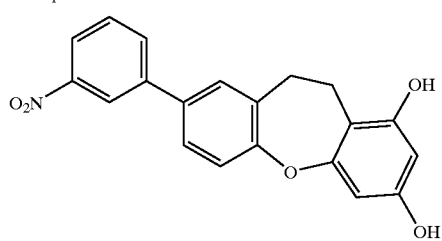

TABLE 1-continued
Example 121
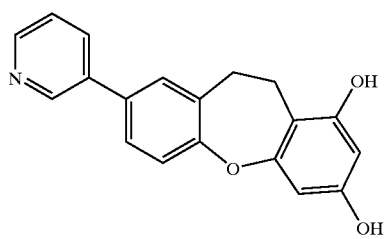
Example 122
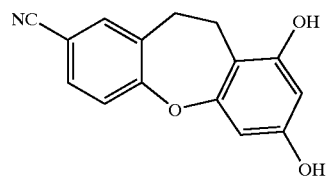
Example 123
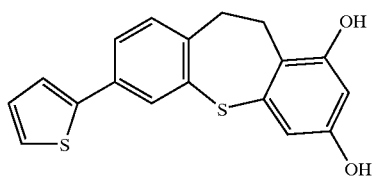
Example 124
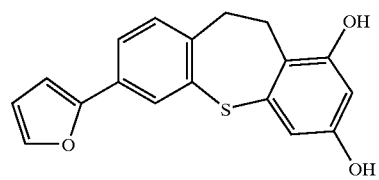
Example 125
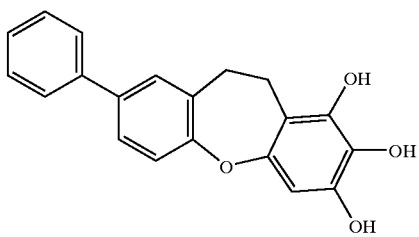
Example 126
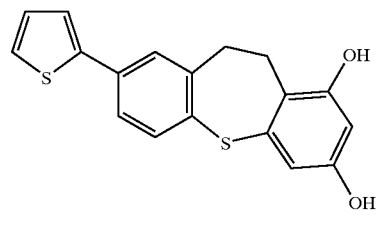
Example 127
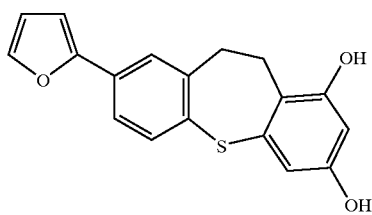
Example 128
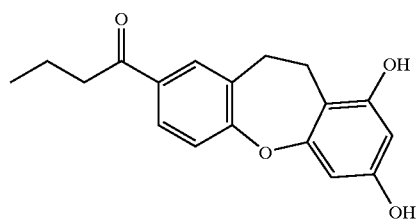
Example 129
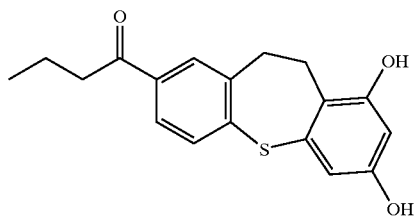
Example 130
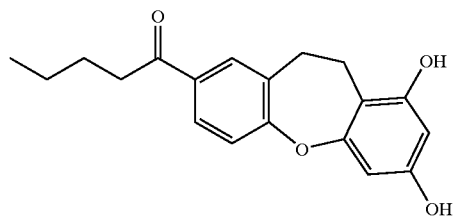
Example 131
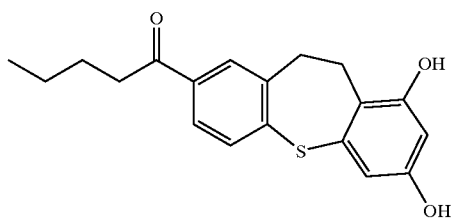
Example 132
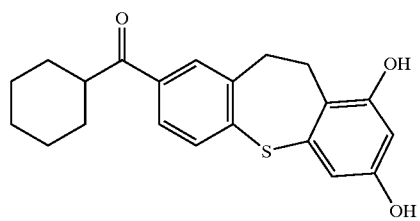

TABLE 1-continued
Example 133
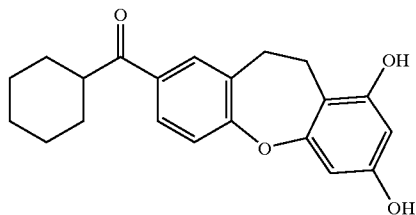
Example 134
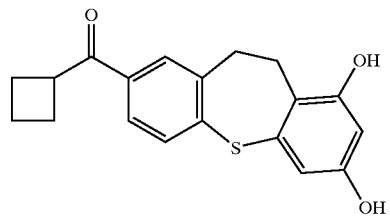
Example 135
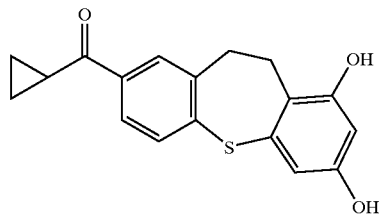
Example 136
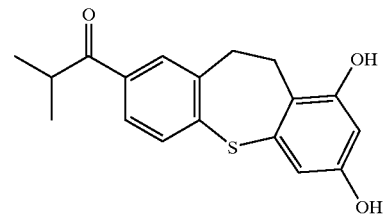
Example 137
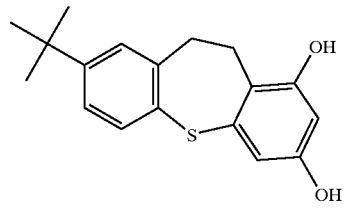
Example 138
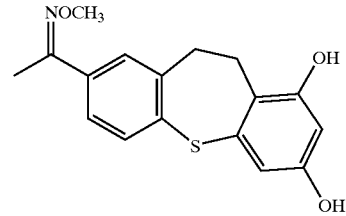
Example 139
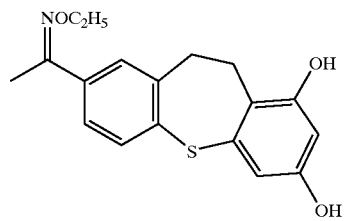
Example 140
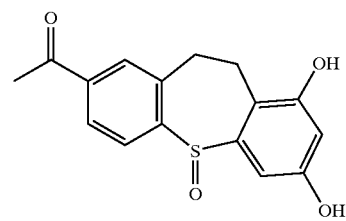
Example 141
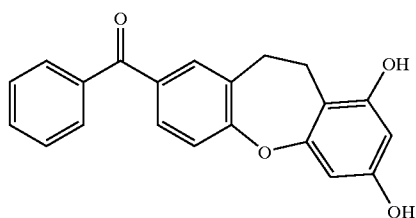
Example 142
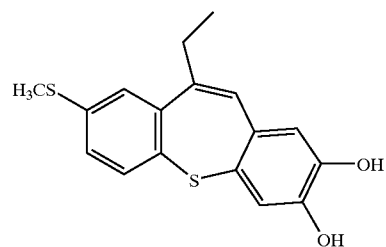
Example 143
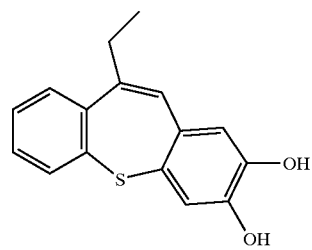
Example 144
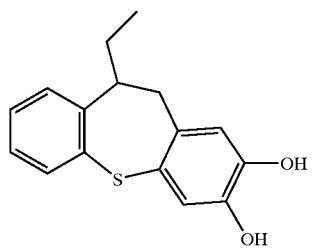

TABLE 1-continued
Example 145
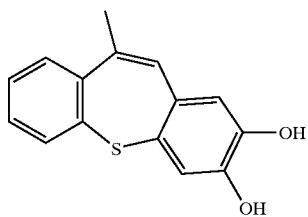
Example 146
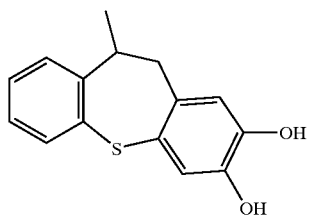
Example 147
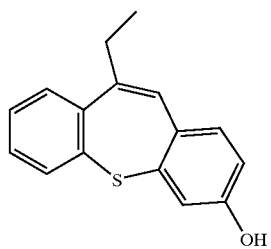
Example 148
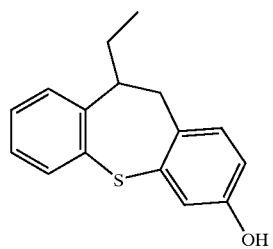
Example 149
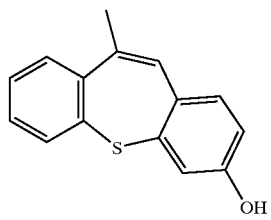
Example 150
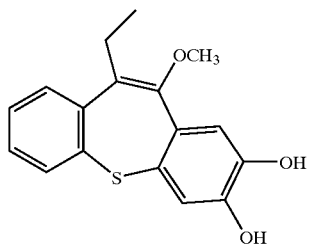
Example 151
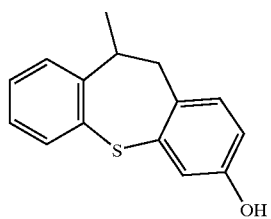
Example 152
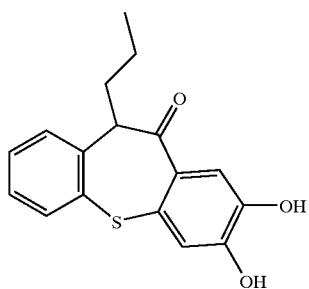
Example 153
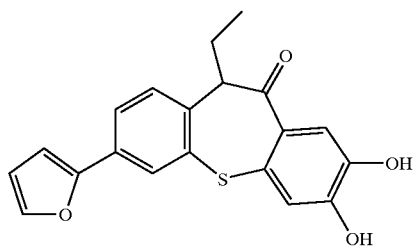
Example 154
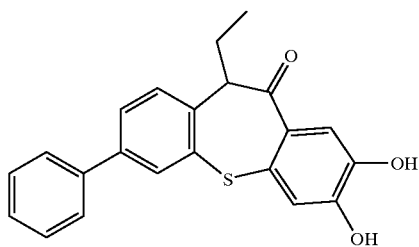

TABLE 1-continued
Example 155
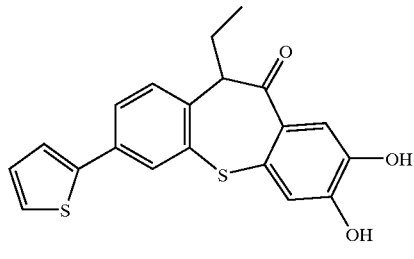
Example 156
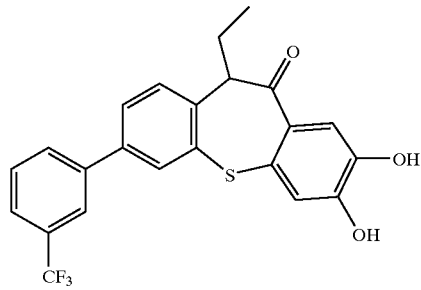
Example 157
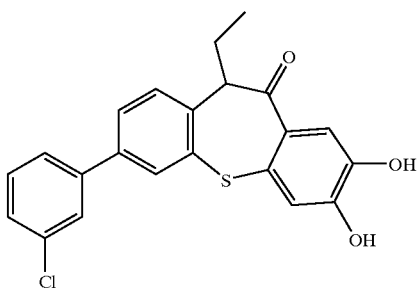
Example 158
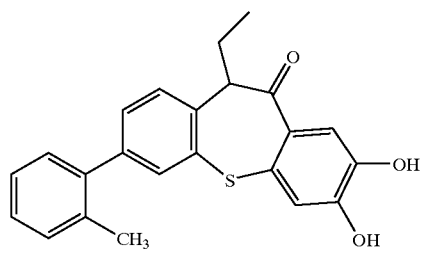
Example 159
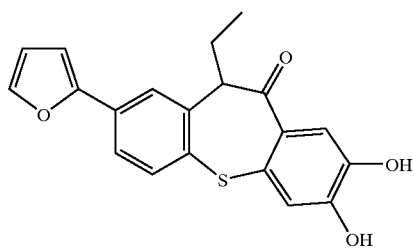
Example 160
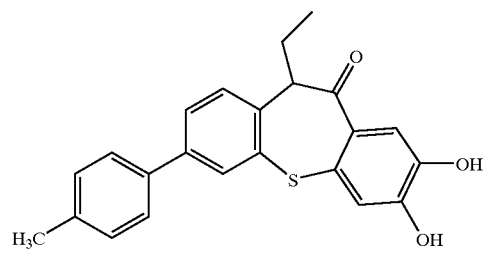
Example 161
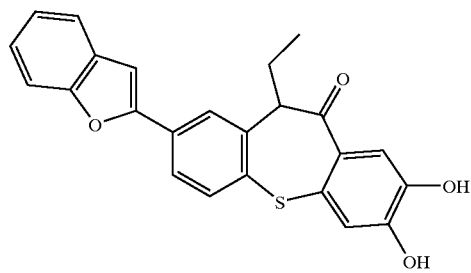
Example 162
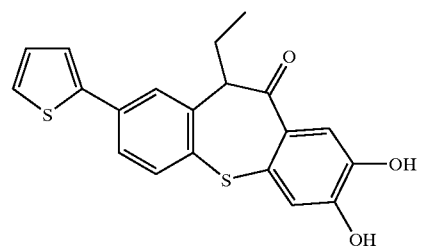
Example 163
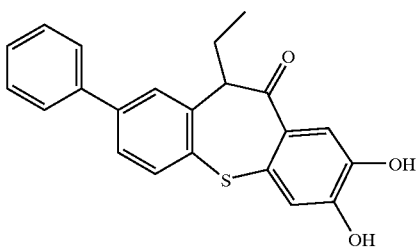

TABLE 1-continued
Example 166
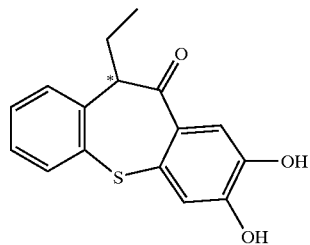
Example 167
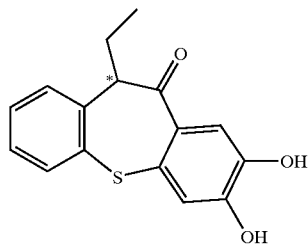
Example 168
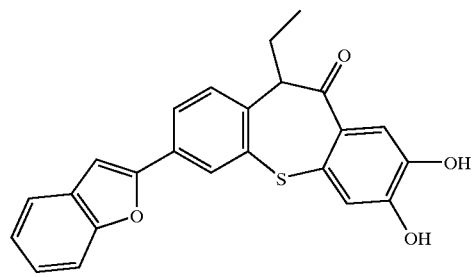
Example 169
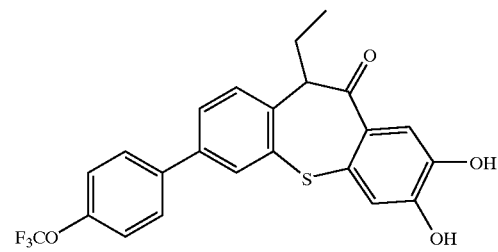
Example 170
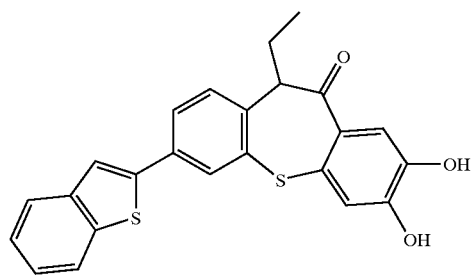
Example 171
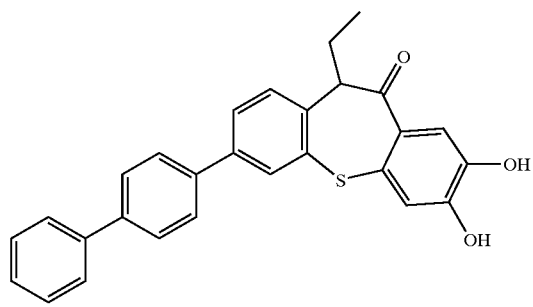
Example 172
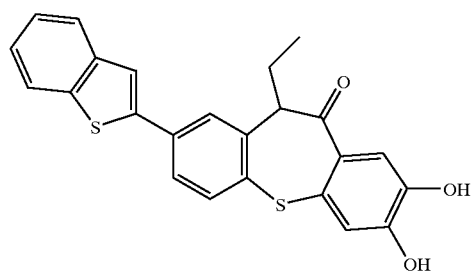
Example 173
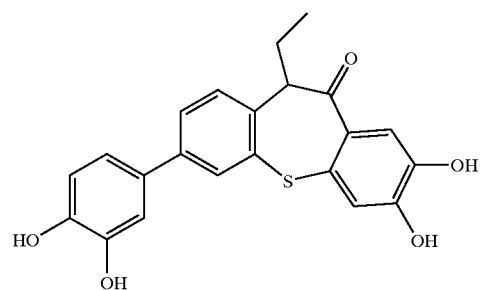
Example 174
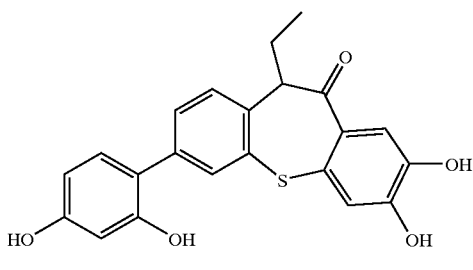
Example 175
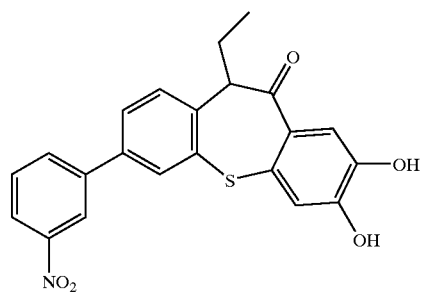

TABLE 1-continued
Example 176
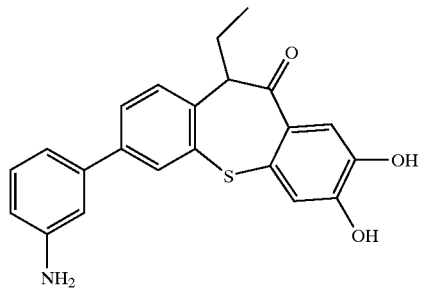
Example 177
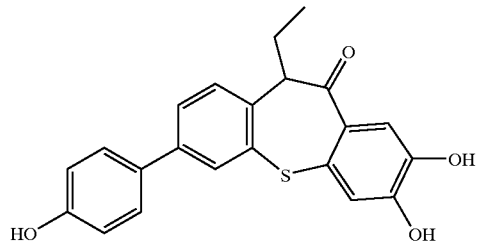
Example 178
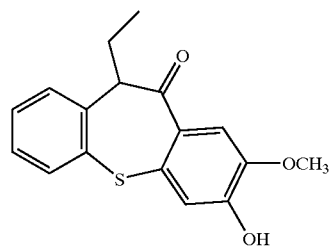
Example 179
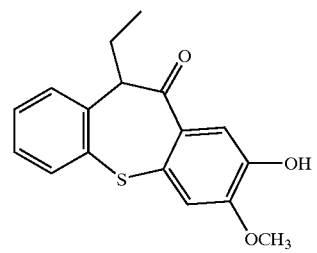
Example 180
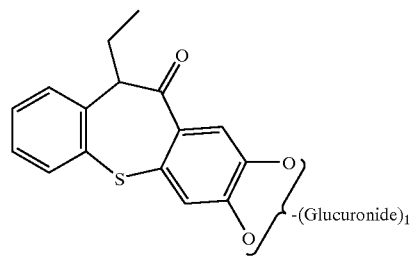
Comparative example
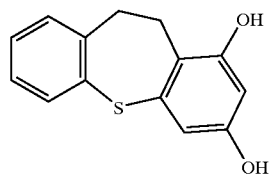

TABLE 2

| Example No | melting point (centi degree) | NMR | NMR solvent | IR | Appearance | Mass | UV |
|---|---|---|---|---|---|---|---|
| 1 | 189.4–191.9 | 2.47(3H, s, CH3)·4.03(2H, s, CH2)·5.86(1H, s, OH)·6.15(1H, d, J=2.5Hz, Ar—H)·6.35(1H, d, J=2.5Hz, Ar—H)·7.15(1H, s, Ar—H)·7.20(2H, d, J=7.8Hz, Ar—H)·12.96(1H, s, OH) | DMSO-d6 | 3213·1611 |  | 332·285 | λ max nm(ε)·243 (23100)·278(27600)·345.6(7900)· |
| 2 | 161.6–163.9 | 2.97–3.00(2H, m, CH2)·3.27–3.30(2H, m, CH2)·6.28(1H, dd, J=2, 2Hz, Ar—H)·6.33(1H, d, J=2Hz, Ar—H)·7.08(1H, d, J=8, 2Hz, Ar—H)·7.23(1H, s, Ar—H)·7.40(1H, d, J=8Hz, Ar—H)·7.62(1H, s, Ar—H)·9.28(1H, brs, OH)·9.49(1H, brs, OH) | DMSO-d6 | 3463·3368·1606 |  |  | ε max 20209(λ max 283.6 nm)·ε max 17842 (λ max 259.6 nm) |
| 3 | 238.0–244.1 | 0.74(6H, t, J=7Hz, CH3)·2.08(1H, q, J=7Hz, CH2)·2.11(1H, q, J=7Hz, CH2) 2.36(1H, q, J=7Hz, CH2)·2.49(1H, q, J=7Hz, CH2)·6.83(1H, s, Ar—H)·6.90(1H, s, Ar—H)·7.27(1H, t, J=7Hz, Ar—H)·7.44(1H, d, J=7Hz, Ar—H)·7.53(1H, d, J=7Hz, Ar—H)·7.64(1H, d, J=7Hz, Ar—H)·9.68(2H | DMSO-d6 | 3467·3267·2973·2963·2957·2934·2875·1646·1596·1508·1451· | needle crystal | 314(M+, base) | ε max 15545(λ max 260.8 nm)·ε max 20821 (λ max 244 nm) |
| 4 | 237.8–239.4 (decomposition) | 0.90(3H, t, J=7.2Hz, CH3)·1.91–1.99(1H, m, J=7.7Hz, CH2)·2.35–2.68(1H, m, J=7.7Hz, CH2)·4.61(1H, t, J=7.1Hz, CH)·6.96(1H, s, Ar—H)·7.23(1H, t, J=7.6Hz, Ar—H)·7.35(1H, d, J=7.6Hz, Ar—H)·7.47(1H, t, J=7.7Hz, Ar—H)·7.49(1H, s, Ar—H)·7.70(1H, d, J=7.6Hz, Ar—H) | DMSO-d6 | 3503·3281·2970·1644·1596·784 | pinkish white needle crystal | 286(M+, Base)·271·257·229 | ε max 6018(λ max 338.4 nm)·ε max 22356 (λ max 257.2 nm)·ε max 23553(λ max 243.2 nm) |
| 5 | 227.6–228.1 | 4.18(2H, s, CH2)·6.16(1H, d, J=2.4Hz, Ar—H)·6.50(1H, d, J=2.4Hz, Ar—H)·7.20(1H, t, J=4.3Hz, Ar—H)·7.51–7.71(5H, m, Ar—H)·11.11(1H, brs, OH)·13.07(1H, s, OH). | DMSO-d6 | 3340·1633·1610·704· | pale yellow needle crystal | 324(M+, Base) | ε max 28742.1(λ max 281.0 nm)· |
| 6 | 182.7–184.4 | 4.21(2H, s, CH2)·6.16(1H, d, J=2.4Hz, Ar—H)·6.5(1H, d, J=2.5Hz, Ar—H)·7.43(8H, m, Ar—H)·11.10(1H, brs, OH)·13.08(1H, s, OH) | DMSO-d6 | 3339·1614·1586 | pale mud yellow needle crystal | 318(M+, Base) | ε max 7353(λ max 321.6 nm)·ε max 15358 (λ max 286.2 nm)·ε max 21057(λ max 256.8 nm) |
| 7 | 179.6–180.4 | 2.85–2.86(2H, m, CH2)·3.09–3.12(2H, m, CH2)·6.18(1H, d, J=2.4Hz, Ar—H)·6.19(1H, d, J=2.4Hz, Ar—H)·7.35–7.53(6H, m, Ar—H)·7.70–7.72(2H, m, Ar—H)·9.25(1H, br, OH)·9.44(1H, br, OH) | DMSO-d6 | 3440·3368·2923·2854·1624·1610·1509·1457 | pale pinkplate crystal | 304(M+, Base) | λ max nm(ε)·207.6(64200)·247.8 (sh 24300) |
| 8 | >250 (decomposition) | 4.36(2H, s, CH2)·6.26(1H, d, J=2Hz, Ar—H)·6.70(1H, d, J=2Hz, Ar—H)·7.37(1H, d, J=8Hz, Ar—H)·7.84(1H, dd, J=8, 1Hz, Ar—H)·8.08(1H, d, J=1Hz, Ar—H)·11.10(1H, brs, OH)·13.48(1H, s, OH) | DMSO-d6 | 3330·1618 |  | 384 (M+, base)·351 (M+, 33)·257 (M+, 127) | ε max 8579.4(λ max 343.0 nm)·ε max 12476.8 (λ max 301.2 nm)·ε max 31556.5(λ max 240.4 nm)·ε max 49370 (λ max 203.0 nm) |
| 9 | >200° C. (sublimation and decomposition) | 4.31(2H, s, CH2)·6.19(1H, d, J=2.3Hz, Res—H)·6.63(1H, d, J=2.3Hz, Res—H)·7.46(1H, d, J=8Hz, Ar—H)·7.61(1H, dd, J=8, 2Hz, Ar—H)·7.86(1H, d, J=2, Ar—H)·11(1H, brs, OH)·13.40(1H, s, OH) | DMSO-d6 | 3338·1599 | white needle crystal | 338(M+, Base)·336·305·303·257· | ε max 7008 (λ max 340.0 nm)·ε max 10843(λ max 301.6 nm)·ε max 9218 (λ max 278.4 nm)·ε max 21932(λ max 238.8 nm) |
| 10 | 159.0–160.3 | 1.05(3H, t, J=7Hz, CH3)·2.79(2H, m, CH2)· | DMSO-d6 | 3361·3197· | pinkish white | 284(M+)·269· | ε max 12965(λ max |

TABLE 2-continued

| Example No | melting point (centi degree) | NMR | NMR solvent | IR | Appearance | Mass | UV |
|---|---|---|---|---|---|---|---|
|  |  | 2.98(2H, q, J=7Hz, CH2)·3.06(2H, m, CH2)· 6.07(1H, d, J=2.5Hz, Ar—H)·6.11(1H, d, J=2.5Hz, Ar—H)·7.18(1H, d, J=8Hz, Ar—H)· 7.78(1H, dd, J=2, 8Hz, Ar—H)·7.83(1H, d, J=2Hz, Ar—H)·9.26(1H, br, OH)·9.41(1H, br, OH) |  | 2944·1660· 1621·1598 | needle crystal | 255(Base) | 260.8 nm)· ∈ max 12364(λ max 245.6 nm)· ∈ max 51685(λ max 207.2 nm) |
| 11 | 215.4–217.5 | 2.11(3H, s, CH3)·2.96(2H, m, CH2)· 3.23(2H, m, CH2)·6.23(1H, d, J=2.4Hz, Ar—H)· 6.28(1H, d, J=2.4Hz, Ar—H)·7.39(2H, m, Ar—H)· 7.51(1H, m, Ar—H)·9.20(1H, brs, OH)· 9.43(1H, brs, OH)·11.20(1H, brs, OH) | DMSO-d6 | 3361·2938· 1607 | pinkish white amorphous | 301(M+, Base) 284 | ∈ max 11366(λ max 291.6 nm)· ∈ max 10157(λ max 273.2 nm)· ∈ max 43942(λ max 211.6 nm) |

TABLE 3

| Example No | melting point (centi degree) | NMR | NMR solvent | IR | Appearance | Mass | UV |
|---|---|---|---|---|---|---|---|
| 12 | 109.5–111.2 | 0.820(3H, t, J=6.4Hz, —CH3)1.23–1.26(6H, m, CH2*3)1.507(2H, t, J=7.0Hz, CH2)2.521(2H, t, J=7.5Hz, CH2)4.040(2H, s, CH2)6.060(1H, d, J=2.3Hz, Ar—H)6.333(1H, d, J=2.3Hz, Ar—H)7.089(1H, dd, J=8.0, 1.3Hz, Ar—H)7.16–7.21(2H, m, Ar—H)10.970(1H, s, Ph—OH)12.997(1H, s, Ph—OH) | DMSO-d6 | 3316-2959-2924-2856-1636-1593-1497-1445 | colorless plate crystal | | ε max 6755(λ max 327.6 nm)·ε max 6396(λ max 312.8 nm)·ε max 13808(λ max 287.2 nm)·ε max 4863(λ max 255.6 nm) |
| 13 | 236.4–237.3 | 4.34(2H, s, CH2)6.17(1H, d, J=2.3Hz, Res—H)6.62(1H, d, J=2.3Hz, Res—H)7.47(1H, d, J=8.3Hz, Ar—H)7.59(1H, d, J=8.3, Ar—H)7.77(1H, s, Ar—H)10.99(1H, s, OH)13.37(1H, s, OH) | DMSO-d6 | 3339-1618-1602 | pale yellow needle crystal | 336(M+, base)303(M+-33)257(M+-79) | λ max nm(ε)206.4(46400)238.5(27700)272.4(13900)300.4(12600)340.0(8800) |
| 14 | 187.5 (sublimation) | 3.90(3H, s, CH3)4.46(2H, m, CH2)6.51(1H, d, J=2Hz, Ar—H)6.85(1H, d, J=2Hz, Ar—H)7.58(1H, d, J=8Hz, Ar—H)7.69(1H, d, J=8Hz, Ar—H)7.89(1H, s, Ar—H)13.50(1H, s, Ph—OH). | DMSO-d6 | 3448-1612-1576 | white needle crystal | 352(M++2, base)350(M+)317(M+-33)271(M+-79) | λ max nm(ε)206.4(44800)239.2(25900)270.7(14100)298.8(11300)340.0(6200) |
| 15 | 217.9–221.6 | 4.43(2H, s, CH2)6.26(1H, d, J=2Hz, Ar—H)6.71(1H, d, J=2Hz, Ar—H)7.43(1H, dd, J=8, 2Hz, Ar—H)7.73(1H, d, J=2Hz, Ar—H)7.75(1H, d, J=8Hz, Ar—H)11.09(1H, brs, OH)13.46(1H, s, OH) | DMSO-d6 | 3338-3089-1602 | needle crystal white | 292(M+, base)259(M+-33) | λ max nm(ε)203.6(53600)269.6(14900)300.8(13100)340.0(9100) |
| 16 | | 4.12(2H, s, CH3)6.26(1H, d, J=2Hz, Ar—H)6.71(1H, d, J=2Hz, Ar—H)7.43–7.75(3H, d, J=8Hz, Ar—H)11.09(1H, brs, OH)12.94(1H, s, OH) | DMSO-d6 | 3368-3227-1634-1615-1498 | | | λ max nm(ε)287.6(7500)326.4(4500) |
| 17 | >200° C. (decomposition) | 4.60(2H, s, CH2)6.27(1H, d, J=2Hz, Ar—H)6.72(1H, d, J=2Hz, Ar—H)7.36(1H, t, J=8Hz, Ar—H)7.64(1H, d, J=8Hz, Ar—H)7.73(1H, d, J=8Hz, Ar—H)11.11(1H, brs, OH)13.42(1H, s, OH) | DMSO-d6 | 3362-1617-1595 | | | ε max 8119(λ max 340.0 nm)ε max 12239(λ max 299.2 nm)ε max 23541(λ max 240.8 nm)ε max 47654(λ max 205.2 nm) |
| 18 | 245.3–246.6 | 2.47(3H, s, CH3)4.03(2H, s, CH2)5.86(1H, s, OH)6.15(1H, d, J=2.5Hz, Ar—H)6.35(1H, d, J=2.5Hz, Ar—H)7.15(1H, s, Ar—H)7.20(2H, d, J=7.8Hz, Ar—H)12.96(1H, s, OH) | DMSO-d6 | 3168-1610-1578 | needle crystal | 320(M+) | λ max nm(ε)203.6(59600)286.8(18800)340.0(13600) |
| 19 | 182.3–184.4 | 2.48(3H, s, CH3)4.27(2H, s, CH2)6.18(1H, d, J=2.4Hz, Ar—H)6.63(1H, d, J=2.3Hz, Ar—H)7.30(1H, d, J=8.0Hz, Ar—H)7.42(1H, d, J=8.0Hz, Ar—H) | DMSO-d6 | 3333-1594 | needle crystal | 304(M+, Base)271-257· | λ max nm(ε)245.2(23900)258.4(24100)298.4(12400)340.0(9400) |
| 20 | >250 | 7.51(1H, s, Ar—H)10.9(1H, br, OH)13.45(1H, s, OH)4.23(2H, d, J=8.1Hz, Ar—H)6.97(1H, s, Ar—H)7.43(1H, d, J=8.1Hz, Ar—H)7.51(1H, s, Ar—H)7.59(1H, dd, J=8.1-1.8Hz, Ar—H)7.88(1H, d, J=1.6Hz, Ar—H)(2H, brs, OH) | DMSO-d6 | 3453-3261-1647-1602-1589-1512-1465 | pale brown needle crystal | 338(M+, Base)336 | ε max 15804(λ max 259.6 nm)ε max 21547(λ max 240.4 nm)ε max 34053(λ max 206.0 nm) |
| 21 | | 2.44(3H, s, CH3)4.16(2H, s, CH2)6.96(1H, s, Ar—H)7.25(1H, m, Ar—H)7.36(1H, d, J=8Hz, Ar—H)7.48(2H, s, Ar—H) | DMSO-d6 | 3542-3344-1638-1591-1506 | | 304(M+)257(M+-SMe) | λ max nm(ε)205.6(28400)249.6(23400)264.4(25900)282.4 |

TABLE 3-continued

| Example No | melting point (centi degree) | NMR | NMR solvent | IR | Appearance | Mass | UV |
|---|---|---|---|---|---|---|---|
| 22 | 285.7 (decomposition) | 4.23(2H, s, CH2)·6.95(1H, s, Ar—H)· 7.41(1H, dd, J=8, 2Hz, Ar—H)·7.48(1H, s, Ar—H)· 7.58(1H, d, J=8Hz, Ar—H)·7.70(1H, d, J=2Hz, Ar—H)· (2H, brs, OH) | DMSO-d6 | 3452·3246· 1652·1604 | plate crystal | 338(M+, Base)·336· 305·303·257· | (25200)·337.6(4900) λ max nm(ε)·246.8 (28400)·283.3(15300)· 337.6(6300) |
| 23 | 232.0–236.9 | 2.45(3H, s, CH3)·4.20(1H, s, CH2)·6.94(1H, s, Ar—H)· 7.10(1H, dd, J=7.2, 1Hz, Ar—H)· 7.32(1H, d, J=1.0Hz, Ar—H)·7.48(1H, s, Ar—H)· 7.55(1H, d., J=8.2Hz, Ar—H) | DMSO-d6 | 3457·3239· 1647·1603· | needle crystal | 304(M+)· 257(M+-SMe) | λ max nm(ε)·203.6 (36000)·248.0(29300)· 260.4(29700)·335.6 (6800) |

TABLE 4

| Example No | melting point (centi degree) | NMR | NMR solvent | IR | Appearance | Mass | UV |
|---|---|---|---|---|---|---|---|
| 24 | 208.0–213.7 | 4.20(2H, s, CH2)6.06(1H, d, J=3Hz, Ar—H)6.29(1H, d, J=3Hz, Ar—H)7.16(1H, ddd, J=7, 7, 2Hz, Ar—H)7.23(1H, dd, J=7, 2Hz, Ar—H)7.27(1H, ddd, J=7, 7, 2Hz, Ar—H)7.34(1H, d, J=7, 2Hz, Ar—H)10.01(1H, br, OH)11.53(1H, br, OH)12.25(1H, brs, OH) | DMSO-d6 | 3390;3339;3223;1618;1599 | colorless needle crystal | 257(M+, Base)211 | ε max 13691(λ max 273.6 nm)·ε max 7662(λ max 253.2 nm)·ε max 32958(λ max 205.2 nm) |
| 25 | | 4.02(3H, s, CH3)4.26(2H, s, CH2)6.16(1H, d, J=2Hz, Ar—H)6.39(1H, d, J=2Hz, Ar—H)7.22–7.41(4H, m, Ar—H)10.21(1H, br, OH)11.63(1H, brs, OH) | DMSO-d6 | 3352(OH)2935(CH)1634(CN)1597(aroma) | pinkish white needle crystal | 271(M+, base)211 | ε max 15241(λ max 283.6 nm)·ε max 7228(λ max 255.2 nm)·ε max 37261(λ max 204.4 nm) |
| 26 | 181.1–184.9 | 2.98–3.01(2H, m, CH2)3.28–3.31(2H, m, CH2)6.30(1H, d, J=2Hz, Ar—H)6.35(1H, d, J=2Hz, Ar—H)7.25(1H, dd, J=8, 2Hz, Ar—H)7.43(1H, d, J=2Hz, Ar—H)7.48(1H, d, J=8Hz, Ar—H)9.31(1H, s, OH)9.55(1H, s, OH) | DMSO-d6 | 3429;3370;1608 | | 278(M+, base)·263(M+–15)·245(M+–33)·210(M+–68) | ε max 11694(λ max 276.8 nm)ε max 58928(λ max 202.0 nm) |
| 27 | 127.3–130.7 | 3.03–3.06(2H, m, CH2)3.42–3.45(2H, m, CH2)6.32(1H, d, J=2Hz, Ar—H)6.36(1H, d, J=2Hz, Ar—H)7.21(1H, t, J=8Hz, Ar—H)7.48(1H, t, J=8Hz, Ar—H)9.35(1H, brs, OH)·9.57(1H, brs, OH) | DMSO-d6 | 3368;1593 | | 278(M+, base)·263(M+–15)·245(M+–33)·243(M+–35)·210(M+–68) | ε max 8881(λ max 275.2 nm)·ε max 55704(λ max 204.4 nm) |
| 28 | 182.9–184.4 | 2.45(3H, s, CH3)6.30(1H, d, J=1.9Hz, Ar—H)6.33(1H, d, J=1, 8Hz, Ar—H)6.79(1H, d, J=12.4Hz, CH=CH)7.05(1H, d, J=12.4Hz, CH=CH)7.20(2H, m, J=5.2Hz, Ar—H)7.29(1H, d, J=3.6Hz, Ar—H) 9.66(1H, s, OH)9.83(1H, s, OH) | | 3340;1599;1575 | plate crystal | 288(M+, Base)256;241 | λ max nm(ε)·239.6(29100)·276.4(26000)·326.4(8300) |
| 29 | 237.4–238.6 | 3.04–3.07(2H, m, CH2)3.27–3.30(2H, m, CH2)6.33(1H, d, J=2Hz, Ar—H)6.37(1H, d, J=2Hz, Ar—H)7.64(2H, s, Ar—H)7.78(1H, s, Ar—H)9.33(1H, s, OH)9.57(1H, s, OH) | DMSO-d6 | 3394;2229;1613;1499;1454 | white needle crystal | 269(M+, base)·254(M+–15)·236(M+–33) | λ max nm(ε)·206.0(49700)·299.6(11400) |
| 30 | | 0.95(3H, t, J=7.3Hz, CH3)1.99–2.05(1H, m, CH2)2.32–2.37(1H, m, CH2)4.31(1H, t, J=6.76Hz, CH)7.21–7.26(1H, m, Ar—H)7.31(1H, s, Ar—H)7.45–7.52(4H, m, Ar—H)7.63(1H, m, Ar—H) | DMSO-d6 | 3386;3082;1671;1586 | pale yellow needle crystal | 302(M+)226(Base) | ε max 6083(λ max 321.6 nm)·ε max 32508(λ max 244.4 nm)·ε max 37486(λ max 210.4 nm) |
| 31 | 194.2–196.1 | 1.67(6H, s, CH3)6.8(1H, s, Ar—H)7.10(1H, s, Ar—H)7.24(1H, t, J=1Hz, Ar—H)7.54(1H, t, J=1.1Hz, Ar—H)7.59(2H, dd, J=8, 1.3Hz, Ar—H) | DMSO-d6 | 3470;3337;1633;1595 | orange prism | 285(M+)272(Base) | ε max 3969(λ max 339.2 nm)·ε max 20771(λ max 260.0 nm)·ε max 21049(λ max 242.0 nm)·ε max 35595(λ max 204.4 nm) |
| 32 | | 1.01(3H, t, J=7.2Hz, CH3)2.02–2.09(1H, m, CH2)2.50–2.58(1H, m, CH2)4.73(1H, dd, J=8.2, 6.0Hz, CH)5.45(1H, s, OH)6.8(1H, dd, J=8.8, 2.5Hz, Ar—H)7.04(1H, d, Ar—H)7.16(1H, t, J=4.4Hz, Ar—H)7.36(1H, d, J=6.8Hz, Ar—H)7.40(1H, dd, J=7.2, 1Hz, Ar—H)7.64(1H, dd, J=8.8, 1.0Hz, Ar—H)8.1 | DMSO-d6 | 3339;2968;2917;2878;1621;1590 | needle crystal | 332;303;285 | λ max nm(ε)·204.4(33400)·246.0(22300)·272.8(sh 16300)·295.2(11200)·340.0(6900) |
| 33 | | 2.83(2H, t, J=6Hz, CH2)3.07(2H, t, J=6Hz, CH2) | DMSO-d6 | 3524;3298 | | 257 | λ max nm(ε)· |

TABLE 4-continued

| Example No | melting point (centi degree) | NMR | NMR solvent | IR | Appearance | Mass | UV |
|---|---|---|---|---|---|---|---|
|  |  | 4.01(2H, s, NCH2) 6.12(1H, d, J=2Hz, Ar—H) 6.18(1H, d, J=2Hz, Ar—H) 7.19(1H, d, J=8Hz, Ar—H) 7.33(1H, d, J=8Hz, Ar—H) 7.39(1H, s, Ar—H) 9.29(1H, s, OH) 9.43(1H, s, OH) |  | 3156-2999- 2897-1624- 1605-1509- 1496-1458 |  | (M+, base)-240 (M+-17) | 206.4(45100)-274.0 (3400) |
| 34 |  | 2.99(2H, t, J=6Hz, CH2) 3.28(2H, t, J=6Hz, CH2) 3.72(2H, s, NCH2) 6.27(1H, d, J=2Hz, Ar—H) 6.34(1H, d, J=2Hz, Ar—H) 7.15(1H, d, J=8Hz, Ar—H) 7.29(1H, s, Ar—H) 7.39(1H, d, J=8Hz, Ar—H) 9.25(1H, s, OH) 9.47(1H, s, OH) | DMSO-d6 | 3433-1595- 1560-1457- |  | 273 (M+, base)-256 (M+-17)-223 (M+-50) | λ max nm(ε)- 204.8(41200)-275.6 (8400) |

TABLE 5

| Example No | melting point (centi degree) | NMR | NMR solvent | IR | Appearance | Mass | UV |
|---|---|---|---|---|---|---|---|
| 35 | 167.4–168.2 | 1.02(3H, t, J=7Hz, CH3) 2.01(1H, sev, J=7Hz, CH2) 2.48(3H, s, SCH3) 2.49(1H, sev, J=7Hz, CH2) 4.83(1H, d, J=7Hz, CH) 6.24(1H, dd, J=8, 2Hz, Ar—H) 6.63(1H, s, Ar—H) 7.04(1H, dd, J=8, 2Hz, Ar—H) 7.17(1H, s, Ar—H) 7.53(1H, d, J=8Hz, Ar—H)?(1H, ?, OH) 13.40(1H, s, OH) | CDCl3 | 3340·2973· 2912·2879· 1618·1594· 1489·1466 | | 332 (M+, base) | λ max nm(ε)244.4 (22900)·280.4(25700)· 348.8(7100) |
| 36 | 199.6–200.5 | 0.96(3H, t, J=7Hz, CH3) 2.00(1H, sev, J=7Hz, CH2) 2.44(1H, sev, J=7Hz, CH2) 2.55(3H, s, SCH3) 4.67(1H, t, J=7Hz, CH) 7.00(1H, s, Ar—H) 7.16(1H, d, J=8Hz, Ar—H) 7.19(1H, s, Ar—H) 7.55(1H, s, Ar—H) 7.67(1H, d, J=8Hz, Ar—H) 9.92(2H, brs, OH) | DMSO-d6 | 3487·3271· 2974·2935· 2914·2877· 1644·1606· 1586·1499· 1456 | brown powder | 332 (M+, base) | λ max nm(ε)207.2 (28200)·248.8(21100)· 264.0(23800)·280.8 (21200)·339.6(4700) |
| 37 | | 1.54(3H, d, J=6.7Hz, CH3) 4.84(1H, q, J=6.7Hz, CH) 6.96(1H, s, Ar—H) 7.24(1H, t, J=7.4Hz, Ar—H) 7.39(1H, d, J=7.7Hz, Ar—H) 7.46(1H, t, J=7.4Hz, Ar—H) 7.51(1H, s, Ar—H) 7.68(1H, d, J=7.5Hz, Ar—H) | DMSO-d6 | 3490·3274· 1645·1601· 1581·1509 | | | λ max nm(ε)204.4 (22800)·243.6(15900)· 257.2(15000)·338.4 (3700) |
| 38 | 175.0–177.5 | 0.98(3H, t, J=7Hz, CH3) 2.05(1H, sev, J=7Hz, CH2) 2.44(1H, sev, J=7Hz, CH2) 4.84(1H, t, J=7Hz, CH) 6.23(1H, d, J=2Hz, Ar—H) 6.70(1H, d, J=2Hz, Ar—H) 7.35(1H, t, J=8Hz, Ar—H) 7.46(1H, d, J=8Hz, Ar—H) 7.57(1H, t, J=8Hz, Ar—H) 7.77(1H, d, J=8Hz, Ar—H) 10.97(1H, brs, OH) 13.30(1H | DMSO-d6 | 3332·2977· 2887·1621· 1591 | | 286 (M+, base) 271(M+−15)·253 (M+−33) | ε max 8811(λ max 340.0 nm)·ε max 13046(λ max 299.6 nm)·ε max 25492(λ max 241.6 nm)·ε max 30052(λ max 202.4 nm) |
| 39 | 152.1–153.4 | 1.62(3H, d, J=7Hz, CH3) 5.09(1H, q, J=7Hz, CH) 6.23(1H, d, J=2Hz, Ar—H) 6.70(1H, d, J=2Hz, Ar—H) 7.35(1H, t, J=8Hz, Ar—H) 7.49(1H, d, J=8Hz, Ar—H) 7.57(1H, t, J=8Hz, Ar—H) 7.76(1H, d, J=8Hz, Ar—H) 10.96(1H, brs, OH) 13.41(1H, s, OH) | DMSO-d6 | 3271·1618· 1594 | | | ε max 8221(λ max 340.0 nm)·ε max 12798(λ max 299.2 nm)·ε max 24627(λ max 241.2 nm)·ε max 44124(λ max 202.4 nm) |
| 40 | 67.5–68.3 | 3.41–3.47(1H, m, CH2) 3.73–3.74(1H, m, CH) 5.38–5.40(3H, m, CH3) 6.23(1H, d, J=2Hz, Ar—H) 6.70(1H, d, J=2Hz, Ar—H) 7.18(1H, t, J=8Hz, Ar—H) 7.26–7.42(5H, m, Ar—H) 7.55(1H, t, J=8Hz, Ar—H) 7.66(1H, d, J=8Hz, Ar—H) 7.75(1H, d, J=8Hz, Ar—H) 11.00(1H, brs, OH) 13.22(1H, s, OH) | DMSO-d6 | 3338·1620· 1583 | yellow powder | 348(M+, base)· 330(M+−18)· 257(M+−91)· 229(M+−119) | λ max nm(ε)241.2 (19600)·300.8(10600)· 340.0(6500) |
| 41 | 190.0–191.6 | 1.68(3H, d, J=6.7Hz, CH3) 4.94(1H, dd, J=13.2, 6.7Hz, CH2) 5.55(1H, s, OH) 6.76(1H, dd, J=8.8, 2.2Hz, CH) 7.05(1H, d, J=2.1Hz, Ar—H) 7.17(1H, td, J=6.8, 2.3Hz, Ar—H) (2H, q, Ar—H) 7.64(1H, d, J=7.7Hz, Ar—H) 8.13(1H, d, J=8.7Hz, Ar—H) | CDCl3 | 3324·1656· 1589 | colorless needle crystal | 256(M+, Base) | ε max 20467(λ max 256.0 nm) |
| 42 | | 1.01(3H, t, J=7.2Hz, CH3) 2.02–2.09(1H, m, CH2) 2.50–2.58(1H, m, CH2) 4.91 (1H, dd, J=8.2, 6.0Hz, CH) 6.1(2H, s, OH) 6.9 (1H, dd, J=8.6Hz, Ar—H) 7.04(1H, d, Ar—H) 7.16 (1H, m, Ar—H) 7.36(1H, m, Ar—H) 7.40(1H, m, Ar—H) 7.64(1H, m, Ar—H) 7.83(1H, d, J=8.6Hz, Ar—H) | CDCl3 | 3398·2969· 2877·1652· 1595·1471 | | 286·253·229 | ε max 20284(λ max 244 nm)·ε max 34443 (λ max 204.4 nm) |
| 43 | | 0.77(6H, t, J=7Hz, CH3) 1.98(2H, six, J=7Hz, CH2) 2.25(2H, six, J=7Hz, CH2) 2.54(3H, s, SCH3) 6.31(1H, d, J=2Hz, Ar—H) 6.34(1H, d, J=2Hz, Ar—H) | DMSO-d6 | 3365·2968· 2923·2879· 1617·1576· 1457 | | 360(M+, base)· 345(M+−15)· 275(M+−85) | λ max nm(ε)254.0 (9717)·284.0(11907)· 362.0(2323) |

TABLE 5-continued

| Example No | melting point (centi degree) | NMR | NMR solvent | IR | Appearance | Mass | UV |
|---|---|---|---|---|---|---|---|
| | | 7.15(1H, dd, J=8, 2Hz, Ar—H) 7.32(1H, d, J=2Hz, Ar—H) 7.55(1H, d, J=8Hz, Ar—H) 9.96(2H, brs, OH) 10.03(2H, br | | | | | |
| 44 | 235.6–237.4 | 0.87(3H, t, J=7.3Hz, CH3) 1.89(1H, sev, J=6.8Hz, CH2) 2.35(1H, sev, J=7.3Hz, CH2) 4.59(1H, t, J=7.1Hz, CH) 6.94(1H, s, Ar—H) 7.41(1H, dd, J=8, 2Hz, Ar—H) 7.44(1H, s, Ar—H) 7.46(1H, s, Ar—H) 7.62(1H, d, J=8Hz, Ar—H) (2H, brs, OH) | | 3517·3294· 2974·2960· 2936·1647· 1597·1586· 1507·1461 | needle crystal pale violet | 366(M+, Base) 364·333·331· 309·307·285 | λ max nm(ε) 246.4 (30500) 258(sh 27400) 280(sh 16200) 340.0 (6800) |

TABLE 6

| Example No | melting point (centi degree) | NMR | NMR solvent | IR | Appearance | Mass | UV |
|---|---|---|---|---|---|---|---|
| 45 | 227.2–229.9 | 0.95(3H, t, J=7.2Hz, CH3)1.96–2.01(1H, m, CH2)2.38–2.44(1H, m, CH2)4.64(1H, t, J=7.2Hz, CH)7.02(1H, s, Ar—H)7.35(1H, d, J=8.4Hz, Ar—H)7.56(1H, s, Ar—H)7.71(1H, dd, J=1.7, 8.4Hz, Ar—H)7.97(1H, d, J=1.7Hz, Ar—H)10.04(2H, brs, OH) | DMSO-d6 | 3516·3307·2968·2877·1645·1596·1506·1463 | pinkish whiteneedle crystal | 366(M+, Base)364 | λ max nm(ε)·337.6(5600)·280.8 (12000)·257.2(25600)·241.6(28100)·205.2 (36100) |
| 46 | 179.8–183.0 | 0.98(3H, t, J=7Hz, CH3)2.04(2H, m, J=7Hz, CH2)2.25(2H, m, J=7Hz, CH2)2.44(1H, sev, J=7Hz, CH)2.47(3H, s, SCH3)4.71(1H, t, J=7Hz, CH)6.40(2H, brs, OH)7.00(1H, m, Ar—H)7.10(1H, m, J=8Hz, Ar—H)7.16(1H, m, Ar—H)7.22(1H, m, Ar—H)7.54(1H, s, Ar—H)7.90(2H, brs, OH)8.01(1H, | DMSO-d6 | 3514·3289·2970·2936·2877·1645·1598·1505 | | | λ max nm(ε) |
| 47 | 121.0–123.0 | 0.850(3H, t, J=7.5Hz, —CH3)1.540(2H, Sx, J=7.5Hz, —CH3)2.509(2H, t, 7.5Hz, —CH2)4.044(2H, s, CH2)6.063(1H, d, J=2.2Hz, Ar—H)6.337(1H, d, J=2.2Hz, Ar—H)7.094(1H, dd, J=8.1, 1.4Hz, Ar—H)7.204(1H, d, J=8.1Hz, Ar—H)7.214(1H, s, Ar—H)10.969(1H, s, Ph—OH) | DMSO-d6 | 3328·2959·2929·2869·1636·1592·1498·1445 | colorless needle crystal | | ε max 7180(λ max 325.2 nm)· ε max 6924(λ max 313.6 nm)· ε max 15843(λ max 287.2 nm)·ε max 4214(λ max 253.2 nm)· ε max 40043(λ max 204.0 nm) |
| 48 | 179.1–180.1 | 1.22(3H, t, J=8Hz, CH3)2.64(2H, q, J=8Hz, CH2)4.35(2H, brs, CH2)5.76(1H, brs, OH)6.25(1H, d, J=2Hz, Res—H)6.67(1H, d, J=2Hz, Res—H)7.06(1H, dd, J=8, 1Hz, Ar—H)7.27(1H, d, J=1Hz, Ar—H)7.52(1H, d, J=8, Ar—H)13.53(1H, s, OH) | CDCl3 | 3315·2964·2931·2872·1618·1594 | colorless needle crystal | 286(M+, base) | λ max nm(ε)·241.2(21400)·262.8 (14700)·301.6 (11200)·340.0 (7800) |
| 49 | | 1.15(3H, t, J=7.1Hz, CH3)2.58(2H, q, J=7.1Hz, CH2)4.03(2H, s, CH2)6.07(1H, d, J=2.5Hz, Ar—H)6.36(1H, d, J=2.5Hz, Ar—H)7.05–7.25(3H, m, Ar—H)11.00(1H, brs, OH)13.00(1H, s, OH) | DMSO-d6 | 3339·2968·2932·1637·1597·1506·1446 | amorphous | 270·241 | λ max nm(ε)·287.2(12600)·327.2 (6700) |
| 50 | 105.6–106.8 | 0.94(3H, t, J=7Hz, CH3)1.33(2H, Sx, J=7Hz, CH2)1.58(2H, quintet, J=7Hz, CH2)2.61(2H, t, J=7Hz, CH2)4.11(2H, s, CH2)6.13(1H, d, J=2Hz, Ar—H)6.40(1H, d, J=2Hz, Ar—H)7.16(1H, d, J=8Hz, Ar—H)7.28(2H, dd, J=8, 2Hz, Ar—H)11.05(1H, brs, Ph—OH)·13.07(1H, s, Ph—OH) | DMSO-d6 | 3314·2956·2929·2860·1636·1498·1445· | white needle crystal | 298 (M+, base)·269 (M+−29)·255 (M+−43)·241 (M+−57) | λ max nm(ε)·204.4(36300)·220.0 (sh, 28100)·287.2 (15000)·326.0 (6900) |
| 51 | 125.9–127.7 | 2.9(4H, m, CH2)4.02(2H, s, CH2)6.16(1H, d, J=2.5Hz, Ar—H)6.36(1H, d, J=2.5Hz, Ar—H)7.0–7.3(8H, m, Ar—H)13.04(1H, s, OH) | CDCl3 | 3482·2923·2859·1636·1507·1447 | colorless amorphous | 346(M+)·255(base) | ε max 7420(λ max 325.2 nm)·ε max 7063 (λ max 312.8 nm)·ε max 14590(λ max 286.8 nm)·ε max 6445(λ max 257.2 nm)·ε max 54184(λ max 204.0 nm) |
| 52 | | 0.91(3H, t, J=6Hz, CH3)1.2–1.7(4H, m, CH2 × 2)·2.59(2H, t, J=7Hz, CH2)4.02(2H, s, CH2)6.0(1H, brs, Ph—OH)·6.16(1H, d, J=2Hz, Ar—H)6.38(1H, d, J=2Hz, Ar—H)6.9–7.3(3H, m, Ar—H)13.04(1H, s, Ph—OH) | CDCl3 | 3310·2959·2933·2860·1636·1595·1508·1445 | oil | 298(M+, base)·241 | ε max 7414(λ max 324.0 nm)·ε max 7140(λ max 313.6 nm)·ε max 15675(λ max |

TABLE 6-continued

| Example No | melting point (centi degree) | NMR | NMR solvent | IR | Appearance | Mass | UV |
|---|---|---|---|---|---|---|---|
| | | | | | | | 286.8 nm)ϵ max 4885(λ max 254.8 nm)·ϵ max 40878(λ max 204.8 nm) |
| 53 | 106.9–108.1 | 0.94(3H, t, J=7Hz, CH3)1.34(2H, qt., J=7, 7Hz, CH2)· 1.58(2H, tt., J=7, 7Hz, CH2)·2.64(2H, t, J=7Hz, CH2)· 4.37(2H, s, CH2)·6.24(1H, d, J=2Hz, Ar—H)· 6.70(1H, d, J=2Hz, Ar—H)·6.19(1H, d, J=8, 2Hz, Ar—H)· 7.41(1H, d, J=2Hz, Ar—H)·7.62(1H, d, J=8Hz, Ar—H)· 11.02(1H, brs, OH)·13.52(1H, s, OH) | DMSO-d6 | 3308·2929· 2859·1618· | pale yellow needle crystal | 314(M+, base) | λ max nm(ϵ)· 204.0(46000)·241.6 (22500)·263.6 (15600)·301.6 (11800)·340.0 (8000) |
| 54 | 170.3–172.0 | 4.25(2H, s, CH2)·6.17(1H, d, J=2Hz, Ar—H)· 6.47(1H, d, J=2Hz, Ar—H)·7.42(1H, tt, J=8, 1Hz, Ar—H)· 7.48(1H, d, J=8Hz, Ar—H)·7.52(2H, t, J=8Hz, Ar—H)· 7.66(1H, dd, J=8, 2Hz, Ar—H)·7.72(2H, dd, J=8, 1Hz, Ar—H)·7.81(1H, d, J=2Hz, Ar—H)·11.10(1H, brs, OH)· 13.10(1H, s, OH) | DMSO-d6 | 3465·3032· 1644·1592 | colorless needle crystal | 318(M+, base) | λ max nm(ϵ)· 204.8(55366)·255.6 (25351)·284.0 (sh, 16957)·320.0 (6840) |

TABLE 7

| Example No | melting point (centi degree) | NMR | NMR solvent | IR | Appearance | Mass | UV |
|---|---|---|---|---|---|---|---|
| 55 | 293.9–300.1 | 4.25(2H, s, CH2)6.16(1H, d, J=2Hz, Ar—H)6.46(1H, d, J=2Hz, Ar—H)7.50–7.55(2H, m, Ar—H)7.73(1H, d, J=8Hz, Ar—H)7.89(1H, s, Ar—H)8.12(1H, d, J=2Hz, Ar—H)8.62(1H, s, Ar—H)8.94(1H, s, Ar—H)11.15(1H, brs, OH)13.08(1H, s, OH) | DMSO-d6 | 3427·1637 | yellow powder | 319 (M+, base) | λmax nm (ε) 203.6 (20952)·256.0 (10308)·279.2 (10274)·317.5 (3383) |
| 56 | 244.3–250.7 | 4.28(2H, s, CH2)6.16(1H, d, J=2Hz, Ar—H)6.47(1H, d, J=2Hz, Ar—H)7.53(1H, d, J=8Hz, Ar—H)7.79–7.83(2H, m, Ar—H)7.99(1H, d, J=2Hz, Ar—H)8.21(1H, d, J=8Hz, Ar—H)8.27(1H, dd, J=8, 2Hz, Ar—H)8.52(1H, t, J=2Hz, Ar—H)11.12(1H, brs, OH)13.09(1H, s, OH) | DMSO-d6 | 3502·3085·1641·1593 | colorless amorphous | 363 (M+, base) | λmax nm (ε) 204.8 (49743)·255.6 (32260)·327.6 (9997) |
| 57 | 171.0–172.7 | 4.15(2H, s, CH2)6.09(1H, d, J=2Hz, Ar—H)6.38(1H, d, J=2Hz, Ar—H)6.59(1H, dd, J=3, 2Hz, Ar—H)6.95(1H, d, J=3Hz, Ar—H)7.38(1H, d, J=8Hz, Ar—H)7.63(1H, dd, J=8, 2Hz, Ar—H)7.75(1H, s, Ar—H)7.78(1H, d, J=2Hz, Ar—H)11.?(1H, brs, OH)13.00(1H, s, OH) | DMSO-d6 | 3543·3468·3062·1641 | pinkish white needle crystal | 308 (M+, base)279 (M—29) | λmax nm (ε) 203.5 (30030)·220.0 (sh, 24545)·282.0 (30829)·320.5 (6430) |
| 58 | 199.9–201.0 | 4.17(2H, s, CH2)6.10(1H, d, J=2Hz, Ar—H)6.38(1H, d, J=2Hz, Ar—H)7.13(1H, dd, J=4, 5Hz, Ar—H)7.37(1H, d, J=8Hz, Ar—H)7.51(1H, d, J=4, 1Hz, Ar—H)7.55(1H, dd, J=5, 1Hz, Ar—H)7.59(1H, dd, J=8, 2Hz, Ar—H)7.76(1H, d, J=2Hz, Ar—H)11.?(1H, brs, OH)13.01(1H, s, OH) | DMSO-d6 | 3369·3111·1645·1601· | pale yellow needle crystal | 324 (M+, base) | λmax nm (ε) 203.6 (3996)·225.0 (sh, 26343)·284.4 (33237)·330.0 (sh, 7905) |
| 59 | >300(decomposition) | 4.23(2H, s, CH2)5.21(2H, brs, NH2)6.15(1H, d, J=2Hz, Ar—H)6.45(1H, d, J=2Hz, Ar—H)6.62(1H, dd, J=8, 2Hz, Ar—H)6.82(1H, d, J=8Hz, Ar—H)6.88(1H, d, J=2Hz, Ar—H)7.14(1H, t, J=8Hz, Ar—H)7.44(1H, d, J=8Hz, Ar—H)7.52(1H, dd, J=8, 2Hz, Ar—H)7.67(1H, d, J=2Hz, Ar—H)?(1H, brs, OH)13.09(1H, s, OH) | DMSO-d6 | 3368·3280·1641·1606 | pale yellow plate crystal | 333 (M+, base) | λmax nm (ε) 206.4 (35877)·229.5 (sh, 27582)·285.0 (12124)·319.0 (sh, 6503) |
| 60 | 174.0–175.0 | 2.34(2H, s, CH3)4.17(2H, s, CH2)6.09(1H, d, J=2Hz, Ar—H)6.39(1H, d, J=2Hz, Ar—H)7.26(2H, d, J=8Hz, Ar—H)7.39(1H, d, J=8Hz, Ar—H)7.54–7.58(3H, m, Ar—H)7.72(1H, d, J=2Hz, Ar—H)?(1H, brs, OH)13.04(1H, s, OH) | DMSO-d6 | 3503·3031·2917·1640·1591 | pale yellow powder | 332 (M+, base) | λmax nm (ε) 206.0 (53935)·260.4 (27534)·320.8 (7109) |
| 61 | 208.9–213.6 | 4.19(2H, s, CH2)6.10(1H, d, J=2Hz, Ar—H)6.40(1H, d, J=2Hz, Ar—H)7.40–7.43(2H, m, Ar—H)7.48(1H, t, J=8Hz, Ar—H)7.63–7.66(2H, m, Ar—H)7.74(1H, d, J=2Hz, Ar—H)7.82(1H, d, J=2Hz, Ar—H)?(1H, brs, OH)13.03(1H, s, OH) | DMSO-d6 | 3503·2919·1645·1593 | pale brown powder | 352 (M+, base) | λmax nm (ε) 212.0 (52265)·258.8 (24168)·280.0 (sh, 17980)·319.0 (6840) |
| 62 | 91.8–94.8 | 2.21(2H, s, CH3)4.16(2H, s, CH2)6.11(1H, d, J=2Hz, Ar—H)6.41(1H, d, J=2Hz, Ar—H)7.18(1H, dd, J=7, 2Hz, Ar—H)7.17–7.21(4H, m, Ar—H)7.39(1H, d, J=8Hz, Ar—H)7.41(1H, d, J=2Hz, Ar—H)?(1H, brs, OH)13.04(1H, s, OH) | DMSO-d6 | 3556·3467·3060·1637·1602 | yellow powder | 332 (M+, base) | λmax nm (ε) 207.6 (50567)·286.8 (14377)·322.0 (6601) |
| 63 | 151.5–155.0 | 1.20(3H, t, J=7.1Hz, CH3)2.2(4H, m, CH2)4.03(2H, s, CH2)6.16(1H, d, J=2.5Hz, Ar—H)6.38(1H, d, J=2.5Hz, Ar—H)6.55(1H, brs, OH)7.0–7.7(8H, m, Ar—H)13.02(1H, s, OH) | DMSO-d6 | 3314·1629 | | 346·332·285·275 | λmax nm (ε)286.8 (14800)· |
| 64 | 191.7–195.0 | 4.21(2H, s, CH2)6.10(1H, d, J=2Hz, Ar—H)6.41(1H, d, J=2Hz, Ar—H)7.45(1H, d, J=8Hz, Ar—H)7.68–7.74(3H, m, Ar—H)7.89(1H, dt, J=8, 2Hz, Ar—H)7.98–8.00 | DMSO-d6 | 3502·3057·1647·1594 | white needle crystal | 386 (M+, base) | λmax nm (ε) 208.0 (50083)·257.6 (23573)·280.0 (sh, 18210)·321.0 |

TABLE 7-continued

| Example No | melting point (centi degree) | NMR | NMR solvent | IR | Appearance | Mass | UV |
|---|---|---|---|---|---|---|---|
| 65 | 274.0–279.0(decomposition) | (2H, m, Ar—H)·?(1H, brs, OH)·13.04(1H, s, OH) 2.67(2H, s, CH3)·4.27(2H, s, CH2)·6.16(1H, d, J=2Hz, Ar—H)·6.47(1H, d, J=2Hz, Ar—H)·7.52(1H, d, J=8Hz, Ar—H)·7.76(1H, dd, J=8, 2Hz, Ar—H)·7.88–7.92(3H, m, Ar—H)·8.09(2H, d, J=8Hz, Ar—H)·?(1H, brs, OH)·13.09(1H, s, OH) | DMSO-d6 | 3195·1677·1641·1606 | pinkish white powder | 360 (M+, base) | (6975) λmax nm (ε)·204.8 (44022)·285.6 (32630) |
| 66 | 173.8–175.8 | 1.60–1.61(4H, m, CH2*2)·2.16(2H, m, CH2)·2.30 (2H, m, CH2)·4.05(2H, s, CH2)·4.11(2H, s, CH2)· 6.13(1H, d, J=2Hz, Ar—H)·6.41(1H, d, J=2Hz, Ar—H)· 7.16(1H, d, J=8, 2Hz, Ar—H)·7.23(1H, t, J=4Hz, CH)· 7.26(1H, d, J=2Hz, Ar—H)·7.29(1H, d, J=8Hz, Ar—H)· 11.0(1H, br, OH)·13.05(1H, s, OH) | DMSO-d6 | 3322·2940·1640·1606 | mud yellow amorphous | 364(M+)·109(Base)·81 | εmax 16815/λmax 286.4 nm)·εmax 10407/λmax 262.4 nm) |

TABLE 8

| Example No | melting point (centi degree) | NMR | NMR solvent | IR | Appearance | Mass | UV |
|---|---|---|---|---|---|---|---|
| 67 | 228.4–230.8 | 2.44(2H, s, Ar—CH3)·2.64(2H, s, CH3)·4.20(2H, s, CH2)·6.10(1H, d, J=2Hz, Ar—H)·6.41(1H, d, J=2Hz, Ar—H)·7.37(1H, dd, J=8, 2Hz, Ar—H)·7.43(1H, dt, J=8Hz, Ar—H)·7.68(1H, dt, J=8, 2Hz, Ar—H)·7.73(1H, dt, J=8, 2Hz, Ar—H)·7.85(1H, d, J=2Hz, Ar—H)·8.05(1H, d, J=2Hz, Ar—H)·11.05(1H, brs, OH)·13 | DMSO-d6 | 3210-2977·2926-1637·1591-1508·1446 | white powder | | λmax nm (ε)·207.6 (46800)·238.0 (sh, 37400)·261.0 (sh, 26300)·284.0 (sh, 19000)·322.4 (9400) |
| 68 | 195.5–195.8 | 1.57–1.61(4H, m, CH2*2)·2.16(2H, m, CH2)·2.31(2H, m, CH2)·4.09(2H, s, CH2)·4.12(2H, s, CH2)·6.14(1H, d, J=2Hz, Ar—H)·6.41(1H, d, J=2Hz, Ar—H)·7.11(1H, d, J=8, 2Hz, Ar—H)·7.21(1H, m, CH)·7.26(1H, m, Ar—H)·7.39(1H, d, J=8Hz, Ar—H)·11.0(1H, br, OH) | DMSO-d6 | 3244-2938·2874-1629·1507-1447 | pale yellow amorphous | 364(M+)·255·109· 81 | εmax 15975(λmax 287.2 nm)·εmax 7762(λmax 261.6 nm)·εmax 46059(λmax 206.0 nm) |
| 69 | 199.9–201.4 | 4.22(2H, s, CH2)·6.16(1H, d, J=2.3Hz, Ar—H)·6.50(1H, d, J=2.3Hz, Ar—H)·7.48–7.83(7H, m, Ar—H)·11.11(1H, brs, OH)·13.08(1H, s, OH) | DMSO-d6 | 3354-1634·1605 | colorless needle crystal | 352(M+, Base)· | εmax 7572(λmax 322.4 nm)·εmax 16068 (λmax 284.4 nm)·εmax 21047(λmax 257.2 nm) |
| 70 | 249.6–250.8 | 4.18(2H, s, CH2)·6.16(1H, d, J=2.1Hz, Ar—H)·6.49(1H, d, J=2.1Hz, Ar—H)·6.67(1H, q, J=1.6Hz, Furyl-H)·7.1(1H, d, J=3.4Hz, Furyl-H)·7.53(1H, d, J=7.9Hz, Ar—H)·7.63(1H, d, J=7.9Hz, Ar—H)·7.72(1H, s, Ar—H)·7.82(1H, s, Ar—H)·11.11(1H, brs, OH)·13.06(1H, s, OH). | DMSO-d6 | 3250-1633·884 | yellow needle crystal | 308(M+), 279(Base) | εmax 10430.2(λ max 320.2 nm)·εmax 30636.9(λmax 279.6 nm)· |
| 71 | 208.8–210.2 | 2.4(3H, s, CH3)·4.2(2H, s, CH2)·6.16(1H, d, J=2.3Hz, Ar—H)·6.49(1H, d, J=2.3Hz, Ar—H)·7.33(2H, d, J=8.0Hz, Ar—H)·7.53–7.69(5H, m, Ar—H)·11.10(1H, brs, OH)·13.09(1H, s, OH) | DMSO-d6 | 3328-1636·1595 | yellow needle crystal | 332(M+, Base) | εmax 7458(λmax 320.6nm)·εmax 23077 (λmax 262.2 nm) |
| 72 | 163.5–165.8 | 2.28(3H, s, CH3)·4.22(2H, s, CH2)·6.16(1H, d, J=1.3Hz, Ar—H)·6.46(1H, d, J=1.2Hz, Ar—H)·7.24–7.56(7H, m, Ar—H)·11.09(1H, brs, OH)·13.1(1H, s, OH) | DMSO-d6 | 3377-1633·1591 | pinkish white amorphous | 332(M+, Base) | εmax 6656(λmax 322.0 nm)·εmax 14655 (λmax 287.0 nm) |
| 73 | 183.0–184.7 | 4.23(2H, s, CH2)·6.17(1H, d, J=2.2Hz, Ar—H)·6.51(1H, d, J=2.1Hz, Ar—H)·7.60–7.85(5H, m, Ar—H)·8.08(2H, d, J=1.9Hz, Ar—H)·11.11(1H, brs, OH)·13.07(1H, s, OH) | DMSO-d6 | 3290-1633·1594-1336 | pale yellow needle crystal | 386(M+, Base) | εmax 7394(λmax 323.2 nm)·εmax 16194 (λmax 286.0 nm)·εmax 21318(λmax 256.2 nm) |
| 74 | 228.3–230.0 | 4.19(2H, s, CH2)·5.22(2H, br s, NH2)·6.16(1H, d, J=2.2Hz, Ar—H)·6.49(1H, d, J=2.4Hz, Ar—H)·6.62–6.65(1H, m, Ar—H)·6.87(2H, t, J=13.8Hz, Ar—H)·7.15(1H, t, J=7.8Hz, Ar—H)·7.46–7.56(3H, m, Ar—H)·11.09(1H, brs, OH)·13.09(1H, s, OH) | DMSO-d6 | 3393-3309·1637-1572 | yellow amorphous | 333(M+, Base) | εmax 9332(λmax 322.0 nm)·εmax 14937 (λmax 287.4 nm)·εmax 34865(λmax 223.4 nm) |
| 75 | 241.0–247.08 | 4.25(2H, s, CH2)·6.15(1H, d, J=2Hz, Ar—H)·6.46(1H, d, J=2Hz, Ar—H)·7.39–7.51(3H, m, Ar—H)·7.55–7.70(2H, m, Ar—H)·7.74(1H, dt, J=8, 2Hz, Ar—H)·7.94(1H, s, Ar—H)·8.38(1H, s, OH)·10.32(1H, s, OH)·11.?(1H, brs, OH)·13.09(1H, s, OH) | DMSO-d6 | crude (containg 20% of CNS-183) | | | crude(containing 20% of CNS-183)·measured |
| 76 | 240.1–246.1 | 4.46(2H, s, CH2)·6.25(1H, d, J=2Hz, Ar—H)·6.72(1H, d, J=2Hz, Ar—H)·7.22(1H, dd, J=5, 4Hz, Ar—H)·7.62–7.68(3H, m, Ar—H)·7.74(1H, d, J=8Hz, Ar—H)· | DMSO-d6 | 3331-3091·1598 | | 340 (M+, base)·307 (M+–33)·279 (M+–61) | λmax nm (ε)·244.4 (22300)·297.2 (30000)·343.0 (sh, 1000) |

TABLE 8-continued

| Example No | melting point (centi degree) | NMR | NMR solvent | IR | Appearance | Mass | UV |
|---|---|---|---|---|---|---|---|
| | | 7.95(1H, s, Ar—H)·11.08(1H, brs, OH)·13.52(1H, s, OH) | | | | | |
| 77 | 212.6–215.7 | 4.49(2H, s, CH2)·6.26(1H, d, J=2Hz, Ar—H)·6.74(1H, d, J=2Hz, Ar—H)·7.46(1H, t, J=7Hz, Ar—H)·7.54(2H, t, J=7Hz, Ar—H)·7.66(1H, dd, J=8, 2Hz, Ar—H)·7.76(2H, d, J=7Hz, Ar—H)·7.81(1H, d, J=8Hz, Ar—H)·7.91(1H, d, J=2Hz, Ar—H)·11.06(1H, brs, OH)·13.55(1H, s, OH) | DMSO-d6 | 3619·3478·3393·3184·1640·1601 | | 350 (M+, base) | λmax nm (ε)·268.0 (19100)·287.6 (20900)·322.0 (7400) |

TABLE 9

| Example No | melting point (centi degree) | NMR | NMR solvent | IR | Appearance | Mass | UV |
|---|---|---|---|---|---|---|---|
| 78 | 190.8–195.3 | 4.49(2H, s, CH2)6.26(1H, d, J=2Hz, Ar—H)6.74(1H, d, J=2Hz, Ar—H)7.46(1H, t, J=7Hz, Ar—H)7.54(2H, t, J=7Hz, Ar—H)7.66(1H, dd, J=8, 2Hz, Ar—H)7.76(2H, d, J=7Hz, Ar—H)7.81(1H, d, J=8Hz, Ar—H)7.91(1H, d, J=2Hz, Ar—H)11.07(1H, brs, OH)13.55(1H, s, OH) | DMSO-d6 | 3332-3073-1598 | | 334 (M+, base)-282.4 (20800)-301 (M+–33) | λmax nm (ε)-246.4 (26400)-282.4 (20800)-344.0 (6900) |
| 79 | >250(decomposition) | 4.27(2H, s, CH2)6.16(1H, d, J=2Hz, Ar—H)6.47(1H, d, J=2Hz, Ar—H)7.43–7.56(4H, m, Ar—H)7.73(1H, dd, J=8, 2Hz, Ar—H)7.79–7.83(6H, m, Ar—H)7.88(1H, d, J=2Hz, Ar—H)11.08(1H, brs, OH)13.01(1H, s, OH) | DMSO-d6 | 3370-1638 | | 394 (M+, base) | εmax 52384.9(λmax 283.0 nm)εmax 88456.4 (λmax 208.4 nm) |
| 80 | >250(decomposition) | 4.51(2H, s, CH2)6.26(1H, d, J=2Hz, Ar—H)6.74(1H, d, J=2Hz, Ar—H)7.77–7.88(3H, m, Ar—H)8.24(1H, d, J=8Hz, Ar—H)8.67(1H, s, Ar—H)8.30(1H, dd, J=8, 2Hz, Ar—H)8.55(1H, d, J=2Hz, Ar—H)11.06(1H, brs, OH)13.55(1H, s, OH) | DMSO-d6 | 3421-3090-2911-2360-1617 | | 379 (M+, base)-346 (M+–33) | λmax nm (ε)-247.6 (45100)-282.7 (27100)-340.0 (10900) |
| 81 | 214.3–215.3 | 4.37(2H, s, CH2)6.21(1H, d, J=2.4Hz, Ar—H)6.69(1H, d, J=2.3Hz, Ar—H)7.14(1H, dd, J=5.2, 3.7Hz, Ar—H)7.54–7.6(3H, m, Ar—H)7.71(1H, dd, J=7.9, 1.9Hz, Ar—H)7.95(1H, d, J=1.9Hz, Ar—H)13.46(1H, s, OH) | DMSO-d6 | 3310-1616-1591-701 | pale yellow amorphous | | εmax 7707(λmax 340.0 nm)εmax 19923 (λmax 286.4 nm)εmax 14694(λmax 241.6 nm)εmax 17445 (λmax 204.8 nm) |
| 82 | 234.9–238.8 | 4.36(2H, s, CH2)6.20(1H, d, J=2.4Hz, Ar—H)6.60(1H, d, J=3.4, 1.9Hz, Ar—H)6.68(1H, d, J=2.4Hz, Ar—H)7.06(1H, d, J=3.2Hz, Ar—H)7.55(1H, d, J=6Hz, Ar—H)7.75(2H, dd, J=7.7, 1.7Hz, Ar—H)7.99(1H, d, J=1.6Hz, Ar—H)13.46(1H, s, OH) | DMSO-d6 | 3226-1611-1575-885 | pinkish white amorphous | 324(M+, Base) | εmax 9678(λmax 340.0 nm)εmax 29245 (λmax 282.0 nm)εmax 17358(λmax 239.2 nm)εmax 17404 (λmax 204.8 nm) |
| 83 | >200(decomposition) | 4.47(1H, s, CH2) 5.25(2H, s, NH2)6.25(1H, d, J=2Hz, Ar—H)6.65(1H, d, J=8Hz, Ar—H)6.73(1H, d, J=2Hz, Ar—H)6.86(1H, d, J=8Hz, Ar—H)6.92(1H, s, Ar—H)7.17(1H, t, J=8Hz, Ar—H)7.54(1H, d, J=8Hz, Ar—H)7.77(2H, m, Ar—H)11.02( | DMSO-d6 | 3364-3295-1582 | | 349 (M+, base) | λmax nm (ε)-204.8 (30900)-243.6 (26500)-281.6 (16100)-337.0 (6400) |
| 84 | 243.5–248.4(decomposition) | 4.45(2H, s, CH2)6.26(1H, d, J=2Hz, Ar—H)6.68(1H, dd, J=3, 2Hz, Ar—H)6.72(1H, d, J=2Hz, Ar—H)7.15(1H, d, J=3Hz, Ar—H)7.67(1H, dd, J=8, 2Hz, Ar—H)7.76(1H, d, J=8Hz, Ar—H)7.85(1H, d, J=2Hz, Ar—H)7.92(1H, s, Ar—H)11.05(1H, s, OH)13.51 (1H, s, OH) | DMSO-d6 | 3338-3075-1598 | | 324 (M+, base)-295 (M+–29)-291 (M+–33)-263 (M+–61) | λmax nm (ε)-238.0 (sh, 49100)-298.4 (26600)-339.0 (21100) |
| 85 | 198.3–203.2 | 4.25(2H, s, CH2)6.15(1H, d, J=2Hz, Ar—H)6.46(1H, d, J=2Hz, Ar—H)7.49–7.52(3H, m, Ar—H)7.69(1H, d, J=8Hz, Ar—H)7.84–7.86(3H, m, Ar—H)11.06(1H, brs, OH)13.09(1H, s, OH) | DMSO-d6 | 3467-3069-1650-1594 | | 402 (M+, base) | λmax nm (ε)-251.7 (19600)-281.5 (sh, 45900)-323.0 (68000) |
| 86 | 228.4–235.2 | 2.34(3H, s, CH3)4.38(2H, s, CH2)6.21(1H, d, J=2.3Hz, Ar—H)6.69(1H, d, J=2.4Hz, Ar—H)7.27(2H, d, J=8Hz, Ar—H)7.58(3H, t, J=7.6Hz, Ar—H)7.71 (1H, dd, J=7.9, 1.8Hz, Ar—H)7.92(1H, d, J=1.8Hz, Ar—H)13.48(1H, s, OH) | DMSO-d6 | 3318-1619-1589 | pale yellow amorphous | 348(M+, Base) | εmax 10566(λmax 342.2 nm)εmax 36653 (λmax 259.4 nm)εmax 70816(λmax 203.8 nm) |
| 87 | 209.7–212.0 | 4.36(2H, s, CH2)6.21(1H, s, CH2)6.7(1H, s, Ar—H)7.39–7.95(7H, m, Ar—H)7.94(1H, s, Ar—H) | DMSO-d6 | 3295-1618-1590 | pale yellow needle | 334(M+, Base) | εmax 8621(λmax 340.0 nm)εmax 13242 |

TABLE 9-continued

| Example No | melting point (centi degree) | NMR | NMR solvent | IR | Appearance | Mass | UV |
|---|---|---|---|---|---|---|---|
| | | 13.48(1H, s, OH) | | | crystal | | (λmax 300.8 nm)ε max 35927(λmax 245.2 nm)εmax 64276 (λmax 205.6 nm) |
| 88 | 124.0–125.8 | 4.19(2H, s, CH2) 6.46(1H, s, Ar—H) 7.36–7.74(8H, m, Ar—H) 12.98(1H, s, OH) | DMSO-d6 | 3401·1640·1600 | yellow needle crystal | 334(M+, Base) | εmax 16414(λmax 295.6 nm)εmax 34018 (λmax 248.8 nm)ε max 71778(λmax 204.4 nm) |

TABLE 10

| Example No | melting point (centi degree) | NMR | NMR solvent | IR | Appearance | Mass | UV |
|---|---|---|---|---|---|---|---|
| 89 | 178.1–198.3 | 2.21(3H, s, CH3)·4.40(2H, s, CH2)·6.21(1H, s, J=2.3Hz, Ar—H)·6.67(1H, s, J=2.3Hz, Ar—H)·7.20–7.62(7H, m, Ar—H)·13.48(1H, s, OH) | DMSO-d6 | 3340·1591 | pale yellow amorphous needle crystal | 348(M+, Base) | εmax 11569(λmax 340.0 nm)·εmax 12408(λmax 300.0 nm)·εmax 36540 (λmax 241.2 nm)·εmax 70476(λmax 203.2 nm) |
| 90 | 180.3–191.6 | 4.46(2H, s, CH2)·6.26(1H, d, J=2.1Hz, Ar—H)·6.74(1H, d, J=2.2Hz, Ar—H)·7.49–8.06(7H, m, Ar—H)·11.07(1H, brs, OH)·13.52(1H, s, OH) | DMSO-d6 | 3329·1617·1594·782 | brown needle crystal amorphous | 368(M+, Base) | εmax 6061(λmax 340.0 nm)·εmax 9184 (λmax 298.4 nm)·εmax 23829(λmax 240.0 nm)·εmax 46353(λmax 210.0 nm) |
| 91 | 225.3–226.5 | 4.48(2H, s, CH2)·6.26(1H, d, J=2.3Hz, CH2)·6.75(1H, d, J=2.4Hz, Ar—H)·7.7–7.90(4H, m, Ar—H)·8.06–8.13(3H, q, Ar—H)·11.08(1H, brs, OH)·13.52(1H, s, OH) | DMSO-d6 | 3314·1615·1588·1335 | pale brown needle crystal | 402(M+, Base) | λmax nm (ε)·254.4 (32300)·301.6(12700)·340.0 (8300) |
| 92 | 251.6–253.8 | 4.48(2H, s, CH2)·6.27(1H, d, J=2.2Hz, Ar—H)·6.77(1H, d, J=2.3Hz, Ar—H)·7.33–7.74(7H, m, Ar—H)·8.03–8.06(1H, q, Ar—H)·8.28(1H, d, J=1.3Hz, Ar—H)·11.13(1H, brs, OH)·13.52(1H, s, OH) | DMSO-d6 | 3209–3180·1610·1575 | orange needle crystal | 374(M+, Base) | εmax 27125(λmax 302.0 nm)·εmax 31051(λ max 236.4 nm)· |
| 93 | >250 | 4.21(2H, s, CH2)·6.15(1H, d, J=2.2Hz, Ar—H)·6.44(1H, d, J=2Hz, Ar—H)·6.86(1H, d, J=8Hz, Ar—H)·6.98(1H, dd, J=8, 2Hz, Ar—H)·7.07(1H, d, J=2Hz, Ar—H)·7.39(1H, d, J=8Hz, Ar—H)·7.50(1H, dd, J=8, 2Hz, Ar—H)·8.08(1H, s, Ar—H)·9.05(1H, brs, OH)·9.13(1H, brs, OH)·11.07(1H, s, Ar—H)·13.09(1H, s, OH) | DMSO-d6 | 3459·3291·3170·1647 | | 350 (M+, base) | εmax 25618(λmax 277.6 nm)·εmax 56647(λ max 206.0 nm)· |
| 94 | 268.4–268.5 | 4.27(2H, s, CH2)·6.17(1H, d, J=2Hz, Ar—H)·6.47(1H, d, J=2Hz, Ar—H)·7.33(1H, t, J=8Hz, Ar—H)·7.39(1H, t, J=8Hz, Ar—H)·7.50(1H, s, Ar—H)·7.53(1H, d, J=8Hz, Ar—H)·7.68(1H, d, J=8Hz, Ar—H)·7.73(1H, d, J=8Hz, Ar—H)·7.93(1H, dd, J=8, 2Hz, Ar—H)·8.08(1H, s, Ar—H)·11.13(1H, brs, OH)·13.07(1H, s, O | DMSO-d6 | 3340·1641 | | | εmax 29487(λmax 322.0 nm)·εmax 41425 (λmax 307.2 nm)·εmax 41043(λmax 291.2 nm)·εmax 56920(λmax 205.6 nm) |
| 95 | 257.9–259.9 | 4.18(2H, s, CH2)·6.10(1H, d, J=2.3Hz, Ar—H)·6.46(1H, d, J=2.4Hz, Ar—H)·7.28(1H, t, J=7.4Hz, Ar—H)·7.33(1H, m, Ar—H)·7.53(1H, s, Ar—H)·7.57(1H, d, J=7.9Hz, Ar—H)·7.65(2H, q, Ar—H)·7.81(1H, dd, J=7.8, 1.5Hz, Ar—H)·7.89(1H, d, J=1.3Hz, Ar—H)·11.10(1H, br, OH)·13.00(1H, s, OH) | DMSO-d6 | 3339.2·1633.9·1609.8·881.6 | yellow needle crystal | 358(M+, Base)·329 | εmax 22612(λmax 323 nm)·εmax 30616(λmax 307.6 nm)·εmax 31103 (λmax 290.0 nm)·εmax 52850(λmax 204.8 nm) |
| 96 | 261.8–263.2 | 4.16(2H, s, CH2)·6.1(1H, d, J=2.2Hz, Ar—H)·6.45(1H, d, J=2.4Hz, Ar—H)·7.4(1H, d, J=7.3Hz, Ar—H)·7.47–7.54(1H, m, Ar—H)·7.62(1H, d, J=1.7Hz, Ar—H)·7.72–7.82(7H, m, Ar—H)·10.97(1H, br, OH)·13.03(1H, s, OH) | DMSO-d6 | 3347·1633·1614 | pale yellow amorphous | 394(M+, Base) | εmax 45218(λmax 281.2 nm)·εmax 83321 (λmax 206.4 nm) |
| 97 | 197.7–200.8 | 4.16(2H, s, CH2)·6.08(1H, d, J=2.0Hz, Ar—H)·6.41(1H, d, J=2.2Hz, Ar—H)·7.44(2H, d, J=8.3Hz, Ar—H)·7.52–7.59(2H, m, Ar—H)·7.69(1H, s, Ar—H)·7.82(1H, d, J=8.6Hz, Ar—H)·11.05(1H, br, OH)·13.02(1H, s, OH) | DMSO-d6 | 3258·1629·1586·1263 | pale yellow needle crystal | 402(M+, Base) | εmax 11227(λmax 322.8 nm)·εmax 20844(λ max 280.4 nm)·εmax 29734(λmax 252.4 nm)·εmax 75178(λmax 203.6 nm) |

TABLE 10-continued

| Example No | melting point (centi degree) | NMR | NMR solvent | IR | Appearance | Mass | UV |
|---|---|---|---|---|---|---|---|
| 98 | 229.8–231.6 | 4.10(2H, s, CH2) 6.08(1H, d, J=2.3Hz, Ar—H) 6.41(1H, d, J=2.3Hz, Ar—H) 6.8(1H, d, J=8.2Hz, Ar—H) 6.96(1H, dd, J=8.2, 2.2Hz, Ar—H) 7.04(1H, d, J=2.2Hz, Ar—H) 7.39(1H, dd, J=7.9, 1.5Hz, Ar—H) 7.43(1H, d, J=7.9Hz, Ar—H) 7.48(1H, d, J=1.2Hz, Ar—H) 9.01(1H, br, OH) 9.13(1H, br, OH) 11.03(1H, | DMSO-d6 | 3288·1641· 1598 | pale brown amorphous | 350(M+, Base) | εmax 24641(λmax 286.4 nm)·εmax 63587(λ max 204.4 nm)· |
| 99 | | | | | pale yellow amorphous | 340(M+)·324· 295(Base) | λmax nm (ε) 207.2 (22300) 227.0(22100)· 239.0(16300) 287.6 (15500) 331.2(6400) |

TABLE 11

| Example No | melting point (centi degree) | NMR | NMR solvent | IR | Appearance | Mass | UV |
|---|---|---|---|---|---|---|---|
| 100 | 239.1–242.6 | 4.09(2H, s, CH2)6.08(1H, d, J=2.3Hz, Ar—H)6.3(1H, dd, J=8.3, 2.3Hz, Ar—H)6.37(1H, d, J=2.2Hz, Ar—H)6.40(1H, d, J=2.3Hz, Ar—H)7.07(1H, d, J=8.4Hz, Ar—H)7.34(1H, dd, J=7.8, 1.3Hz, Ar—H)7.37(1H, d, J=7.9Hz, Ar—H)7.44(1H, d, J=0.9Hz, Ar—H)9.38(1H, br, OH)9.47(1H, s, OH)11(1H, br, O H)13.04(1H, s, OH) | DMSO-d6 | 3467·3256·1638·1593 | pale brown needle crystal | 350(M+, Base) | εmax 21818(λmax 287.6 nm)εmax 20338 (λmax 265.6 nm)ε max 6304(λmax 202.4 nm) |
| 101 | 189.4–191.1 | 4.23(2H, s, CH2)6.17(1H, d, J=2.4Hz, Ar—H)6.48(1H, d, J=2.4Hz, Ar—H)7.4–7.6(8H, m, Ar—H)11.2(1H, brs, OH)13.04(1H, s, OH) | DMSO-d6 | 3348·1633·1609·1505 | pale yellow amorphous | 342(M+, Base) | εmax 40436(λmax 283.6 nm)εmax 18280 (λmax 249.2 nm)εmax 56341(λmax 204.4 nm) |
| 102 | 135.6–137.6 | 0.833(3H, t, J=6Hz, CH3)1.15–1.35(6H, m, CH2)1.504(2H, t, J=6Hz, CH2)2.482(2H, t, J=8Hz, CH2)2.728(2H, t, J=6Hz, CH2)2.955(2H, t, J=6Hz, CH2)6.026(1H, d, J=2Hz, Ar—H)6.072(1H, d, J=2Hz, Ar—H)6.91–6.97(2H, Ar—H)6.700(1H, s, Ar—H)9.127(1H, s, Ph—OH)9.302(1H, s, OH) | | 3434·3364·2956·2924·2855·1624·1498·1457 | colorless amorphous | | εmax 3707(λmax 275.2 nm)·εmax 3404(λmax 262.8 nm)·εmax 52641(λmax 206.4 nm) |
| 103 | 153.3–154.8 | 1.66(2H, quintet, J=3Hz, CH2)2.49–2.54(2H, m, CH2)0.73(2H, t, J=5Hz, CH2)2.49–2.54(2H, m, CH2)4.41(1H, t, J=4Hz, R—OH)6.02(1H, s, Ar—H)6.07(1H, s, Ar—H)6.95(2H, s, Ar—H)7.01(1H, s, Ar—H)9.12(1H, s, Ph—OH)9.31(1H, s, Ph—OH) | | 3423·3318·2939·1618·1497·1461 | colorless amorphous | | λmax nm(ε)206.0 (52200)·275.2 ( 3800) |
| 104 | | 0.73(3H, t, J=7Hz, CH3)1.13(3H, d, J=7Hz, CH3)1.50(2H, quintet, J=7Hz, CH2)2.49(1H, m, CH)2.73(2H, t, J=6Hz, CH2)2.97(2H, t, J=6Hz, CH2)6.03(1H, d, J=2Hz, Ar—H)6.07(1H, d, J=2Hz, Ar—H)6.96(2H, m, Ar—H)7.01(1H, m, Ar—H)9.13(1H, s, Ph—OH)9.31(1H, s, Ph—OH) | DMSO-d6 | 3338·2961·2928·2873·1624·1496·1458 | | 284 (M+, base)· 269 (M+-15)·255 (M+-29) | λmax nm (ε)·206.0 (53000)·274.4 ( 3900) |
| 105 | 125.2–126.9 | -0.03(9H, s, TMS) 0.78(2H, t, J=8Hz, CH2)2.49–2.53(2H, m, CH2)2.72(2H, m, CH2)2.94(2H, m, CH2)6.01(1H, d, J=2Hz, Ar—H)6.06(1H, d, J=2Hz, Ar—H)6.95(2H, m, Ar—H)7.03(1H, m, Ar—H)9.14(1H, s, Ph—OH)9.32(1H, s, Ph—OH) | DMSO-d6 | 3360·2954·2923·2854·1623·1496·1457 | pale orange needle crystal | | λmax nm (ε)·205.6 (57600)·271.2 ( 4200) |
| 106 | | 2.86–2.89(2H, m, CH2)3.12–3.15(2H, m, CH2)6.18(1H, d, J=2.4Hz, Ar—H)6.21(1H, d, J=2.4Hz, Ar—H)7.41–7.43(1H, m, Ar—H)7.55–7.60(2H, m, Ar—H)7.80(1H, t, J=8Hz, Ar—H)8.20–8.27(2H, m, Ar—H)8.48–8.49(2H, m, Ar—H)9.25(1H, br, OH)9.44(1H, br, OH) | DMSO-d6 | 3402·2926·2858·1623·1508·1458 | yellow oil | 349(Base, M+)· (60000) 252.8 (28700) | λmax nm (ε)·204.4 |
| 107 | | 2.56–2.57(2H, m, CH2)3.08–3.11(2H, m, CH2)5.19(2H, br s, NH2)6.17(1H, d, J=2.4Hz, Ar—H)6.18(1H, d, J=2.4Hz, Ar—H)6.61(1H, dd, J=8, 2Hz, Ar—H)6.82(1H, d, J=8Hz, Ar—H)6.89(1H, d, J=2Hz, Ar—H)7.14(1H, t, J=8Hz, Ar—H)7.32(2H, m, Ar—H)7.42(1H, m, Ar—H)9.25(1H, br, OH)9.43(1H, br, OH) | DMSO-d6 | 3378·2921·2851·1623·1509·1457 | pale yellow oil | 319(Base, M+) | λmax nm (ε)·206.0 (57700) |
| 108 | 169.1–174.9 | 2.79–2.82(2H, m, CH2)2.89(4H, s, CH2*2)3.01–3.04(2H, m, CH2)6.11(1H, d, J=2.1Hz, Ar—H)6.15(1H, d, J=2.1Hz, Ar—H)6.97–7.35(8H, m, Ar—H)9.21(1H, br, OH)9.39(1H, br, OH) | DMSO-d6 | 3469·3368·1621 | | 332(M+)·241 (Base) | εmax 2548(λmax 340.6 nm)· |
| 109 | 176.7–179.2 | 2.85–2.89(2H, m, CH2)3.13–3.16(2H, m, CH2)· | DMSO-d6 | 3437·3361· | | 304(M+, base) | εmax 21325.6(λmax |

TABLE 11-continued

| Example No | melting point (centi degree) | NMR | NMR solvent | IR | Appearance | Mass | UV |
|---|---|---|---|---|---|---|---|
|  |  | 6.15(1H, d, J=2Hz, Ar—H)·6.17(1H, d, J=2Hz, Ar—H)·7.21(1H, d, J=8Hz, Ar—H)·7.39(1H, t, J=8Hz, Ar—H)·7.48–7.52(3H, m, Ar—H)·7.58(1H, d, J=2Hz, Ar—H)·7.68(2H, d, J=8Hz, Ar—H)·9.25(1H, s, OH)·9.44(1H, s, OH)· |  |  |  |  | 258.0 nm)εmax 68335.7 (λmax 204.6 nm) |
| 110 | 194.2–195.6 | 2.79(2H, t, J=6.3Hz, CH2)·3.02(2H, t, J=6.3Hz, Ar—H)·6.13(2H, t, J=2.8Hz, Ar—H)·7.07–7.14(1H, m, Ar—H)·7.26(1H, d, J=7.8Hz, Ar—H)·7.35–7.38(2H, m, Ar—H)·7.51–7.54(2H, m, Ar—H)·9.21(1H, s, OH)·9.4(1H, s, OH) | DMSO-d6 | 3440·3368·2923·2856·1623·698 | pale gray needle crystal | 310(M+, Base) | εmax 12818(λmax 282.8 nm)εmax 35269 (λmax 205.2 nm)· |

TABLE 12

| Example No | melting point (centi degree) | NMR | NMR solvent | IR | Appearance | Mass | UV |
|---|---|---|---|---|---|---|---|
| 111 | 188.3–191.4 | 2.83–2.87(2H, m, CH2)-3.10–3.13(2H, m, CH2)-6.14(1H, d, J=2Hz, Ar—H)-6.17(1H, d, J=2Hz, Ar—H)-7.16–7.19(2H, m, Ar—H)-7.48–7.51(2H, m, Ar—H)-7.55–7.58(2H, m, Ar—H)-9.25(1H, s, OH)-9.45(1H, s, OH)- | DMSO-d6 | 3369-687- | | 310 (M+, base) | εmax 22325 (λmax 284.4 nm)-εmax 64475 (λmax 204.4 nm) |
| 112 | 195.1–197.1 | 2.33(3H, s, CH3)-2.8(2H, t, J=6.3Hz, CH2)-3.09(2H, t, J=6.3Hz, CH2)-6.12(2H, dd, J=6.1, 2.4Hz, Ar—H)-7.24–7.36(5H, m, Ar—H)-7.54(2H, d, J=8.1Hz, Ar—H)-9.23(1H, s, OH)-9.41(1H, s, OH) | DMSO-d6 | 3432-3362-1625-1612 | pale pink needle crystal | 318 (M+, Base) | εmax 21032 (λmax 256.4 nm)-εmax 56257 (λmax 207.6 nm) |
| 113 | 151.8–152.7 | 2.78–2.84(2H, m, CH2)-2.88–2.91(4H, m, CH2)-3.01–3.04(2H, m, CH2)-6.10(1H, d, J=2Hz, Ar—H)-6.14(1H, d, J=2Hz, Ar—H)-7.01–7.07(2H, m, Ar—H)-7.12(1H, d, J=2Hz, Ar—H)-7.21–7.25(1H, d, J=2Hz, Ar—H)-7.27–7.28(2H, d, J=2Hz, Ar—H)-7.31–7.35(2H, d, J=2Hz, Ar—H)-9.20(1H, s, OH)-9.39(1H, s, OH) | DMSO-d6 | 3440-3368 | | 332 (M+)-241 (M+ -91, base) | εmax 4037.3 (λmax 275.4 nm)-εmax 69082.7 (λmax 206.2 nm) |
| 114 | 163.6–173.9 | 2.83–2.86(2H, m, CH2)-3.10–3.15(2H, m, CH2)-6.13(1H, d, J=2Hz, Ar—H)-6.16(1H, d, J=2Hz, Ar—H)-6.63(1H, m, Ar—H)-6.91(1H, d, J=3Hz, Ar—H)-7.19(1H, d, J=8Hz, Ar—H)-7.55(1H, dd, J=8, 2Hz, Ar—H)-7.63(1H, d, J=2Hz, Ar—H)-7.77(1H, s, Ar—H)-9.25(1H, s, OH)-9.45(1H, s, OH) | DMSO-d6 | 3432-3370 | | 294 (M+, base) | εmax 24574.5 (λmax 283.0 nm)-εmax 52361.3 (λmax 204.8 nm) |
| 115 | 198.6–201.1 | 2.79(2H, m, CH2)-3.02(2H, t, J=6.3Hz, CH2)-6.12(2H, s, Ar—H)-6.58(1H, dd, J=3.3, 1.8Hz, Ar—H)-6.94(1H, d, J=3.4Hz, Ar—H)-7.26(1H, t, J=4.1Hz, Ar—H)-7.39–7.41(2H, m, Ar—H)-7.72(1H, d, J=1.6 Hz, Ar—H)-9.25(1H, brs, OH)-9.43(1H, brs, OH) | DMSO-d6 | 3456-3362-2924-2856-1622-874 | colorless needle crystal | 294 (M+, Base) | εmax 25034 (λmax 282.2 nm)-εmax 39332 (λmax 207.8 nm) |
| 116 | | 2.23(3H, s, CH3)-2.82(2H, t, J=6.3Hz, Ar—H)-3.06(2H, t, J=6.3Hz, Ar—H)-6.10(2H, dd, J=11.2, 2.3Hz, Ar—H)-7.02–7.29(8H, m, Ar—H)-9.22(1H, s, OH)-9.43(1H, s, OH) | DMSO-d6 | 3410-3348-2923-2847-1622–751 | pale pink oil | 318 (M+, Base) | εmax 23012 (λmax 228.2 nm)-εmax 22380 (λmax 221.8 nm) |
| 117 | 150.2–152.6 | 2.81(2H, t, J=6.3Hz, CH2)-3.07(2H, t, J=6.3Hz, CH2)-6.12(1H, d, J=2.4Hz, Ar—H)-6.15(1H, d, J=2.4Hz, Ar—H)-7.35(1H, d, J=7.82Hz, Ar—H)-7.45–7.50(2H, td, Ar—H)-7.67–7.73(2H, m, Ar—H)-7.96–7.99(2H, m, Ar—H)-9.24(1H, brs, OH)-9.43(1H, brs, OH) | DMSO-d6 | 3370-2923-2853-1624-1336-1174-1129 | pale pink amorphous | 372 (M+, Base) | εmax 18307 (λmax 253.2 nm)-εmax 56560 (λmax 206.6 nm) |
| 118 | 137.1–143.2 | 2.81(2H, t, J=6.3Hz, CH2)-3.05(2H, t, J=6.3Hz, CH2)-6.12(1H, d, J=2.4Hz, Ar—H)-6.15(1H, d, J=2.4Hz, Ar—H)-7.31(1H, d, J=7.8Hz, Ar—H)-7.4–7.49(4H, m, Ar—H)-7.63(1H, dd, J=6.4, 1.3Hz, Ar—H)-7.72(1H, t, J=1.8Hz, Ar—H)-9.24(1H, s, OH)-9.43(1H, s, OH)- | DMSO-d6 | 3445-3370-2922-2855-1622-785 | colorless amorphous | 338 (M+, Base) | εmax 20038 (λmax 253.2 nm)-εmax 61114 (λmax 207.6 nm) |
| 119 | 197.2–199.3 | 2.85–2.88(2H, m, CH2)-3.11–3.14(2H, m, CH2)-5.17(2H, br, N—H2)-6.14(1H, d, J=2Hz, Ar—H)-6.17(1H, d, J=2Hz, Ar—H)-6.59(1H, d, J=8Hz, Ar—H)-6.79(1H, d, J=8Hz, Ar—H)-6.86(1H, s, Ar—H)-7.13(1H, t, J=8Hz, Ar—H)-7.18(1H, d, J=8Hz, Ar—H)-7.49(1H, dd, J=8.2Hz, Ar—H)-7.45(1H, s, Ar—H)-9.25(1H, b | DMSO-d6 | 3371-3224-3059-2885-2622-1618- | | 319 (M+, base) | λmax nm (ε)-307.0 (sh, 12300) |
| 120 | 199.6–201.8 | 2.87–2.90(2H, m, CH2)-3.16–3.19(2H, m, CH2)-6.16(1H, d, J=2Hz, Ar—H)-6.18(1H, d, J=2Hz, Ar—H)-7.28(1H, d, J=8Hz, Ar—H)-7.64(1H, dd, J=8, 2Hz, Ar—H)-7.72–7.74(1H, m, Ar—H)-7.78–7.82(1H, m, Ar—H)-8.18(1H, d, J=8Hz, Ar—H)-8.25(1H, dd, J=8, 2Hz, Ar—H)-8.47(1H, s, Ar—H)-9.27(1H, s, OH)-9.47( | DMSO-d6 | 3401-2920-1626 | | 349 (M+, base)-322 (M+ −17)- | λmax nm (ε)-260.8 (26800)-323.5 (3500) |
| 121 | | 2.88(2H, t, J=6Hz, CH2)-3.16(2H, t, J=6Hz, CH2)-6.16(1H, s, Ar—H)-6.18(1H, d, J=2Hz, Ar—H)-7.26(1H, d, J=8Hz, Ar—H)-7.51(1H, dd, J=8, 4Hz, Ar—H)-7.55(1H, d, J=8Hz, Ar—H)-7.65(1H, s, Ar—H)-8.09(1H, d, J=8Hz, Ar—H)-8.60(1H, d, J=4Hz, Ar—H)-8.91(1H, s, Ar—H)-9.26(1H, s, OH)-9.46(1H, s, OH)- | DMSO-d6 | 3369-1624-1476 | | | λmax nm (ε)-204.0 (57600)-261.6 (16600) |

TABLE 13

| Example No | melting point (centi degree) | NMR | NMR solvent | IR | Appearance | Mass | UV |
|---|---|---|---|---|---|---|---|
| 122 | 211.8–217.3 | 2.84–2.87(2H, m, CH2)-3.09–3.12(2H, m, CH2)-6.15(1H, d, J=2Hz, Ar—H)-6.19(1H, d, J=2Hz, Ar—H)-7.34(1H, d, J=8Hz, Ar—H)-7.72(1H, dd, J=8, 2Hz, Ar—H)-7.80(1H, s, Ar—H)-9.33(1H, s, OH)-9.55(1H, s, OH)- | DMSO-d6 | 3373-2237-1608 | | 253 (M+, base)-236 (M+ −17) | λmax nm (ε)-226.5 (sh, 52500)-281.0 (sh, 13900)- |
| 123 | 196.1–198.5 | 2.99(2H, q, J=3.8Hz, CH2)-3.23(2H, q, J=3.9Hz, CH2)-6.26(1H, d, J=2.4Hz, Ar—H)-6.34(1H, d, J=2.4Hz, Ar—H)-7.12(1H, dd, J=5.0, 3.6Hz, Ar—H)-7.3(1H, d, J=8Hz, Ar—H)-7.51–7.54(3H, m, Ar—H)-7.67(1H, d, J=1.9Hz, Ar—H)-9.29(1H, s, OH)-9.52(1H, s, OH) | DMSO-d6 | 3429-3370-1609-692 | pale brown amorphous | 326 (M+, Base) | εmax 27602 (λmax 279.6 nm)-εmax 54275 (λmax 207.6 nm) |
| 124 | 148.5–149.6 | 3.04(2H, q, J=4.1Hz, CH2)-3.29(2H, q, J=3.9Hz, CH2)-6.31(1H, d, J=2.3Hz, Ar—H)-6.39(1H, d, J=2.4Hz, Ar-H-6.64(1H, dd, J=3.6, 1.7Hz, Ar—H)-7.03(1H, d, J=3.1Hz, Ar—H)-7.36(3H, d, J=8.0Hz, Ar—H)-7.62(1H, dd, J=7.6, 1.8Hz, Ar—H)-7.79(2H, d, J=1.7Hz, Ar—H)-9.3(1H, s, OH)-9.53(1H, s, OH) | DMSO-d6 | 3428-3366-1605-829 | pale orange amorphous | 310 (M+, Base) | εmax 22619 (λmax 275.6 nm)-εmax 57427 (λmax 205.6 nm) |
| 125 | 175.1–178.3 | 2.92(2H, q, J'3.7Hz, CH2)-3.15(2H, t, J=6.2Hz, CH2)-6.26(1H, s, Ar—H)-7.19–7.68(8H, m, Ar—H)-8.08(1H, brs, OH)-8.37(1H, brs, OH)-9.06(1H, brs, OH) | DMSO-d6 | 3494-3462-3421-1627 | pare brown amorphous | 320 (M+, Base) | εmax 24764 (λmax 254.4 nm)-εmax 64910 (λmax 204.4 nm) |
| 126 | 207.3–208.1 | 3.03–3.06(2H, m, CH2)-3.33–3.36(2H, m, CH2)-6.30(1H, d, J=2Hz, Ar—H)-6.36(1H, d, J=2Hz, Ar—H)-7.19(1H, dd, J=5, 3Hz, Ar—H)-7.47(1H, d, J=8Hz, Ar—H)-7.50(1H, d, J=8Hz, Ar—H)-7.57(1H, d, J=3Hz, Ar—H)-7.61(1H, d, J=5Hz, Ar—H)-7.62(1H, s, Ar—H)-9.28(1H, s, OH)-9.25(1H, s, OH) | DMSO-d6 | 3435-3369-1607 | | | εmax 21933 (λmax 308.0 nm)-εmax 61186 (λmax 202.4 nm) |
| 127 | 213.7–214.7 | 3.02–3.05(2H, m, CH2)-3.32–3.35(2H, m, CH2)-6.30(1H, d, J=2Hz, Ar—H)-6.36(1H, d, J=2Hz, Ar—H)-6.65(1H, dd, J=3, 2Hz, Ar—H)-7.01(1H, d, J=3Hz, Ar—H)-7.49–7.54(1H, m, Ar—H)-7.67(1H, s, Ar—H)-7.80(1H, s, Ar—H)-9.28(1H, s, OH)-9.52(1H, s, OH) | DMSO-d6 | 3447-3376-1607- | | | εmax 26495 (λmax 301.2 nm)-εmax 55066 (λmax 207.6 nm) |
| 128 | 157.6–157.9 | 0.90(3H, t, J=7Hz, CH3)-1.60(1H, tq, J=7, 7Hz, CH2)-2.94(2H, t, J=7Hz, CH2)-2.79(2H, m, CH2)-3.08(2H, m, CH2)-6.07(1H, d, J=2Hz, Ar—H)-6.11(1H, d, J=2Hz, Ar—H)-7.18(1H, d, J=8Hz, Ar—H)-7.78(1H, dd, J=2, 8Hz, Ar—H)-7.83(1H, d, J=2Hz, Ar—H)-9.23(1H, br, OH)-9.43(1H, br, OH) | DMSO-d6 | 3353-3170-2964-1652-1622-1597 | colorless needle crystal | 298 (M+)-255 (Base) | εmax 13003 (λmax 261.2 nm)-εmax 12385 (λmax 245.6 nm)-εmax 53218 (λmax 206.8 nm) |
| 129 | 151.8–152.8 | 0.90(3H, t, J=7Hz, CH3)-1.60(1H, tq, J=7, 7Hz, CH2)-2.94(2H, t, J=7Hz, CH2)-2.99(2H, m, CH2)-3.25(2H, m, CH2)-6.25(1H, d, J=2Hz, Ar—H)-6.30(1H, d, J=2Hz, Ar—H)-7.50(1H, d, J=8Hz, Ar—H)-7.68(1H, dd, J=2.8Hz, Ar—H)-7.80(1H, d, J=2Hz, Ar—H)-9.30(1H, br, OH)-9.48(1H, br, OH) | DMSO-d6 | 3360-2959-1679-1591 | pale pink amorphous | 315 (M+)-271 (Base) | εmax 9626 (λmax 315.6 nm)-εmax 5918 (λmax 276.4 nm)-εmax 44639 (λmax 208.4 nm) |
| 130 | 119.8–121.7 | 0.88(3H, t, J=7Hz, CH3)-1.32(2H, tq, J=7, 7Hz, CH2)-1.56(2H, tt, J=7, 7Hz, CH2)-2.79(2H, m, CH2)-2.95(2H, t, J=7Hz, CH2)-3.06(2H, m, CH2)-6.07(1H, d, J=2Hz, Ar—H)-6.11(1H, d, J=2Hz, Ar—H)-7.18(1H, d, J=8Hz, Ar—H)-7.78(1H, dd, J=2, 8Hz, Ar—H0-7.83(1H, d, J=2Hz, Ar—H)-9.23(1H, br, OH)-9.43(1H | DMSO-d6 | 3367-3203-2946-1656-1597 | colorless needle crystal | 312 (M+)-255 (Base) | εmax 12405 (λmax 260.0 nm)-εmax 12019 (λmax 245.6 nm)-εmax 51546 (λmax 206.4 nm) |
| 131 | 155.1–158.7 | 0.88(3H, t, J=7Hz, CH3)-1.31(2H, tq, J=7, 7Hz, CH2)-1.56(2H, tt, J=7, 7Hz, CH2)-2.94(2H, t, J=7Hz, CH2)-2.99(2H, m, CH2)-3.25(2H, m, CH2)-6.25(1H, d, J=2Hz, Ar—H)-6.30(1H, d, J=2Hz, Ar—H)-7.50(1H, d, J=8Hz, Ar—H)-7.68(1H, dd, J=2, 8Hz, Ar—H)-7.80(1H, d, J=2Hz, Ar—H)-9.28(1H, br, OH)-9.49(1H | DMSO-d6 | 3429-3370-2957-1678-1591 | pinkish white amorphous | 328 (M+)-271 (Base) | εmax 10260 (λmax 314.8 nm)-εmax 6421 (λmax 276.8 nm)-εmax 48033 (λmax 208.8 nm) |

TABLE 14

| Example No | melting point (centi degree) | NMR | NMR solvent | IR | Appearance | Mass | UV |
|---|---|---|---|---|---|---|---|
| 132 | | 1.38–1.44(5H, m, cyclo-hex)-1.77–1.83(5H, m, cyclo-hex)-3.06(2H, m, CH2)-3.32(2H, m, CH2)-3.34(1H, m, cyclo-hex)-6.32(1H, d, J=2.4Hz, Ar—H)-6.37(1H, d, J=2.4Hz, Ar—H)-7.58(1H, d, J=8.1Hz, Ar—H)-7.75(1H, dd, J=1.6, 8.1Hz, Ar—H)-7.85(1H, d, J=1.6Hz, Ar—H-9.33(1H, br, OH)-9.57(1H, br, O | DMSO-d6 | 3348-2930-2853-1660-1589 | oil | 354 (M+)-271 (Base) | εmax 9403 (λmax 299.2 nm)-εmax 6935 (λmax 277.6 nm)-εmax 47934 (λmax 208.0 nm) |

TABLE 14-continued

| Example No | melting point (centi degree) | NMR | NMR solvent | IR | Appearance | Mass | UV |
|---|---|---|---|---|---|---|---|
| 133 | | 1.17(1H, m, cyclo-hex)-1.25–1.46(4H, m, cyclo-hex)-1.62–1.78(5H, m, cyclo-hex)-2.79(2H, m, CH2)-3.06(2H, m, CH2)-3.34(1H, m, cyclo-hex)-6.07(1H, d, J=2Hz, Ar—H)-6.11(1H, d, J=2Hz, Ar—H)-7.18(1H, d, J=8Hz, Ar—H)-7.78(1H, dd, J=2, 8Hz, Ar—H)-7.82(1H, d, J=2Hz, Ar—H)-9.23(1H, br, OH)-9.4 | DMSO-d6 | 3370-2931-2855-1661-1601 | oil | 338 (M+)-255 (Base) | εmax 12018 (λmax 261.6 nm)-εmax 11355 (λmax 246.0 nm)-εmax 51180 (λmax 206.4 nm) |
| 134 | 141.2–141.7 | 1.83(1H, m, cyclo-bu)-2.07(1H, m, cyclo-bu)-2.20–2.32(4H, m, cyclo-bu)-3.06(2H, m, CH2)-3.32(2H, m, CH2)-4.15(1H, dddd, J=8.5Hz each, cyclo-bu)-6.32(1H, d, J=2.5Hz, Ar—H)-6.37(1H, d, J=2.5Hz, Ar—H)-7.58(1H, d, J=8Hz, Ar—H)-7.68(1H, dd, J=2, 8Hz, Ar—H)-7.79(1H, d, J=2Hz, Ar—H)-9.33(1H | DMSO-d6 | 3359-2944-1669-1591 | pinkish white amorphous | 326 (M+)-271 (Base) | εmax 11180 (λmax 317.2 nm)-εmax 6902 (λmax 277.2 nm)-εmax 51325 (λmax 208.4 nm) |
| 135 | 142.2–143.5 | 1.02(4H, m, cyclo-pro)-2.85(1H, m, cyclo-pro)-3.00(2H, m, CH2)-3.27(2H, m, CH2)-6.26(1H, d, J=3Hz, Ar—H)-6.31(1H, d, J=3Hz, Ar—H)-7.53(1H, d, J=8Hz, Ar—H)-7.75(1H, dd, J=2, 8Hz, Ar—H)-7.88(1H, d, J=2Hz, Ar—H)-9.26(1H, brs, OH)-9.51(1H, brs, OH) | DMSO-d6 | 3371-1660-1591 | pinkish white amorphous | 312 (M+, Base)-271 | εmax 10456 (λmax 317.6 nm)-εmax 6176 (λmax 277.2 nm)-εmax 47193 (λmax 208.8 nm) |
| 136 | | 1.07(6H, d, J=6.8Hz, CH3*2)-3.00(2H, m, CH2)-3.26(2H, m, CH2)-3.59(1H, q, J=6.8Hz, CH)-6.25(1H, d, J=2.4Hz, Ar—H)-6.30(1H, d, J=2.4Hz, Ar—H)-7.50(1H, d, J=8.1Hz, Ar—H)-7.69(1H, dd, J=1.6, 8.1Hz, Ar—H)-7.79(1H, d, J=1.6Hz, Ar—H)-9.26(1H, br, OH)-9.50(1H, br, OH) | DMSO-d6 | 3332-2972-1664-1589 | oil | 314 (M+)-271 (Base) | εmax 8618 (λmax 316.0 nm)-εmax 5596 (λmax 276.8 nm)-εmax 41069 (λmax 208.4 nm) |
| 137 | 151.7–153.7 | 1.29(9H, s, CH3*3)-3.11(2H, m, CH2)-3.39(2H, m, CH2)-3.34(1H, m, cyclo-hex)-4.8(1H, br, OH)-4.9(1H, br, OH)-6.19(1H, d, J=2Hz, Ar—H)-6.54(1H, d, J=2Hz, Ar—H)-7.15(1H, dd, J=2, 8Hz, Ar—H)-7.22(1H, d, J=8Hz, Ar—H)-7.38(1H, d, J=2Hz, Ar—H)- | CDCl3 | 3373-2963-1604 | pinkish white amorphous | 300 (M+, Base)-285 | εmax 10084 (λmax 274.4 nm)-εmax 7945 (λmax 261.2 nm)-εmax 46454 (λmax 204.0 nm) |
| 138 | 176.7–177.6 | 2.13(3H, s, CH3)-2.95(2H, m, CH2)-3.23(2H, m, CH2)-3.90(3H, s, CH3)-6.23(1H, d, J=2.4Hz, Ar—H)-6.28(1H, d, J=2.4Hz, Ar—H)-7.40(2H, m, Ar—H)-7.52(1H, m, Ar—H)-9.20(1H, br, OH)-9.43(1H, br, OH)- | DMSO-d6 | 3461-3370-1607 | pale pink plate crystal | 315 (M+, Base)-300-284 | εmax 16817 (λmax 296.0 nm)-εmax 13182 (λmax 274.8 nm)-εmax 50814 (λmax 210.4 nm) |
| 139 | 110.7–112.4 | 1.30–1.33(3H, m, CH3)-3.01–3.04(2H, m, CH2)-3.30–3.32(2H, m, CH2)-4.20–4.26(2H, m, CH2)-6.32(1H, d, J=2.4Hz, Ar—H)-6.35(1H, d, J=2.4Hz, Ar—H)-7.48(2H, m, Ar—H)-7.59(1H, m, Ar—H)-9.2(1H, br, OH)-9.5(1H, br, OH)- | DMSO-d6 | 3452-3371-2938-1607 | colorless amorphous | 329 (M+, base)-284 | εmax 14745.1 (λmax 296.4 nm)-εmax 14631.9 (λmax 258.0 nm) |
| 140 | | 3.00–3.04(2H, m, CH2)-3.14–3.18, 3.45–3.47(2H, m, CH2)-6.41(1H, d, J=2.4Hz, Ar—H)-6.68(1H, d, J=2.4Hz, Ar—H)-7.79(1H, d, J=8.1Hz, Ar—H)-7.94(1H, dd, J=1.5Hz, Ar—H)-8.02(1H, dd, J=1.5, 8.1Hz, Ar—H)-9.63(1H, s, OH)-9.83(1H, s, OH) | DMSO-d6 | 3276-2924-1674-1611-1057 | colorless amorphous | TMS, 447 (M + 1) | εmax 16018 (λmax 256.4 nm)-εmax 14603 (λmax 244.8 nm)-εmax 45362 (λmax 206.4 nm) |
| 141 | | 2.87–2.90(2H, t, J=6Hz, CH2)-3.13–3.16(2H, t, J=6Hz, CH2)-6.17(1H, d, J=2Hz, Ar—H)-6.20(1H, d, J=2Hz, Ar—H)-7.31(1H, d, J=8Hz, Ar—H)-7.59–7.64(3H, m, Ar—H)-7.71–7.74(2H, m, Ar—H)-7.78(2H, d, J=7Hz, Ar—H)-9.31(1H, s, OH)-9.51(1H, s, OH) | DMSO-d6 | 3366-2924-1626-1599- | white | | λmax nm (ε)-268.2 (11100)-253.2 (12400) |
| 142 | | 1.09(3H, t, J=7Hz, CH3)-2.52(3H, s, SCH3)-2.70–2.85(1H, m, CH2)-6.71(1H, s, Ar—H)-6.85(1H, s, Ar—H)-6.93(1H, s, Ar—H)-7.23(1H, d, J=8Hz, Ar—H)-7.33(1H, s, Ar—H)-7.44(1H, d, J=8Hz, Ar—H)-?(1H, ?, OH)-?(1H, ?, OH)- | DMSO-d6 | 3369-2966-2923-2872-1595-1575-1501-1458 | | 316 (M+, base)-301 M+ −15)-283 (M+ −33)-269 (M+ −47) | λmax nm (ε)-205.2 (31900)-218.8 (32000)-271.6 (29000) |

TABLE 15

| Example No | melting point (centi degree) | NMR | NMR solvent | IR | Appearance | Mass | UV |
|---|---|---|---|---|---|---|---|
| 143 | 37.9–41.5 | 1.15(3H, t, J=7.6Hz, CH3)-2.75(2H, br, CH2)-5.25(2H, s, OH)-6.73(1H, s, Ar—H) 6.88(1H, s, Ar—H)-7.00(1H, s, Ar—H)-7.21–7.29(2H, m, Ar—H)-7.37(1H, d, J=7.5Hz, Ar—H)-7.51(1H, d, J=7.1Hz, | CDCl3 | 3499-3262-1588 | orange needle crystal | 270 (M+, Base) | εmax 36839 (λmax 219.2 nm)-- |

TABLE 15-continued

| Example No | melting point (centi degree) | NMR | NMR solvent | IR | Appearance | Mass | UV |
|---|---|---|---|---|---|---|---|
| 144 | | Ar—H) 0.99(3H, t, J=7.2Hz, CH3)-1.62–1.73(2H, m, CH2)-3.08(1H, dd, J=14.8, 10.3Hz, CH2)-3.25(1H, dd, J=14.8, 3.6Hz, CH2)-3.42(1H, m, CH)-5.24(1H, brs, OH)-5.32(1H, brs, OH)-6.71(1H, s, Ar—H) 6.98(1H, s, Ar—H)-7.04(1H, t, J=7.2Hz, Ar—H)-7.12(1H, d, J=7.13Hz, Ar—H)-7.17(1H, t, J=7.6 | CDCl3 | 3379-2962-2932-2873-1598-1504 | orange oil | 272 (M+, Base) | εmax 8392 (λmax 273.6 nm)-εmax 45531 (λmax 205.2 nm)- |
| 145 | 68.2–70.1 | 2.40(3H, s, CH3)-5.31(1H, s, OH)-6.71(1H, s, Ar—H)-6.92(1H, s, Ar—H)-7.00(1H, s, Ar—H)-7.24–7.29 (3H, m, Ar—H)-7.38(1H, d, J=1.5Hz, Ar—H)-7.50 (1H, d, J=Hz, Ar—H)- | CDCl3 | 3393-3216-1589 | orange needle crystal | 256 (M+, Base) | εmax 19345 (λmax 265.6 nm)-εmax 39937 (λmax 219.2 nm)-- |
| 146 | | (3H, t, J=Hz, CH3)-2.98(1H, dd, J=14.8, 9.8Hz, CH2)-3.39(1H, dd, J=14.8, 3.9Hz, CH2)-(1H, q, CH)-5.12(1H, s, OH)-5.24(1H, s, OH)-6.70(1H, s, Ar—H) 7.00(1H, s, Ar—H)-7.02–7.06(1H, m, Ar—H)-7.16 (2H, s, Ar—H)-7.40(1H, d, J=7.6Hz, Ar—H) | CDCl3 | 3369-2962-2927-1598-1506-1472 | pale yellow oil | 258 (M+, Base) | λmax nm (ε)-206.0 (47400)-273.2 (8700) |
| 147 | | 1.16(3H, t, J=7.6Hz, CH3)-2.77(2H, d, J=6.6Hz, CH2)-4.74(1H, s, OH)-6.72(1H, dd, J=8.4, 2.4Hz, CH)-6.94(1H, s, Ar—H)-6.98(1H, d, J=2.3Hz, Ar—H)-7.09(1H, d, J=8.4Hz, Ar—H) 7.23(1H, dd, J=7.2, 0.9Hz, Ar—H)-7.29(1H, td, J=7.1, 1.2Hz, Ar—H)-7.38(1H, d, J=7.7Hz, Ar—H)-7.52(1H, dd, | CDCl3 | 3213-2962-2926-2869-1593 | pale red oil | 254 (M+, Base) | λmax nm (ε)-212.0 (40800)-sh 230 (27300)-263.6 (20200)-292.8 (sh 7000) |
| 148 | | 0.99(3H, t, J=7.4Hz, CH3)-1.59–1.77(2H, m, CH2)-3.06(1H, dd, J=15.2, 10.2Hz, CH2)-3.29(1H, dd, J=15.2, 3.2Hz, CH2)-3.47(1H, q, CH)-4.62(1H, s, OH)-6.63(1H, dd, J=8.2, 2.6Hz, Ar—H)-6.94(1H, d, J=2.5Hz, Ar—H)-7.01(1H, d, J=8.3Hz, Ar—H)-7.07(1H, td, J=7.8, 7.8Hz, Ar—H) 7.15(1H, d, J= | CDCl3 | 3360-2962-2931-2873-1601-1493 | colorless oil | 256 (M+)-213 (Base) | λmax nm (ε)-203.6 (31900)-274.0 (6800) |
| 149 | | 2.40(3H, s, CH3)-4.86(1H, s, OH)-6.71 (1H, dd, J=8.4, 2.5Hz, Ar—H)-6.98(2H, s, Ar—H)-7.07(1H, d, J=8.4Hz, Ar—H)-7.23–7.31(2H, m, Ar—H)-7.4(1H, dd, J=7.7, 1.0Hz, Ar—H)-7.51 (1H, d, J=7.5, 0.9Hz, Ar—H)- | CDCl3 | 3369-1598-1489-1473 | red oil | 240 (M+, Base) | εmax 17324 (λmax 264.4 nm)-εmax 35918 (λmax 208.0 nm) |
| 150 | | 1.06(6H, t, J=7.5Hz, CH3)-2.51–2.56(1H, m, CH2) 3.31–315(1H, m, CH2) 5.39(2H, brs, OH)-6.99(1H, s, Ar—H) 7.03(1H, s, Ar—H)-7.15–7.16(1H, m, Ar—H)-7.24–7.26(1H, m, Ar—H)-7.37–7.38(1H, m, Ar—H)-7.47–7.48(1H, m, Ar—H)- | CDCl3 | 3491-3308-2978-2969-2933-2871-2834-1608-1584-1503- | | 300 (M+, Base)-285-267-254 | εmax 19832 (λmax 266.8 nm)-εmax 28582 (λmax 239.6 nm)-εmax 44022 (λmax 206.0 nm)- |
| 151 | | 1.29(3H, d, J=7.0Hz, CH3)-2.98(1H, dd, J=15.1, 9.9Hz, CH2)-3.38(1H, dd, J=15.1, 3.2Hz, CH2)-3.72–3.78(1H, m, CH)-4.7(1H, s, OH)-6.64(1H, dd, J=8.4, 2.6Hz, Ar—H)-6.96(1H, d, J=2.5Hz, Ar—H)-7(1H, d, J=8.3Hz, Ar—H)-7.05–7.10(1H, m, Ar—H)-7.19(2H, d, J=3.0Hz, Ar—H)-7.43(1H, d, J=7.7Hz, Ar—H) | CDCl3 | 3361-2962-2927-2874-1601-1494 | colorless oil | | λmax nm (ε)-205.6 (36500)-272.4 (8300) |
| 152 | | 0.98(3H, t, J=7.6Hz, CH3)-1.34–1.42(2H, m, CH2)-1.95–2.05(1H, m, CH2)-2.43–2.48(1H, m, CH2)-4.82(1H, t, J=8Hz, CH)-7.06(1H, s, Ar—H)-7.14(1H, t, J=8Hz, Ar—H)-7.33–7.40(2H, m, Ar—H)-7.58(1H, s, Ar—H)-7.65(1H, d, J=7.6Hz, Ar—H) | CDCl3 + CD3OD | 3372-3270-2959-2937-2873-1647-1595-1582-1506-1462 | | | |
| 153 | 242.9–248.4 | 0.91(3H, t, J=7.2Hz, CH3)-1.92–2.01(1H, m, CH2)-2.33–2.43(1H, m, CH2)-4.61–4.65(1H, m, CH)-6.59–6.60(1H, m, Furyl-H)-6.98(1H, s, Ar—H)-7.04(1H, d, J=3.3Hz, Furyl-H)-7.39(1H, d, J=8.2Hz, Ar—H)-7.50(1H, s, Ar—H)-7.77(2H, m, Ar—H, Furyl-H)-8.01(1H, s, Ar—H)- | DMSO-d6 | 3504-3288-2968-2935-2877-1645-1596-1503-1465 | orange needle crystal | 352 (M+, Base)-323 | λmax nm (ε)-205.2 (28400)-244.4 (24400)-260.0 (22500)-280.4 (21200)-328.8 (sh 7500) |

TABLE 16

| Example No | melting point (centi degree) | NMR | NMR solvent | IR | Appearance | Mass | UV |
|---|---|---|---|---|---|---|---|
| 154 | 274.3–276.1 | 0.99(3H, t, J=7.2Hz, CH3)-2.01–2.08(1H, m, CH2)-2.39–2.51(1H, m, CH2)-4.72(1H, t, J=7.0Hz, CH)-7.04(1H, s, Ar—H)-7.44(1H, t, J=7.2Hz, Ar—H)-7.51(3H, q, J=7.6Hz, Ar—H)-7.57(1H, s, Ar—H)-7.73(2H, d, J=7.5Hz, Ar—H)- | DMSO-d6 | 3480-3343-1645-1600-1508 | orange amorphous | 362 (M+, Base) 335- | λmax nm (ε)-204.4 (54900)-246.4 (37300)-260.8 (40400)-332.4 (6200) |

TABLE 16-continued

| Example No | melting point (centi degree) | NMR | NMR solvent | IR | Appearance | Mass | UV |
|---|---|---|---|---|---|---|---|
| 155 | 270.3–271.9 | 0.98(3H, t, J=7.2Hz, CH3)-1.98–2.05(1H, m, CH2)-2.41–2.49(1H, m, CH2)-4.69(1H, t, J=7.1Hz, CH)-7.04(1H, s, Ar—H)-7.2(1H, dd, J=4.7, 4.0Hz, Ar—H)-7.43(1H, d, J=8.2Hz, Ar—H)-7.57(1H, s, Ar—H)-7.63(1H, dd, J=2.6, 2.5Hz, Ar—H)-7.78(1H, dd, J=8.1, 1.5Hz, Ar—7.81(1H, dd, J=8.1, 1.4Hz, Ar—H)-8.02(1H, d, J=1.4Hz, Ar—H)- | DMSO-d6 | 3509-3282-2974-2934-2875-1645-1597-1506 | red needle crystal | 368 (M+, Base)- | λmax nm (ε)-205.6 (30200)-246.4 (28900)-260 (sh 24700)-285.2 (25800) |
| 156 | 109.7–111.9 | 1.03(3H, t, J=7.2Hz, CH3)-2.08–2.15(1H, m, CH2)-2.49–2.56(1H, m, CH2)-4.79(1H, t, J=7.2Hz, CH)-6.03(1H, s, OH)-7.16(1H, s, Ar—H)-7.22(1H, s, OH)-7.42(1H, d, J=8.1Hz, Ar—H)-7.54(1H, t, J=7.8Hz, Ar—H)-7.60–7.62(2H, m, Ar—H)-7.71(1H, d, J=7.6Hz, Ar— | CDCl3 | 3325-2970-2939-2879-1649-1602-1507-1336 | pale brown needle crystal | 430 (M+, base) | λmax nm (ε)-334.8 (4800)-260.4 (36100)-248.4 (sh 31600)-205.6 (43800) |
| 157 | 175.5–176.8 | 1.03(3H, t, J=7.5Hz, CH3)-2.07–2.14(1H, m, CH2)-2.49–2.56(1H, m, CH2)-4.77(1H, t, J=6.8Hz, CH)-7.14(1H, s, Ar—H)-7.31–7.42(4H, m, Ar—H)-7.52(1H, s, Ar—H)-7.58(1H, d, J=8.1Hz, Ar—H)-7.87(1H, d, J=1.6Hz, Ar—H)-7.95(1H, s, Ar—H) | CDCl3 | 3494-3302-2967-2936-2877-1646-1595-1581-1508-1466 | pale brown amorphous | 396 (M+, Base)-363- | λmax nm (ε)-334.4 (6200)-260.8 (41000)-246.4 (sh 35500)-209.2 (49700) |
| 158 | 179.2–181.1 | 1.00(3H, t, J=7.2Hz, CH3)-2.00–2.07(1H, m, CH2)-2.26(3H, s, Ar—CH3)-2.46–2.54(1H, m, CH2)-4.68–4.72(1H, m, CH0-7.03(1H, s, Ar—H)-7.24–7.34(4H, m, Ar—H)-7.46(1H, d, J=8.1Hz, Ar—H)-7.51(1H, dd, J=8.1, 1.2Hz, Ar—H)-7.58(1H, s, Ar—H)-7.70(1H, d, J=1.2Hz, CH)-9.65(1H, s, OH)-10.26(1H, s, OH | DMSO-d6 | 3511-3293-2970-2935-2877-1645-1599-1507-1455 | dark red amorphous | 376 (M+, Base) | λmax nm (ε)-337.2 (5300)-290 (sh 11200)-258.4 (31000)-244.4 (32500)-207.6 (46600) |
| 159 | 238.7–241.7 | 3.04(2H, q, J=4.1Hz, CH2)-3.29(2H, q, J=3.9Hz, CH2)-6.31(1H, d, J=2.3Hz, Ar—H)-6.39(1H, d, J=2.4Hz, Ar—H)-6.64(1H, dd, J=3.6, 1.7Hz, Ar—H)-7.03(1H, d, J=3.1Hz, Ar—H)-7.36(3H, d, J=8.0Hz, Ar—H)-7.62(1H, dd, J=7.6, 1.8Hz, Ar—H)-7.79(1H, d, J=1.7Hz, Ar—H)-9.3(1H, s, OH)-9.53(1H, s, OH) | DMSO-d6 | 3478-3430-2974-1644-1600-1500 | | 352 (M+, Base)-295-319- | λmax nm (ε)-301.6 (33200)-286 (sh 31400)-239.6 (25800)-204.4 (33600) |
| 160 | 271.9–273.3 | 0.99(3H, t, J=7.2Hz, CH3)-2.02–2.05(1H, m, CH2)-2.39(3H, s, CH3)-2.45–2.48(1H, m, CH2)-4.70(1H, t, J=7.2Hz, CH)-7.04(1H, s, Ar—H)-7.32(2H, d, J=7.9Hz, Ar—H)-7.46(1H, d, J=8.2Hz, Ar—H)-7.57(1H, s, Ar—H)-7.63(2H, d, J=8.0Hz, Ar—H)-7.79(1H, d, J=8.0Hz, Ar—H)-7.99(1H, d, J=1.0Hz, Ar—H)-9.9 | DMSO-d6 | 3494-3315-2970-2878-1645-1599-1505 | orange needle crystal | 376 (M+, Base) | λmax nm (ε)-262.4 (40933)-245.6 (37746)-204.4 (63180) |
| 161 | 277.4–279.2 | 0.94(3H, t, J=7.4Hz, Ch3)-2.04(2H, m, CH2)-4.66(1H, t, J=6.0Hz, CH)-6.97(1H, s, Ar—H)-7.27–7.34(2H, m, Ar—H)-7.51(1H, s, Ar—H)-7.61–7.67(3H, m, Ar—H)-7.78–7.82(3H, m, Ar—H)-9.62(1H, brs, OH)-10.09(1H, brs, OH) | DMSO-d6 | 3509-3288-2965-2874-1647-1597-1506-1450 | needle crystal | 402 (M+, Base) | λmax nm (ε)-336 (sh 33900)-318.8 (46200)-241.2 (30200)-207.6 (46100) |
| 162 | 225.7–227.4 | | | 3507-3282-1645-1598-1583-1502 | needle crystal | | λmax nm (ε) |
| 163 | 225.7–227.3 | | | | needle crystal | | λmax nm (ε) |

TABLE 17

| Example No | melting point (centi degree) | NMR | NMR solvent | IR | Appearance | Mass | UV |
|---|---|---|---|---|---|---|---|
| 166 | | 0.90(3H, t, J=7.2Hz, CH3)-1.91–1.97(1H, m, CH2)-2.35–2.41(1H, m, CH2)-4.61(1H, t, J=7.2Hz, CH)-6.96(1H, s, Ar—H)-7.23(1H, t, J=7.6Hz, Ar—H)-7.35(1H, d, J=7.7Hz, Ar—H)-7.45–7.49(2H, m, Ar—H)-7.70(1H, d, J=7.6Hz, Ar—H) | DMSO-d6 | | | | εmax 6269 (λmax 338.8 nm)-εmax 23173( λmax 257.6 nm)-εmax 23680 (λmax 243.6 nm)- |
| 167 | | 0.90(3H, t, J=7.2Hz, CH3)-1.92–1.95(1H, m, CH2)-2.36–2.41(1H, m, CH2)-4.61(1H, t, J=7.2Hz, CH)-6.96(1H, s, Ar—H)-7.23(1H, t, J=7.2Hz, Ar—H)-7.35(1H, d, J=7.7Hz, Ar—H)-7.45–7.49(2H, m, Ar—H)-7.70(1H, d, J=7.6Hz, Ar—H)- | DMSO-d6 | | | | εmax 6426(λmax 339.2 nm)-εmax 23731 (λmax 257.6 nm)-εmax 24247 (λmax 243.6 nm) |
| 168 | 293.2 (decomposition) | 0.99(3H, t, J=7.2Hz, CH3)-2.01–2.08(1H, m, CH2)-2.45–2.2.52(1H, m, CH2)-4.75(1H, t, J=7.2Hz, CH)-7.07(1H, s, Ar—H)-7.33(1H, t, J=7.6Hz,)-7.40(1H, t, J=7.6Hz,)-7.54(1H, d, J=8.3Hz, Ar—H)-7.58(1H, s, Ar—H)-7.59(1H, s, Ar—H)-7.69(1H, d, J=8.2Hz, Ar—H) | DMSO-d6 | | pale brown amorphous | 402 (M+, Base) | λmax nm (ε)-310.4 (32461)-245.6 (31228)-206.4 (48450) |

TABLE 17-continued

| Example No | melting point (centi degree) | NMR | NMR solvent | IR Appearance | Mass | UV |
|---|---|---|---|---|---|---|
| 169 | 216.8–219.1 | 7.72(1H, d, J=7.6Hz, Ar—) 0.99(3H, t, J=7.4Hz, CH3)-2.01–2.08(1H, m, CH2)-2.39–2.51(1H, m, CH2)-4.72(1H, t, J=7.2Hz, CH)-7.05(1H, s, Ar—H)-7.49–7.51(3H, m, Ar—H)-7.57(1H, s, Ar—H)-7.82–7.84(1H, m, Ar—H)-7.86–7.88(2H, m, Ar—H)-8.06(1H, s, Ar—H)-10.04(2H, brs, OH) | DMSO-d6 | pale brown needle crystal | 446 (M+, Base) | λmax nm (ε)-260.4 (36913)-245.2 (35410)-204.0 (59710) |
| 170 | >312 (decomposition) | 0.99(3H, t, J=7.2Hz, CH3)-2.01–2.08(1H, m, CH2)-2.44–2.51(1H, m, CH2)-4.73(1H, t, J=7.2Hz, CH)-7.07(1H, s, Ar—H)-7.41–7.52(3H, m, Ar—H)-7.58(1H, s, Ar—H)-7.90(2H, d, J=7.9Hz, Ar—H)-8.01–8.05(2H, m, Ar—H)-8.16(1H, s, Ar—H)-9.68(1H, s, OH)-10.30(1H, s, OH) | DMSO-d6 | brown amorphous | 446 (M+, Base) | λmax nm (ε)-302.8 (21641)-209.6 (44871) |
| 171 | >300 | 1.0(3H, t, J=6.8Hz, CH3)-2.04–2.07(1H, m, CH2)-2.45–2.52(1H, m, CH2)-4.73(1H, t, J=7.2Hz, CH)-7.06(1H, s, Ar—H)-7.42–7.56(4H, m, Ar—H)-7.58(1H, s, Ar—H)-7.77–7.89(7H, m, Ar—H)-8.09(1H, s, Ar—H) | DMSO-d6 | pinkish white amorphous | 438 (M+, Base) | λmax nm (ε)-279.6 (33361)-245.6 (25555)-205.6 (59442) |
| 172 | 251.4–255.5 (decomposition) | 0.94(3H, t, J=7.2Hz, CH3)-1.98–2.07(2H, m, CH2)-4.66(1H, t, J=7.1Hz, CH)-6.96(1H, s, Ar—H)-7.35–7.40(2H, m, Ar—H)-7.51(1H, s, Ar—H)-7.60–7.66(2H, m, Ar—H)-7.77(1H, d, J=8Hz, Ar—H)-7.85(1H, d, J=8Hz, Ar—H)-7.97–8.01(2H, m, Ar—H)-9.68(1H, s, OH)-10.30 (1H, s, OH) | DMSO-d6 | pinkish white amorphous | 418(M+, Base)-361-385 | λmax nm (ε)-233.2 (38900)-250.0 (33300)-312.0 (29900)-340.0 (21700) |
| 173 | | 0.92(3H, t, J=7.2Hz, CH3)-1.94–1.99(1H, m, CH2)-2.37–2.41(1H, m, CH2)-4.61(1H, t, J=7.1Hz, CH)-6.79(1H, d, J=8.1Hz, Ar—H)-6.94(1H, dd, J=8.1, 1.8Hz, Ar—H)-6.98(1H, s, Ar—H)-7.01(1H, d, J=1.8Hz, Ar—H)-7.35(1H, d, J=8.1Hz, Ar—H)-7.50(1H, s, Ar—H)-7.60(1H, dd, J=8.1, 1.3Hz, Ar—H)-7.79(1H, | DMSO-d6 | pale brown oil | 349 (M+, Base) | |
| 174 | | 0.92(3H, t, J=7.2Hz, CH3)-1.94–1.99(1H, m, CH2)-2.35–2.42(1H, m, CH2)-4.60(1H, t, J=7.2Hz, CH)-6.29(1H, dd, J=8.4, 2.0Hz, Ar—H)-6.39(1H, d, J=2.0Hz, Ar—H)-6.96(1H, s, Ar—H)-7.06(1H, d, J=8.3Hz, Ar—H)-7.30(1H, d, J=8.1Hz, Ar—H)-7.50(1H, s, Ar—H)-7.56(1H, d, J=8.1Hz, Ar—H)-7.79(1H, s, Ar— | DMSO-d6 | pale orange oil | 394 (M+, Base) | |
| 175 | 221.8–225.0 | 0.94(3H, t, J=7.2Hz, CH3)-1.98–2.01(1H, m, CH2)-2.39–2.47(1H, m, CH2)-4.69(1H, t, J=7.2Hz, CH)-7.01(1H, s, Ar—H)-7.48(1H, d, J=8.2Hz, Ar—H)-7.53(1H, s, Ar—H)-7.75(1H, t, J=8Hz, Ar—H)-7.87(1H, dd, J=8, 1.9Hz, Ar—H)-8.11(1H, d, J=1.9Hz, Ar—H)-8.16(1H, d, J=7.7Hz, Ar—H)-8.21-8.23(1H, m, Ar | DMSO-d6 | yellow needle crystal | 407 (M+, Base)- | λmax nm (ε)-260.4 (52815)- |
| 176 | 245.5–246.4 | 0.93(3H, t, J=7.2Hz, CH3)-1.95–1.99(1H, m, CH2)-2.39–2.42(1H, m, CH2)-4.62–4.65(1H, m, CH)-5.15(2H, s, NH2)-6.56(1H, dd, J=7.9, 1.6Hz, Ar—H)-6.77(1H, d, J=7.8Hz, Ar—H)-6.84(1H, d, J=1.6Hz, Ar—H)-6.98(1H, s, Ar—H)-7.08(1H, dd, J=7.9, 7.8Hz, Ar—H)-7.39(1H, d, J=8.2Hz, Ar—H)-7.51(1H, s, Ar | DMSO-d5 | pinkish white amorphous | 377 (M+, Base) | λmax nm (ε)-243.2 (43705)-206.4 (49928) |

TABLE 18

| Example No | melting point (centi degree) | NMR | NMR solvent | IR Appearance | Mass | UV |
|---|---|---|---|---|---|---|
| 177 | 155.4–159.4 | 0.93(3H, t, J=7.2Hz, CH3)-1.95–1.99(1H, m, CH2)-2.38–2.41(1H, m, CH2)-4.60–4.64(1H, m, CH)-6.83(2H, d, J=9.3Hz, Ar—H)-6.70(1H, s, Ar—H)-7.36(1H, d, J=8.2Hz, Ar—H)-7.50(3H, d, J=9.3Hz, Ar—H)-7.66(1H, dd, J=8.2, 1.9Hz,, Ar—H)-7.86(1H, d, J=1.9Hz, Ar—H)- | DMSO-d6 | pinkish white needle crystal | 378 (M+, Base) | |
| 178 | | 1.00(3H, t, J=7.2Hz, CH3)-2.03–2.06(1H, m, CH2)-2.53–2.57(1H, m, CH2)-3.97(3H, s, OCH3)-4.71–4.74(1H, m, CH)-5.54(1H, s, OH)-7.01(1H, s, Ar—H)-7.13–7.16(1H, m, Ar—H)-7.34–7.41(2H, m, Ar—H)-7.65(1H, d, J=7.6Hz, Ar—H)-7.76(1H, s, Ar—H)-- | CDCl3 | colorless needle crystal | 300 (M+, Base)-285 | |
| 179 | | 1.01(3H, t, J=7.2Hz, CH3)-2.02–2.09(1H, m, CH2)-2.51–2.58(1H, m, CH2)-3.89(3H, s, OCH3)-4.70–4.73(1H, m, CH)-6.08(1H, s, OH)-7,12(1H, s, Ar—H)-7.14–7.16(1H, m, Ar—H)-7.33–7.41(2H, m, Ar—H)-7.65(1H, d, J=7.7Hz, Ar—H)-7.71(1H, s, Ar—H)-- | CDCl3 | pale orange needle crystal | 300 (M+, Base)-285 | |
| 180 | | 0.90(3H, t, J=7.3Hz, CH3), 1.97(1H, m, CH2CH3), 2.42(1H, m, CH2CH3), 3.3–3.5(7H, m, Glu-H), 4.03(1H, m, Glu-H), 4.61(1H, m, 11-H), 5.29(0.5H, d, J=7.3Hz, anomeric), 5.18(0.5H, d, J=7.3Hz, anomeric), 7.2–7.8(6H, m, aromatic) | DMSO-d6 | | | UV|max: 244 nm (e 25,100), 272 (12,700), 337 (4,000) |

Example 164

Preparation of 11-Ethyl-7,9-dihydroxy-10,11-dihydrodibenzo[b,f]thiepin-10-one (Compound of Example 4)

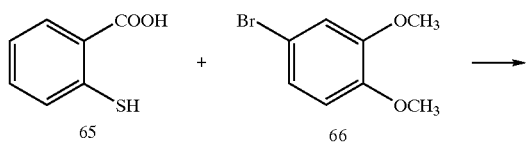

65          66

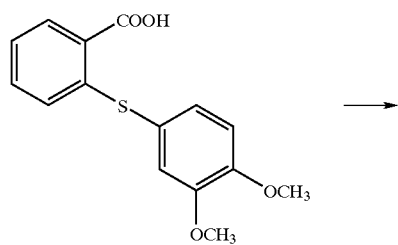

67

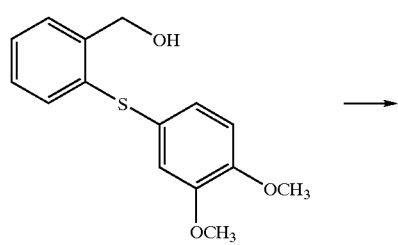

68

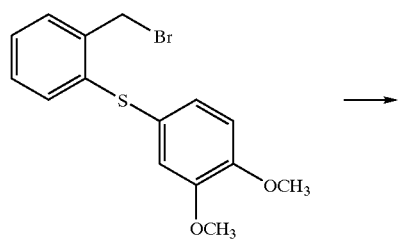

69

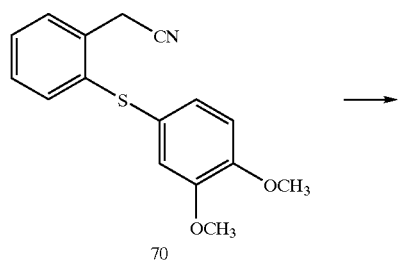

70

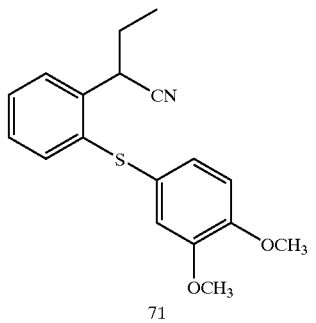

71

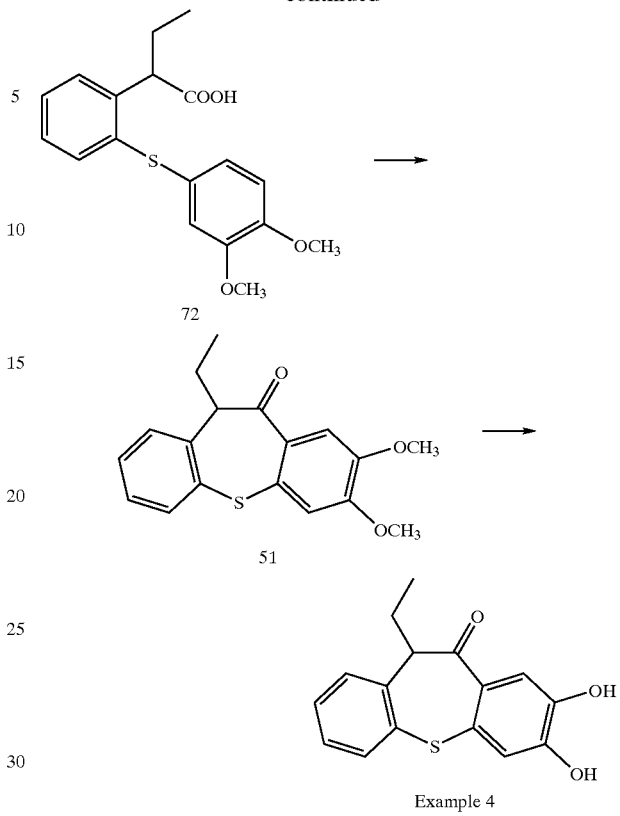

Example 4

Synthesis of Carboxylic Acid (67)

A mixture of 39.3 g (F.W. 154.19, 255 mmol) of thiosalicylic acid (65), 55.4 g (F.W. 217.06, 255 mmol) of 4-bromoveratrole, 1.90 g (F.W. 63.55, 30.0 mmol) of copper (powder), 5.7 g (F.W. 190.45, 30.0 mmol) of copper (I) iodide, 45.0 g (F.W. 138.21, 326 mmol) of potassium carbonate and 120 mL of N-methyl-2-pyrrolidone was stirred at 150° C. for four hours. After the reaction, the reaction solution was cooled by standing to 70 to 80° C., and ice water was added thereto and the resulting solution was made pH 2 with hydrochloric acid. The deposited crude crystals were collected by filtration, washed with water, diisopropyl ether and hexane in the order named and dried to obtain 74.4 g of a crude product. This product was recrystallized from 1,4-dioxane to obtain 55 g of carboxylic acid (67). Ethyl acetate was added to the crude carboxylic acid obtained by concentrating the mother liquor, and the resulting solution was filtered and then, the residue was washed with ethyl acetate to obtain 6.1 g (total yield 83%) of carboxylic acid (67).

Synthesis of Alcohol (68)

To a solution of 75.2 g (F.W. 290.34, 259 mmol) of carboxylic acid (67) in 200 mL of tetrahydrofuran, 10.4 g (F.W. 37.83, 274 mmol) of sodium borohydride was added at 0° C. and then, 37.0 mL (F.W. 141.93, d=1.154, 301 mmol) of boron trifluoride diethyl etherate was added dropwise thereto at the same temperature, and the resulting solution was stirred at room temperature for one hour. To this reaction solution was slowly added ice water and the resulting solution was extracted with ethyl acetate and the extract was washed with water and then with a saturated sodium chloride aqueous solution. The obtained reaction solution was dried with anhydrous magnesium sulfate and then, the solvent was removed under reduced pressure to obtain 73.4 g of crude alcohol (68).

Synthesis of Bromide (69)

To a solution of 73.4 g (F.W. 276.36) of crude alcohol (68) in 100 mL of methylene chloride, 8.5 mL (F.W. 270.70, d=2.850, 89.0 mmol) of phosphorus tribromide was added at 0° C. After stirring at room temperature for 30 minutes, this reaction solution was added onto crushed ice. The solution was further stirred at room temperature for 30 minutes and then, water was added thereto and the resulting solution was extracted with methylene chloride and the extract was washed with water and a saturated sodium chloride aqueous solution. The obtained solution was dried with anhydrous magnesium sulfate and then, the solvent was removed under reduced pressure. As the result, 83.4 g of a crude product was obtained. This crude bromide was recrystallized from methylene chloride-hexane to obtain 75.2 g of bromide (69). The yield was 86% in two steps.

Synthesis of Nitrile Compound (70)

To 15 mL of water was dissolved 1.76 g (F.W. 49.01, 36.0 mmol) of sodium cyanide and then, 20 mL of ethanol was added thereto. To the resulting solution was slowly added 10.2 g (F.W. 339.25, 30.0 mmol) of bromide (69) at room temperature. This mixed solution was heated to 80° C. and stirred at the same temperature for 30 minutes. This reaction solution was cooled by standing to room temperature while vigorously stirring. Ethanol was removed under reduced pressure and water was added to the remaining solution. The deposited crude crystals were collected by filtration and washed with water. After drying, 8.13 g of a crude nitrile compound was obtained. These crude crystals were recrystallized from ethyl acetate-hexane to obtain 7.30 g (yield 85.3%) of nitrile compound (70).

Synthesis of Ethylated Compound (71)

To a solution of 22.8 g (F.W. 285.37, 80.0 mmol) of nitrile compound (70) in 50 mL of methylene chloride was added dropwise 6.72 mL (F.W. 155.95, d=1.94, 84.0 mmol) of ethyl iodide and stirred. Furthermore, 27,2 g (F.W. 339.54, 80.0 mmol) of tetrabutylammonium hydrogen sulfate was added thereto to completely dissolve nitrile compound (70). To this solution was added dropwise a 20% sodium hydroxide aqueous solution (80 g) and then, stirred at room temperature for one hour. Under cooling with ice, the reaction was neutralized by addition of 4N hydrochloric acid and then, extracted with methylene chloride and the organic layer was washed with water and a saturated sodium chloride aqueous solution. The obtained solution was dried with anhydrous magnesium sulfate and then, the solvent was removed under reduced pressure to obtain an oily product. To the residue was added a 3:1=hexane:ethyl acetate mixture to remove tetrabutylammonium iodide deposited by filtration. The filtrate was removed under reduced pressure to obtain 27.0 g of crude ethylated compound (71).

Synthesis of Phenylacetic Acid (72)

To a mixture of 27.0 g (F.W. 313.41, 77.2 mmol) of crude ethylated compound (71) and 66 mL of ethylene glycol was added a 30% sodium hydroxide aqueous solution (42.7 g). The resulting solution was stirred at 150° C. overnight. To the reaction solution was added ice and the resulting solution was neutralized with 4N hydrochloric acid. The neutralized solution was extracted with ethyl acetate and the extract was washed with water and then with a saturated sodium chloride aqueous solution. The obtained solution was dried with anhydrous magnesium sulfate and then, the solvent was completely removed under reduced pressure to obtain 29.0 g of crude phenylacetic acid (72). This crude phenyacetic acid was recrystallized from ethyl acetate-hexane to obtain 23.0 g of phenylacetic acid (72). The yield was 87% in two steps.

Synthesis of Cyclized Compound (51)

To 10.0 g (F.W. 332.41, 30.1 mmol) of dried phenylacetic acid (72) was added 50 mL of methanesulfonic acid to dissolve phenylacetic acid (72) and then, stirred at room temperature overnight. To the reaction solution was added water under cooling with ice and then, the resulting solution was partitioned with ethyl acetate and water, and the organic layer was washed with water and then with a saturated sodium chloride aqueous solution. The obtained solution was dried with anhydrous sodium sulfate and then, the solvent was removed under reduced pressure to obtain 9.52 g of a crude product. A small amount of ethyl acetate was added to this crude product which was then collected by filtration then, the residue was washed with a small amount of ethyl acetate to obtain 8.84 g (yield 93.4%) of cyclized compound (52).

To 25.0 g (F.W. 314.40, 80.0 mmol) of cyclized compound (51) was added 150 g of pyridine hydrochloride and stirred at 200° C. for two hours. To the reaction mixture was added diluted hydrochloric acid and ethyl acetate and the resulting solution was extracted, and the organic layer was washed with water and then with a saturated sodium chloride aqueous solution and dried with anhydrous magnesium sulfate. The concentrated residue was dissolved in 800 mL of ethyl acetate and polar substances were adsorbed on 50 g silica gel and 25 g of Florisil and then, filtered. Ethyl acetate in the filtrate was concentrated and then, the residue was recrystallized from ethyl acetate-hexane to obtain 19.9 g (yield 87%) of the title compound.

Example 165

Preparation of 11-Ethyl-7,9-dihydroxy-10,11-15 dihydrodibenzo[b,f]thiepin-10-one (Compound of Example 4)

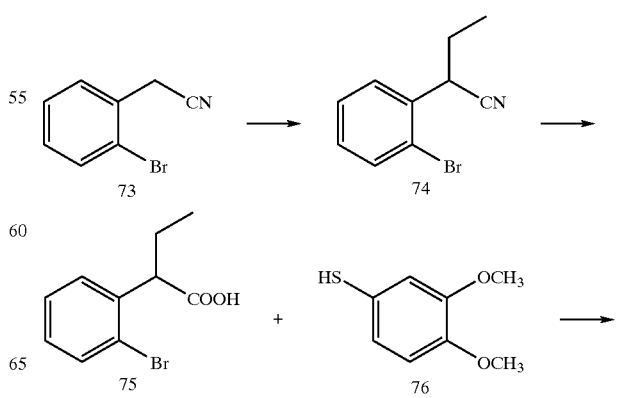

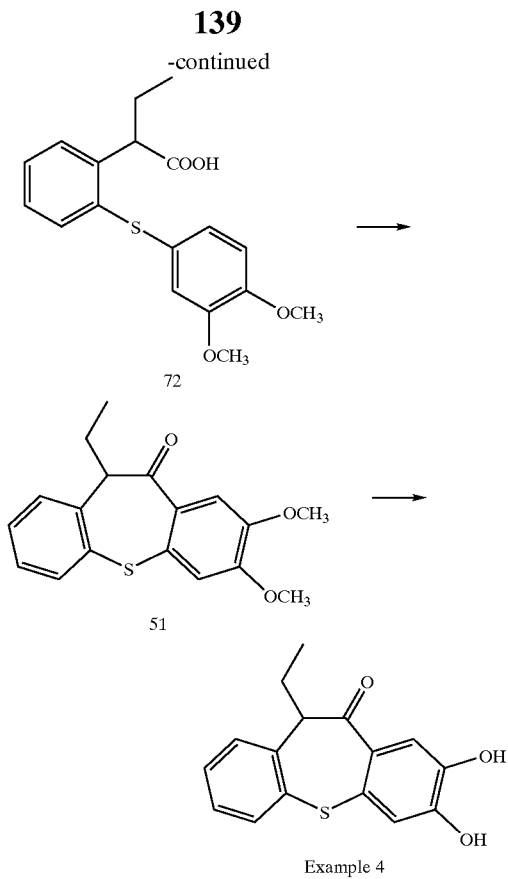

Example 4

Synthesis of Ethylated Compound (74)

To a solution of 30.0 g (F.W. 196.05, 153 mmol) of nitrile compound (73) and 13.6 mL (F.W. 155.97, d=1.94, 169 mmol) of ethyl iodide in 50 mL of toluene was quickly added a suspension of 51.8 g (F.W. 339.54, 153 mmol) of tetrabutylammonium hydrogen sulfate and a 20% sodium hydroxide aqueous solution (300 g) on an ice bath and stirred at room temperature for two hours. The crystals of tetrabutylammonium iodide produced were separated by filtration and the crystals were washed with 200 mL of toluene. The organic layer was washed with water and then with a saturated sodium chloride aqueous solution and dried with anhydrous magnesium sulfate. The solvent was removed under reduced pressure to obtain 34.4 g of ethylated compound (74).

Synthesis of Carboxylic Acid (75)

To 34.4 g (F.W. 224.10) of ethylated compound (74) were added a 6N sodium hydroxide aqueous solution (75.0 mL) and 75.0 mL of ethanol and stirred at 100° C. for two days. Ethanol was removed under reduced pressure and then, to the resulting solution was added toluene to effect partition. To the aqueous layer was added concentrated hydrochloric acid and the resulting solution was made pH 3. The solution thus obtained was extracted with ethyl acetate and washed with water and then with a saturated sodium chloride aqueous solution. After drying with anhydrous magnesium sulfate, the solvent was removed under reduced pressure to obtain about 38 g of a crude product. This crude product was recrystallized from hexane to obtain 33.5 g of carboxylic acid (75). The yield was 90% in two steps.

Synthesis of Phenylacetic Acid (72)

A mixture of 26.7 g (F.W. 243.10, 110 mmol) of carboxylic acid (75), 18.7 g (F.W. 170.23, 110 mmol) of 3,4-dimethoxythiophenol (76), 3.50 g (F.W. 63.55, 55.0 mmol) of copper (powder), 10.5 g (F.W. 190.45, 55.0 mmol) of copper (I) iodide, 18.2 g (F.W. 138.21, 132 mmol) of potassium carbonate and 140 mL of N-methyl-2-pyrrolidone was stirred at 140° C. for 3.5 hours. To the reaction solution was added ice and the resulting solution was made pH 6 to 7 with concentrated hydrochloric acid under cooling with ice. Toluene and water were added thereto to dissolve the product, and insolubles were separated by filtration. To the filtrate was added a 20% sodium hydroxide aqueous solution to effect partition. The organic layer was separated and further extracted with a 2% sodium hydroxide aqueous solution and then, combined with the aqueous layer and made pH 2 to 3 with concentrated hydrochloric acid under cooling with ice. The obtained solution was extracted with ethyl acetate and the organic layer was washed with water, and dried with anhydrous sodium sulfate and then, the solvent was removed under reduced pressure to obtain 35.1 g of a crude product. This product was washed with a small amount of diisopropyl ether and then, dried to obtain 28.7 g (yield 78.6%) of phenylacetic acid (72).

Synthesis of Cyclized Compound (51)

To 28.6 g (F.W. 332.41, 86.0 mmol) of dried phenylacetic acid compound (72) was added 140 mL of methanesulfonic acid and stirred at room temperature overnight. The reaction solution was added dropwise to ice water and the deposit was collected by filtration and then, washed with water. After drying, 26.9 g (yield 99.4%) of cyclized compound (51) was obtained.

To 18.9 g (F.W. 314.40, 60.0 mmol) of cyclized compound (51) was added 56.6 g of pyridine hydrochloride and stirred at 185° C. for six hours. The reaction mixture was completely cooled to room temperature and then, ice water and ethyl acetate were added thereto and the resulting solution was extracted therewith. The organic layer was washed with water and a saturated sodium chloride aqueous solution, subsequently dried with anhydrous sodium sulfate, and the solvent was removed under reduced pressure to obtain 16.2 g of a crude product. This crude product was recrystallized from 60% isopropyl alcohol to obtain 15.9 g (yield 92.4%) of the title compound.

Example 166

Preparation of (+)-11-Ethyl-7,9-dihydroxy-10,11-dihydrobenzo[b,f]thiepin-10-one [Optical Isomer (+) of Compound of Example 4]

Compound of Example 4 was subjected to optical resolution by a column under the conditions as described below to obtain a frontal peak. This compound had a specific rotation $[\alpha]_D$ (20° C.) of +16.7.

Column: CHIRALPAK AD

Mobile Phase: n-hexane/ethanol/acetic acid=40/60/0.1 (vol/vol)

Example 167

Preparation of (−)-11-Ethyl-7,9-dihydroxy-10,11-dihydrobenzo[b,f]thiepin-10-one [Optical Isomer (−) of Compound of Example 4]

Compound of Example 4 was subjected to optical resolution by a column under the conditions as described below to obtain a rear peak. This compound had a specific rotation $[\alpha]_D$ (20° C.) of −16.7.

Column: CHIRALPAK AD
Mobile Phase: n-hexane/ethanol/acetic acid=40/60/0.1 (vol/vol)

Example 178

Preparation of α-Ethyl-2-bromophenylacetic Acid (75)

It was confirmed that the title compound obtained by the same method as described in Example 165 of up to the second step had the following properties.

Description: Colorless plate crystals
Melting Point: 37–39° C. (cold hexane) $^1$H NMR (400 MHz, CDCl$_3$) δ: 0.94 (3H, dd, J=7.4, 7.4 Hz), 1.83 (1H, ddq, J=14.9, 7.4, 7.4 Hz), 2.10 (1H, ddq, J=14.9, 7.4, 7.4 Hz), 4.14 (1H, dd, J=7.4, 7.4 Hz), 7.12 (1H, ddd, J=8.0. 7.5, 1.6 Hz), 7.29 (1H, ddd, J=7.8, 7.5, 1.2 Hz), 6.94 (1H, dd, J=7.8, 1.2 Hz), 7.38 (1H, dd, J=8.0, 1.6 Hz) EIMS m/z: 244, 242 (M+), 199, 197, 171, 169, 163; IR (KBr)cm$^{-1}$: 1705; UV $\lambda_{max}$ (EtOH) nm (ε): 274 (40), 264 (300).

Example 179

Preparation of α-Ethyl-2-[(3,4-dimethoxyphenyl)thio]phenylacetic Acid (72)

It was confirmed that the title compound obtained by the same method as described in Example 164 of up to the sixth step and in Example 165 of up to the third step had the following properties.

Description: Light brown amorphous powder
Melting Point: 115.2–117.0° C. (Dec.); $^1$H NMR (400 MHz, CDCl$_3$) δ: 0.92 (3H, dd, J=7.4, 7.4 Hz), 1.79 (1H, ddq, J=14.8, 7.4, 7.4 Hz), 2.12 (1H, ddq, J=14.8, 7.4, 7.4 Hz), 3.79 (3H, s), 3.87 (3H, s), 4.33 (1H, dd, J=7.4, 7.4 Hz), 6.80 (1H, d, J=8.3 Hz), 6.88 (1H, d, J=1.9 Hz), 6.94 (1H, dd, J=8.3, 1.9 Hz), 7.14–7.26 (3H, m), 7.37; (1H, d, J=1.8, Hz); EIMS m/z: 332 (M$^+$, Base); IR (KBr) cm$^{-1}$: 1705, 1585, 1504, 1442; UV $\lambda_{max}$ (EtOH) nm (ε): 250 (15200), 283 (8000).

Example 180

To a mixture of 1.00 g (F.W. 286.37, 3.50 mmol) of the compound of Example 4 and 1N NaOH (4 mL) was added 6 mL of acetone dissolving 1.40 g (F.W. 397.2, 3.50 mmol) of methyl acetobromoglucuronate in small portions at 0° C. and stirred at room temperature for six hours while adjusting the pH to around 6 with 1N NaOH. After concentration, 20% NaOH (11.2 mL) was added to the concentrated solution and stirred at room temperature for 30 minutes. After cooling, to the obtained solution was added 5 mL of concentrated hydrochloric acid attentively and the resulting solution was made pH 2 to 3 with 1N hydrochloric acid and desalted with a column packed with "HP-20". The column was thoroughly washed with water, and then, the desired fraction was eluted with 100% methanol. The starting material was removed from 2.57 g of the obtained crude product by silica gel chromatography (silica gel 8 g; eluent; 33% ethyl acetate:hexane→20% ethanol:ethyl acetate). After concentration, the obtained crude product was further purified by HPLC (detection; 280 nm; mobile phase, 50% MeCN-H$_2$O containing 0.2% of AcOH). The concentrated oily substance was dissolved in dioxane and freeze-dried to obtain 463 mg (yield 36%) of the title compound.

TEST EXAMPLES

It will now be shown that the compounds of the present invention have excellent pharmacological activities with reference to Test Examples.

Test Example 1

Dilating Action on Contraction of Tracheal Smooth Muscles

With the use of pig tracheal muscles, the action of the compounds of the present invention on contraction of tracheal muscles has been investigated. The method refers to "Smooth Muscle Manual" (published by Bun'eido Publishing Co.), pp. 125–137. The trachea cartilage mucous membrane and submucous tissue of a pig trachea were removed to prepare a specimen of tracheal smooth muscles having a major diameter of about 10 mm and a minor diameter of about 1.5 mm. This specimen was suspended in a Magnus tube which was aerated with a mixed gas of 95% of oxygen and 5% of carbon dioxide and contained nutrient solution at 37° C. and a load of 0.8 g was applied to this specimen, and after the tension of the specimen was stabilized, the nutrient solution was replaced with a high concentration K+ solution (72.7 mM) to provoke K+ contraction. The procedure of replacing the solution in the Magnus tube with the nutrient solution to wash the solution and provoking K+ contraction with the high concentration K+ solution was repeated again until the contraction force became constant. When the tension of the K+ contraction became constant, each of the compounds described in Table 19 (the structural formula of the Comparative Example being described in the right side of the compound of the above described Example 180) was added to the high concentration K+ solution as the test substance to measure the change in tension. The test substance was dissolved in dimethyl sulfoxide at a predetermined concentration and added to the high concentration K+ solution in such a manner that the final concentration came to 10 mM. Further, the final concentration of dimethyl sulfoxide added was made 0.3% or less. The change in tension was led to a strain pressure amplifier ("AP-621G", manufactured by Nippon Koden Kogyo) through a FD pickup transducer ("TB-611T", manufactured by Nippon Koden Kogyo) and recorded on a recorder ("R-64V", manufactured by Rika Electric). When the tension before replacement with the high concentration K+ solution was regarded as 0% and the last tension which was generated by the high concentration K+ solution before the addition of a test substance was regarded as 100%, the contraction force of the tracheal smooth muscle two hours after addition of a test substance was shown as relative percentage. Further in this instance, the contraction by the high concentration K+ solution was approximately constant for at least two hours after the tension had been stabilized. The results are shown in Table 19.

TABLE 19

| Example No. | Relative Contraction Force (%) |
| --- | --- |
| 1 | 0 |
| 4 | 2.7 |
| 17 | 0 |
| 27 | 1.4 |
| 37 | 7.5 |
| 82 | 22.4 |
| 110 | 10.9 |
| 124 | 30.3 |
| ComparativeExample | 54.5 |

Test Example 2

Inhibition of Immediate Asthmatic Response, Late Asthmatic Response and Infiltration of Inflammatory Cells into Lung of Guinea Pigs It is reported [Pepys, J. and Hutchcroft, B. J., Bronchial provocation tests in etiologic diagnosis and analysis of asthma, *Am. Rev. Respir. Dis.*, 112, 829–859 (1975)] that when asthmatic patients are allowed to inhale an antigen, immediate asthmatic response (hereinafter referred to as "IAR") whose peak is 15 to 30 minutes after inhalation is provoked and recovery from this response is within two hours; however, in 60% of the asthmatic patients late asthmatic response (hereinafter referred to as "LAR") appears 4 to 12 hours after the inhalation of the antigen. LAR is considerably prolonged and is similar to a natural attack of asthma, particularly an attack of intractable asthma and thus, it is thought very important for the therapy of bronchial asthma to clarify the pathology. On the other hand, it is known that when the guinea pigs actively sensitized with an antigen are allowed to inhale the antigen again, biphasic airway responses are caused. Accordingly, as the animal model line of IAR and LAR which are recognized in the above described asthmatic patients, the asthmatic model using guinea pigs is widely used in the evaluation of drugs for asthma and the like. Furthermore, it is known that in the IAR and LAR model of guinea pigs, when actively sensitized guinea pigs are exposed to an antigen, infiltration of inflammatory cells into the airway occurs together with the biphasic airway contraction to cause various inflammatory disorders to airway tissues thereby. Therefore, the number of inflammatory cells in the bronchoalveolar lavage fluid is widely used as the index for the infiltration of inflammatory cells into the airway. Each of the above described actions in the IAR and LAR model of guinea pigs was examined with the compounds of the present invention.

Experimental Method (1) Sensitization

Guinea pigs were allowed to inhale a 1% ovalbumin ("OVA", sigma-Aldrich Co., U.S.A.) physiological saline for 10 minutes daily continuously for 8 days using of an ultrasonic nebulizer ("NE-U12", Omron, Japan).

(2) Challenge

One week after the final sensitization, the guinea pigs were allowed to inhale a 2% "OVA" physiological saline for 5 minutes using of the nebulizer. Twenty-four hours and one hour before challenge, the guinea pigs were dosed with metyrapone (10 mg/kg, Sigma-Aldrich Co., U.S.A.) intravenously, and dosed with pyrilamine (10 mg/kg, Sigma-Aldrich Co., U.S.A.) intraperitoneally 30 minutes before challenge.

(3) Preparation of Test Substance and Method of Administration

Each of the test substances (Compounds of Examples 1 and 4) was formed into a suspension with a 0.5% carboxymethyl cellulose sodium salt (hereinafter referred to as "CMC-Na") solution at a concentration of 2 mg/mL. One hour before challenge, the guinea pigs were orally dosed with the suspension of the test substance with such a dose so as to be 10 mg/kg. For the control group the medium (a 0.5% CMC-Na solution) was used.

(4) Measurement of Airway Resistance

The specific airway resistance (hereinafter referred to as "sRaw") was measured, 1 minute, 10 minutes and 30 minutes after challenge and furthermore, 1 hour, 2 hours, 3 hours, 4 hours, 5 hours, 6 hours, 7 hours, 8 hours and 24 hours, each time for the duration of 1 minute with the use of airway resistance measuring equipment ("Pulmos-1", M.I.P.S., Japan).

(5) Measurement of Number of Inflammatory Cells in Broncho-alveolar Lavage Fluid Twenty-three to twenty-four hours after the antigen challenge, the abdominal aorta of the guinea pigs was cut under intraperitoneal anesthesia with "Nembutal" (50 mg/kg) to remove blood and the chest was opened. A tube was inserted in the bronchus and fixed thereto and through this tube, 5 mL (37° C.) of a physiological saline was injected and sucked therethrough; this procedure was repeated twice (10 mL in total) and the recovered fluid was regarded as the bronchoalveolar lavage fluid (hereinafter referred to as "BALF"). BALF was centrifuged at 1,100 rmp at 4° C. for 10 minutes to obtain a precipitate (a pellet). This pellet was suspended in 1 mL of a physiological saline and a Turkliquid was added thereto and the number of leukocytes per $\mu$L was counted with a leukocyte counter plate. Centrifugation was repeated under the above described conditions and rabbit serum was added to the obtained pellet to prepare a smear preparation. After drying, the preparation was subjected to the May Grdnwald-Giemsa stain. The number of leukocytes was counted by a microscope and the ratio to the total number of cells of neutrophils, eosinophils, macrophages and lymphocytes was obtained and the number of cells per $\mu$L was calculated on the basis of this ratio.

(6) Statistical Analysis

The obtained test results were shown by mean values and standard deviations and the student's t-test was carried out. The level of significance was set to 5% or less. The number of animals used in each test group was 6.

Results (1) Antigen Induced Immediate and Late Asthmatic Responses

As shown in FIG. 1, with the actively sensitized guinea pigs, the airway resistance quickly increased by inhalation of "OVA" and increased after one minute, on average, by 475% of that before the challenge. Thereafter, the airway resistance quickly was reduced and decreased to 52% after three hours. Furthermore, the airway resistance increased again and reached 156% after 6 hours. The area under the response curve (hereinafter referred to as "AUC") from 4 hours to 8 hours was 466%·hr. From this, the biphasic response of the immediate asthmatic response which occurred within 30 minutes after the challenge (IAR) by the "OVA" inhalation and the late asthmatic response which occurred several hours (LAR) after the challenge was recognized.

Figure 2:
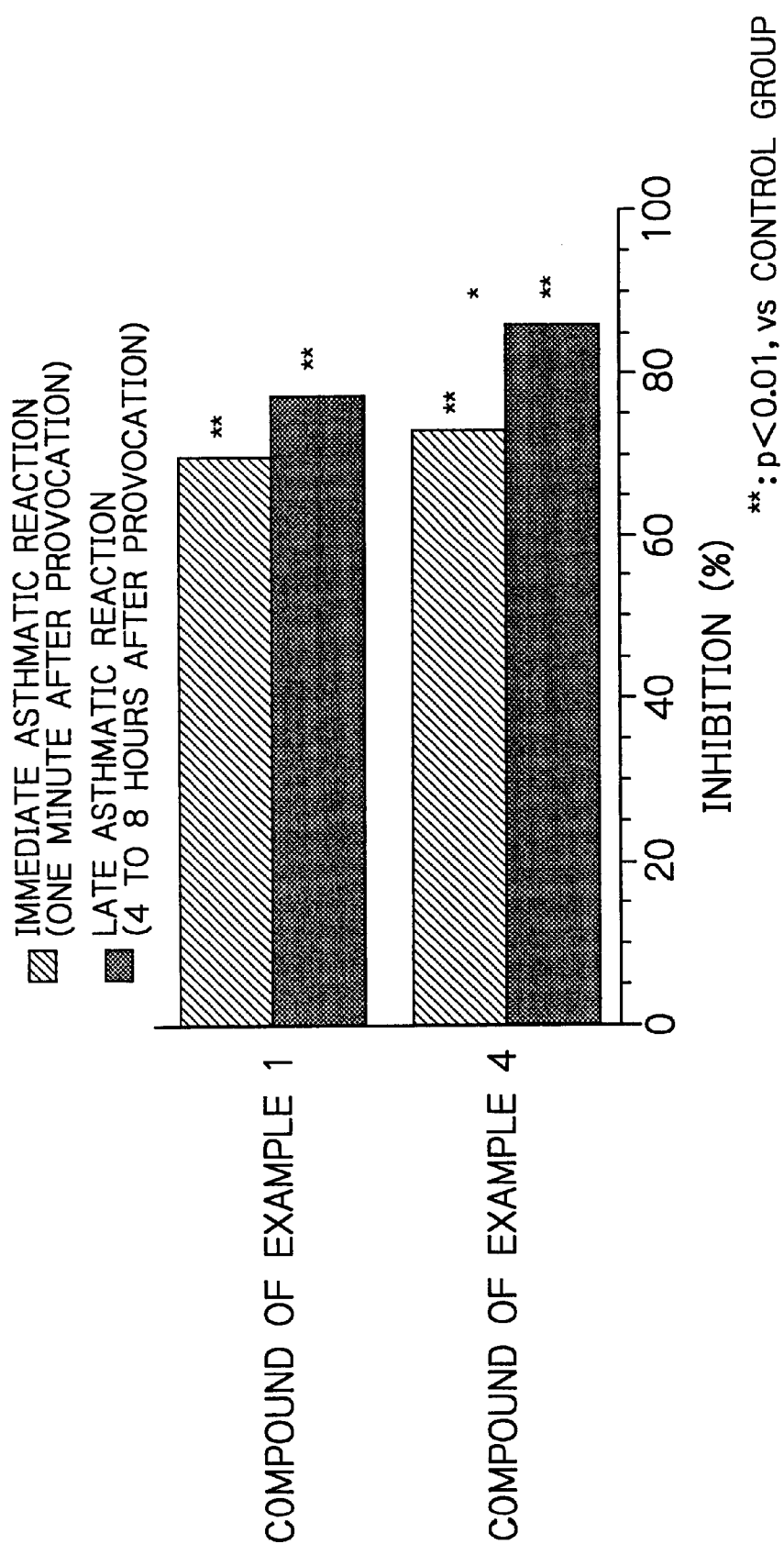
FIG. 2 is a graph showing the inhibitory effects of the compounds of the present invention on the immediate and late asthmatic responses in actively sensitized guinea pigs.

Here, when Compounds of Examples 1 and 4 were orally dosed with 10 mg/kg one hour before the "OVA" challenge, each IAR (% change in sRaw) was inhibited by 70% and 73%, and LAR (AUC) was inhibited by 77% and 86% compared to the control group (FIG. 2).

(2) Number of Cells in Bronchoalveolar Lavage Fluid

Figure 3:
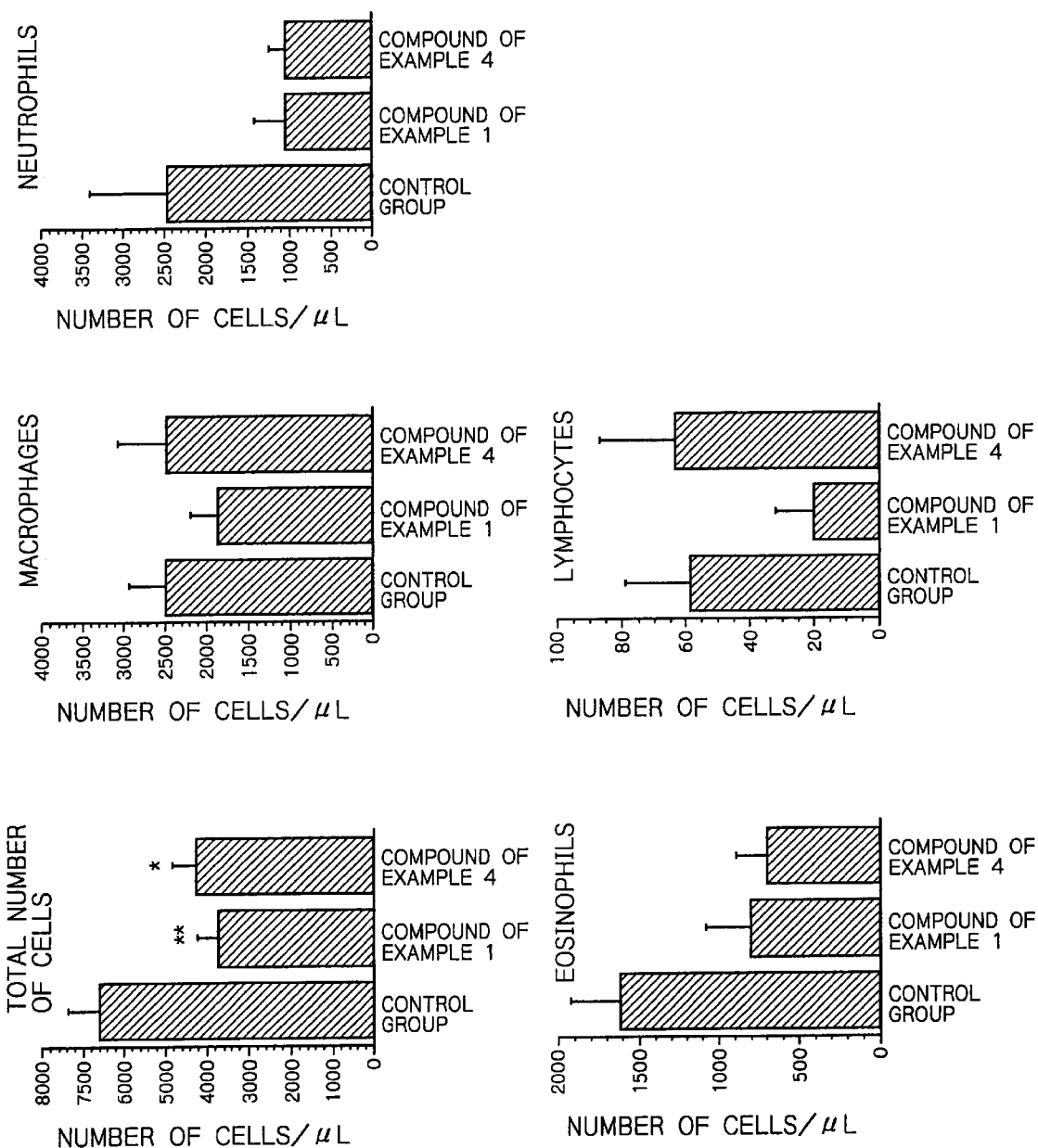
FIG. 3 is a graph showing the inhibitory effects of the compounds of the present invention on the number of inflammatory cells in the bronchoalveolar lavage fluid 24 hours after challenge with an antigen in actively sensitized guinea pigs.

The results are shown in FIG. 3. In the actively sensitized guinea pigs by the "OVA" inhalation, the total number of cells in the bronchoalveolar lavage fluid 24 hours after the antigen challenge was, on average, 6,667/$\mu$L, and the numbers of cells of macrophages, neutrophils, eosinophils and lymphocytes were, on average, 2,499, 2,487, 1,622 and 59/$\mu$L, respectively.

When Compound of Example 1 was orally dosed with 10 mg/kg one hour before the "OVA" challenge, the total number of cells was, on average, 3,775/$\mu$L, and the numbers of cells of macrophages, neutrophils, eosinophils and lymphocytes were, on average, 1,872, 1,072, 810 and 21/$\mu$L, respectively; a significant decrease in the total number of cells and a tendency for the numbers of cells of neutrophils, eosinophils and lymphocytes to decrease compared to the control group were recognized. On the other hand, when Compound of Example 4 was orally dosed with 10 mg/kg one hour before the "OVA" challenge, the total number of cells was, on average, 4,304/$\mu$L, and the numbers of cells of macrophages, neutrophils, eosinophils and lymphocytes were, on average, 2,478, 1,062, 700 and 64/$\mu$L, respectively; a significant decrease in the total number of cells and eosinophils and a tendency for the numbers of cells of neutrophils to decrease compared to the control group were recognized.

From the above results, both Compounds of Examples 1 and 4 exhibited inhibition against the immediate and late asthmatic responses of guinea pigs and, in addition, inhibition against the increase in the number of inflammatory cells in the bronchoalveolar lavage fluid and suggested a possibility that they would become promising drugs for the therapy of asthma in clinical trials.

Test Example 3

Action on Antigen Induced Airway Hypersensitivity in Actively Sensitized Guinea Pigs Bronchial asthma is a disease characterized by bronchial contraction, airway hypersensitivity and infiltration of inflammatory cells into the airway. Airway hypersensitivity is a condition in which the airway sensitively produces a contraction response to various slight stimuli. Particularly, airway hypersensitivity is considered to be a common feature among patients suffering from allergic bronchial asthma. This experimental system in which actively sensitized guinea pigs are used is useful as a airway hypersensitivity model.

(1) Sensitization

Guinea pigs were allowed to inhale a 1% "OVA" (Sigma Aldrich Co., U.S.A) physiological saline for 10 minutes daily continuously for 8 days with the use of an ultrasonic nebulizer ("NE-U12", Omron, Japan).

(2) Challenge

One week after the final sensitization, the guinea pigs were allowed to inhale a 2% "OVA" physiological saline for 5 minutes. Twenty-four hours before challenge and one hour before challenge, the guinea pigs were dosed with metyrapone (10 mg/kg, Sigma-Aldrich Co., U.S.A.) intravenously, and dosed with pyrilamine (10 mg/kg, Sigma-Aldrich Co., U.S.A.) intraperitoneally 30 minutes before challenge.

(3) Preparation of Test Substance and Method of Administration

Test substance (Compound of Example 4) was formed into a suspension with a 0.5% CMC-Na solution at each predetermined concentration. In two groups of guinea pigs, one hour before challenge, the guinea pigs of the each group were orally dosed with the suspension of the test substance with a dose set at 10 mg/kg or 30 mg/kg respectively and in other one group, the guinea pigs were orally dosed with the test substance twice, 16 hours before challenge and 2 hours before challenge, with a dose set at 30 mg/kg. Dexamethasone was formed into a suspension with a 0.5% CMC-Na solution which was then dosed twice, 16 hours before the antigen-challenge and 2 hours before the antigen-challenge, with a dose set at 10 mg/kg. For the control group the medium (a 0.5% CMC-Na solution) was used. The doses were all set at 5 mL/kg.

(4) Measurement of Airway Resistance

The specific airway resistance (sRaw) of wake guinea pigs was measured by the double flow plethysmography with the use of airway resistance measuring equipment ("Pulmos-1", M.I.P.S., Japan).

(5) Measurement of Airway Reactivity

For two hours, from twenty-two to twenty-six hours after the antigen challenge, the guinea pigs were placed in an animal chamber and allowed to inhale a physiological saline and acetylcholine (hereinafter referred to as "ACh") solutions of 0.0625, 0.125, 0.25, 0.5, 1 and 2 mg/mL, respectively, in the order named, each for one minute until sRaw came to the value at least twice the baseline sRaw (sRaw after the inhalation of the physiological saline). The ACh concentration (hereinafter referred to as "$PC_{100}ACh$") necessary for 100% increase in the baseline sRaw was calculated from the concentration of ACh and sRaw-resistance curve.

(6) Statistical Analysis

The obtained test results were shown by mean values and standard deviations and the student's t-test was carried out. The level of significance was set to 5% or less. The number of animals used in each test group was 6.

Results

Figure 4:
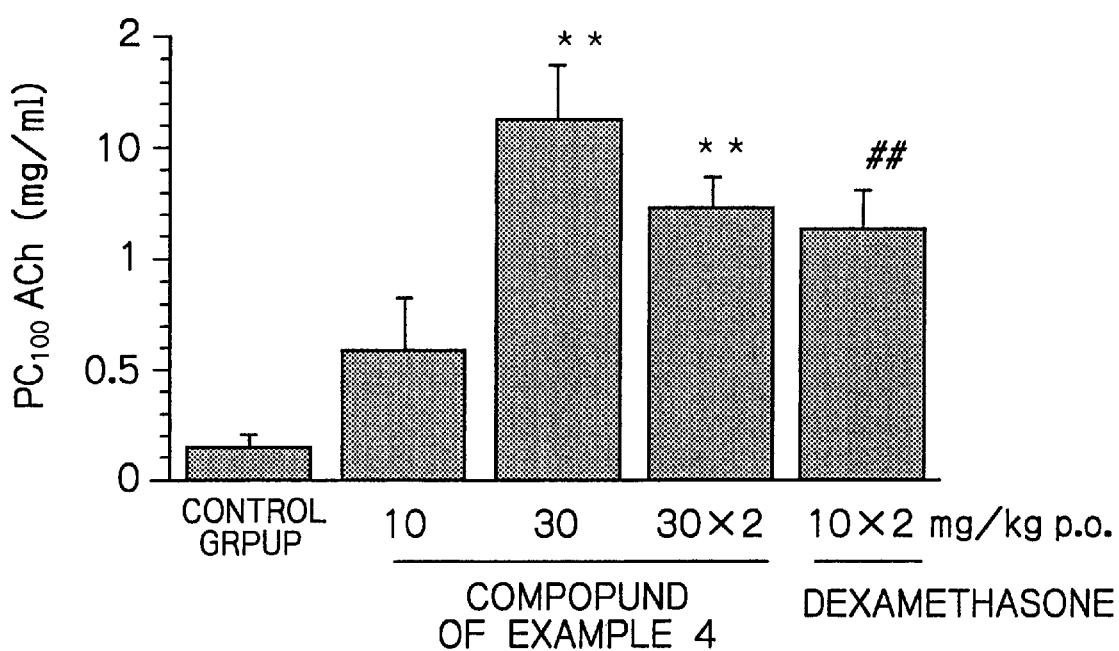
FIG. 4 is a graph showing the inhibitory effects of the compound of the present invention on the airway reactivity to acetylcholine 22 to 26 hours after challenge with an antigen in actively sensitized guinea pigs.

The results are shown in FIG. 4. In the guinea pigs actively sensitized by the "OVA" inhalation, the airway reactivity to ACh 22 hours to 26 hours after the challenge of antigen-antibody reaction was measured. The $PC_{100}ACh$ of the control group using the medium alone was 0.15 mg/mL. According to the report [Fuchikami, J-I, et al, Pharmacological study on antigen induced immediate and late asthmatic responses in actively sensitized guinea-pigs, *Jap, J. Pharmacol.*, 71, p196 (1996)] on the same system, the $PC_{100}ACh$ of guinea pigs challenged by a physiological saline in the guinea pigs actively sensitized by the "OVA" inhalation was, on average, 1.20 mg/mL and thus, in the control group of the present experiment the antigen induced airway hypersensitivity was clearly recognized. Further, when dexamethasone used as the positive control was orally dosed with 10 mg/kg 16 hours and 2 hours before the "OVA" challenge, the $PC_{100}ACh$ was 1.14 mg/mL, the airway hypersensitivity was significantly inhibited compared to the control group. On the other hand, when Compound of Example 4 was orally dosed with 10 and 30 mg/mL, respectively, one hour before the "OVA" challenge, the $PC_{100}ACh$ was 0.59 and 1.63 mg/mL, respectively, and exhibited a dose-dependent inhibition. Further, when Compound of Example 4 was orally dosed with 30 mg/kg twice 16 hours and 2 hours before the "OVA" challenge, the $PC_{100}ACh$ was 1.24 mg/mL, and the airway hypersensitivity was significantly inhibited compared to the control group.

From the above results, it is clear that Compound of Example 4 has a strong inhibition against the hypersensitivity in sensitized guinea pigs and, and it has suggested a possibility that Compound of Example 4 would become a promising anti-asthmatic drug even in clinical trials.

Test Example 4

Toxicity Study of Two-week Repeated-dose Oral Administration with Rats

In order to study the toxicity by repeated-dose administration of compounds, the compounds were dosed orally to Sprague-Dawley line rats (three male rats per group) with 0, 125 and 500 mg/kg/day (a 0.5 w/v % CMC-Na solution) repeatedly for two weeks. The results are shown in Table 20.

TABLE 20

| Example No. | Results |
| --- | --- |
| Comparative Example | Kidney damage were observed with 125 mg/kg or more. |
| Example 1 | No abnormalities were recognized in any dosed group. |
| Example 4 | Tendency to weight inhibition was recognized in the group with 500 mg/kg. |

INDUSTRIAL APPLICABILITY

The compounds of the present invention have a wide range of pharmacological actions such as an excellent tracheal smooth muscle relaxing action, an inhibition of airway hypersensitivity and an inhibition of infiltration of inflammatory cells into the airway and also high safety and accordingly, are very promising as drugs.

What is claimed is:

1. A compound represented by formula (1),

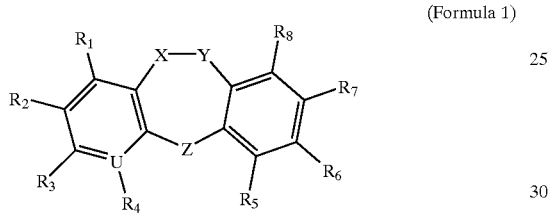

(Formula 1)

wherein
when the X—Y bond is a single bond, X and Y are independently selected from the group consisting of: $CW_1W_2$ wherein $W_1$ and $W_2$ are independently selected from the group comprising one of a hydrogen atom, a halogen, a hydroxyl group, a lower alkyl group, a substituted lower alkyl group, a lower alkoxy group, a cycloalkyl group and a cycloalkenyl group, C=O, and C=NOW$_3$ wherein $W_3$ comprises a hydrogen atom or a lower alkyl group;

when the X—Y bond is a double bond, X and Y independently comprise $CW_4$ wherein $W_4$ comprises any one of a hydrogen atom, a halogen, a hydroxyl group, a lower alkyl group, a substituted lower alkyl group, a lower alkoxy group and an acyloxy group;

Z comprises any one of S, S=O and $SO_2$;
U comprises C;
$R_1$ to $R_4$ are independently selected from the group consisting of a hydrogen atom, a lower alkyl group, a substituted lower alkyl group, a cycloalkyl group, a substituted cycloalkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_1W_5$, a nitro group, an amino group, a substituted amino group, a cyano group, an acyl group, an acylamino group, a substituted acyl group, a substituted acylamino group, an aromatic ring, a substituted aromatic ring, a heterocycle and a substituted heterocycle wherein
$V_1$ comprises any one of S, S=O and $SO_2$,
$W_5$ comprises any one of a hydrogen atom, a lower alkyl group, a substituted lower alkyl group, a lower alkylcarbonyl group and a substituted lower alkylcarbonyl group, an acyloxy group and a trihalomethyl group;

$R_5$ to $R_8$ are independently selected from the group consisting of a hydrogen atom, a lower alkyl group, a substituted lower alkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_2W_7$, a nitro group, an amino group, a substituted amino group, an acylamino group, an aromatic ring, a substituted aromatic ring, a heterocycle and a substituted heterocycle; wherein
$V_2$ comprises one of S, S=O and $SO_2$,
$W_7$ comprises one of a hydrogen atom, a lower alkyl group, a substituted lower alkyl group, a lower alkylcarbonyl group, a substituted lower alkylcarbonyl group and a trihalomethyl group,
wherein:
when X is $CHW_0$, $CW_0W_0$ or $CW_0$ at least one of $R_5$ to $R_8$ is a hydroxyl group, provided that at least one of $R_5$, $R_7$ or $R_8$ is a hydroxy group when the X—Y bond is $CH(C_2H_5)CO$ and $R_6$ is a hydroxyl group and
when X is other than $CHW_0$, $CW_0W_0$ or $CW_0$ at least one of $R_5$ to $R_8$ is a hydroxyl group and, at the same time, at least one of the other $R_5$ to $R_8$ is a group of OR wherein
$W_0$ is any one selected from a lower alkyl group and a substituted lower alkyl group and
R is any one selected from the group consisting of a hydrogen atom, a lower alkyl group, a substituted lower alkyl group, a lower alkylcarbonyl group and a substituted lower alkylsilyl group; and
when X—Y comprises $CH_2CH_2$, $CHBrCH_2$, $CH_2CO$, CHBrCO, CH=CH, CH=COCOCH$_3$ or CH=COCH$_3$,
at least one of $R_1$ to $R_4$ is an aromatic ring, a substituted aromatic ring, a heterocycle or a substituted heterocycle provided that when both $R_6$ and $R_7$ are hydroxyl groups, any one of $R_1$ to $R_4$ is not a phenyl group; or
at least one of $R_1$ to $R_4$ comprises $SW_8$ or $S(O)W_9$ wherein $W_8$ and $W_9$ independently comprise a lower alkyl group or a substituted lower alkyl group; or
$R_2$ comprises either a lower alkyl group or a substituted lower alkyl group and, at the same time, $R_8$ comprises a hydroxyl group; or
at least one of $R_1$ to $R_4$ comprises a lower alkylcarbonyl group provided that the number of carbon atoms of the lower alkyl group is 3 or more, a cycloalkylcarbonyl group or a cycloalkenylcarbonyl group and, at the same time, $R_8$ is a hydroxyl group; or
at least one of $R_1$ to $R_4$ comprises a cyano group; or
at least one of $R_1$ to $R_4$ comprises a halogen and, at the same time, Z is any one of S, S=O and $SO_2$; or
$R_5$ and $R_6$ comprise hydroxyl groups and, at the same time, Z is S; or
at least one of $R_1$ to $R_4$ comprises —C(=NOR)CH$_3$ wherein R comprises a hydrogen atom or a lower alkyl group, an optical isomer thereof, a conjugate thereof or a pharmaceutically acceptable salt thereof.

2. The compound according to claim 1, wherein $R_6$ is a hydroxyl group.

3. The compound according to claim 1, wherein $R_6$ and $R_7$ are hydroxyl groups.

4. The compound according to claim 1, wherein $R_6$ and $R_8$ are hydroxyl groups.

5. The compound according to claim 1, wherein $R_5$ and $R_6$ are hydroxyl groups.

6. The compound according to claim 1, wherein the X—Y bond is a single bond and X comprises $CW_1W_2$ or the X—Y bond is a double bond and X comprises CW, wherein
   at least one of $W_1$ and $W_2$ is selected from a lower alkyl group, a substituted lower alkyl group, a cycloalkyl group and a cycloalkenyl group and
   W is one of a lower alkyl group, a substituted lower alkyl group, a cycloalkyl group and a cycloalkenyl group.

7. The compound according to claim 1, wherein Y comprises CO.

8. The compound according to claim 6, wherein the lower alkyl group is any one of a methyl group, an ethyl group, a n-propyl group, an isopropyl group, an n-butyl group, a sec-butyl group, an isobutyl group and a tert-butyl group.

9. The compound according to claim 1, wherein $R_2$ or $R_3$ is any one of a heterocycle, a substituted heterocycle, an aromatic ring and a substituted aromatic ring.

10. The compound according to claim 1, wherein the heterocycle is an aromatic heterocycle.

11. The compound according to claim 1, wherein $R_2$ or $R_3$ is $SW_8$ or $S(O)W_9$, wherein
    $W_8$ is a lower alkyl group or a substituted lower alkyl group, and
    $W_9$ is a lower alkyl group or a substituted alkyl group.

12. The compound according to claim 11, wherein the lower alkyl group comprises any one of a methyl group, an ethyl group, a n-propyl group, an isopropyl group, an n-butyl group, a sec-butyl group, an isobutyl group and a tert-butyl group.

13. The compound according to claim 1, wherein Z comprises S.

14. The compound according to claim 1 wherein the compound comprises 7,8-dihydroxy-1-ethyl-10,11-dihydrodibenzo[b,j]thiepin-10-one.

15. The compound according to claim 1 wherein the compound comprises 11-diethyl-7,8-dihydroxy-10,11-dihydrodibenzo[b,j]thiepin-10-one.

16. The compound according to claim 1 wherein the compound comprises 7,9-dihydroxy-2-methylthio-10,11-dihydrodibenzo[b,j]thiepin-10-one.

17. A method of preparing a compound represented by formula (1),

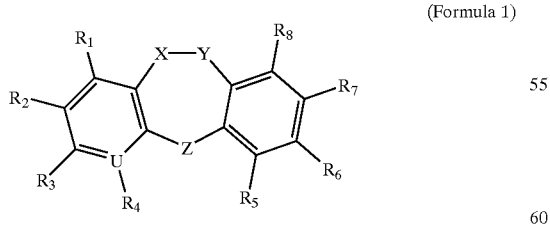

(Formula 1)

wherein
   when the X—Y bond is a single bond, X and Y are independently selected from the group consisting of:
   $CW_1W_2$ wherein $W_1$ and $W_2$ are independently selected from the group comprising one of a hydrogen atom, a halogen, a hydroxyl group, a lower alkyl group, a substituted lower alkyl group, a lower alkoxy group, a cycloalkyl group and a cycloalkenyl group,
   C=O, and
   $C=NOW_3$ wherein $W_3$ comprises a hydrogen atom or a lower alkyl group;
when the X—Y bond is a double bond, X and Y independently comprise $CW_4$ wherein $W_4$ comprises any one of a hydrogen atom, a halogen, a hydroxyl group, a lower alkyl group, a substituted lower alkyl group, a lower alkoxy group and an acyloxy group;
Z comprises any one of S, S=O and $SO_2$;
U comprises C;
$R_1$ to $R_4$ are independently selected from the group consisting of a hydrogen atom, a lower alkyl group, a substituted lower alkyl group, a cycloalkyl group, a substituted cycloalkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_1W_5$, a nitro group, an amino group, a substituted amino group, a cyano group, an acyl group, an acylamino group, a substituted acyl group, a substituted acylamino group, an aromatic ring, a substituted aromatic ring, a heterocycle and a substituted heterocycle wherein
   $V_1$ comprises any one of S, S=O and $SO_2$,
   $W_5$ comprises any one of a hydrogen atom, a lower alkyl group, a substituted lower alkyl group, a lower alkylcarbonyl group and a substituted lower alkylcarbonyl group, an acyloxy group and a trihalomethyl group,
$R_5$ to $R_8$ are independently selected from the group consisting of a hydrogen atom, a lower alkyl group, a substituted lower alkyl group, a lower alkenyl group, a substituted lower alkenyl group, a lower alkynyl group, a substituted lower alkynyl group, a halogen, a lower alkylcarbonyl group, a substituted lower alkylcarbonyl group, a trihalomethyl group, $V_2W_7$, a nitro group, an amino group, a substituted amino group, an acylamino group, an aromatic ring, a substituted aromatic ring, a heterocycle and a substituted heterocycle; wherein
   $V_2$ comprises one of S, S=O and $SO_2$,
   $W_7$ comprise one of a hydrogen atom, a lower alkyl group, a substituted lower alkyl group, a lower alkylcarbonyl group, a substituted lower alkylcarbonyl group and a trihalomethyl group,
wherein:
   when X is $CHW_0$, $CW_0W_0$ or $CW_0$ at least one of $R_5$ to $R_8$ is a hydroxyl group, provided that at least one of $R_5$, $R_7$ or $R_8$ is a hydroxy group when the X—Y bond is $CH(C_2H_5)CO$ and $R_6$ a hydroxyl group and
   when X is other than $CHW_0$, $CW_0W_0$ or $CW_0$ at least one of $R_5$ to $R_8$ is a hydroxyl group and, at the same time, at least one of the other $R_5$ to $R_8$ is a group of OR wherein
      $W_0$ is any one selected from a lower alkyl group and a substituted lower alkyl group and
      R is any one selected from the group consisting of a hydrogen atom, a lower alkyl group, a substituted lower alkyl group, a lower alkylcarbonyl group and a substituted lower alkylsilyl group; and
   when X—Y comprises $CH_2CH_2$, $CHBrCH_2$, $CH_2CO$, CHBrCO, CH=CH, $CH=COCOCH_3$ or $CH=COCH_3$, at least one of $R_1$ to $R_4$ is an aromatic ring, a substituted aromatic ring, a heterocycle or a substituted heterocycle provided that when both $R_6$ and $R_7$ are hydroxyl groups, any one of $R_1$ to $R_4$ is not a phenyl group; or at least one of $R_1$ to $R_4$ comprises $SW_8$ or $S(O)W_9$ wherein $W_8$ and $W_9$ independently comprise a lower alkyl group or a substituted lower alkyl group; or $R_2$ comprises either a lower alkyl group or a substituted lower alkyl group and, at the same time, $R_8$ comprises a hydroxyl group; or at least one of $R_1$ to $R_4$ comprises a lower alkylcarbonyl group provided that the number of carbon atoms of the lower alkyl group is 3 or more, a cycloalkylcarbonyl group or a cycloalkenylcarbonyl group and, at the same time, $R_8$ is a hydroxyl group; or at least one of $R_1$ to $R_4$ comprises a cyano group; or at least one of $R_1$ to $R_4$ comprises a halogen and, at the same time, Z is any one of S, S=O and $SO_2$; or $R_5$ and $R_6$ comprise hydroxyl groups and, at the same time, Z is S; or at least one of $R_1$ to $R_4$ comprise —C(=NOR)CH$_3$ wherein R comprises a hydrogen atom or a lower alkyl group, an optical isomer thereof, a conjugate thereof or a pharmaceutically acceptable salt thereof, which comprises, in any order, the reaction steps of (1) bonding a ring A to a ring C by the Ullmann reaction as shown in formula 2 and (2) bonding a ring A to a ring C by the Friedel-Crafts reaction or photoreaction as shown in formula 3, (Formula 2)

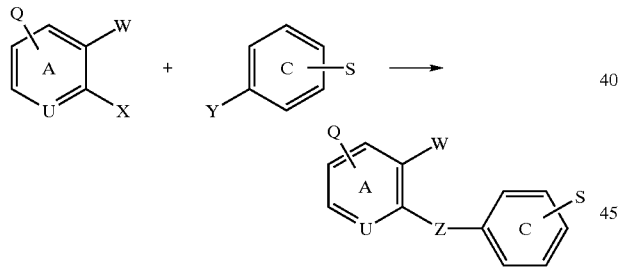

(Formula 3)

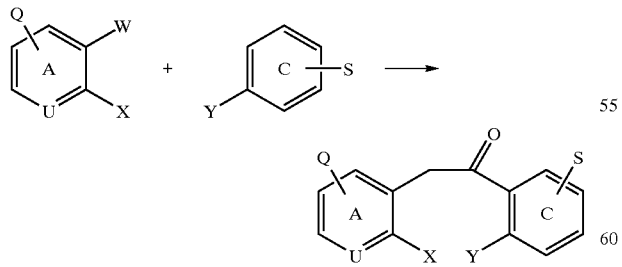

wherein
Q, S and W are each any substituent;
U is C;
one of X and Y is a leaving group and the other is a nucleophilic group; and Z is any one of S, SO and $SO_2$.

18. The method according to claim 17 further comprising at least one of a carbon atom increasing reaction, a conversion reaction of a substituent, an introduction reaction of a substituent, a removal of the protection of a substituent, forming a salt, and performing optical resolution.

19. A pharmaceutical composition comprising an effective amount of the compound of claim 1 and a pharmaceutically acceptable carrier or diluent.

20. The pharmaceutical composition according to claim 19 wherein the pharmaceutical composition utilizes the tracheal smooth muscles relaxing action of the compound.

21. The pharmaceutical composition according to claim 19 wherein the pharmaceutical composition utilizes the inhibitory effect on airway hypersensitivity of the compound.

22. The pharmaceutical composition according to claim 19 wherein the pharmaceutical composition utilizes the inhibitiory effect on inflammatory cells infiltration of the compound.

23. The pharmaceutical composition according to claim 19 wherein the pharmaceutical composition is used as the anti-asthmatic drug.

24. The compound of claim 1 wherein X and Y are the same.

25. The compound of claim 1 wherein X and Y are different.

26. The compound of claim 1 wherein $W_1$ and $W_2$ are the same.

27. The compound of claim 1 wherein $W_1$ and $W_2$ are different.

28. The compound of claim 1 wherein $R_1$ to $R_4$ are the same.

29. The compound of claim 1 wherein $R_1$ to $R_4$ are different.

30. The compound of claim 1 wherein $R_5$ to $R_8$ are the same.

31. The compound of claim 1 wherein $R_5$ to $R_8$ are different.

32. The compound according to claim 2, wherein the X—Y bond is a single bond and X comprises $CW_1W_2$ or the X—Y bond is a double bond and X comprises CW, wherein
at least one of $W_1$ and $W_2$ is selected from a lower alkyl group, a substituted lower alkyl group, a cycloalkyl group and a cycloalkenyl group and
W is one of a lower alkyl group, a substituted lower alkyl group, a cycloalkyl group and a cycloalkenyl group.

33. The compound according to claim 3, wherein the X—Y bond is a single bond and X comprises $CW_1W_2$ or the X—Y bond is a double bond and X comprises CW, wherein
at least one of $W_1$ and $W_2$ is selected from a lower alkyl group, a substituted lower alkyl group, a cycloalkyl group and a cycloalkenyl group and
W is one of a lower alkyl group, a substituted lower alkyl group, a cycloalkyl group and a cycloalkenyl group.

34. The compound according to claim 4, wherein the X—Y bond is a single bond and X comprises $CW_1W_2$ or the X—Y bond is a double bond and X comprises CW, wherein
at least one of $W_1$ and $W_2$ is selected from a lower alkyl group, a substituted lower alkyl group, a cycloalkyl group and a cycloalkenyl group and
W is one of a lower alkyl group, a substituted lower alkyl group, a cycloalkyl group and a cycloalkenyl group.

35. The compound according to claim 5, wherein the X—Y bond is a single bond and X comprises $CW_1W_2$ or the X—Y bond is a double bond and X comprises CW, wherein at least one of $W_1$ and $W_2$ is selected from a lower alkyl group, a substituted lower alkyl group, a cycloalkyl group and a cycloalkenyl group and W is one of a lower alkyl group, a substituted lower alkyl group, a cycloalkyl group and a cycloalkenyl group.

36. The compound according to claim 2, wherein Y comprises CO.

37. The compound according to claim 3, wherein Y comprises CO.

38. The compound according to claim 4, wherein Y comprises CO.

39. The compound according to claim 5, wherein Y comprises CO.

40. The compound according to claim 6, wherein Y comprises CO.

41. The compound according to claim 1, wherein the lower alkyl group is any one of a methyl group, an ethyl group, a n-propyl group, an isopropyl group, an n-butyl group, a sec-butyl group, an isobutyl group and a tert-butyl group.

42. The compound according to claim 2, wherein the lower alkyl group is any one of a methyl group, an ethyl group, a n-propyl group, an isopropyl group, an n-butyl group, a sec-butyl group, an isobutyl group and a tert-butyl group.

43. The compound according to claim 3, wherein the lower alkyl group is any one of a methyl group, an ethyl group, a n-propyl group, an isopropyl group, an n-butyl group, a sec-butyl group, an isobutyl group and a tert-butyl group.

44. The compound according to claim 4, wherein the lower alkyl group is any one of a methyl group, an ethyl group, a n-propyl group, an isopropyl group, an n-butyl group, a sec-butyl group, an isobutyl group and a tert-butyl group.

45. The compound according to claim 5, wherein the lower alkyl group is any one of a methyl group, an ethyl group, a n-propyl group, an isopropyl group, an n-butyl group, a sec-butyl group, an isobutyl group and a tert-butyl group.

46. The compound according to claim 7, wherein the lower alkyl group is any one of a methyl group, an ethyl group, a n-propyl group, an isopropyl group, an n-butyl group, a sec-butyl group, an isobutyl group and a tert-butyl group.

47. The compound according to claim 2, wherein $R_2$ or $R_3$ is any one of a heterocycle, a substituted heterocycle, an aromatic ring and a substituted aromatic ring.

48. The compound according to claim 3, wherein $R_2$ or $R_3$ is any one of a heterocycle, a substituted heterocycle, an aromatic ring and a substituted aromatic ring.

49. The compound according to claim 4, wherein $R_2$ or $R_3$ is any one of a heterocycle, a substituted heterocycle, an aromatic ring and a substituted aromatic ring.

50. The compound according to claim 5, wherein $R_2$ or $R_3$ is any one of a heterocycle, a substituted heterocycle, an aromatic ring and a substituted aromatic ring.

51. The compound according to claim 2, wherein the heterocycle is an aromatic heterocycle.

52. The compound according to claim 3, wherein the heterocycle is an aromatic heterocycle.

53. The compound according to claim 4, wherein the heterocycle is an aromatic heterocycle.

54. The compound according to claim 5, wherein the heterocycle is an aromatic heterocycle.

55. The compound according to claim 2, wherein $R_2$ or $R_3$ is $SW_8$ or $S(O)W_9$, wherein $W_8$ is a lower alkyl group or a substituted lower alkyl group, and $W_9$ is a lower alkyl group or a substituted alkyl group.

56. The compound according to claim 3, wherein $R_2$ or $R_3$ is $SW_8$ or $S(O)W_9$, wherein $W_8$ is a lower alkyl group or a substituted lower alkyl group, and $W_9$ is a lower alkyl group or a substituted alkyl group.

57. The compound according to claim 4, wherein $R_2$ or $R_3$ is $SW_8$ or $S(O)W_9$, wherein $W_8$ is a lower alkyl group or a substituted lower alkyl group, and $W_9$ is a lower alkyl group or a substituted alkyl group.

58. The compound according to claim 5, wherein $R_2$ or $R_3$ is $SW_8$ or $S(O)W_9$, wherein $W_8$ is a lower alkyl group or a substituted lower alkyl group, and $W_9$ is a lower alkyl group or a substituted alkyl group.

59. The compound according to claim 54, wherein the lower alkyl group is any one of a methyl group, an ethyl group, a n-propyl group, an isopropyl group, an n-butyl group, a sec-butyl group, an isobutyl group and a tert-butyl group.

60. The compound according to claim 55, wherein the lower alkyl group is any one of a methyl group, an ethyl group, a n-propyl group, an isopropyl group, an n-butyl group, a sec-butyl group, an isobutyl group and a tert-butyl group.

61. The compound according to claim 56, wherein the lower alkyl group is any one of a methyl group, an ethyl group, a n-propyl group, an isopropyl group, an n-butyl group, a sec-butyl group, an isobutyl group and a tert-butyl group.

62. The compound according to claim 57, wherein the lower alkyl group is any one of a methyl group, an ethyl group, a n-propyl group, an isopropyl group, an n-butyl group, a sec-butyl group, an isobutyl group and a tert-butyl group.

63. The compound according to claim 2, wherein Z comprises S.

64. The compound according to claim 3, wherein Z comprises S.

65. The compound according to claim 4, wherein Z comprises S.

66. The compound according to claim 5, wherein Z comprises S.

67. The compound according to claim 6, wherein Z comprises S.

68. The compound according to claim 7, wherein Z comprises S.

69. The compound according to claim 8, wherein Z comprises S.

70. The compound according to claim 9, wherein Z comprises S.

71. The compound according to claim 10, wherein Z comprises S.

72. The compound according to claim 11, wherein Z comprises S.

73. The compound according to claim 12, wherein Z comprises S.

74. A pharmaceutical composition comprising an effective amount of the compound of claim 2 and a pharmaceutically acceptable carrier or diluent.

75. A pharmaceutical composition comprising an effective amount of the compound of claim 3 and a pharmaceutically acceptable carrier or diluent.

76. A pharmaceutical composition comprising an effective amount of the compound of claim 4 and a pharmaceutically acceptable carrier or diluent.

77. A pharmaceutical composition comprising an effective amount of the compound of claim 5 and a pharmaceutically acceptable carrier or diluent.

78. A pharmaceutical composition comprising an effective amount of the compound of claim 6 and a pharmaceutically acceptable carrier or diluent.

79. A pharmaceutical composition comprising an effective amount of the compound of claim 7 and a pharmaceutically acceptable carrier or diluent.

80. A pharmaceutical composition comprising an effective amount of the compound of claim 8 and a pharmaceutically acceptable carrier or diluent.

81. A pharmaceutical composition comprising an effective amount of the compound of claim 9 and a pharmaceutically acceptable carrier or diluent.

82. A pharmaceutical composition comprising an effective amount of the compound of claim 10 and a pharmaceutically acceptable carrier or diluent.

83. A pharmaceutical composition comprising an effective amount of the compound of claim 11 and a pharmaceutically acceptable carrier or diluent.

84. A pharmaceutical composition comprising an effective amount of the compound of claim 12 and a pharmaceutically acceptable carrier or diluent.

85. A pharmaceutical composition comprising an effective amount of the compound of claim 13 and a pharmaceutically acceptable carrier or diluent.

86. A pharmaceutical composition comprising an effective amount of the compound of claim 14 and a pharmaceutically acceptable carrier or diluent.

87. A pharmaceutical composition comprising an effective amount of the compound of claim 15 and a pharmaceutically acceptable carrier or diluent.

88. A pharmaceutical composition comprising an effective amount of the compound of claim 16 and a pharmaceutically acceptable carrier or diluent.

* * * * *